US007720614B2

(12) United States Patent
Davidson et al.

(10) Patent No.: US 7,720,614 B2
(45) Date of Patent: May 18, 2010

(54) METHOD FOR IDENTIFICATION OF CIS-REGULATORY MODULES VIA COMPUTATIONAL ANALYSIS OF SINGLE POLYNUCLEOTIDE POLYMORPHISMS (SNPS) AND INSERTIONS/DELETIONS (INDELS)

(75) Inventors: Eric H. Davidson, Pasadena, CA (US); Robert Andrew Cameron, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/297,293

(22) Filed: Dec. 7, 2005

(65) Prior Publication Data

US 2006/0141513 A1      Jun. 29, 2006

Related U.S. Application Data

(60) Provisional application No. 60/634,196, filed on Dec. 7, 2004.

(51) Int. Cl.
*G01N 33/48* (2006.01)
(52) U.S. Cl. .............................. 702/20; 703/2; 703/11; 706/45; 707/6; 707/7; 435/6; 435/320.1; 536/24.2; 211/41.12
(58) Field of Classification Search ........................ None
See application file for complete search history.

(56) References Cited

U.S. PATENT DOCUMENTS

| 6,470,277 | B1 | 10/2002 | Chin et al. | |
|---|---|---|---|---|
| 6,772,069 | B1 | 8/2004 | Eisenberg et al. | |
| 2002/0081688 | A1* | 6/2002 | Kamb et al. | 435/189 |
| 2002/0142468 | A1* | 10/2002 | Sundstrom | 435/484 |

OTHER PUBLICATIONS

Grad et al. Bioinformatics, vol. 20, pp. 2738-2750, May 4, 2004.*
Kohn et al. Molecular Biology and Evolution, vol. 21, pp. 374-383, Available Dec. 5, 2003.*
Sinha et al. BMC Bioinformatics, vol. 5, pp. 1-12, Sep. 2004.*
Elkon et al. Nucleic Acids Research, vol. 32, pp. 4955-4961, Sep. 23, 2004.*
Mayor et al., Bioinformatics, vol. 16, pp. 1046-1047, 2000.*
Cameron et al., PNAS, vol. 102, pp. 11769-11774, 2005.*
Sinha et al. Molecular Biology and Evolution, vol. 22, pp. 874-885, Jan. 19, 2005.*
Balhoff et al. PNAS, vol. 102, pp. 8591-8596, Jun. 2005.*
Emberly et al. BMC Bioinformatics, vol. 4, pp. 1-11, Nov. 2003.*
Arnone and Davidson, "The Hardwiring of Development: Organization and Function of Genomic Regulatory Systems," Development (1997) 124:1851-1864.
Britten, "Divergence Between Samples of Chimpanzee and Human DNA Sequences is 5%, Counting Indels," Proc Natl Acad Sci USA (2002) 99:13633-13635.

Britten et al., "Majority of Divergence Between Closely Related DNA Samples is Due to Indels," Proc Natl Acad Sci USA (2003) 100:4661-4665.
Chechetkin et al., "Sequencing by Hybridization with the Generic 6-mer Oligonucleotide Microarray: An Advanced Scheme for Data Processing," J Biomol Struct Dyn (2000) 18(1):83-101.
Davidson, *Genomic Regulatory Systems: Development and Evolution*, Academic Publishing, San Diego, CA (2001) pp. 17, 58-61.
Fujiyama et al., "Construction and Analysis of a Human-Chimpanzee Comparative Clone Map," Science (2002) 295:131-134.
Hatzigeorgiou, et al., "Functional Site Prediction on the DNA Sequence by Artificial Neural Networks," In *Proceedings of the IEEE International Joint Symposia on Intelligence and Systems*, (1996) pp. 12-17 (IEEE Computer Society Press, Los Alamitos, CA).
Kim et al., "Hox Cluster Genomics in the Horn Shark, Heterodontus Francisci," Proc Natl Acad Sci USA (2000) 97:1655-1660.
Kirchhammer and Davidson, "Spatial and Temporal Information Processing in the Sea Urchin Embryo: Modular and Intramodular Organization of the CyIIIa Gene cis-Regulatory System," Development (1996) 122:333-348.
Kirchhamer et al., "Modular cis-Regulatory Organization of Developmentally Expressed Genes: Two Genes Transcribed Territorially in the Sea Urchin Embryo, and Additional Examples," Proc Natl Acad Sci USA (1996) 93:9322-9328.
Langeland and Carroll, "Conservation of Regulatory Elements Controlling Hairy Pair-Rule Stripe Formation," Development (1993) 117:585-596.
Ludwig et al., "Functional Analysis of Eve Stripe 2 Enhancer Evolution in Drosophila: Rules Governing Conservation and Change," Development (1998) 125:949-958.
Shashikant et al., "Comparative Studies on Mammalian Hoxc8 Early Enhancer Sequence Reveal a Baleen Whale-Specific Deletion of a cis-Acting Element," Proc Natl Acad. Sci USA (1998) 95:15446-15451.
Tümpel et al., "Conservation and Diversity in the cis-Regulatory Networks that Integrate Information Controlling Expression of Hoxa2 in Hindbrain and Cranial Neural Crest Cells in Vertebrates," Dev Biol (2002) 246:45-56.
Williams et al., "Organization of Wing Formation and Induction of a Wing-Patterning Gene at the Dorsal/Ventral Compartment Boundary," Nature (1994) 368:299-305.

(Continued)

*Primary Examiner*—Carolyn L. Smith
(74) *Attorney, Agent, or Firm*—DLA Piper LLP (US)

(57) ABSTRACT

A computational method is described which uses the process of cis-regulatory module evolution to identify conserved sequence patches which exhibit suppression of change by snp/indel occurrence, including determining sequence similarities significantly greater than random expectation on selected genome sequences from two or more species in sequences that lie outside of protein coding regions, sorting the similarities for conserved patches of single nucleotide polymorphisms (SNPs) and insertion/deletions (indels). and selecting such patches to identify cis-regulatory modules. Further, the disclosed method is practiced in the absence of having to execute multiple interspecific sequence comparison analysis, where such identified cis-regulatory modules are used to produce libraries and arrays containing such cis-regulatory modules.

16 Claims, 88 Drawing Sheets

OTHER PUBLICATIONS

Yuh et al., "Complexity and Organization of DNA-Protein Interactions in the 5regulatory Region of an Endoderm-Specific Marker Gene in the Sea Urchin Embryo," Mech Dev (1994) 47:165-186.

Yuh et al., "Modular Cis-Regulatory Organization of Endo16, a Gut-Specific Gene of the Sea Urchin Embryo.. Development," Development (1996) 122:1069-1082.

Yuh et al., "Quantitative Functional Interrelations within the Cis-Regulatory System of the *S. purpuratus* Endo16 Gene," Development (1996) 122:4045-4056.

Yuh et al., "Genomic cis-Regulatory Logic: Functional Analysis and Computational Model of a Sea Urchin Gene Control System," Science (1998) 279:1896-1902.

Yuh et al., "cis-Regulatory Logic in the endo16 Gene: Switching from a Specification to a Differentiation Mode of Control," Development (2001) 128:617-628.

Lee et al., "A Distal Enhancer in the Interferon-$\gamma$ (IFN-$\gamma$) Locus Revealed by Genome Sequence Comparison." *J. Biol. Chem.*, 279:4802-4810 (2004).

Kellis et al., "Sequencing and Comparison of Yeast Species to Identify Genes and Regulatory Elements." *Nature*, 423:241-254 (2003).

Ellrott et al., Identifying Transcription Factor Binding Sites through Markov Chain Optimization. Bioinformatics, 18:S100-S109 (2002).

\* cited by examiner

Brachyury Alignments

_Bra Active 1:_

```
bra_Sp_117A03            AGAAGAGAAAAGCCAGGGTGGTCGAAGTTTTGTCAATAAAAGCCCACCAA
bra_Sf_024017_Contig1b   A------AAAAGCCAGGGTGGTCGAAGTTTTGTCAATAAAAGCCCCCCAA
                         *      ****************************************  ** bra_Sp_117A03            AAGTCCTTTTCATTCGTGATCGCCGAATAAACATTCGCACTTGCGACGTG
bra_Sf_024017_Contig1b   AAGTCCTTTTCATTCGTGATCACCGAATAAACATTCGCACTTGCGACGTG
                         ******************* ************************** bra_Sp_117A03            AAACGAGACTTACGCCGGAGAGAAAAGGAGAAAGTGACGAAAGCACCACC
bra_Sf_024017_Contig1b   AAACGAGACTTACGCCGAAGAGAAAAGGAGAAAGTGACGAAAGCACCACC
                         *************** ****************************** bra_Sp_117A03            C   (SEQ ID NO:1)
bra_Sf_024017_Contig1b   C   (SEQ ID NO:2)
                         *
```

_Bra Active 2:_

```
bra_Sp_117A03            CTTGTCAAGGAAAAA-AAGCCTTTGATCTCGCATCTCACCGCCAATAATT
bra_Sf_024017_Contig4b   CTTGTCAAAGAAAAACAAGCCTTTGATCTCGCATCGCACCGCCAATAATT
                         ****** ** *************** ************ bra_Sp_117A03            AGTAAACAATAGCGGAGCACATGGCCTATCTCAGCTTTTATAGTTTGGAC
bra_Sf_024017_Contig4b   AGTAAACAATAGCAGCGCACATGGTCTATCTCAGCTTTTATAGTTTGGAC
                         ************* * ****** *********************** bra_Sp_117A03            TTTCTTTGTCGATCTCTTATAATATAAACTGGTTATCACGCCACGCGTAG
bra_Sf_024017_Contig4b   TTTCTTTGTCGATCTGTTATA---TAAACTTGTTATCACGCCACGCGTAG
                         ************* *   ** ***************** bra_Sp_117A03            TAAAA-GACAGGCATAAAACTGGGCGGTCGGTTGCCTGTATTCTGTTCTG
bra_Sf_024017_Contig4b   TAAAAAGACAGGCATAAAACTAGGCGGTTCGTTGCGTGTATTCTGATCCA
                         *** *********** ** * ***** bra_Sp_117A03            TTCCCAAACACAATGTCCCGATTATCCAACGGACCTTTTCAGGTTGATTT
bra_Sf_024017_Contig4b   GTGCCGAACACAATGTCCCGATTATCCAACGAACCTTTTCAGGTTGATTT
                         *  ********************** **************** bra_Sp_117A03            TACACCGGTCAATTAAAACGAAAATCATTGTCAACCAAACAAAGGGG-C
bra_Sf_024017_Contig4b   TACACCGGTCAATTAAAACGAAAATCATTGTCAACCAAACAAAGGGGGC
                         *********************************************** * bra_Sp_117A03            GGCGGGACTTCAAAGGAAAAGGCGCTTTGAAGTGAAGAAAGAAAATAATA
bra_Sf_024017_Contig4b   GGCGGGACTTCAAAGGAACAGGCGCTTTGAAG-----AAAGAAAATAATA
                         **************** *********     *********** bra_Sp_117A03            GAAATGGGATTCCTTCTTTCTGTAAAGCCCTTA--GATGAGTCATGGTGA
bra_Sf_024017_Contig4b   GAAATGGGATTCCTTCTTTCTGTAAAGCCCTTATAGATGAGTCATAGTGG
                         ******************************* ****** * bra_Sp_117A03            AATAAAAGATGTTTTATGAGATAGTTTGGAAGGGGTTATAATGTTTCCAA
bra_Sf_024017_Contig4b   AATAAAAGATATTTTACGAGATAGTTTGGAAGGGGTTATAATGTTTCCAA
                         ********** ***** *********************************
```

Figure 5a

```
bra_Sp_117A03              TTCCGCTCTGGAGCACATAATGTATCCGTTGGCTTTTATTTTTATTTTTT
bra_Sf_024017_Contig4b     TTCCGCTCTAGAGGACATAATGTATCCGCTGGCTTTTATTTTGAT-----
                           ****** * ************ ********** bra_Sp_117A03              ATTTTGAGGGTGGCAGGCCAGATAGACTTTGTTTGAACTTCCCGATTTTT
bra_Sf_024017_Contig4b     --TTTGAGGGTGGCAGGCCAGATAGACTTTGTTTGAACTCCCCGATTTTT
                             ************************************ ****** bra_Sp_117A03              ATGAATGAAATGAACCCGGTAAAATGTGGAATAATTGATCCATTGGCATT
bra_Sf_024017_Contig4b     ATGAATGAAATGAACTCGGTAAAAGGTAGAATAATTGATCCATTGACATT
                           ************* ****  *************** * bra_Sp_117A03              CTTGAGACTGGCCTTGTTTACATTGCCAAATTCACGATGTGATTGCCGGT
bra_Sf_024017_Contig4b     CTTGAGACTTGCCTTGTTTACATTGCCAAATTCACGATGTGATTGCCGTT
                           ******* ************************************ * bra_Sp_117A03              GAGAAT   (SEQ ID NO:3)
bra_Sf_024017_Contig4b     GAGAAT   (SEQ ID NO:4)
                           ******

Bra_Flanking_1:

bra_Sp_117A03              GTAAGGAAGTTTTAATTTATTACATTTTTTAACTTGTTAGATTGCTACCA
bra_Sf_024017_Contig1d     GTAAGGAAGTTTTGATTTATTACATTTTTCAACTTGTTATGTAG------
                           *********** ***********  ******  * * bra_Sp_117A03              TCATGACTATGATTTTTTATCATTTTTAAAGAGTTAGATATTACAAGAAT
bra_Sf_024017_Contig1d     --ATTGCTAGGATTCTTTATCATT--TAAAGAGTTTAATATTAAACGAAT
                               *  ** *****  ****  **** * **** bra_Sp_117A03              ATATAT-TTTTGAAGCAATGCGATTACCCCAAAATGCGTTTAGACGTTAT
bra_Sf_024017_Contig1d     ATATATATTTTTTAGCAATACGTTTACCCCATATTGCATTTAGACATTAT
                           ****   **  ******   * ***** ** bra_Sp_117A03              TTAATTTTTAGGTGTTATTTGATGTTATATGAATGCTCTTATTACATCTC
bra_Sf_024017_Contig1d     TTG-TGGCATGCTGATGTTCGTTAAACTAT-AATGTTCTTGTTAAATATC
                           **  *     *  ** * **  * * *  * ** * bra_Sp_117A03              ATGGACTTGTCAATAACTTTGAATCTTTTTAAATGTTACAACCTAGACAA
bra_Sf_024017_Contig1d     TTGGACTTGTCACTAACTTGGAATCTTTTCAAATGTTACAACCTATAGAA
                           ******** ** ***** ***********    * ** bra_Sp_117A03              ---TAAGGGAGTCGTTCTATGCAAATTCAAATTGTAGATTACTATGAATG
bra_Sf_024017_Contig1d     AATTAAGGAGGTCATTCTATGCGAATTTAAGTTGTAGACGACTATAAATG
                              *****  * * ******   ****      ** bra_Sp_117A03              AAGTAATTTTCTTAACCACATGTTGATTAGTTTGATAATCTGTAT-----
bra_Sf_024017_Contig1d     AAATAACTTTCTTAACCAAATGTTGATTAGTTTGATAATCTGTATATATA
                            * ******** *********************** bra_Sp_117A03              -------GGTAATGGTGTTGACTTGCTACAATATTCAAACACTTTGATGA
bra_Sf_024017_Contig1d     TATATATGGTAATGGTGAGTTGCCACAATATTCAAACACTTTGATGA
                                  **********    ********************* bra_Sp_117A03              TGTTGAACAATTTTATGCGGAGATGGTCTT--------GTTTTTAGCGCA
bra_Sf_024017_Contig1d     TATTAAACAATTTCATGCGGAGATAGACTCCTTTTAGGCTTTTAGCGCA
                           * ** ******** ********** * **  * **   * *********
```

Figure 5b

```
bra_Sp_117A03      TAGATGGACGATAGAGGTGAA------ATTTC-------ACGTGCATT--
bra_Sf_024017_Contig1d  TAGATGGACGATAATAGTAAACTCCATATTTCTAAGAGAAAATATATTGT
                   **********        ***       *  *   *** bra_Sp_117A03      ---------------------TGATGAGATGCTTTGATATTTTGTTTAA
bra_Sf_024017_Contig1d  TCACCTTTTACTTGGCACTTTATAACAAGATGCTTTGATATTTTGTTTGA
                                         * *   ******************** * bra_Sp_117A03      CACTATTTGGTATTTTTTCATAATGTTATTCGTAATCAATTTT-------
bra_Sf_024017_Contig1d  AAATATTTGGTACTTTTTCATAATGTTATTTGAAATCAAATTTCATTGAT
                    * ******* ************ *  **** * bra_Sp_117A03      ---------TTTATAATTATGTTGCATAGAAGCCTACTGAAGA------T
bra_Sf_024017_Contig1d  TAAGTGAACTTTATGATTATGTTGTATAGAAGCCTACTGTAGAAGCATAT
                            *** ***** ********** *      * bra_Sp_117A03      AGTGTATATTTCTTTATTAATTAAGTTTATGTAAAGTCATAACGAAGTGG
bra_Sf_024017_Contig1d  AGTATATATTTCTTTATTAATTGATTTAATGTAAAGTAAAA--GAAGTGG
                   * **************   *********  *  * ******* bra_Sp_117A03      CATCGAACTTGGGGAAGTTATAAAGAAAACGACTTGAAACTTTTTAAGGC
bra_Sf_024017_Contig1d  NATGGAATTTGGGGGAAGTG-ATTAAAAATGATTTGAAG-TTTTTAAGGG
                     * ******  *  *   **     * ******* bra_Sp_117A03      ATTACCTGATGTCTATTTTTATGGAAAACGTCTCCCCACACTT-GTTTGG
bra_Sf_024017_Contig1d  AATACCTGATGT-TAAATTTATGGAAAACTCTCCCCACACTTAGTGTGA
                    * ********   ********** *********  ** bra_Sp_117A03      AACTTTCACAGTTTTAAAAGTTGGAAAATATGGTT
bra_Sf_024017_Contig1d  AACTTTAAAAATTTAAAAAGTTGGA--ATTTGGTT
                   ******  *  * ******  ***** bra_Sp_117A03      GATCTTTT  (SEQ ID NO:5)
bra_Sf_024017_Contig1d  GATTTTTT  (SEQ ID NO:6)
                   *** ****

Bra_Flanking_2:

bra_Sp_117A03      GGGG-------TAATGAATTACATTATTTTAAAAAGTAATATATCTCGTT
bra_Sf_024017_Contig2a  GGGGGGGGGGGCTAATAAAT-AAATTATTTGTAAAAGTAGTATATCTCGTT
                   **        *  *****  *** ********** bra_Sp_117A03      GTT--CGTTTCTCAA---ATTGATGTCCATCATAATAATATATCGACTTT
bra_Sf_024017_Contig2a  GTTTTCGTATCTCATGTTATTGATGTCCATCATAATT-TAGATCGACTTT
                   *  * ****     ************   ******** bra_Sp_117A03      TACGTCATAATAGCCAAC--ATTTGAA------ATAGGTGAAATATGTTC
bra_Sf_024017_Contig2a  CACGTCATAACCCAAAACCCGTTTAGACTGTTAGTAGGTGACATATGTTA
                    *******    *   *       ***** ***** bra_Sp_117A03      A---------GGTTACTGTATCATCTTTATCAATATCACGGTTTGACAAT
bra_Sf_024017_Contig2a  AATATTTATTGGTTACTGTATCAA-TTTATGAATAACACTGTTTTACAGC
                   *         *********** *  * *   * bra_Sp_117A03      GCTTTTACAAAAGAGTATTATATAGACATTAGATAATG-TAATACGATTG
bra_Sf_024017_Contig2a  ACATTTACAAAATAGTT-----TAGACAACAGAGAATGATAGCACGATTA
                    * *******        **  * *   ****** bra_Sp_117A03      GATTGGAAATTAATAAAGCATGAACAAAGACATAGTCGAGCATTAACAGA
bra_Sf_024017_Contig2a  CAC-----ATCAACAAAACACGAACAAGAACATAATCGTGCATTCAAAGG
                     *    ** ** *** ** ******  ***** *** ***** ** **
```

Figure 5c

```
bra_Sp_117A03           TGATGATACAGAAGGGCTACATCCAAGGCACATCTTGACATGCTTGTAGT
bra_Sf_024017_Contig2a  TGATTATATAGAAGGGCTACATCCTAGGCATAGTTTGATATGCTTGTAGT
                        ** *  ************* *** *  ** ******** bra_Sp_117A03           CCAGAAATATTGAGTTCAT---AAACA----CAAGTCAAATAGTTACTTA
bra_Sf_024017_Contig2a  CCAGAAACATTGATTTCATCACAAATATTACCAAGTCAAATGGTT---TA
                        ***** * *    * *   ******** *   ** bra_Sp_117A03           GTTACAAGGAATCGAGAGGGGGTAATGATAAGGAGAAATGGGGTGGGGC-
bra_Sf_024017_Contig2a  CGTACAAGGAATGGAGAGGGGGTAATAGTAAGGAGGGATGTGGTGGGGGA
                         ********* *********** * **** * * **** bra_Sp_117A03           TTTCCAGTATAGCAAACGCCTCAATGCGAAAGACAAAACGAAATGTAGAC
bra_Sf_024017_Contig2a  TTTCCAGTATAACAAACGTTTCAATGCGAAAGACAAAACGAAATGTAGAG
                        *********  **** * ***************************** bra_Sp_117A03           ACAAGGTAGATGTGCATAATCACTTCATGTCGACTTGCTACCTTATGCAA
bra_Sf_024017_Contig2a  ACAAGGTAGTTGTTCAGAATCACTCCATGTCGACTTGCTACCTTATGGCA
                        ******* *  *** ******************** * bra_Sp_117A03           TTAAAGTCTCCGAAAAACTCTCATCTACACGATTTGCACGAACACGTCCC
bra_Sf_024017_Contig2a  TTGA-GTCTCCGACAAACTCTCATCTACACGATTTGCACGAACACGTTCC
                        **  * ***** ***************************** bra_Sp_117A03           ACTCTCTCTTCAAATATTCTCCGTCAAAAAGAGCAACAACTGAATCAAC
bra_Sf_024017_Contig2a  ACTCTCTCTTCAAATATTCACCGTCAAAAAGAGTAGCAACTGAATCAAC
                        ***************** *********** *  ************ bra_Sp_117A03           ATCGAAAACCTGCCCAGGAATATCATTTCTGAAGATGAATAACGTAAAGC
bra_Sf_024017_Contig2a  ATCGAAAACCTGCCCAGGAATATCACTTATGAAGATGAATAACGTAAAGC
                        ***********************  ********************* bra_Sp_117A03           TGTTGGTTTACTTTCTGCTCGAGAATTTCAAGTGGGGATAAAAACTGAAT
bra_Sf_024017_Contig2a  TGTTAGTTTATTTTAAGCTCGAGAATTTCAAGTGGGGATAAAAGTTGAAT
                        ** * *   ************************* * **** bra_Sp_117A03           TGATTTTCAAGGGATCTTTCGAAATCAATAAAAATGTGTCTTATTATCTG
bra_Sf_024017_Contig2a  TGATTTTCAAGGGATTTTTCAAAATCAATAAAA-TGTGAGTTATTATCTG
                        *************  * *********  ******* bra_Sp_117A03           TATCACTGACACTTTTAAGACGGGATAAGGGCAAATTTAATCGAGGTTAA
bra_Sf_024017_Contig2a  TATCACTGACATTTTTAAGACGGGATAAGGGCAAATTTAATCGAGGTTAA
                        ********* ************************************ bra_Sp_117A03           ATTGATTATCCGTATTTCGTTTTCCCAAAAGAAGTATCTTGATTTTGTCA
bra_Sf_024017_Contig2a  CTTAATTATCCGTATTTCGTCTTCCCAAAAGAAGCGTCTTCACT----CA
                          ************ ********  *      ** bra_Sp_117A03           AATTAAATTTAGGGTCGATCTGCGGGGAATTTAGTTTGCTTTCAATTGTG
bra_Sf_024017_Contig2a  AATTAAATTTAGGGTCGATCTGCGGGAAT--AGCTTGCTTTCAATTTTG
                        ************************     * ********** bra_Sp_117A03           GATGTCTTTTCATTAAACTTGTTCTGACACACT----TATATAATGAAAC
bra_Sf_024017_Contig2a  GATGTCTTTTCATTAAAGTTATTTTGACACACTATAATTTATTATGATAA
                        ***************   *******    * * ** * bra_Sp_117A03           GTTTTTGCTATGAATGAATGAATGAATGAATAAAAGGTTTTAAGTTATTA
bra_Sf_024017_Contig2a  ATATTTGCTATGAATGAAATAACGAATG----AAGGGT----AGAAATTA
                        *  ************** *   *****    ** ***    ** * ****
```

Figure 5d

```
bra_Sp_117A03            TTTATGCTTTTTGTTTCATA-TGATTATTTCTTCCTTATAGCTTTTTAAG
bra_Sf_024017_Contig2a   TTTGTGCTCTTTGTTTTATAGTCAGTCTTTCTTTCTTA--GCTTTTTAAG
                         *  *** * * * * ****    ******* bra_Sp_117A03            AAATAAAGTCACTGATGGCATTATTTCTTCTTTTTAATGAAATAATGAAC
bra_Sf_024017_Contig2a   AAATGAATTCACTGATGGCATTTTTT----TTTTTAATGAAATGATGATC
                         **  ************ *    ********** ** * bra_Sp_117A03            ATGTTTTGAAAATTAATGTAAAAGAGTGATTTATTTGAAGGAAT-ATTTA
bra_Sf_024017_Contig2a   ATGTTTTGAAAATTACTTTAAAAAAGTGATTTATCTGACAGAATTAATCA
                         *************** * *** ****** * ****  * * * bra_Sp_117A03            ACATTACAGATGATAAATGGAAGCATTTAATATAGGTAAACTTTATCAAA
bra_Sf_024017_Contig2a   ACATTACAGATGATGAATGGAAGTATTACATAAAGGTAAACTTTATCAAA
                         ************ *** * *   * ************* bra_Sp_117A03            CATTTTAAGTTGCTAAGCGATATTTGTTCATTTTAAGCAAAACTTATGCC
bra_Sf_024017_Contig2a   TATTTTAAGTTGCTCAACGATAGT-GTTCGTTTTAAGCAAAACTTAGGCC
                         ************* * ***** *  ** ************ * bra_Sp_117A03            TATA-ATGTTCGAAATTATGACATCTGAAGATC--TTATAATGATGATGT
bra_Sf_024017_Contig2a   TATGGATGTTAGAAATTGCGATATCTGAAGATCGATGACGATGACGATGA
                         *  * **   **********   *    **  ** bra_Sp_117A03            CCCTTTGTCAAAGTTTCCTAAATTCAGAAAAGTAACAGTCCGTCAAAAGG
bra_Sf_024017_Contig2a   CCCTTTGTCAAAGTTTCCTAAATTCAGAAAAGTAACGGTCCGACAAAAGG
                         ********************************** * ***** bra_Sp_117A03            ATTTTTTTTAACTTCATCATCATTTCATTTCCATATTCTCTTCTTCC---
bra_Sf_024017_Contig2a   ATTTTGTTCAACCTCATCATGATTTTGTTTCCATATTCTCTTCTTCCAAC
                         ***  * ***   *** **** *** bra_Sp_117A03            ---------------GTTAGAGTTTTA-----------------------
bra_Sf_024017_Contig2a   TCTTACGATCATCAAGCGAATGTTTTAAATGAATAATCGTGGTAAATTTT
                                        * *  ****** bra_Sp_117A03            ----CGATCATCATACTCATTAA-----------TCTCTCTGCTCTTAAC
bra_Sf_024017_Contig2a   CACTCAAAGACTTTACTCATCAAACTAGTTTTATTCCCTCTCCTCTCAAC
                          *   *   * *****               * bra_Sp_117A03            TACCACCCTTAACA    (SEQ ID NO:7)
bra_Sf_024017_Contig2a   TATCACCACCAACA    (SEQ ID NO:8)
                         ** ****   ****

Bra Flanking 3:

bra_Sp_117A03            ACGAAAAAGAGAAATTTCACTTTGCTTATGTTATGCTCATACTGTATAGG
bra_Sf_024017_Contig3a   ACGAATAAGAGAAATTTCACTATACTTATGTTGTGCTTATACTGTATAGG
                         *** ************* * ******  ********** bra_Sp_117A03            CGACTTCTGGAAACTTTTTGATCGATAGAAAACATTTCAAAATGAAATCA
bra_Sf_024017_Contig3a   CGACTT-TGGAAACTTTTTGATCGATAGAAAATATTCCAAAATGAAATCA
                         **** ********************* * ************ bra_Sp_117A03            GTACAAAATGAAATAATACTTTTGATACTGACTTCAATATGAAAAATAAA
bra_Sf_024017_Contig3a   GAACTTAATGAAATAACACTTTTGGAACTGACTTCCATATAAACAATTAA
                         * **  ********** *******  ********* **** ** *** **
```

Figure 5e

```
bra_Sp_117A03           AAAGGCCTTGGAATTACAACATTTTCATTTTTT-TGCTATT----TATTA
bra_Sf_024017_Contig3a  AAAGGCCTTGGATTTACAACATTTTTAAATGTTGTACTTTTGCTATATAA
                        ********** ********** *  * ** *       *** * bra_Sp_117A03           ATGTTGCATCCATCATTTTAAAAGTT--AAATGTATCCCATTTTGAATAC
bra_Sf_024017_Contig3a  ATGTTGCATCCAGCATTTTAAAAGTTTAAAATGTATCCCATTTTGTATAC
                        ********** ********  *************** ** bra_Sp_117A03           GCTCTTGC-TCCTTGGCCCTGTTTAATGTTAACCCGTGCATTTTCCGAGT
bra_Sf_024017_Contig3a  GTTATTACACCCTTGCCTCTCTTTAATGTTAATCCGTTGATTCATCGAGT
                        * * ** * ***** *   ******  *   ***** bra_Sp_117A03           CTTGGAATATACCCATTACATTGTATTCTTATCTTTATGTTCTTTCTCAG
bra_Sf_024017_Contig3a  CTTGGAATATACCCATTACATGTTATTCTTATCTCTATATTCTTTTTCAG
                        ******************* ******* * **** ** bra_Sp_117A03           A  (SEQ ID NO:9)
bra_Sf_024017_Contig3a  A  (SEQ ID NO:10)
                        *

Bra_Flanking_4:

bra_Sp_117A03           AGTAAGTATAAACATATTTCATAATCAATATATCATTTCAAAACTCTTAT
bra_Sf_024017_Contig3c  AGTAAGTATAAACATAATCCATAATCAATATATTATTTCAAAACCCTTA-
                        **************** * ***********  *****  ** bra_Sp_117A03           TAAGTTCTGTTTTCCCTTCTCTTTCTCAAAGTCTTATCCGATCAATATTA
bra_Sf_024017_Contig3c  --AGTTCTATCTTCCCTTCTCTTTCTCAAAGTCTTATCTGATCAAT----
                        ****** * ****************** *** **** bra_Sp_117A03           CCCATTACCTAGAAAATATTTGTATGTTTCAAGACTAGTAT-TGGAAAAA
bra_Sf_024017_Contig3c  -----TACCTAGAAAATATTTGTATGTTGAAACTTGAAAGTGTTGAAAAA
                             *******************    * *    * * ****** bra_Sp_117A03           TGTTAATAAATGTCTTTCACACAGCTATAAAACAAACGTTTAGTTCTATT
bra_Sf_024017_Contig3c  TGTTAATAAGTGTGTTTCACGCAGCTATAAAACAGACGTTTAGTTCGATT
                        ******* * **** ********* *******  * bra_Sp_117A03           GTTATGTCAAAGTTCTTGAATAGATTTGTATATATTTCTTAATGTGTATA
bra_Sf_024017_Contig3c  GTTATATCAAAGTTCTTGAATAGCTTTATATTTATTTTGTAATGTGTATA
                        *** ************* * * *    ******** bra_Sp_117A03           TTGTTATTATCATTGTATGTTATCTACATGACATTGTCTGAC--------
bra_Sf_024017_Contig3c  TTGTTATTATCGTTGTATGAAATCTACATGAAATCGTCTTATCATATAGA
                        ********* ***** *  ******  **** * bra_Sp_117A03           --AATAGTAATCGGTCTTTAAATTACAAGAGCAATTTACATGTAAGAAGA
bra_Sf_024017_Contig3c  GTGATAATAATCGGTCTTTAAATTACAAGTGCAAGTTACATGTA-GAAGA
                          * ******************   ***** *** bra_Sp_117A03           AAGTCAACGTCGTTAAAATCGTTTTGGGAATCGCGATGATATATTTTATC
bra_Sf_024017_Contig3c  AAGCCAACATGGATTAAATCTTTTTGGGGGA-------------------
                        *  **  *  *  *  *** ***** bra_Sp_117A03           ACCTGACGAAGTGTAGCAGCTGCACACGAACCGTCGTGATCTTTTAGATC
bra_Sf_024017_Contig3c  --------------------------------------------------
```

Figure 5f

```
bra_Sp_117A03              CCTTGTTGACCGTACATTGCGAGACAAACGAATGTCACTAGCGATATTAT
bra_Sf_024017_Contig3c     ---------------ATTGCGA----------------------TGAT
                                          ******                      * ** bra_Sp_117A03              TTTCGATAAATTTTCTTATTTCCTGTTCATTTTATTTTATTTTCAAGTAG
bra_Sf_024017_Contig3c     TCTAATTATATATCCTTATTTCCTGTTTCATTTTTATTCCCTTTATGAGG
                           * *    * ***********    * *     * *  * bra_Sp_117A03              A   (SEQ ID NO:11)
bra_Sf_024017_Contig3c     A   (SEQ ID NO:12)
                           *

Bra Flanking 5:

bra_Sp_117A03              TGTAAGTATTCGAGGTTTTCTCTCACAAT
bra_Sf_024017_Contig3e     TGTAAGTATTCGAGGTTCATTCTCACAAT
                           ***************  ******* bra_Sp_117A03              CACTAAATAGAT    (SEQ ID NO:13)
bra_Sf_024017_Contig3e     CATCAAATGGAT    (SEQ ID NO:14)
                           **  **** ***

Bra Flanking 6:

bra_Sp_117A03              CTGCTAATAACAAGGTAATCAAACCGCATTAATAATGCAAGGCGCTCTAC
bra_Sf_024017_Contig4a     CTGCTAATAACAAGGCAATCAAACCGCACTAATAATGCAAGGCGCTCTAC
                           ************* ******** ******************* bra_Sp_117A03              ATCAAACGAAATCTTATTGGGGAGACCCTTTCCGATTTCTATAACTCGAA
bra_Sf_024017_Contig4a     ATCAAACGAAATCTTAT-GGGGAGAGCCTTTCCGTTTTCTTAACTCAAA
                           ***************  **  *** * * bra_Sp_117A03              CGAGCACATTAAACGGCGACGCTTTGTAGAATTGATGATGACACAGATAC
bra_Sf_024017_Contig4a     CGAGCACATTAAACGGCGTCGCTTTATAGAATTGATGATGACACAGATAC
                           **************** **  ********************* bra_Sp_117A03              AGACGTATGGGACAGTGATTGCGGTCCACAGACCACCCTATTAGCAACCA
bra_Sf_024017_Contig4a     ACACGTATGGGACTGTCATTGCGGTGCACGGACCACCCTATTAGCAACGA
                           * *********  ****** * ****************** * bra_Sp_117A03              AACTAAAGCCCGTGTAACAATAAAGAGATATCGTTAAATTAACGCCATAA
bra_Sf_024017_Contig4a     AACTATAGGCCGTGTAACAATGAAGAGCTATCGTAAAATTAACGCCATAA
                           ***   ********* * ** ************* bra_Sp_117A03              ATTCCAGTCGGAAACCAATGCTGTATATGGGGGGTATTGGTAAATAAGG-
bra_Sf_024017_Contig4a     ATTCCAGTCGGAAACCAATGCTTTATATGGGCGGTATTGGTAAATAAGAA
                           ******************** **** ************* bra_Sp_117A03              TGTGACGTCAACGCAAGCTGTCATAAAAAG-CGCTAGCCTTTTGACACAT
bra_Sf_024017_Contig4a     TGTGACGTCAACGCGAGCTGTCATAAAAAAACGCTAGCCTTTTGACACTT
                           ************ **********  ************** * bra_Sp_117A03              TAAATGAGTGGTTTGATTTCAGAATTGAAATACA--TTTTTTATTGGAAC
bra_Sf_024017_Contig4a     TAAATGAGTGGTTTGATTTCACAATTGAAAGATTGTTTTTTTATTGGAAC
                           ********************* ********    *  *************
```

Figure 5g

| | |
|---|---|
| bra_Sp_117A03<br>bra_Sf_024017_Contig4a | GAGCAGTGGGATTTTGGTAGAAAAAA-TATCAAACGAAAACATTCCCCAG<br>GAGCAGCG--ATTTGGGTAGAAAAAAATATCAAACGAAAACATTCGCCGG<br>****** * **** ********** ******************* ** * |
| bra_Sp_117A03<br>bra_Sf_024017_Contig4a | TGAACTCTGACTTACATTTGAATGTATTCGACGACACCATTTTAAAAATG<br>TGAACTTTGACTTACATTAGAATGTATTCGACGAAACCATTCTAAAAATG<br>****** ********** **************** ****** ******** |
| bra_Sp_117A03<br>bra_Sf_024017_Contig4a | CTTACTTTGTACTCTAGATAAACC----GATAATTGTTTAGATCCAAATA<br>CTTACTTTTTACTCTAAAAAAAAAAGAAGATAATTGTTTAGATCCAAGTC<br>******** ****** * *** ****************** * |
| bra_Sp_117A03<br>bra_Sf_024017_Contig4a | TCCTTTCGACCATCCCCCCAAATTCGAGACAGTCATGATCGCACCACTCC<br>TCCTTTCGTCCCTTCCCCCAAATTCAGGACAGACATGATCGCGCCACTCC<br>******** ** * *********** ***** ********* ******* |
| bra_Sp_117A03<br>bra_Sf_024017_Contig4a | CTCTCATTTCTCAAAGTCTGAATCTCTTTGTTTTGTGATTATTTTGTGTA<br>CTCTCAATTCTCCAAGTCTGGACCTCTTTGTTTGTTTTTTTTTTTTTTAA<br>****** ***** ******* * ********* * ** **** * * |
| bra_Sp_117A03<br>bra_Sf_024017_Contig4a | TGTCATCCGATTATTTACTATTTCTTGATGAGAAAGTAAG----------<br>TGTTAACCGATCATTTCTTATTTCTTGAAGAAAAAGTAAAAAAACAAAAAC<br>*** * ***** **** ********** ** ****** |
| bra_Sp_117A03<br>bra_Sf_024017_Contig4a | ---------------------------GGTATT-------------<br>TCTTACTAAAATTTCTCGGAATATGATTAATGGTTTTTTTTTATTTTAAA<br>*** ** |
| bra_Sp_117A03<br>bra_Sf_024017_Contig4a | ACGGTATTACAAAAACATGCACAAACATT-AAAATCATACCCT-TTTACT<br>ACATTATAACAAAACCATGCACAAACTTTCAAAATCATACCCCGCTTACT<br>** *** ****** ************ ** *********** ***** |
| bra_Sp_117A03<br>bra_Sf_024017_Contig4a | CCTTTGAAACTCACCTTTGAATTCAATTTTTCAAAAT-------TCATCT<br>CCTTTGAAAGTCGACTTTGAATTCATTTTTTTTAATGCATACATCATCT<br>********* ** *********** ***** *** ****** |
| bra_Sp_117A03<br>bra_Sf_024017_Contig4a | -TTAT----AAAAACTTG-AAAATAATTGAATGTTTGGCAGTA---TCAC<br>GTTATGTTAATGAACCAGTAGAATGAATCAATATTTGGCAGTAATATAAT<br>**** * *** * * *** * * *** ********** * * |
| bra_Sp_117A03<br>bra_Sf_024017_Contig4a | TTGATAACAACAGCTGAATCGATTTGTTTTGTCGGTGTCAATTTTAT-AA<br>CATTTAACAGCAGCTGAATTGATTTGTTTTTTCAGTGTCAATTTTGTTAA<br>***** ********* ********* ** *********** * ** |
| bra_Sp_117A03<br>bra_Sf_024017_Contig4a | TTGTGAAGAAAA----AGTACTAGTTTGTTT--AAATGATTTTGTCGTCT<br>TGGTTAAAACAATTCAAGTACTAGTTTGTTTTTAAATGAATTTGTCGTAT<br>* ** ** * ** ************** ****** ********* * |
| bra_Sp_117A03<br>bra_Sf_024017_Contig4a | GGCTCTT--ACCAGCACAAATATATATTTGGCGAAAATTGTCATTCTCGT<br>TGCTCTTTTACCAACAAAAATATATATTTGGCGAAAAATGTCGATTCCGT<br>****** **** ** ******************* **** * *** |
| bra_Sp_117A03<br>bra_Sf_024017_Contig4a | AT-----AGGCCTATATTACTTTGTAGTTGTTGAATTTTTGAATAGTTAG<br>GTGTGGTAGGCCTATA--ACTTTGTAGTTGTTGAAATTTTGAACAGATTG<br>* ********* ****************** ******* ** * * |
| bra_Sp_117A03<br>bra_Sf_024017_Contig4a | ATTTTCACCC-CATAACCTAACTACTTG----ATTAATGTTTAAGTTCGT<br>AATTTTACTCACATCCTTAAACTCCTTGCATTATCAAAGTTTAAGTTCGT<br>* *** ** * *** **** **** ** ** ************ |

Figure 5h

```
bra_Sp_117A03           TGAGCGGGGAATCATATAGCATCCCACAATAA
bra_Sf_024017_Contig4a  TGAGAGGGGAATCCTATAGCATCCCACAATAA
                        **  *** **************** bra_Sp_117A03           CAACGCAAATC  (SEQ ID NO:15)
bra_Sf_024017_Contig4a  CAACGCAAATC  (SEQ ID NO:16)
                        ***********

Bra_Flanking_7:

bra_Sp_117A03           TGGGTCCAGGGGGTGTTTCACAAAGATCCTAACTTGAACTTATCTCTAAG
bra_Sf_024017_Contig4c  TGGGTCCAGA-----CTTCGTAAAGAATTTGG--TAGATTGGGACCTCTG
                        ********     *   *****    *   *  *   **     * bra_Sp_117A03           TTGGACTAATCAATTATGGAAAGCCGTTGGCATTGATGAAAATATTTTGT
bra_Sf_024017_Contig4c  ATGTAACCA-CATTTATAAAATCATATTCTCATT--------TACTCTGA
                         * *   *  *                  * ** bra_Sp_117A03           AAAAGTTATCTTAAAAGGCATAAAATGTTGATTCGAATCATTCATATTTT
bra_Sf_024017_Contig4c  AATACTTGTTCCTTGAT-CATGTAACATCAAT-------GTTCATAGTTT
                        **  * **  *        *    *        ** * bra_Sp_117A03           CTATTATGAAGGAGATTTCATGTTCTTGACGTGAAATTTATAAAGAGTCT
bra_Sf_024017_Contig4c  C-ATCATAAAGTA-ACGTCAAATTATCGAA-------TTATAAAGAAT--
                        *  *  *  *  *   * *        ******* * bra_Sp_117A03           AAGATACTTGAATTTTCGCTTTTGAATATATTTTATTTTAAGGCTGCAAA
bra_Sf_024017_Contig4c  ---------AAATTGTTGCT---GCAAATTTCTTAATTT-----------
                                 **** * *    *  * *** * ***** bra_Sp_117A03           TGGCTCTCCAAAATGTTGAAGTCTCAAGAGTTAAGTTCGATTTAGGATCT
bra_Sf_024017_Contig4c  ---CTTTCAAATGTAATTTGATTTAAATTGTCACTTTTGCACTGCAATC-
                             **  *   *    *    *   **  *    *** bra_Sp_117A03           TTGTGAAACACCCCCAGTATTAGTAATGAATTTAGTAGATTGTGACCCCT
bra_Sf_024017_Contig4c  -------AGATTTTCAGGAT--GCCATGAAACAGATATATCGTTAC----
                               *   *   *     **** * bra_Sp_117A03           GCTATTGAATAATTACGCTCGAACATGACTTGTAACATCAATGTTCCCAG
bra_Sf_024017_Contig4c  --------------------AAAGAAGTCTATAA----AATAC-----G
                                            **    * *** * *  ***     * bra_Sp_117A03           TTTTATCATAAAGTAATGTCAATGACAAGCACCTCGCGCTGTACGAACAT
bra_Sf_024017_Contig4c  CTTCATCTCA--------TCAATGACAACGACCTCAAACTGTACAAATAT
                          *  *          ******** *  **  ** bra_Sp_117A03           --CTCTTCAAAATTAATTTCTTCGTTTTCCATCTTTAAAAAAAAAAACCC
bra_Sf_024017_Contig4c  AATCGCTCTGAAACAGATTCTTCGTTTTCCATATGTCTTTAA----CGC
                              *  * * ************** *  *   **    * * bra_Sp_117A03           TTTCATCTTACCCTAATATTCTTTATTTAGGCCCTATACGTGTTTTCCTT
bra_Sf_024017_Contig4c  GTTTATCTTACCCCACTAATCTTTAT----ACCTT-----TGTTTTCCTT
                          *****  * ******    * *     ******** bra_Sp_117A03           CTATATCTTGTATTGTTGAGCATTTGGATTTTATTAATGTTGTGTTTTTG
bra_Sf_024017_Contig4c  TATTTTCTGTTATTGTTGAACATTTGGAGTTTACTCATTTTGTAT-----
                          ***  ******** **** ********  ***  * * *** ****  *
```

Figure 5i

```
bra_Sp_117A03              ATTCATAAAATATAAACAAGCAAGGATGTGTAATTTTCATATTTTGTTG
bra_Sf_024017_Contig4c     ------------------------------------------------- bra_Sp_117A03              GTGCATTATCGGTACATTTGGGGAAGATTGATTTGTTGTACTTACAGTTA
bra_Sf_024017_Contig4c     ---------------ATTTGGGAAAGATTGATTTGTTACACTT-TAGTTA
                                          ***** ********    *** bra_Sp_117A03              AAGTCAAATTATTTT-GTTTCTTTTTTGATTTA    (SEQ ID NO:17)
bra_Sf_024017_Contig4c     TTGTTAAGTTATTTTTGTTTCTCTTTCGATTTA    (SEQ ID NO:18)
                           ** ** ****** ****** *** ******

Bra_Flanking 8:

bra_Sp_117A03              TTTGATCAATTGGCA-GAATACAATAAACCTCTGGGAATAACTAAGGTTA
bra_Sf_024017_Contig5a     TTTGTTCAATTGGCAAGAATCCAATAAATTTTTGAGAATAAATAA--TTG
                           ** ******  ***** *  **** * bra_Sp_117A03              TTTTTTTAGGGTGAAGTTTCCTTTAAATTCATATTGGCAAGGTATTTACT
bra_Sf_024017_Contig5a     ATTTCTTGGGGTGAGGTTTCATTTCAATTTAAATTGGCAAGGC-TTTCTT
                            *  **** * * **** *  ********  * * bra_Sp_117A03              TCGAGCATGAAAGATGATTATTGAAACCTTAT-AAAACCCGAACGCTATT
bra_Sf_024017_Contig5a     TCGAGCCCGAAAGATGATTATTGAAACCTAATGAAAATCAAAACGCTATT
                           ****   ****************** *  ****  * ******** bra_Sp_117A03              AAACAACCAGCTTAAAAAGTGATCTGAGACTGA------AACCTCCATGA
bra_Sf_024017_Contig5a     AAACAACCAGCTTAATAAGTAATCTGAAACTGATTAATAGACCTCTATAA
                           *************  ** *      *  * bra_Sp_117A03              AGATGAGTATATGTCAACCGCCTGGATTCGTCTCTCTGCTTGGATATTAT
bra_Sf_024017_Contig5a     AGATGACTTTATTTCAACCTTCTGGATTCGTCTCTCTGCTTAGATTTTAT
                           ****** * * **  **************** * **** bra_Sp_117A03              TTCAAATTTAGGCCTACGACATGAATCGTTCCAAAAAAGGGCCACAACTT
bra_Sf_024017_Contig5a     TTCAAACTTAGGCATACGACATGAATCGATACAAAAAGGGGCCACAACTT
                           **** ** ************ * ****** * ********** bra_Sp_117A03              AGTGAGGAGTTATAGTGCATTGATTATATTAGTGCAATATCGGCACGCAT
bra_Sf_024017_Contig5a     AGTGAGGAGTTATGGCACCTTGAG---------GCAATATTGGCAAACAT
                           ************* *  * **          ***  * bra_Sp_117A03              AAACTTTCAGGACAAGATATTT---ATATAGGGCTAAAGTGATCCCAAAC
bra_Sf_024017_Contig5a     AAACCTCCTGGACAGGATATTTTATATATAGGGCTAAACAGATCACAATC
                           ****  * * *** **   **********  * * bra_Sp_117A03              AT--TGTTTATCAAAATGGCAACAATAATAAATATCTGACATTGTTCTAA
bra_Sf_024017_Contig5a     ATGTTGTTCTTCAAATTGACAACACTAATAATTATCTGACATTGTTCTAA
                              **  ***  ** *************** bra_Sp_117A03              TACTATTCAATGTCTCTGAAAACAATATACATGGCTAGAAACTTAGTTGA
bra_Sf_024017_Contig5a     TAAAATGTAATGTCTCTGAAAACATTATACATGGCTAGAAACTTTGTTGG
                               ************ **************** ** bra_Sp_117A03              AAAGTTGAAATATGCAACATTTTAATCGCACTTCGAACCTCTCAATGTGT
bra_Sf_024017_Contig5a     AAAATTGAAAAATGTCAAATTTGATCCAATTTTGAACTTCTTAATGTGG
                           *** ****** ***  * ****  * **  *** ***  ***  ***** 
```

Figure 5j

```
bra_Sp_117A03          TGCCAATTTAAGAATTTTAAGCCTTATTTCCTTTTTTGTTAATTCCTGG
bra_Sf_024017_Contig5a TACCAATCTAATAATTTTAAGT---------TTTTTTTTTAATTCCTGG
                       * *** * *******         *** ******** bra_Sp_117A03          TATCGAACGCAGTATGGTTATGCA-CAGAGATGGGTACATTGTGTGCAGA
bra_Sf_024017_Contig5a TATCTAGGGCAGTATGGTTATGCAGCAATGATGGGTGCAGTGTGTGCAGA
                       **** * ***************  *****  ********** bra_Sp_117A03          AATGTTTACCCTTTCTAGTCATTCATCCGGTATAATTTTTTAAGGCTCTG
bra_Sf_024017_Contig5a AAT-TTTTCACACTCTACTCATGCATCTGGTTTGATTTCT-AACGCTCTG
                       * * * * **   * * **** *  **** bra_Sp_117A03          AATCGAACGTTATTAAGCCAAAACAAAAAATGTGGAAGTTTTCATGAAAG
bra_Sf_024017_Contig5a AATC-------------------------------------ATGAAAG
                       **                                         ***** bra_Sp_117A03          GGTTTAAGAGAA-GAAAAAAGTTTGTAAAGAGCTTTCTCCTTAGTTTGTT
bra_Sf_024017_Contig5a GGTTTAAGAGAAAGAAAAAAGTTTTAAAAGAGCTTTCTCCTTCGTTTGTT
                       ********** ******* * ******** ***** bra_Sp_117A03          TTAGGGGCCATCTACTATACAAACCTGATCTCACCTGGGCTTTATTTACA
bra_Sf_024017_Contig5a TTACGGGCCATCTACTATACAAACCAAGTCTCACAGGGGCTTTATTTACC
                       * **************** ** *********** bra_Sp_117A03          CGATGACTAATTCAAACTTTGTCTCAGGCTCTTCTTCTCTTTACGATGTA
bra_Sf_024017_Contig5a CGGTGACTAATTCAAACTTCGTCTAAA-TGTTCTTCTCTTTACGATGT-
                        ************ ** *    * ****************** bra_Sp_117A03          TAGCCTCTTTCCTTTTATTGTTCCCGGGTTC-TTTGA
bra_Sf_024017_Contig5a -AGCCTTTTCCCTTTTATTGTTCCCGGGTCCCTTTGA
                       ***  **************** *** bra_Sp_117A03          CGTACCATTTTA    (SEQ ID NO:19)
bra_Sf_024017_Contig5a CGCACCCATTTT    (SEQ ID NO:20)
                       ** *** ***
```

Figure 5k

Delta Alignments

Delta Active 1:

```
delta_Sp_046A16           CATGCCAACATGAAGATGCACACGGGTGAATCTCAACGTGCACTTAGTGG
delta_Sf_035H04_Contig1b  CATAAGTACATAAAGATGCACGCGGGTGAATCTCAACGTGCACTTAGTGG
                          *      **** ************************** delta_Sp_046A16           AACGAGATTTCGGAAAGAAAACACCAAGAACTCGTCAAGCTTCTGCTTTG
delta_Sf_035H04_Contig1b  AACGAGATTTTGGAAAGAAAACACCAAGAACTCGTCAAGCGCTTGCTTTG
                          ******** **************************  * **** delta_Sp_046A16           ATTGGAACAGCAGGCTTTCCTCAAGTTTTTGTTTCAATCCCCTTTTCGCA
delta_Sf_035H04_Contig1b  ATTGGAACAGGAGGCTTACCTCAAGTTTTCGTTTCAATCCCCTTTTTGCA
                          ******** ** ******* ************ * *** delta_Sp_046A16           TCTAATAATCATTCTTTGTCTGAACTTCATAAAATGTA----GAGTAGTC
delta_Sf_035H04_Contig1b  TCTACTAATAATTCTTTGCCTTAAATTCATAAATCGTATTAGGTATAGTC
                          **   **    * ****** *        ***** delta_Sp_046A16           TTGAGTTGGATGTGAGATGAGAAAGGAGAAAGATAAGTAAAATATGATAT
delta_Sf_035H04_Contig1b  TTGAGCTGGATGTGAGATGAGTAAGGAGAAAGATAAGTAAAATATGATAT
                          *** *********** ************************** delta_Sp_046A16           CATGAGACATGAAGAACAAAGAAAAAAAGGAAGGGGGTTGGGTTAAGTG
delta_Sf_035H04_Contig1b  CATAAGACATGAAGAACAAACAAAAGAGGGA--GGGGTTGAGTTAGGTG
                          * ************ **  * *   **  * delta_Sp_046A16           TTGGTGAGGGCATTGGATTACCAGATAAAACTTGCACGTACATCACATCC
delta_Sf_035H04_Contig1b  TTGGTGAGGGCATTGGATTACTAGATAGAACTTGCACGTACATCACATCC
                          ******************* * ********************* delta_Sp_046A16           ACTTCAACAAAACAT-CAACCTTCGGATGTTGAATAGGGGATCGGAGAAG
delta_Sf_035H04_Contig1b  ACTTTAATAAAACATTCAACCTTACGATAC--------------GAGAAG
                          **  ***** ***  *                ****** delta_Sp_046A16           GTCGAGTCCTATCCCATCAAAATACTAGGAAGTCACATGACAGACTGATA
delta_Sf_035H04_Contig1b  GTCAAGTCCTATCCCATCAAAATACTAGGAAGTCATGTGACAGACTGATA
                          * **************************  *********** delta_Sp_046A16           AACAAGACAGTTATCCAAATCATTCCATGAGTTCAAGCAGCGTGCAATCA
delta_Sf_035H04_Contig1b  AACAAGACAGTTATCCAATTCATTTCATGAGTTCAAGCAGCGTGCAATCA
                          **************** * *********************** delta_Sp_046A16           CGTGTTAATGAAGCATCAACATAGTGATGCCAACCACAAAAATTATGGCG
delta_Sf_035H04_Contig1b  CGTGTTAATGAAGCATCAACAAAGTGATGCCAACCACAAAAATTATGGCG
                          ******************* ************************** delta_Sp_046A16           CCCTTTATACTATGTCTACAGTGAACACCCGTTTCCATTATTCAATGAAT
delta_Sf_035H04_Contig1b  CCCT----ACCATGTCTACAGTGAACACCCATTTCAATTATTCGATGAAT
                          **     *****************  *** **** delta_Sp_046A16           CTATGCTATGAGTTCGTCTTTACCAATGACACTTAGC-------------
delta_Sf_035H04_Contig1b  CTATGCTATGAGTTCGTCTTTACCAATGACGTTTAGCTTGCGACATTAAA
                          **************************** *** delta_Sp_046A16           -----------AGGATCCATCTGAAAGGTACAAATTTAATCCTCATATA
delta_Sf_035H04_Contig1b  GTTAATGGAAACATGATCCA-CTGAAAGGTACAGATTCAATCCTCATATA
                                     * ******* *********** *** *************
```

Figure 6

| | |
|---|---|
| delta_Sp_046A16 | CACCCACATACTAAATATTATAGACTTTGGTGTTGCCTTCTTAGAATTCT |
| delta_Sf_035H04_Contig1b | C--CCACATACTATAAAATATAGACTTTGGTGTTGCTTTCTTAGAATTCT |
| | * ********* * * ****************** ************* |
| delta_Sp_046A16 | TTCCCCTTCATAGAAATTGGTAAATG--------CGAACAAGCAATCTCC |
| delta_Sf_035H04_Contig1b | TTCCCCTTCATCGAAATTGGTAAATGAATGCGTGCGAACAAGCAATCTCC |
| | *********** **************                 ****************** |
| delta_Sp_046A16 | GTTTATTGATCACTATTCTGTGATTGTCGTCTGTCTGACTCACTCACTCC |
| delta_Sf_035H04_Contig1b | GTTTATTGATCACTATTTTGTGATTGTCGTCTGACTCACTCACTCCCACT |
| | ***************** ************** ** ******* * * |
| delta_Sp_046A16 | CACACCTAGTTCATGCAGAAGCGCGCAAACCATAATATTAGCACACCTTT |
| delta_Sf_035H04_Contig1b | CACTCCCACACCT--CAGAAGCGCGCAAACCATAATATTAGCCCACCTTT |
| | *** ** *   *   ****************************** ******* |
| delta_Sp_046A16 | ATTTCAAAGCAAGGAAACTTCCTATTAAGACTTGTGCATGCTAATCTGGA |
| delta_Sf_035H04_Contig1b | ATTTCAAAGCAAGGAAACTTCCTATTAAGATTTGTGGATGCTAATCTTGA |
| | ****************************** ***** ********** ** |
| delta_Sp_046A16 | CTTCAATTCATATTATTTCTTTTTGTAATCATGGTAATGACCTTAGTTAT |
| delta_Sf_035H04_Contig1b | CTTCAATTCATATTATTTCTTTTTGTAATCATGGTAATGACCTTAGTTAT |
| | ************************************************** |
| delta_Sp_046A16 | TTGACTCCCCGTAAAAATAATCGTACAATTGGTCGAAAATTTGTGAGCAG |
| delta_Sf_035H04_Contig1b | TTGACTCCCCGTAAAAATAATCATACAATTGGTCGAAAATTTGTGAGCAG |
| | ********************** ************************** |
| delta_Sp_046A16 | GAAATGGCCGATGACCTGTGAATATGGGTGACGAAAGGAACGATTAGAAT |
| delta_Sf_035H04_Contig1b | GAAATGGCAGATGACCTGTGAATACGGGCGACGAAAGGAACAATTAGAAT |
| | ******** *************** *** ************ ******* |
| delta_Sp_046A16 | CAATGTTCTTTCCACATGGTTTGAACAGGCGACCTGACAATGACCGAATG |
| delta_Sf_035H04_Contig1b | AAATGTTCTTTCCACATGGTCTGAACAGGCGACCTGACAATGACCGAATG |
| |  ******************* ***************************** |
| delta_Sp_046A16 | AGTGAGTTCCGATTGACAAATGTATCTTTTCAGACTATAATTATAGCACC |
| delta_Sf_035H04_Contig1b | AGTGAGTTCCGATTGACAAATGTATCTTTTCAAACTATAATTATAGCACC |
| | ******************************** ***************** |
| delta_Sp_046A16 | ATTCATCCATTGAAAAACAATGTAATTCATTTTCCCCTTATGATTTTGTT |
| delta_Sf_035H04_Contig1b | ATTCATCCATTGAAAAACAAGGTAATTCATTTTCCCCTTATGATTTTGTA |
| | ******************** ******************************* |
| delta_Sp_046A16 | TAGAAACATATCATCATCATCTTTAATGGGAGTGTGCTCAGTAAATGAAA |
| delta_Sf_035H04_Contig1b | TAGAAACATATCATCATCATCTTGAATAGGAGTGTGCTCAGTAAATGAGA |
| | *********************** *** ****************** * |
| delta_Sp_046A16 | ATTGGGAGAAGGTACAGAGAATATTTTGAACTATTGTTAAAGATTTTGCA |
| delta_Sf_035H04_Contig1b | ATTGGGAGAAAGTACAGAGAGCATTTGA-----TACTAA---------- |
| | ********** ******* ******  *   *** |
| delta_Sp_046A16 | TTATTATGGACAATAACATTGAAAACAATAGGGTTTTGGCTGCACGCTCT |
| delta_Sf_035H04_Contig1b | -CATTGCACACAAT-----------AATAGGGTTTGGGCAGCACGCTGT |
| | ***   *****           ********** *** ******* * |
| delta_Sp_046A16 | TCCATCGTATTATTTTCTGTTTTTATCTTTTGAAGTCTAGCTGACTAAAT |
| delta_Sf_035H04_Contig1b | TCCATCGTACTATTTTCTGTTTTTATCTTTTGAAGTCAAGCTGAGTAAAT |
| | ********* *************************** ****** ***** |

Figure 6a

```
delta_Sp_046A16            TTCAGAGAATGAGAAAGACCAACAACAACA------AATCAGTAAGAAAA
delta_Sf_035H04_Contig1b   TTTAGAGAATGAGAAAGATAAACATCAACACCAAAAAATCTATGAGAACA
                            **********   *       **  * **** * delta_Sp_046A16            ATACCATTTGATTATTCAAACTTGATCTGGTCAACATGAATACGCGGCTC
delta_Sf_035H04_Contig1b   ATACCATTTGATTATTCGAACTTGATTTGTTCAAAATGAATACGCGACTC
                           *************** ****   ** ****** * delta_Sp_046A16            CTTTACTCGTTCTTACTATATAT--ATTCATAATA------AGTCATGT
delta_Sf_035H04_Contig1b   CTTTACTCGTTTATTGCTATATATTCATAAGTAAACTTGCATAGTCATTT
                           *********   ******  *   *      **** * delta_Sp_046A16            TATCAGTACTCTTCTTTCTAAAGCCAGTATTGAATTTGTTTTCTTGGTCA
delta_Sf_035H04_Contig1b   TATCCGTACTCTTCTTTCTAAAGCCAGTATTCAATTTGTTTTCTAGGTCA
                           ** ********************** ******* *** delta_Sp_046A16            TTTGTATTCTCATTGCTTCATCTGGTTTGTTCTTCTCT-GTGATTGTGTT
delta_Sf_035H04_Contig1b   TTGGTATTCTCATTGCTCAATCTGATTTGTTCTTCTCTAGTGATTTTGTT
                            ********** *  ********* ** ** delta_Sp_046A16            TTGAAATCAGAGATGCCTGATCTCAAAATGAAATTAAAATGAGAAGAATT
delta_Sf_035H04_Contig1b   ATGAAATCAGAGATGCCTGATCCCAAATTGAAATTAAAATGAGAAGAATT
                            ******************   ********************* delta_Sp_046A16            GATGAATAGCTATCATGCACAATAGATTCGCGTGAAGAATAGATCGAAGA
delta_Sf_035H04_Contig1b   GATGAATAGCTATTATGCACAACAGATTTGCGTGAAGAATAGATCGAAGA
                           *********** **** * ******************* delta_Sp_046A16            TTATGTTACAGCCAACTTCGTGACGTCGAATTGGCAACAGCTTTGTATTA
delta_Sf_035H04_Contig1b   TTATGTTACAGCCAACTTCGTGACGTCGAATTGGCAACAGCTTTG---TA
                           ******************************************* delta_Sp_046A16            AGCTGCTATCGATCATAAGTCACATGATCTAGTTTACCTTGACACCGGTA
delta_Sf_035H04_Contig1b   AGCTGCAATCGATCATAAGTTACATGATCTAGTTCACCTTGACACCGGTA
                           **** ********* ********* ************* delta_Sp_046A16            GCATTTCGTCTGGCCGTCAAATTATGTCAACCTCAAGACAACGATCGTTT
delta_Sf_035H04_Contig1b   GCATTTAGTCTGGCCGTCATCGCATGTCAACCTCAAGACAACGATCGTTT
                           **** ********    ************************** delta_Sp_046A16            GCAGACGACCTTTAATTACAATCGCTTTTGTTCTCATGTATTCATCGACA
delta_Sf_035H04_Contig1b   GCAGACGACCTTTAATTACAATCACTTTTGTTCTCATGTATTCATCGACA
                           ********************* ************************ delta_Sp_046A16            TTTACTAATCGAATAATGAGTATTCCAATCGCAAGAGGCCTATGTAATGC
delta_Sf_035H04_Contig1b   TGTACTAATCGAATAATGAGTATTCCAATCGCAAGATGCCTATGTAATGC
                           * ******************************** *********** delta_Sp_046A16            TATCTTGAGTAGGCCAAATCTGTAAGCGATCAAACGCGAAATCAGAAGAC
delta_Sf_035H04_Contig1b   TATCTTGAGTAGGCCAAAACTGTATCCGATGAAACGCGAAATTAGATGAC
                           ****************     ******* * *** delta_Sp_046A16            AAAAAGGGTT-TGTTTTTGTCTAATTTTATGAAAGCATTTTTTCTTATGT
delta_Sf_035H04_Contig1b   AAAAGGTTTTGTTTTTTTGTTTAATATTATGAAAGCATATTTTCTTATGT
                           **   * * ****   ******* ********** delta_Sp_046A16            GATCGCTTAACATGGTTCCCGCCAAAACCAACGGGCGCCAAACAGAGTGA
delta_Sf_035H04_Contig1b   GCTCGCTTAACATGGTTCCCGCCAAAACCAACGGGCGCCAAACAGAGGGA
                           * ********************************************* **
```

Figure 6b

```
delta_Sp_046A16           ATCTGATGATGCAGCTGCAATGCTTCACATCTCCGACTTGACTAGATTTC
delta_Sf_035H04_Contig1b  ATCTGATGATGCAGCTGCAATGCTTCACATCTCCGACTTCACTAGATTTC
                          ************************************* ******* delta_Sp_046A16           TCTCCAAATCATCGGCCATGGTGGGATGATCAGAAACAATGCACAGTCAT
delta_Sf_035H04_Contig1b  TCTCCGAACCATCGGCCATGGTGGGATGATCAGAAACAATGCACAATCAT
                          ***  ********************************** ** delta_Sp_046A16           TCGTCCATCTCAGGAAACTGAGAGAATAAAAAAAAGGGGAAAAGGGGAAG
delta_Sf_035H04_Contig1b  TCGTCCATCTCAGGAAACTGAGAGAATTAAAAAA----GAAAAA---AAG
                          ************************* **    *   * delta_Sp_046A16           AAGTGACAATTGGCATGGATGATATGCAGCCAATGCATGACGACTCACAA
delta_Sf_035H04_Contig1b  AAGTGACAATTCGCATGG-----ATGCAGTCGATGCATGACGACTCACAA
                          ********* **     **** * ****************** delta_Sp_046A16           AAGACAC-CATTTCCCTCATCTCGCGTGCT------------------A
delta_Sf_035H04_Contig1b  AAGACACTCATTTCCCCATCTCGCGTGCTCTCTTTTATATCAACAGCCA
                          ***** *  *************                  * delta_Sp_046A16           TCTTTGCTCTGAGGATGAACCCTAGTGATCAAGCTACCTTGACGATGTGC
delta_Sf_035H04_Contig1b  TCTTTGCTCTGAGGATGAACCCTTGTGATCAAGCTACCTTGACGATGTGC
                          ********************* ************************ delta_Sp_046A16           TGATTGTGGTTTGCATTCATGCTCATAAATAGACGTCAAGGTATTCATAT
delta_Sf_035H04_Contig1b  TGATTGTGGTTTGCATTCATACTCATAAATAGACGTCAAGGTATTCATAT
                          ****************** *************************** delta_Sp_046A16           CATATCACCCGTTCTCTATTCATTACAAAATCTTCTCTCTAAACTGCCAC
delta_Sf_035H04_Contig1b  CATATCACCCGTTCTCTATTCATTACAAAATCTTCTCTCTAAACTGCCAC
                          ************************************************** delta_Sp_046A16           CAGAGATTACCATCCCGCCCTAA-CCGTATAATTAGCTGCCTTTTCCAGC
delta_Sf_035H04_Contig1b  CAGAGATTACCATCCCGCCCTAAACCGTATAATTAGCTGCCTTTTCCAGC
                          ********************* ************************ delta_Sp_046A16           AAGCTTTATGGCGGCATGGCGACAAAGTGTAACTTCCGGCGCGAGCCACT
delta_Sf_035H04_Contig1b  AAGCTTTATGGCGGCATGGCGACAAAGTGTAACTTCCGGCGCGAGCCACT
                          ************************************************** delta_Sp_046A16           CACAAAACGCGTGCTAAACCCTTCAAAACGGACCAAACCACGAACCCCTT
delta_Sf_035H04_Contig1b  CACAAAACGCGTGCTAAACCCTTCAAAACGGTCCAAACCACGGACCCCTT
                          ***************************** ***** ***** delta_Sp_046A16           TTTCAAACCTCGTGTAGCTTAAGCCGGAAGGACATGTCCCATGGACTTAC
delta_Sf_035H04_Contig1b  TT-CAAACCTC-TGTAGCTTAAGCCGGAAGGACATGTCCTATGGACATAC
                           **** *********************** ** * delta_Sp_046A16           TGTATACTACGGTTCTTCTATGAAAAGACTGGTA---TAACAAACATAAT
delta_Sf_035H04_Contig1b  TATATACCACGGGTCTTCCATGAAAAGACTGGTAATATAACAAACACAAT
                          * ***   * **********    **** * delta_Sp_046A16           TTCCATTTTTTTTTCTTCACTACGTGCACGTCGATGACGACGAAGATCA
delta_Sf_035H04_Contig1b  TTCCATTTTTTTTT------CTACGTGCACGTCGATGACGACGAAGATCA
                          ************      ***************************** delta_Sp_046A16           GTTTTTATTTCACCCATCCCCGTGAATCAATTAAAGCAAACCGACGAGGC
delta_Sf_035H04_Contig1b  GTTTTTATTTCACCCATTCCCGTGAATCAATTAAAGCAAACCGACGAGGC
                          ***************** ********************************
```

Figure 6c

```
delta_Sp_046A16           TTATTCAAGCTTTCAATAGAGGCAATTAAAGGTTCATTGTGCGCCCATCG
delta_Sf_035H04_Contig1b  TTATTCAAGCTTTCAATAGAGGCAATTAAAGGTTCATTGTGCGCACATCG
                          ***************************************** *** delta_Sp_046A16           TCGTTGATACTCGAGTTTTAATGAAGATTGAATTTGGGGTTGATTAAACG
delta_Sf_035H04_Contig1b  TCGTTGATACTCGCGTTTTAATGAAGATTGAATTTGGGGTTGATTAAACG
                          *********** ********************************** delta_Sp_046A16           AGACGAGACGTG    (SEQ ID NO:21)
delta_Sf_035H04_Contig1b  AGACGAGACGTG    (SEQ ID NO:22)
                          ************

Delta Flanking 1:

delta_Sp_046A16           GGGATGAAAGGGAGATGATAATTGGCCATATGGTATGACAAATCAATCAA
delta_Sf_035H04_Contig1a  -GGGCGGA--GGATATGATA-TTGACCATATGGTATGACAA-TCAATCAA
                           **  *  *  * ** * ************** ***** delta_Sp_046A16           CATCACCATCCAGACCAAGTCGGCCATCTGGGATGGTCTGAGAGGGAGAC
delta_Sf_035H04_Contig1a  CATCACCATCCAGACCAAGCCGACCATCTGGGATGGTCTAAGAGGGAGAA
                          *****************  ************** ****** delta_Sp_046A16           GGGGGCATCTTCGATCTCAGGTACATCTAGTGGTGTAAAAGGAGAAGAAA
delta_Sf_035H04_Contig1a  GGGGGCATCTTTAATCTAAGGTATATCTAGTGGTGTTAAAGGAGAAGAAA
                          *********     ******** ********** delta_Sp_046A16           AGCCCCCATTGATGACGAATATTGTAAGTATTTTGTTTAAGATTCCATGT
delta_Sf_035H04_Contig1a  AGCCCC-ATCGAGGACGAATATTTAAAGTCTTTTGTTTAAGATTCCATGT
                          ****   ******   ****************** delta_Sp_046A16           TTAATCATGTTCATAGTTGATTGTTTATATTACAAGAGTGCTAACGAATC
delta_Sf_035H04_Contig1a  TTGATC-----------GAT------------------------------
                           *           *** delta_Sp_046A16           AAGTATTTGTTTAAAAGAAATTTCATTTAGGGTTGAAATCTTATAGAATA
delta_Sf_035H04_Contig1a  -------------------------------------------------- delta_Sp_046A16           GTTAAATTGAGTGAATGTCTTACCTGACTAGCTCAAGATCGAACTGATCT
delta_Sf_035H04_Contig1a  -------------------------------------------------- delta_Sp_046A16           ACATCTGTACAATTAAAACCAGAACAATTTGCGACATGAAACGTTCGCGA
delta_Sf_035H04_Contig1a  -----------------------------------------------CGA
                                                                         *** delta_Sp_046A16           TACTGGACCACTCAAGAGATTCGCAACAAAATTTGGTTTTAAATCACATT
delta_Sf_035H04_Contig1a  TACTGGACCACTCAAGAGATTCGCAACGAATTCTGGTTTTACATCACATC
                          ************************* ** * ****** ***** delta_Sp_046A16           CCCAAATGTTTGCAGAAAACATGTGGTACAAAGTCATTTGTCGAAAGGAT
delta_Sf_035H04_Contig1a  CTCAAATGTTTGCATAAAGCATGTGGTGCGAAATCATTTCTCGAAAGGAT
                          * ********* *  ******** * * * ******* delta_Sp_046A16           CTAAGATTTCTTTAAAGAAAAAGTAATAAATAAACAGACAA----GACTG
delta_Sf_035H04_Contig1a  CTGACATTTCATTAAAGAAAA-GTAGTAAATAAACAGACCACGTAGATTG
                          ** * *****  ********* *** ************* *      ** **
```

Figure 6d

```
delta_Sp_046A16            TGATTGATTACGTGATTACAAAATAATGTTTCAAGTATTTTTTGCTATT
delta_Sf_035H04_Contig1a   TGATTGATTACGTGTTTACAAAATACTGTTTCAAGTATGTTCTTGCAAGT
                           ************ ***** ********  **** * * delta_Sp_046A16            GGTGAATCGTCCCGTTGCTTTCCGATGTAAA--CTAGGATCATGGAACGA
delta_Sf_035H04_Contig1a   GGTGAATCGCCCCGTTGCTTTCCGATGTATTTCTTGGATCATGGAACGA
                           ******* ***************     ************** delta_Sp_046A16            AATCCGTTTGATTTTGATGCTTTTCACAAACCAGACCATATCT-----CC
delta_Sf_035H04_Contig1a   AATCCGTTTGATTTTGAAGCTAATCACAAACCAGACCATCTCTTGCTTCC
                           *************** * ************* *     ** delta_Sp_046A16            AATAGATAATCCTAATAACAACTGAACATGATATAGCGATGGGATATTTT
delta_Sf_035H04_Contig1a   AATAGATCATTCTAATCATAACTGAACATGATA--GTGATGGGATATTTT
                           *****  ***** * **************  * ************* delta_Sp_046A16            TCATGCAGGGATATCCCATCACTATAGGTATAAGGTTCGGCCTGGCTCGG
delta_Sf_035H04_Contig1a   TCATGCGGGGATAC----------AAGGTATAATGTTCGGCCTGGCTCGG
                           **** **             *** ************** delta_Sp_046A16            TGTCTTGTGATGCAACAGTCTTCATCTTTCAGCGCTTCGTGATTACGATA
delta_Sf_035H04_Contig1a   TGTCTTGT-ATGCAACAGTCTTCATCTTTCAGCGCTTTGTGATTATGATA
                           ******  ********************** **** ** delta_Sp_046A16            CAGGGATTAAAAAGATAGGGACTATAAGGGAAGGAGGCAAGCAACACCAA
delta_Sf_035H04_Contig1a   CAGGGATTAAAAAGCTAGGGACTAT--GGGAGAGAGGCAAGCAACACCAA
                           ************ *****  ** * **************** delta_Sp_046A16            GGAAAATATCTAGAGCGAACAGATCTAGGGGTCAAGTCCACACAATGCGT
delta_Sf_035H04_Contig1a   GGAAAATATCTAGAGCGAACAGATCTAGGGGTCAAGTCCACACAAAGCGT
                           ******************************************* ** delta_Sp_046A16            TATTGAAATAGATAGGCCTATATGGTTCATGTTCGGATTGAAACGAGACT
delta_Sf_035H04_Contig1a   TATTGAAATAGATAGGACTGTATGG----------ATTGAAACAAGACT
                           **************   ***           *** *** delta_Sp_046A16            AGAGTGTCCTCGTCGTATG--GTCTCAGCTCCTCTGAAGGCTCTACATAA
delta_Sf_035H04_Contig1a   ACAGTGTCCTCATCGTATATAGTGTCAGCTCATCTCAAGGATCTATATAA
                           * ******* **** *   *** * **  ** delta_Sp_046A16            TAACGAGAATAATAATGTTTATATTAATTTGGTTTAACTAGCCAGGTAAG
delta_Sf_035H04_Contig1a   TAATAAGAATAATAATGTAGATACTAATTTTGTTTAACTAGCCAGGTAAG
                           *  ********  *  **** ***************** delta_Sp_046A16            ACTCATCAGCATCATTGCTATTCTTTCCGAGGGCGCTGCAATTAATATTA
delta_Sf_035H04_Contig1a   ATGCATCAGTATCAATGCTGTTCTTTCAGAGGGCCCTGCAATTT------
                           *  ****    **  * ****** delta_Sp_046A16            CCCCGGCAATTACCAGGTACCCATTTACACCTG--GGTGGAGAGGGGCAA
delta_Sf_035H04_Contig1a   ------------CCAGGTACCCATTTACACCTATAGGTAGAGAGGGGCAA
                                       ****************    * ********** delta_Sp_046A16            ATGTGTATTACAGGCTTGTCAAAGGACAATACTGCCGGGCTAGGATTCGA
delta_Sf_035H04_Contig1a   ATGTGAATTAAAGGCTTGTCAAAGGACATTACTGCCGGGCTGGGATTCGA
                           ***  ************* ******* ****** delta_Sp_046A16            ACCCTCGATCTTTGGATTGGGAGTCAAGTGAATTAAGTACTATA-----C
delta_Sf_035H04_Contig1a   ACCCTCAACCCTTGGATTGAGAGTCAAGTGAATGAACTACTATAATATAC
                           ******  * * ******* ************* ** *******     *
```

Figure 6e

| | |
|---|---|
| delta_Sp_046A16 | CACGATACTTCCACCATTCTCACGATTCACATTCACAAGATAATGTAGGC |
| delta_Sf_035H04_Contig1a | CACGATACCTCCACTATTTTTATGATGCCCATTCGCAA----ATGTAGGC |
| | ******* ***** *** * * *** * ***** ***    ******* |
| delta_Sp_046A16 | CTACAGTGTGATTGAATTGGATTGAATTGAATTTATTTTCTTCTGCAACA |
| delta_Sf_035H04_Contig1a | CTATTGTG------------------------------------------ |
| | *** *** |
| delta_Sp_046A16 | TACACATCGAATTACATTTCAGCGATGCAACATATACCAAAACTGTTTTG |
| delta_Sf_035H04_Contig1a | -------------------------------------------------- |
| delta_Sp_046A16 | TATACACAGTATAATAATAATAAAAAATACGTCATTGAAACAAAATGTAA |
| delta_Sf_035H04_Contig1a | -------------------------------------------------- |
| delta_Sp_046A16 | ATGATATCACACTACCAATAATTATTGAAAGCATTGTCACTTGATTTTCC |
| delta_Sf_035H04_Contig1a | ----------------ATGATCAT---------GTCACTTCATTTTCC |
| | ** ** ** ******* ******* |
| delta_Sp_046A16 | CATGCATGTCGAAACTGTTCAAACATGACACTACAGTACAAAGATTCGCG |
| delta_Sf_035H04_Contig1a | CATGCATGTCAAAACTATTCAAACATGAGACTACAGTACAAAGATTCGCG |
| | ********** ***** *********** ********************* |
| delta_Sp_046A16 | AATCATTGGATGGATCAGA-------TAAAAGAGTGTT--CCCCGAGGCA |
| delta_Sf_035H04_Contig1a | AATCATTGGATCAGATAAAGCAGTATTGGAATGGTGGTTGCCCCGAGGCA |
| | ***********  * *    *  ** *** * ********* |
| delta_Sp_046A16 | ATCATCATTGATTGTCACAACAAAGATCAATATTATGTGAAACTATTTCA |
| delta_Sf_035H04_Contig1a | ATCATCATTGATTGTCACAATAAAGATCAATATTACGTGAAACTATTTCA |
| | ******************** ************** ************* |
| delta_Sp_046A16 | TCTTATTCATAATTCTCATCATCAAACGTTTGAACTGATATCTGTTTTCA |
| delta_Sf_035H04_Contig1a | TCTTATTCATA-TTCTCATCATCAAACGTTTGAGCTGATACCTGTTTTCA |
| | *********** ********************* ****** ******** |
| delta_Sp_046A16 | GTTCAAATAATCGATGTTGTACTTCATTCGAAACCGTATACATATAGATG |
| delta_Sf_035H04_Contig1a | GTTCAACTAATCGATTTTGTACTTCATTCGAAACTGTATGCAT--AGATG |
| | ****** ******* ****************** **** ***  ***** |
| delta_Sp_046A16 | ACATGATTCATCACTAAATACGAAAATGAATCCGCAAAATATGTTGAAAT |
| delta_Sf_035H04_Contig1a | ACATGATTCATCACTAAATATGGAAATGAATCCGCAAGAATTGTTGAAAT |
| | ******************** * *************  **  ******* |
| delta_Sp_046A16 | ATCAATCAGGGAGTTGGACCATGGACCTGT--AACTTGTTGAA--ACAAA |
| delta_Sf_035H04_Contig1a | GTCAATCAGGGAGTTAGACCTAGACCTTGTTGAAACCATGGGCCTACTAA |
| | **************  ****  *  *  ***  **  *    ** ** |
| delta_Sp_046A16 | GAGGGGTGCTATATA--------------------TTCTGGAAATAAAA |
| delta_Sf_035H04_Contig1a | GACGGATGCTATATCCTTAATTATTCACCTGTATGTTTCTGGAAAGCAAA |
| | ** ** ********                    ********  *** |
| delta_Sp_046A16 | CTGTATCGACATTAAGCGATGATGGTTTAGTGCTGGCTAATCGTCGTGAT |
| delta_Sf_035H04_Contig1a | CTGTATCTACATAAAGCTCCGATGGTTCAGTGCTGGCCAATCATCGTGAT |
| | ******* **** ****    ******* ******** **** ****** |
| delta_Sp_046A16 | ACTCTTCACACTATCGACTTCAAGAGAATCCGGCCAGGTCCAGTGTTCGT |
| delta_Sf_035H04_Contig1a | ATTCTTCACACTGTCGACTTCACGAGAATCCGGCCAGTCCCGGTGTTCGT |
| | * ********** ******** ************** ** ******** |

Figure 6f

```
delta_Sp_046A16           AAACTGTTGAAAAGATCCACCAAATAGACAACAACCTACTATCTTTCCAA
delta_Sf_035H04_Contig1a  AAACTGTTAAAAAGATTCACCAAATAGACAACAACCTACTATCTTTCCAA
                          ****** *  **************************** delta_Sp_046A16           TATTTTATTTT---CATTTTGGTCTTCACAAACCGATCGATTTTAGCACG
delta_Sf_035H04_Contig1a  TATCTTATTTTTTTCATTTTGGTCTTCACAA-CCGATCGATTTTAGCACG
                          * ***   ************* **************** delta_Sp_046A16           GTTGTACCGGATTTCTAATTTCCCAGGGATGTTTATTTGGAGGACCCTGG
delta_Sf_035H04_Contig1a  GTTGTACCGGATTTCTAATTTCCCAGGTGAGTTTGTTTGGAGGACCCTGG
                          *************************    ******** delta_Sp_046A16           ACAAAGCCTTTTACGTCATAAACGTGGAGAATGTGCTGCAACAA------
delta_Sf_035H04_Contig1a  ACATAGCCTTTTACGTCATAAACGTGAAGAATGTGCTGCGACATAGGCCT
                          * ****************** ******** * delta_Sp_046A16           ------CACTAGATATACTAACACAATGATTTCACACGAGATAATCATAT
delta_Sf_035H04_Contig1a  TTACATCACGAGACATACTAACGCAATGATTTCACACGAGATAATCATAT
                                * **** ************************** delta_Sp_046A16           TATTTTCCCAGACTGTGAGAATTCAAATAAA-GTACATACTCCTACCATT
delta_Sf_035H04_Contig1a  TATTTTACCAGAGTGTGAGAATTTTAATAAAAGTACATACTCCTGCCATT
                          ****    ****     *  ******** *** delta_Sp_046A16           TTGTTGCGATTAGTATCTTTTTCAAGTTTGTTTGTTCGTTTTTATTTCCG
delta_Sf_035H04_Contig1a  CTGTTGCGATTAGTATATTTTTCAGGT-----------------------
                           ************** *** delta_Sp_046A16           AAATCCATAATACATGCAAGTTTTAAAAACATGCACAATACATTTCAAAT
delta_Sf_035H04_Contig1a  -------------------------AAACAT-------------------
                                                   ****** delta_Sp_046A16           GATAAGTTGTGTAAAGTATAGACAAACGGTAGGATAGCCCGTTTCAGGAC
delta_Sf_035H04_Contig1a  -------------------------------------------------- delta_Sp_046A16           CATTTTCAAAATGGTCCTGTTCTTTCAGGATTAGGACTAAGTGATTACAA
delta_Sf_035H04_Contig1a  ---------------TCTGTT----------TAGGATTAAGTGATTACAA
                                         ***          * *********** delta_Sp_046A16           TCAACCATAAAATTGCAGGTATAGTTACTGAAAGCTTGCCTCGGAATCAT
delta_Sf_035H04_Contig1a  TCAACCATAAAATTGCACTTATAGTTACTGAAAGCTTGCCTTG-AATCAT
                          *************** ********************* * ****** delta_Sp_046A16           ATA--TGGTCTAGTTGGTATAGGACCGTGAGAGTTTCTCACCAGACTCCT
delta_Sf_035H04_Contig1a  ATACTTGGTCTAGTTGG-GTAGGACCGTGAGAGTTTCTCTTCAGACTCCT
                          *   ******** **************** ******* delta_Sp_046A16           AACACTGGTTGTCGATGGCTCCTTTGTTTATGTCATGGAGAGCGTGATCT
delta_Sf_035H04_Contig1a  ACCACTGATTGTCGATGGCTCCTTTGTTTATGTCATGGAGAGCGTGATCA
                          * *** *************************************** delta_Sp_046A16           GTGAGTGGCCTTCCCTA--CTTATCGATCCAAAGACCAAAATTTTCCTGG
delta_Sf_035H04_Contig1a  GTGAGTGGCCTTCCCTATACTTATCGATCCAAAGACCAAAATTTTCCTGG
                          ***************  ***************************** delta_Sp_046A16           GAAAGCAGTGATTGATTGGAGAGATTTTGTCCTTCGATCAACTCGTTGGA
delta_Sf_035H04_Contig1a  GAAAGCAGTGATTGATTGGAAAGGTTTTGTCCTTCGATCAACTCGTTGGA
                          ******************** *  **************************
```

Figure 6g

```
delta_Sp_046A16          CGTGTCAAATCGTTGGGATCCCACGCACACACCAACAACACGAGGTGTCG
delta_Sf_035H04_Contig1a CGTGTCAAATCGTTGGGATCCCACGCACACACCAACAACACGAGGTGTCG
                         ************************************************** delta_Sp_046A16          TGTGGCCCACCAGCTGGCGTGTGCTACTGGGGTCAACATCAAGAACCCCA
delta_Sf_035H04_Contig1a TGTGGCCCACCAGCTGGCGTGTGCTCCCGGGGTCAACATCAAAAACCC-A
                         ************************* * ************ *** * delta_Sp_046A16          AGTTCAATTGCAGGGGTCAGAGGATGGATGGGGGAATTAGAACTGGACCG
delta_Sf_035H04_Contig1a AGTTCAATTCCAGGGGTCAGAGGATGGATGGGGGAATTAGAACTGGACCG
                         ******* ************************************** delta_Sp_046A16          TCATGTTGGTCCTGTGCTTGGGATACACAATACTCATTAACCTCATTCGT
delta_Sf_035H04_Contig1a TCATTTTGGTCCTGTGCTTAGGAAACACAATACTCATTAAACTCATTCCT
                         ** ********** * ************* ***** * delta_Sp_046A16          GTATCATGAACATTGGGCTCACAGGGATATGTATACACATAAAATAAGAC
delta_Sf_035H04_Contig1a GTATCATATTTATTGTGCTCACCGGTCTATGTATACAAGTAAGCTAAGGC
                         *****       ******** *   *   * * delta_Sp_046A16          AGCAGTTTTTTTCC-------TTTTCATTTTACGGTGTTTAATCAATTAT
delta_Sf_035H04_Contig1a AGAAGGTTTTTTTTCTTCCCATTTTCATTTGCGGTGTTAAATCAATTAT
                            ****        ****** ** ****** delta_Sp_046A16          AGTAAGGCCTATCGATCCTTCATCAAATGTTTCAACAGTGAGTCATACAA
delta_Sf_035H04_Contig1a AGTAAGGCCTATCGATCCGTCATCACATTTGTCAACAGTGAGTCATA---
                         **************** **  * * ************** delta_Sp_046A16          AATAATGAGAGATAAATGTCAAAAACTCGATCATGATTCTTAATGAAAA-
delta_Sf_035H04_Contig1a -ACAATGAGAGATAAATGTCAAAAACCAGATCATGATTCGTAATGAAAAA
                          * ******************** ******** ******* delta_Sp_046A16          TCAGCTAATGTTGTTTAATGTTGTTAAATCAACATGATTTCAAGCCTGAA
delta_Sf_035H04_Contig1a TCAGCTA----------TGTTGTTAAATCAACATGATTTCAAGCCTGAA
                         *****           ****************************** delta_Sp_046A16          TTAATTACCATACTGATTATCTATTCTTAATCTATAAGAAAATGAAAGAG
delta_Sf_035H04_Contig1a TTAATTACCATACTTATTATCTAATCTTAATCT--AAAGACATGAAAGAG
                         ************ *** ****   **  * ******* delta_Sp_046A16          AACCATCCAAGCTGATGCGATGGTCTAACCCATACAAAGTTAAGACCATG
delta_Sf_035H04_Contig1a GA----CCAAGAAGGTGCAATGGTCTAACCCATACAAAGTTAAAACCATG
                         *     ***   * *********************** **** delta_Sp_046A16          TTCGAGTAGATGGGTGTAAGTTGTTACGTTTGGATATCAGCCAAAAGTAA
delta_Sf_035H04_Contig1a TTCAATTAGATGGATAAAAGTTGTTACGTTTG-ATATCAGTC--------
                         *** * ******* *  ************* ***** * delta_Sp_046A16          CCCGGCAGCATTCCCAAAACGAGCAATAAACAAGAAAATATTGAAAACAA
delta_Sf_035H04_Contig1a --------------TAAAACGAGCAATAAACAAGAAAACAATGAAAACAA
                                       ********************** * ******** delta_Sp_046A16          ATAAATTGAATACATGACGATTCTGTATAAGTGTAATAAGTTTAGTGTCA
delta_Sf_035H04_Contig1a ATAAATTGAATACATGACGATTCTGTATAAGTGTAAGAAGGATAGTGTCA
                         ********************************** *    ****** delta_Sp_046A16          ATACAGTCCCGGCATGAAACCCATCATCTATGTATTACAAGGATGCGCAG
delta_Sf_035H04_Contig1a ATACAGTCCCGGTATGAATACCATCATCTGTTTATTACAAGGATGCCGAA
                         ************ ***** ********* * ************** *
```

Figure 6h

```
delta_Sp_046A16         CAGATCGACCTACGTCATAAATACAGGACGAAACTTTCTTCATTAGAGTT
delta_Sf_035H04_Contig1a CA----GACCTACGTCATAAACACAGGACGAAACTTTCTTCATTAGAGTT
                            *********** ************************** delta_Sp_046A16         GGTGTTGACGATATAGAATCGACAGCTCTTTAGCGCATTGTCACTTTCCA
delta_Sf_035H04_Contig1a GGTGTTGACGAC-TCGAATCGACAGCTCTTTAGCGCATTGTCACTTTCCA
                        ***********  * *********************************** delta_Sp_046A16         CCAAAATCATGTCCTTGTACTTAGGTTGACCAGATACACTTGGCTATGAC
delta_Sf_035H04_Contig1a CCAAAATCATGTCCTTGTACTTAGGTTGACCAGATACACTTGGCTATGAC
                        ************************************************** delta_Sp_046A16         TCTCGCCTTATAATTGATTTTTCTATCTTCACCACTGTTCACTCGATCGC
delta_Sf_035H04_Contig1a TCTCGCCTTATAATTGATTTTTCTATCTTCACCACTGTTCACTCGATCGC
                        ************************************************** delta_Sp_046A16         TAGGGCTAT--GCCCTTGGACGCAGTTATATGCATAAGTGTATATTGTGA
delta_Sf_035H04_Contig1a TGGGGCTATATGCCCTTGGACGCAGTTAGATGTATAGGTGTATATTGTGT
                        * *****  ************* * * ********** delta_Sp_046A16         GGAAGTAGTTTAATCTATTAGTATTAGTTAAATGTATTCCTATGATGGGG
delta_Sf_035H04_Contig1a GGACGTAG--TAATTAGCC--TATGAGTTAAGCGTATTCCTATGCTGGGG
                        *      *  * ** *******  ** delta_Sp_046A16         TTCCAGTATTCGTTATCAGCCTGACGACACCTGATTTTTTCTTATAGGTA
delta_Sf_035H04_Contig1a TTCCAGTATTCGTTGTCAGTCAGACGACACACGAATTTTTCTTCTAGGTA
                        ************ ** * ******  ******* **** delta_Sp_046A16         CATTTCGCTTGAATTAACTATATTAATGTGATATAAAAATCGATATTCAT
delta_Sf_035H04_Contig1a CATTTCGCTTGAATTAACTATATTAATGTAATACGAAAATCGATATTCAT
                        *************************** * * ************** delta_Sp_046A16         AAACAACATCAAATCGTGTTTTGAGATACGTGTTAATATAATACAACTTG
delta_Sf_035H04_Contig1a AAACAACATAAAATTGTGTTTTGAGATATGTGTTAATAGAATACAACT--
                        *******  ********* ***** ******* delta_Sp_046A16         AATCAGTAGATTAGGTAGATGAGATAAGCGTATGTGCTAATTTTAAACGG
delta_Sf_035H04_Contig1a --ACAGTAGATTAGGTAGATATGAC-------------------------
                          **************** delta_Sp_046A16         GGTGGAGGCGGTTGACGTCTCGTGCCCGAATATCAAATTAAAATCGTAAG
delta_Sf_035H04_Contig1a --------TGGCTGACGTCTCGTGCCCGAATATCTAATCAAAATTTTATG
                                  ****************   ***   * delta_Sp_046A16         TAATTTAGTGAAATCCAAATCCTGATATAAAAGTATTTTCATCTAAACAA
delta_Sf_035H04_Contig1a TAATTTATTGAAATCCAAATCCTGATATAGAAGGATTATCAT--AAAAAA
                        *****  **************** * *      ** delta_Sp_046A16         ACAAACAAACAAAACAAAATGAAAAAAAGTGAAACAAATTTAAGGTATGC
delta_Sf_035H04_Contig1a ACAAACAAACAAAACAAA-CAAAACAAAGTGAAACAAATTTAAGAGATGC
                        ****************  *  ****************** * *** delta_Sp_046A16         TGAATAGGAACAAAAGCATCAACAAAGCAAATGCGAATATTGTTTAAAAA
delta_Sf_035H04_Contig1a TGAATAGGAA-AAAAGCCTCAACAAAGCAAAGCGAAT--TGTTTAAAAA
                        ******** ** ********* *  ******** delta_Sp_046A16         CAAAATTGTACATAATTATGATCGCATTGCACTCGACAAAATTAGTTCAA
delta_Sf_035H04_Contig1a CGATACTGTACATAATTATGATCGCATTGCACTCGACAAAATTAGTAATA
                        *   * ******************************************** *
```

Figure 6i

```
delta_Sp_046A16         TCAAAATAAAAA-------------CACATGCAGGAGGAAA-------AT
delta_Sf_035H04_Contig1a CACACATGACATGTATTTTCATCATCACATTCAAAATAAAACACAGGAGG
                          *  ** * *              ***    *   *** delta_Sp_046A16         GTAGTGTAGTGGATATATACAATACCTCGACAAA--AAAGGTAGGCCTAT
delta_Sf_035H04_Contig1a GGAATGTAGAGGATATAAACAATACCTCAACAAACCAAAAGTTGTATTGT
                        * * ***  *** ****** *  *      * * delta_Sp_046A16         AT-TGTATAAA-----------TAAATAAAAAATAAATTT----------
delta_Sf_035H04_Contig1a ATACAAATAAAGTTATTTTATTTGTATACAATACAACTTTTGGTTTGTTG
                           ***            *  *   *   * delta_Sp_046A16         -ATTAACTAAGTTATCAACTTTCCAGTT----TCCAAAT--TCGAGA---
delta_Sf_035H04_Contig1a AGGTAACTAACTTATCAACTTTCCAGTTGCTGCCCAAATATTTAAAATTT
                         **** **************    ****  *  *  * delta_Sp_046A16         --GCGGGGGGGGGGGGGGGGCTGCACCCTCTTATGTTCTCCTTGCACAC
delta_Sf_035H04_Contig1a CGGGGAGGGGGGGGGGGGGGGGCTGCACCCTCTTATATTCTCCTTGCACGC
                          *  ******************** **** ********* * delta_Sp_046A16         CTATGATGATGATGATTTAGTTAAGATGGAATTATGCGTACTTTATTGTT
delta_Sf_035H04_Contig1a CTAGGATGATGATTATTTAGTTAAGATGTACTTATGCGTACTTTCTTGTT
                        *  ***** **********  * ********** *** delta_Sp_046A16         ATGAGCTTTTCTTCTTTTCGTGATATTTAGTCCTTTTT-TTTAAAGATAT
delta_Sf_035H04_Contig1a ATGA-TTTTTCTTCTTTGCGTGATGTTTAGTCCCTATAGTTTTAAGATAT
                        **  ******* ** ****** *  *  * ***** delta_Sp_046A16         CATTTTATTGAAAAGCTAATAATG---TAATTTGCAAAGGGTCACCACAC
delta_Sf_035H04_Contig1a CGCTTTATTCAAAAGCTAATAATGATCTCATTTGCGAAGGGTCATCACAC
                        *  **** ************    * **** **** *** delta_Sp_046A16         GTGTCCAGAAAA-ATAGTTCATAATATATAGTTCA-------TTCTGTAT
delta_Sf_035H04_Contig1a GTGTCCAGGAAATATAGTTCATAATAGTTCATTTGAAATGACTTTTGTAT
                        ****** *  ************* *          ***** delta_Sp_046A16         GACTCAAAATCGACAATGGGACTGATTTAAAATGTCAGAATAATTGAACG
delta_Sf_035H04_Contig1a GACTCAAAATCAACAATGGGACTGATTCAAAATGTTAGAATAATTGAAAG
                        *********  ********** *** ********** * delta_Sp_046A16         TGACATGGCAGTACCATGGGAGTCTAGACTGTTGGACAATCAGTGAATTA
delta_Sf_035H04_Contig1a TGACATGGCAGTACCATGGGAGTCTAGACTGTTGGACAATCAGTGAATTA
                        ************************************************** delta_Sp_046A16         AGAGATGATGATTCGGAAACCTCTAAGGTCTTAAGAACAGGGTGTCTCAT
delta_Sf_035H04_Contig1a AGAGATGATGATTCGGAAACCTCTAAGGTCTTAAGAACAGGGTGTCTCAT
                        ************************************************** delta_Sp_046A16         GAAAATGATCACAGGAGTCAATGTTTTTTCTTCACCCAATCTCTATCAC
delta_Sf_035H04_Contig1a GAAAATGATAATAGGAGTCAATGTTTTTTCTTCACCCAATCTCTATCGC
                        ********* *  ************************************** delta_Sp_046A16         TTATATATAGCGTAAGTAA-TACGAAACATTACTTGAGTGTGAATAAAAG
delta_Sf_035H04_Contig1a TTAT-TATAGTGTAAGTAACTACGAAACATTAATTGTTGTGAAGAAAAG
                        **  * ******* *****  *  **** *** delta_Sp_046A16         AATGCATTATTCTTAATAGAGATATTCT---------------------
delta_Sf_035H04_Contig1a AATATATTATTCTTAATAAAGATATTCTTGTTTCTATGAATATGATATGT
                        ***   ************* *********
```

Figure 6j

```
delta_Sp_046A16      ------------------------------------------------------
delta_Sf_035H04_Contig1a  TGAACAACGTCAAATTAATACGTCGCCCACAAGTTTGCAGTATCTACAAT delta_Sp_046A16      ------------------------------------------------------
delta_Sf_035H04_Contig1a  TGAACGATATTTTGTATATATATCTGTCGGGTCTATATTGAATTTGCGTG delta_Sp_046A16      ---------------------------------------------------
delta_Sf_035H04_Contig1a  GGTATATCCCATAACAAGTGTTCTGGAATGCATGTTATTGATTGTAAGGT delta_Sp_046A16      ---AATGTTAGAATATGATGATTGTAAAATATTCATGAGTAAATTAACGT
delta_Sf_035H04_Contig1a  GATAATGTTAGAATATGATGATTGTAAAATATTCATGAGTATATCAACGT
                        ****************************************  ***** delta_Sp_046A16      CCAGGCCACTGTTTTAGAAAAGTCTACTTACCCTGTAGACGGAGCTACGC
delta_Sf_035H04_Contig1a  CCAGGCCATTGTTTTAGAAAAGTCTACTTACCCTATAAACGGAGCTGCGC
                        ****** ********************  ****** * delta_Sp_046A16      ATTTGGTTTGGGACTACGCGTTTGGGAC-TAGACGAAACGTACCGAAGAA
delta_Sf_035H04_Contig1a  ATTGC----------CGTGTTTGGGACCTAGACGAAACGTACCGAAGAA
                        *               ******* ****************** delta_Sp_046A16      AGAAGTGAGGAAATAACCAGTATCCTACCACCTTAACCCCGGTCTAGGGG
delta_Sf_035H04_Contig1a  AGAAGTGAGGAAATAACCAGTATCCTACCGCCTTAACCCCGGTCTAGGGG
                        *************************** ****************** delta_Sp_046A16      ACAAAATATGTAGTCCTTGAAGAAT-AATCGAATAGGGAATATCATTAGA
delta_Sf_035H04_Contig1a  ACAAAATATATAGTCCTTGAAGACTTAATCGAATAGGGAATATCATTAGA
                        ******* *********** * ************************ delta_Sp_046A16      TGTGGAGAGATGAATTATCTCATTTTCCTAACGAGTTGATTTCATTTTAA
delta_Sf_035H04_Contig1a  TGTGGAGAGATGAATTATCTCATTTTCCTAACGAGTTGATTTCATATTAA
                        ****************************************** ** delta_Sp_046A16      AACACAATGGTAG---GGGCTGGTGATTTGAAAGAAGCACGC--------
delta_Sf_035H04_Contig1a  AACACAATGGTAGCCAGGGCAGGTGATCTGAAAGAAGCACGTCACCTGCA
                        ***********    ** ********** delta_Sp_046A16      ---GTGGCCATTGAGTGAGGTGCG----GGGAAAATCTATATCTTTTCTA
delta_Sf_035H04_Contig1a  CGTGTGGCCATTGAGTGAGGTGTGCAATGGGGAAATCTA--GCTTTTCTA
                        ******************* *    * ***   ***** delta_Sp_046A16      ATTGTAGGACGAACATGTGATAATTGAAATTGCCGATTTGGTTTACTTAT
delta_Sf_035H04_Contig1a  ATTGTAGGACCAACATGTGATAATTGAAATTGCCAATTTGGTTTACTTAT
                        ******** ******************* ************* delta_Sp_046A16      TTCTGAGTGACTGGATTATATCGCATTGAATGGTGCTGAAAATAGGCATG
delta_Sf_035H04_Contig1a  TTCTGAGTGACTGGATTATACTTCATTGAATGATGATGAAAATGAACATG
                        ******************   ****  *****   **** delta_Sp_046A16      ACCAGGGCATGATTAGTCAGTTCAAATTTTGTACCTTGATGATTATGATT
delta_Sf_035H04_Contig1a  ACCAGGGCATGATTA-------------TGAAC-----TAATTATGA--
                        *************               **       * ******* delta_Sp_046A16      AGTTTTGGAATTATAATTGATATGTTGGGTATACAATTTAGTTGCGTTTC
delta_Sf_035H04_Contig1a  --------------------------------------------------
```

Figure 6k

```
delta_Sp_046A16          ACTTTGGGAAATAATTTCTTTTTTGATTTTCTCTTCTTTTTACTCCCATA
delta_Sf_035H04_Contig1a ---------ACTAATTTCTTCTTTGGTTTTTCTCTTTTTT---TTCCATC
                                  * ******    **    * ****    * **** delta_Sp_046A16          TAACCCCATACTGTCCTACGTAATTAAT--------ATATGCAAATGAAT
delta_Sf_035H04_Contig1a CAACTTCAGACTGTCCTACGTATACAATTTATGTGTATACGCAAATGAAC
                          *   *********** *      *  * ********* delta_Sp_046A16          TATTATTGTCAAAATAAGTAATGTTCCCGAGCTCCTAACATAGCTCTTCA
delta_Sf_035H04_Contig1a TATAATTGTCAAAATTAGTAACGTTCCTCAGCTCCTAATATAGCTCTTCA
                         * ******* * * ***** ********* delta_Sp_046A16          TTATTCCCATCAGTGTCACTGATGTGTGGTGTACAATATCTCCATTCCTG
delta_Sf_035H04_Contig1a TTATGCCCAT---TGTCACTGGTGTGTTGTGTACAATATCTCCATTCCTG
                         ** *    **** * ****************** delta_Sp_046A16          CGTGCTGCCCGGTATTTTGATGTATGCACGGTTGTTCGGAATACAAATTT
delta_Sf_035H04_Contig1a CGTGCTGCCCGGTATTTAAT-TATGCATG------CACAGTTGTATTTT
                         ***************    ******        *  *  *  *** delta_Sp_046A16          GGCGACCACAATGGCTTACTGCATCTGGGTCCCATTCTCGCCTGGGTAGG
delta_Sf_035H04_Contig1a GGCGACTGCAATGGCTTATTGTATCTGGGTC--------GCCTGGGTAGG
                         ****  ******  *******        ******** delta_Sp_046A16          TAGTGGCAAGTACAGATTGATGTCTCTCTCGTGA--ACGTTAGCTTCGTA
delta_Sf_035H04_Contig1a GAGTGGCAAATACAGATTGATGTCTCTCTCTTGAGAAAGTTAGCTTCGTA
                          ******  ***************  *   * *********** delta_Sp_046A16          TATGGGGAGTTGAGAAGTTTTCACATCCACGAGACCAGAGATCACGAAA
delta_Sf_035H04_Contig1a CGTGGGAAGTTGAGCATGTCGCATCCATC-------AGATTACGAAA
                            *** ***** *   **          **** delta_Sp_046A16          CCATTCTATAAAGTATTCAGCTTCACCGTCGTTCACATCACCACTTCATC
delta_Sf_035H04_Contig1a CCATTATATAAAGTATTCATCTCCACCGTCGTTCACATCACCACTCCATC
                         *** ********   ******************** ** delta_Sp_046A16          TGCTTTTCTCTCAAATTCCGATATCAAAATTTTTGCTCCAAACAGTCAAA
delta_Sf_035H04_Contig1a TGTTTTTCTCTCAAATTCCGATATCAAT-TTTTTGCTTCAAACCGTCAAA
                          ********************    ** ** * ***** delta_Sp_046A16          CAAAAGGCTAGAAATCTGAAGTGTATCCACCGAGTCTTCGTCACCTCCAC
delta_Sf_035H04_Contig1a CAAAAGGCTAGAAATCTGAAGTGTATCC---GAGTCTTCGTCACTTCCAC
                         **************************    ******** *** delta_Sp_046A16          CTCTCCATGTTTGCACAGCCAAGACATCAATGCAAGTAATTACATTTAAA
delta_Sf_035H04_Contig1a CTCTCCATGTTTGCACAGGCAAGACATCAATGCAAGTAATTACATTTAAA
                         **************** ***************************** delta_Sp_046A16          GCATCCCGCTAAAGAAAACAACTCTTCCGCTTTCGTTTGTCGACAAACTT
delta_Sf_035H04_Contig1a GCATCCCGCTACAGAAAACAACTCTTCCGCTTTCGTTTGTCGACAAACTT
                         ******** ************************************ delta_Sp_046A16          GACTGGACCCGTCTCGATTGTTCAAACAAGAGAATGGAGAAATTGGTGAG
delta_Sf_035H04_Contig1a GACCAGGCCCGTCTCGATTGTTCAAATAAGAGAATGGAGACATTGGTGAG
                         ***  * ***************** ********* ******* delta_Sp_046A16          GGGAGGGGAGTTCGTTTGGCCATCACATTAACTTTGTATTTGTATTGTAT
delta_Sf_035H04_Contig1a GGGAGGGGAGTTCGTTTGGACATCACATTAACTTTGTATTTGTACTGAAT
                         ******************* ************************ ** **
```

Figure 61

```
delta_Sp_046A16        CTTATTTGTACTGCTTTCCATCCCGTCTTCATCCTTTTCTCTGTTCATTA
delta_Sf_035H04_Contig1a CTTATTTGTATTGCTTTCCATCCCATCTTCATCCTCTTCTTTGTTCATTA
                       ******** ********* ****  ******* delta_Sp_046A16        CCAACAAAAGGACA-GATTTTACTAACCATTGATGAAAGGAAAGTTATCA
delta_Sf_035H04_Contig1a TCAACGAAAGGGCATAATTTTACGAGCCTTTGATGAAAGGGCAATTATCA
                       ** *   ******* *   ******* *  ****** delta_Sp_046A16        TAATTGCTAAATATTCTA---------TCTACAAG---------------
delta_Sf_035H04_Contig1a TAATTGCTAATTATTCTAGGCCTATCATCTACAAGTTTAGAGAGAGAAAA
                       ******** ***         ****** delta_Sp_046A16        -----------------------AGAGAGAGAAGGAAAGAGAGAGAGAGA
delta_Sf_035H04_Contig1a AAAAAGGATAGGGAGAGAGATAGAGAAAGAGAAAGAGAGAGAGAGAGAGA
                                              * **  ************* delta_Sp_046A16        GAGAGAG------------AGAGATAGACACAAAAATC----------
delta_Sf_035H04_Contig1a GAGAGAGGTAAAAAAGAGAGAGAGAGAGACAGAGAGATAGAGAGAGATAG
                       *****             * *** * * ** delta_Sp_046A16        --------------------------------------------------
delta_Sf_035H04_Contig1a AGAAAGAGATAGAGTGAAAGAAAGAGAGAGAGAGAGAGAGAGAGAGACAG delta_Sp_046A16        ATATAGGCC-----------TTGTTTGACAAATGAAT------AATTTTT
delta_Sf_035H04_Contig1a AGATAGACACGAACATCAGATAGTTCGACAAATCAATGTTTAAAAATAAT
                        * **** *            * * *** *       ** *  * delta_Sp_046A16        TTAAAGATAGCAATCGTGATTCCTAAGTATCTTATCATTTGATTTTATCT
delta_Sf_035H04_Contig1a GAAATTATAGCTATCGTGATTCCTGAATATCTTATCATTTGATTTTATCT
                          * ********** * *********************** delta_Sp_046A16        TTAACATTTCTGAAATTTAAATGTTCATG-AAGGTTTGGGACTCCTGTGA
delta_Sf_035H04_Contig1a TTGAAATTTCTGAAATTTAAATGTTCATGTAAATTTTGGGACTCACGTGC
                        ** * **********************  ********* * *** delta_Sp_046A16        TATTATGATAAACAAAATTAACCCCTGGTGATAACAGT-AGTCATGGACT
delta_Sf_035H04_Contig1a TATTATGATCA-CAAAATTAGCTCCTGGGGATAACGGTCGGCCATGGACT
                        ********* * ******** * **** *   * ******** delta_Sp_046A16        CTAAAACGATTGTATCTCTGTGGGCCGGCAAAGCCTATATATGATTATGG
delta_Sf_035H04_Contig1a CTAAATCGGTTGTATCTCTGTGGGTCGGCATATACCCTATAT------GG
                        ***  ************ ***     *  *** delta_Sp_046A16        TTATTATCTACACATCTTCGATTGTAAAAATAAGCTAAAATACTGAATGG
delta_Sf_035H04_Contig1a TTATTATCTACAGGTCTTCGATTGTAAAA-TAAGCTAAATACTGAATGG
                        **********   ********* *** ********* delta_Sp_046A16        GATACATCAATAAATAACACGTACTTCTAATACTACTTCTACTTGCAAGA
delta_Sf_035H04_Contig1a GATACATCGATAAAGAACACGTACTTCTAAAACAACTTCTACT-GCAAAA
                        ****** * **********  ******* ** * delta_Sp_046A16        TAATGGCGTTGGTAAAAAA-AAAAATGTTGTTATTAAAAAGGCGATCTCC
delta_Sf_035H04_Contig1a TAATGGCGCGAGTTGGTAACAAAAAGGTTGTTATTAAAAAGGCGATCTCC
                        ******       * ********************** delta_Sp_046A16        GAA-CATTTGGCGGTTAACAACTGGGGTGGTGTCACTTCTTGGCTGAAGT
delta_Sf_035H04_Contig1a GAAACATTTGGCGGTTAACAACTGGGGTGGTGTCACTTCTTGGCTGAAGT
                        *** **********************************************
```

Figure 6m

```
delta_Sp_046A16            AATTGGCTCGCGTGCCATTCATTAACAGCGATGGCTGGTGTGAGTTAGGC
delta_Sf_035H04_Contig1a   AATTGGCTCGCGTGCCATTCATTAACGGCGATGGCTGGTGTGAGTTAGGC
                           ************************ ******************** delta_Sp_046A16            CAATTTAAAATGGAATTAGTGATAGGAGTGGTGGTAGGGCTGAGAAGGAT
delta_Sf_035H04_Contig1a   CAATTTAAAATGAAATTAGTTATAGGAGTGGTGGTAGGGGTGAGAAGGAT
                           ********** *** ************* ******** delta_Sp_046A16            CCCCGCTACTTCAAGTCGACCATA------CAATTCATGGATATTCTCTC
delta_Sf_035H04_Contig1a   CCCCGCTACTTCAAGTCCACCATATTAACACAATTCATGGAC-TTCTCTC
                           *************** **      ********* * ***** delta_Sp_046A16            CAAAAGGATGGAGAGGATTCGACCCTTCTTTGTCGCGCTCAGTTTAACGT
delta_Sf_035H04_Contig1a   CAAAAGGATGGGTC--ATTCGACCCTTCTTTGTCGCGTTCAGTTTAGCGT
                           *********    ***************** **** * delta_Sp_046A16            GATTGTGGATA----TATTGAGTTCGATGACATATTTCTAACTTGATTAG
delta_Sf_035H04_Contig1a   GATTGTGGATAATTATATTGAGTTCGATGACATATTTCCAACAGTATTAG
                           *********    ******************* *   **** delta_Sp_046A16            AAAACAGTTCAATGTATC-CTTTCACGTCAACAGGTTACCAACACAATAG
delta_Sf_035H04_Contig1a   AAAAAGGTTCAATGTATCATTTTCACGTCAACAGGTTACCGACACAAC--
                           **  ******** **************** **** delta_Sp_046A16            TGATAAACAGTATTTGCATGACAGACATATTTTAATGTTTTGTTTTTTAT
delta_Sf_035H04_Contig1a   TCATAAGCAGTATTTGCATGACAT-TTCATTTGAACAATTAGG----TAT
                           * ** ************               *** delta_Sp_046A16            TTGAACAATTAGGTATGTGAGAATCTCAGAAACCTATGACGGAGTGGAAG
delta_Sf_035H04_Contig1a   GTGAGAGTGTGAGACAGTGAG-----TAGAAACCTATGTCGGAGTGGAAG
                           ***      *  *   ***     ******** ******** delta_Sp_046A16            CTTCTGGTTCACCGGGATGCAGGCCAAGCACAAAACAGCAGGGAGAAAAT
delta_Sf_035H04_Contig1a   CTTCTGGTTCACCGGGATGCAG-CCAAGCACAAAACAGCAGGGAGAAAAT
                           ******************** ************************* delta_Sp_046A16            GTTTGTGGCATACTGGCATCCCATACACGGTGGGACCTCGTGCATGTGTT
delta_Sf_035H04_Contig1a   GTGTG---------GCATCCCATACACGATGGGACCTCGTGCGTGTGTT
                                     ************ ********* **** delta_Sp_046A16            GCTGCGAAGTTGCCGACACATACTGA---CCAATTCGAATGTGTACTCAT
delta_Sf_035H04_Contig1a   GCTGCGAAGTTGCTGACACATACTGAGTGCCAATTTGAATGTTTACTCAT
                           *********** ********   ** ** ***** delta_Sp_046A16            GTTGTCGAAGTGTATGTTGCTTGTGGAATTGTTTACCTGTTGCTCGTGAC
delta_Sf_035H04_Contig1a   GTTG--------------CTTGTGGAATTGTTTACCTGTTGCTCGTGAC
                           **              ****************************** delta_Sp_046A16            CAAGCGCCATAGGTCCCCTGTCATAGCCAACACTAA--ATAGGTATCACT
delta_Sf_035H04_Contig1a   CAAGCAC--TAACTTTGTAATTA-ACCCTTCAATGGCGGTAGGTCCCCTG
                           ***      *  *   ** *   **    *     *****  * delta_Sp_046A16            TAAT-TA--TTATCAAGAGCGTCATTAAACATTTTGCATGCAAATTTGA
delta_Sf_035H04_Contig1a   TCATATAGCCTATCACTAAATAGGTATAACATTTCTACATGCAAATTTGA
                           *     *****  *      * ******   *********** delta_Sp_046A16            AATTCTGAACAACCCTTTTGGGGGCGGTTGGAGGGGACGGTTGGAGGGGA
delta_Sf_035H04_Contig1a   AATTATGAGGTACCCTTTTTTGGGGGGGGGAGGGG----CGGGGGTTTC
                           **** ***  ******* *** **  **  *****    *  *   *
```

Figure 6n

```
delta_Sp_046A16          CGGGGAAAGAAATCGACTAGGACTAACTTGAATGATGGTACATTTTTT-C
delta_Sf_035H04_Contig1a CTGAAGAAAAAATTGACTAGGCCTAACTTGGATGATAGTACATTTTTTC
                         *  *    *** *** * ********* * delta_Sp_046A16          GACAAAATTAATAGCCGCAATGGTCTTGTGACGACAGTGACTTGATACTT
delta_Sf_035H04_Contig1a GACAA-----ATAGCCGCAAAGGTCCAGTGACGACAATGACTTAATACTT
                         ***     ******  **** ** **** delta_Sp_046A16          GACAATATTACTTTAAAGCCTCACCTCTTCTCTTTGAATAAAAAAGGCGT
delta_Sf_035H04_Contig1a AACAATATTACTTTACAGCCTCACCTCTTCTCTTTTAATTAAAC-GGCGT
                          ************ *************** * *  ** delta_Sp_046A16          ACATCTTACCATGGAATTCCTCCTTCATTTTACTGATGGCATCTCTTTTG
delta_Sf_035H04_Contig1a ACATCTTACCATGGAATTCCTCCTTCATTTTACTGATGGCATCTCTTTTG
                         ************************************************** delta_Sp_046A16          TACCGGTCAGAGAATCTCCTTTCCTCCGGAAGGA
delta_Sf_035H04_Contig1a TACCGGTCAGAGAATTTCCTTTCCTCCTGAAAGA
                         ************* ******* * ** delta_Sp_046A16          TTAAGTATTATAC   (SEQ ID NO:23)
delta_Sf_035H04_Contig1a TTAAGTATTATAC   (SEQ ID NO:24)
                         *************

Delta Flanking 2:

delta_Sp_046A16          GCTCAATACTTAGCTTCAAGCACCAATCAACAGATAACTTATTTTCAGTA
delta_Sf_035H04_Contig1c GCTCAATACTTAGCTTCAAGCACCAATCAACAGATAACTTATTTGCAGTA
                         ****************************************** *** delta_Sp_046A16          TTAACAAAAAAAGAAGGAGAAGGGGATGAGATAAGGCTTGTAGAGGATCA
delta_Sf_035H04_Contig1c TTA---CAAAAAGAAGGAAAAGGGGGTGAGATAAAGCTTGTAGATGATCA
                         *    ****** *** ***** **** *** delta_Sp_046A16          GGGGTGGGGAATGACA--GGGGGGGGGGGGTATAAAGAATGATAATAAGC
delta_Sf_035H04_Contig1c GGGGTGGGGAATGAGATGGGGGGGGGGGGGATGTCAAAAATGATAGTAGCG
                         ************** *  *********** *  *   *** delta_Sp_046A16          CTTTGTAGTCACTTATTGGACTCGCATGCTTGATTAGCACGTGGCCATTG
delta_Sf_035H04_Contig1c GTTTGTAGTCAGTTATTGGACTCGCATGCTTGATTAGCACGTGACCATTG
                         ********  ************************** **** delta_Sp_046A16          TAACGAAGGACATTGTCTTCTATACACA   (SEQ ID NO:25)
delta_Sf_035H04_Contig1c TGACGAAGGACATTGTCTGAT-CACACT   (SEQ ID NO:26)
                         * **************** *  ****
```

Figure 6o

Gatae Alignments

<u>Gatae Active 1:</u>

```
gatae_Sp_040I09              AGATTATTAGTCACCGCTTGAAGAACATCGGGAAGAGAATGCGGCGCTAA
gatae_Sf_021N05_Contig3b     AAATTATTAGTCACCGCCTGGAGAA-GTTACTAAGAAAATGCGGCGCTGA
                             * ************  ****  *   ** ******** * gatae_Sp_040I09              TCAAAA--------AGGTTGTAATCCCAAGCTACCCTTTTATTCTAGCAT
gatae_Sf_021N05_Contig3b     TCAAAACGTTCTAAGGGTTGTAATCCCAAACTACCCCTTTATTCTAACAT
                             ****         ********** ** ***** * gatae_Sp_040I09              TTGTCCAGGTTCACCCATTAATCTCTTACTAATCCCTTGTAACTGTACAA
gatae_Sf_021N05_Contig3b     TTGTCCAGGTTCGCTCATTAATCTCTTACTAATCCCTTGTAACTGTACGG
                             ************ * ******************************** gatae_Sp_040I09              GATCGCTTTCATAGAAGTACAAAGCTTTACAAAGCAAAGTGAATTGTCTG
gatae_Sf_021N05_Contig3b     GATCGCTTACATAAAG---------TTACAAAGCAAAGTGAATTGTCTG
                             ****** ** *          ************************ gatae_Sp_040I09              CTTGCGATGGCATTCATAAAACACAGTTCACATGATTCATACGATTTGTT
gatae_Sf_021N05_Contig3b     CTAGCGATGGCTTTCATACAAGACAATTCACATGATTCATAAGATTTGTT
                              ****  *  *  ********** ***** gatae_Sp_040I09              TTCAGCAGTTTGCGCCGGAGTGTTTTCTTTGTAGTGCTGTGATTATTTCG
gatae_Sf_021N05_Contig3b     TTCAGCAGTTTGCACCGGAGTGTTTTCTTTGTAGTGCTGTGATTATTTCG
                             *********** ********************************** gatae_Sp_040I09              CGGCTCAAGTGCGGCGACAAACAACATACGTATTTGCTCGATGAACAACG
gatae_Sf_021N05_Contig3b     CGGCTCAAGTGCGGCGACAAACAACGCACGTATTTGCTCGAGGAACAACG
                             ***********************  ********* ****** gatae_Sp_040I09              ATACACGGGTAGAAGAACAAACCAACTTCAAAATCAAATTTAGCGACAAA
gatae_Sf_021N05_Contig3b     ATACACTGGTAGAGGACCAAACTAACTTCAATATCAAATTTAGCGACAAA
                             **** **  *** *** ***************** gatae_Sp_040I09              AGAGAAAAAA-GGAGGTGGGAGAATGAGTGTATGTAAGGATGGTGCCAGT
gatae_Sf_021N05_Contig3b     AAAGAAAAAAAGGAGGTGGGAGAAGAAGTGTATGTAAGGATGGTGCCAGT
                             * ****** ********    ********************* gatae_Sp_040I09              AGAATGACTACAAAGCTTACCGCCAATCTACGGGTACACGTGCCAAGATT
gatae_Sf_021N05_Contig3b     ATGATGACTACAAAGCTTACCGCCAATGTACGGGTACACGTGCCAAGATT
                             *  ********************** ******************** gatae_Sp_040I09              TATGTTTGAGTTCGTGTGCTTTAGCCCGCCGGTTTGCCGCTAAAACAAAA
gatae_Sf_021N05_Contig3b     TATGTTTGAGTTCGTGTGCTTTAGCCCGCCGGTATGCCGCTAAAACAAAA
                             ******************************* ************** gatae_Sp_040I09              ACGGATTTTGCTCAAAGTTCCAGAATATTGAATATTGATTTAGTGATGTA
gatae_Sf_021N05_Contig3b     ACCGATTTTACTCAAAGTTCCTGAATATTGAATATTGATTTAGTGATGTA
                              ** ******* ************************** gatae_Sp_040I09              AAACTAATTTATCAAAGTAATGGCTTCTGCGAGT
gatae_Sf_021N05_Contig3b     CAACCGATTAATCAAAATAATGGCTTCTGCGAGT
                              *   *  ** *************** gatae_Sp_040I09              GGTGAATACAAATCT    (SEQ ID NO:27)
gatae_Sf_021N05_Contig3b     GGTGAATACAAATCC    (SEQ ID NO:28)
                             **************
```

Figure 7

Gatae_Active_2:

```
gatae_Sp_040I09            ATGCATGGTTGTATAACGTTTGAACATGTGAAAGTGGAGCGTCCATTAAG
gatae_Sf_021N05_Contig4c   ATGCATGGTTGTATAAAGTTTGAACATGTGAAAGCAGAGCGTCCATTAAG
                           **************  **********  ************** gatae_Sp_040I09            TTGGCATAACTCTGCCAATCAAATCCTTGACTTGGCTTTTCCTCTTATCT
gatae_Sf_021N05_Contig4c   TTGGCATAACTCTGCCAATCAAATCCTTGACTTGGCTTTTCCTCTTATCT
                           ************************************************** gatae_Sp_040I09            CGAATAAATGAATGAGGAGAATGCGACAGATGCGTGTTGGTTAGATAAGA
gatae_Sf_021N05_Contig4c   CGAATAAATGAATGAGGAGAATGCGACAGATGCGTGTTGGTTAGATAAGA
                           ************************************************** gatae_Sp_040I09            GAAGCGGAAGATGACTTCAGAAGATGTCCCATGCAAACCATTTTCATCTG
gatae_Sf_021N05_Contig4c   GAAGCGGAAGATGACTTCAAAAGATGTCCCATGCAAACCATTTTCATCTG
                           *****************  *************************** gatae_Sp_040I09            CTCCCATCCCC-TTTGTCTTCTCCTGGCTCCTTAAAGGGACATGAGATAT
gatae_Sf_021N05_Contig4c   CTCTCATCCCCCTTTGTCTTCTCCTGGCTCCTTAAAGGGACATAAGATTT
                           * ***  ************************* * * * gatae_Sp_040I09            TTTAAAGGGAC   (SEQ ID NO:29)
gatae_Sf_021N05_Contig4c   TTTAAAGGGAC   (SEQ ID NO:30)
                           ***********
```

Gatae_Flanking_1:

```
gatae_Sp_040I09            CGCAAGTCAAATATTTGCACCGGTTTTAAGAACCCGCCTCTTCTTCAGCT
gatae_Sf_021N05_Contig1a   GGGGGAATACATATTTGCACCGGATTTTAGAACCCGCCTCTTCTTCTGCT
                           *          ********** * **************** * gatae_Sp_040I09            AGTA-----ACATTTACCATTGTCTTAATGACTCGCTAACCATTTGAGGT
gatae_Sf_021N05_Contig1a   AATATGGGAACATTTACCATTGTCTTAATGACTCGCTAACCATTTGAGGT
                           *      *************************************** gatae_Sp_040I09            ACTCGAGTA---AATCCAGTTCTTAGGAATTCAATCAAAAATGATTGTAT
gatae_Sf_021N05_Contig1a   ACTCGAGTATTAACTCCAGTTCTTAGGAATTCCATCAGAAATATATGTCT
                           *********   * ****************     * * gatae_Sp_040I09            GCGCTGGGAGGGCGGGTAATATAACCT-CAACAATTCTTTTTTTTTCTTC
gatae_Sf_021N05_Contig1a   GTGCATGGCCTGTGTGGTGGGAGGAGTGGTAATATAACCTCAGCAAAG
                           *         *  *   **  *       ***         * gatae_Sp_040I09            TACTTTTTTTGAGGGTGTGTGGATAATAAAGTCATTACGGACAGTTCTTA
gatae_Sf_021N05_Contig1a   TTTGTTTTTTTGTTTTCTGTGGATAATAAAGTCATGACGGACAGTTCTTA
                           *  ******  * **** *************** ******** gatae_Sp_040I09            ATATACTCATTTATGTACCTAATGACAATCATTAACAGTTCAGTTATTAA
gatae_Sf_021N05_Contig1a   ATATACTCATGTATGTACTTAATGACAATCATTAACAGTT---------
                           ******** *** ******************* gatae_Sp_040I09            ATGTAATGTTCAGTAAGTTGAATATTTAATCAATATCCGTTTATCCAGGG
gatae_Sf_021N05_Contig1a   ---TAATGTTCA-AAGTTGAATATTTAACCAATATCCGTTTATCCAGGG
                              ******  ***********  ****************** gatae_Sp_040I09            TTCTAAACTCACTTTCTGCACATGGATTTCAATTTCAAGGTCGATATACT
gatae_Sf_021N05_Contig1a   TTCTACATT-ATTTTCTGCACAGGGATTTGAATTTCAAGGTCGATATACT
                           *****  *   ********** * ***** ********************
```

Figure 7a

```
gatae_Sp_040I09            TACGCCCCCTAAAATTCTAAATTTGGGGGTTCCGGAGTCAGTGAAATCCG
gatae_Sf_021N05_Contig1a   TACGCCCCCTAAAATTCTAAATTTGGGGGTTTTGGAGT---TGAAATCCG
                           ************************** *   ****** gatae_Sp_040I09            AGGGCCTGATATTTCACAATTATTAGTGTGAAATAGGTTTTTAGTAATTT
gatae_Sf_021N05_Contig1a   AGAGCCTGATTTTTCACTA------TGTGCAATAGGTTTTTTAATTTTT
                            *** **** *      ** ******    * gatae_Sp_040I09            TTTGATGAAAATGCGGTCGTTATGGCAAAA-CAATATTGCATATCATTAA
gatae_Sf_021N05_Contig1a   TTTAATGAAAATGCGGTCGTTATTGCAAAAACAAAATAGCCTATCATTAA
                           * *************** ** *   ******** gatae_Sp_040I09            CC------------------------ATTCAAGTGAATATCCGATAAAT
gatae_Sf_021N05_Contig1a   CCTTGCTACAGTCCAATGTCTAAAACCATTCAAGTGAATATCCGATAAAG
                                                   ****************** gatae_Sp_040I09            TCTGAAAGATT-----TGTAACTATGGGGAAAATTACAATTTAACAAGA
gatae_Sf_021N05_Contig1a   TCTGAAGGATTAATTTTGTAACTATGGGG-AAAATGAAAATTTATCGAAA
                           ****      ********* *** * ****** * * * gatae_Sp_040I09            GAATAT--CTTAGCGGAATATTTATCGAAATTGTTCAAGTTTTCTTGAAA
gatae_Sf_021N05_Contig1a   GAATATACCTAAGCGGAATATTTATCAAAATTTGTCAAGTTTTCTTGAAA
                           ****   ************ *  ************** gatae_Sp_040I09            GTTAGGAAAGGGCGTTTCGGTTAATTTTTTAAATAATATTTTTCTTTTTC
gatae_Sf_021N05_Contig1a   GTTAGGAAATGGCGTTTCGGTTAATTTTTCTAATAATGTTTTTCTTGTTC
                           ******* *************** ** **** * gatae_Sp_040I09            ATAAAAGATAAAATTTAAACTACACTCTTTTTAATAGCGTTTGTAATGTT
gatae_Sf_021N05_Contig1a   ATAAAAATGAAAATTAAACTACATTATTTTGAATAGCGTTTGTAATTTG
                           ****  ********   **** * *************  * gatae_Sp_040I09            TGTAATTCAAATGTGTACAGTCAGAACGCGTTCAAACTTTAAGGATATTC
gatae_Sf_021N05_Contig1a   TGTAATTCAAATGTGTACATTCAGAATGCGTTCAAACTTTAAGGACATTC
                           ***************** ** ************* ** gatae_Sp_040I09            CCTGGGGGCCCGTGTACGCATATCTGACCACTGTTGGTGTCTAACTAAAA
gatae_Sf_021N05_Contig1a   CCTGGGGTCCCATGTACGCCTATCTGACCTCGGTTGGTGTCTAACTAAA-
                           ***** * ***** ******* * ***************** gatae_Sp_040I09            TAAAGGAAGTTAATACAGTGGCACGGGACTCGAATCCGAGTCAGTAGTGC
gatae_Sf_021N05_Contig1a   TAAAGGAAGTAAGTACAGTGGCA-GGGACTCGAATCCGGGTCAGTAGTGC
                           ********** * ******** ********** ******** gatae_Sp_040I09            GGAGGCCTTTCCAACTGACCATACAACCTCTAAAATCCACCAGGT-----
gatae_Sf_021N05_Contig1a   GGAGACCTATCCAACTGACCACACAACCTCTAAAATCCGACAAATGTGGT
                           ** * ********** ************   * gatae_Sp_040I09            -ATATTCCGTGTGATTTAACTACTTCTGTATTGAGCCGATTCAACAAGAT
gatae_Sf_021N05_Contig1a   AATATTCCGTGTGATTTAACGACTTCTGTTTTGAGCCGATTCTACAGAAG
                            ***************** ***** * ********* * * gatae_Sp_040I09            GGACAGAGAATCCGGTAGGACACTCCGAAAGCTGCATCGAATCGATACAG
gatae_Sf_021N05_Contig1a   GGACAGAGAATCCGGTAGGTCACTCCGAAATCTGCATGGAATCGATACAG
                           ***************** ****** ** ********** gatae_Sp_040I09            CGCCTCAAACTTTGAAAAGC    (SEQ ID NO:31)
gatae_Sf_021N05_Contig1a   CGTCTCAAACTTTAAAAAGC    (SEQ ID NO:32)
                           ** ********** ******
```

Figure 7b

Gatae Flanking 2:

```
gatae_Sp_040I09           ATGATTGTTTGAACAAGATTCTAAACAAGCCATGAACTACATATACAAGG
gatae_Sf_021N05_Contig2a  -TGATTGGTTTGACAAGATTCTAAACAAGCCATGAACTACATATACAAGG
                           ****  **************************************** gatae_Sp_040I09           ATATATTTACATGAGGAAGTTTATTTCACTTAAACGTGTTCTTACTACCT
gatae_Sf_021N05_Contig2a  ATATATTTACATGCGGAAGTTTATTTCACTTAAACGTGTTCTTACTACCT
                          *********** ********************************** gatae_Sp_040I09           TGATGAGTTAAAGGGTACAGCACTGGTTTATATGCTTGGCTTGGTTCCTC
gatae_Sf_021N05_Contig2a  TGATGATTTAAAGGATACAGCACTGGTTTCTATGCTTGACTTGGTTCCTC
                          **** *** ********** **** ********* gatae_Sp_040I09           GGATGGAAGCGCATTCTA--AATGCTGAATCTGTCATTCTTAATGTTGTA
gatae_Sf_021N05_Contig2a  GGGTCGAAGAGCATTCTATAAATGCTGAATCTGCCATTCTTAATTTTATA
                          ** * ** ****  ********* ******  ** gatae_Sp_040I09           TCATACAATCAAACAACTAGAAGAGATTA---------------------
gatae_Sf_021N05_Contig2a  TCGTACAATTAAACAACTAGAAGAGATTATTATGAAATGTTATATAATGG
                           ** ***************** gatae_Sp_040I09           ---------ATT-TTTTGCGCCTTCAGAAGTTCAGCTCACTTAAATACCA
gatae_Sf_021N05_Contig2a  TAGAGGAGGATTATTCTGTGCCTTCAGAAGTTCAGCTCACTTAA-TACCA
                                   *   ********************** *** gatae_Sp_040I09           AATATCAGAATAACTGAAAAAGTCAATTCAAATGTCCGT-TGGGAAGACG
gatae_Sf_021N05_Contig2a  ACTATTAGAATCACTGAAAAAGTCGACTGAAATGTCCATGCGGGAAGACG
                          * * * ********** * * ******** *  ********* gatae_Sp_040I09           GT-CAGACTGCCGTTGTGAGTGGCCGCATAATCA-----------AGTA
gatae_Sf_021N05_Contig2a  GTGCAGACTGCCGTTGTTAGTGGTCGCATTATCAGCAGTTAAAGAAAGTA
                           ********** * *               ** gatae_Sp_040I09           CGATTACAATGATCTTGTTAATACGACAAATCTAGATAGCAGATTCATTC
gatae_Sf_021N05_Contig2a  CGATTACAATGATCTTGTTAGTACGAAAAATCTAGATAGCAGATGGATTC
                          ****************** * ************** * **** gatae_Sp_040I09           GAGTGATAACGAAGATTATTATAATAATGATAATCATAATAAGAATAATG
gatae_Sf_021N05_Contig2a  GGGTGATAATGATAATTATCATATTAATGATAAGAAGAAGGAAAAGAAGA
                          * *****   *** * ********* * *  * gatae_Sp_040I09           ATAAGAGGAAAAGGAAGAAGAAGAAGAAGTAGAAGAAAACGAAGAAAGAA
gatae_Sf_021N05_Contig2a  AAAAGAAAAAGAAGAAGAGGAAGGAGAAGAAGAAGAAGTAGAAGAAGAAG
                          * **   * ***   * ***  ****   * gatae_Sp_040I09           AAGAAAAGAAGAGGAAGAAGAGGAAGAAGA       (SEQ ID NO:33)
gatae_Sf_021N05_Contig2a  AAGG--AGAAGAAGAAGAAGAAGAAGAAGA       (SEQ ID NO:34)
                          ****  ****** ******** ********
```

Gatae Flanking 3:

```
gatae_Sp_040I09           AAAAATTGATTAGATCCTCATTTAAAGTAAATGCATCTTTCATAATTCTT
gatae_Sf_021N05_Contig3a  AAAAATTGATTCGATCCTCATTAAAAGTAAATATATCTTTCATTATTCTT
                          ********* ******    *****  ****** gatae_Sp_040I09           TCAAAGTTTTGGAATTTAAACATTATGATATTATAATTGATTTACGGCCG
gatae_Sf_021N05_Contig3a  TCAAAGTTTTGGAATATAAACATTATGTTATTAT---TGGTTTACTGTCA
                          *************** *********** ******   ** ***** * *
```

Figure 7c

```
gatae_Sp_040I09           AATCGTAAA--AAATATGAATTAAGCATTAATGATTCCTCGATTTATATT
gatae_Sf_021N05_Contig3a  AATCGTTAACAAAATATAAATTAAGCGCTATTTAGACCTCGATTCATATT
                          ****   **** ****   *   ****** *** gatae_Sp_040I09           TAATTCCATCTGTCAAAT-TTAAGGTACAAACTGAATCTTTATTATAATT
gatae_Sf_021N05_Contig3a  TTATTCTCTCTGTCAAACCTTAAGTTTGAAATTGAATCTTTAGTATAAAT
                          * **  ***** *** *  * ****** *** * gatae_Sp_040I09           TGTAATTGTATATTTTCTTATAGCGAAATGGTATTAAACCAATCGATCGG
gatae_Sf_021N05_Contig3a  T-----TGTAT---TTCTTGCAGCGAAATGGTAT--AACCAATCGACCGG
                          *     ***   * ********   ****** * gatae_Sp_040I09           TCTCCTATACCACCGCTGTGCCGTGCCATAACATAACCAGGTCGGAACCT
gatae_Sf_021N05_Contig3a  TCTC--ATACCACCGCTGTACTGTGCCATAACATAACCAGATCGGAATCT
                          **  *********** * **************** * gatae_Sp_040I09           GAATTGTACA---TGTTTGTCGGACGA---TGAACATTA-----------
gatae_Sf_021N05_Contig3a  AGATTGTATAGAATGTATGTGGGACGGCCGTGAACATGAGTGGTGGTTAT
                           ******* *   * *  **    **** gatae_Sp_040I09           ----------ACAT------------------------------------
gatae_Sf_021N05_Contig3a  TTTTGTTTTACGTGACTGCTAAGAAAGCATAAATGCTTGTTGGTAACCAA
                                    ** * gatae_Sp_040I09           ---------TTTTTTTCGCCTCTTTAAT--TCAGGTGAAGGGTTATTATT
gatae_Sf_021N05_Contig3a  CCAGCAACATTTTCTTTGCCTTTTCAATCATCAGGTGAAATGTAATTATT
                                   ** *    *  ****   ****** gatae_Sp_040I09           TTATTATAAAATCCACATATTTTCCAGACAAACAGGACATAGAATAGCAT
gatae_Sf_021N05_Contig3a  TT-TTATAAAATCCATATATTTTCAAGACAAACAGGACATAATATAATAT
                           ******** **** ************     ** gatae_Sp_040I09           GTATCTGCAAGATTATTAGTCACCGCTTGAAGAACA
gatae_Sf_021N05_Contig3a  GTATCCGCAAAATTATTAGTCACCGCCTGGAGAA-G
                          ***  ***********  **** gatae_Sp_040I09           TCGGGAAGAGAATG    (SEQ ID NO:35)
gatae_Sf_021N05_Contig3a  TTACTAAGAAAATG    (SEQ ID NO:36)
                          *    **** ****

Gatae Flanking 4:

gatae_Sp_040I09           TAACATTGTAACAATTCCAATATATTAATACTTGCAGTATTTCCAAGTTT
gatae_Sf_021N05_Contig3c  CAAC--------AATTCCAATCAACTAATACTTGCAGTATTTTCAAGCTT
                           *        ******  *  *************** gatae_Sp_040I09           TTCCCATTTATCATTTTAATTTCGTTCATCATAATTATTTTAAAGTGAAA
gatae_Sf_021N05_Contig3c  TTCCCATTTACACTTTTAAGT--GTTCAT-------ATTTTAAAGTCAAA
                          ********  **** *   ****       ****** * gatae_Sp_040I09           TATAGAAGATAACAAGAGAGTAGAGCTAAATTCTTTTCATTAAAT----T
gatae_Sf_021N05_Contig3c  TATAGAAG-------AGAGTAGAGCTAAATTCCTAACATTAAATAATTT
                          ******       **************  *  ********    * gatae_Sp_040I09           AATGCGATAAAAACACCCAGACAGCCTATCGTATATATGCACTATTAGCG
gatae_Sf_021N05_Contig3c  AATGCGATAAAAACACACAGACAGCCTATCGTCACTAT---CAATTATCA
                          **************** *************** ***    * **** *
```

Figure 7d

```
gatae_Sp_040I09          TCTTATCACAATTACTACAAGTGACATTAAAATTAGAGTACGATTTATCG
gatae_Sf_021N05_Contig3c TCTTATCAAAATAACTACAAATGACATTAAAATCAGAGTACGATTTAGCG
                         ****** * ***** ********* ******** gatae_Sp_040I09          GTATGATAAATTGTGATAAAATAGATGATACGTCAACATTTTATCTTGTT
gatae_Sf_021N05_Contig3c GTATGATAAATTGTGATAAAATAGATTATTCGTCAACATTTTATCTTGTT
                         ************************  ******************* gatae_Sp_040I09          AACCGTTTACTGCTAATTTAATGGCATTGATGTTGATAAGGTGACAGTGC
gatae_Sf_021N05_Contig3c AACCGTTTACTGCTAATTTAATGGCAATAGTGTTGATAAGGTGAAAA---
                         ************************** *  ************* * gatae_Sp_040I09          AGTATAGAGCCCACTGACTGACTGGTCTAGTAAGACTCCACA-ATAGAGC
gatae_Sf_021N05_Contig3c ---GTAGACCC----GACTGACGGGTCTAGAGAGACTTCACATACTGACA
                            ** *    ***** **    * **  * ** gatae_Sp_040I09          TACACATATTT-CAAAGTTTATTACCTTTTTAATTTCTTTCTCTGTTACG
gatae_Sf_021N05_Contig3c TAGACATATTTTCAAAGTTTATTTCCTTTTTAATTCCTTTCTCTGCTACA
                          **** ******* ******* ***** * gatae_Sp_040I09          GATTTGACCATTTTTATTCTGATCCACTTTCCTTTCAACCTGGAATAAAG
gatae_Sf_021N05_Contig3c GATTTGACCATTTT-ATTTTGATCCACTT-CCCTTCAACCAGGAATCAAA
                         ************ * ********  ***** * gatae_Sp_040I09          TGGTATAATTCGTGT-AGGTCGATATTTTATTGAACAATGAAAGGGATTT
gatae_Sf_021N05_Contig3c TGGTAAAATTTGTGTTAGGTTGATA-----TTAAGCAATGAAAGGGATTT
                         ***          * ************** gatae_Sp_040I09          AAGTATCG-AAATTCGAAAT-TTAATAATTT--------CTTTTCAGAAC
gatae_Sf_021N05_Contig3c AAGTATCTCAAATTCGAAATGTTAAAAATTTACTCTTTTCTTTTCAGAAC
                         *****  *******           ******** gatae_Sp_040I09          CCTACCATATTCAGATGAAGATTATTTTACTTAATATCCATTTAAGTTTT
gatae_Sf_021N05_Contig3c CCTACCATATTCAGATGAAGATTATTGTACTCAATATCCATTT-------
                         ************************  ******** gatae_Sp_040I09          TAACTAAATGTGTAAATTCGGCATCCATTCACGACCGGTAATAGCAATAA
gatae_Sf_021N05_Contig3c TAACTAA-TGTGTAGTTTCGGCATTCATTCACGACTGGTGA---------
                         *****  * **** ******* * * gatae_Sp_040I09          ATATAGGCCTATATCATATTTAAAAAGTAAAATTTAATATATCAG----G
gatae_Sf_021N05_Contig3c ATAAAGGCATATAGCATTTTGGAAAGTAAAACTGAATGTATCAGTTAGG
                         *   * *  ******* * * ****    * gatae_Sp_040I09          GCCAAGAACAAGAGAACAGATTATTTCTCCATCAAAATTTCGTTCGTAAA
gatae_Sf_021N05_Contig3c GCCAAGAACATGTGAACATGCT-CATCGGAAAGGAAATAT-ACCCGTATT
                         **********  * ***** *   ***    * **** *  * * gatae_Sp_040I09          AGTACTGCACGGATTCACCTCACCAAAAAGCTCGATAGTTCTCTGTCACA
gatae_Sf_021N05_Contig3c --CACGTCTCTGATAGATTTTACT------TTCATTAATTTATCTACATA
                           **   *  * **   *  *           **  * * * gatae_Sp_040I09          ACTCATGATATTGTTTGATAATAATTTTGTCTCTTC
gatae_Sf_021N05_Contig3c A-TCAGGAATCAGGATAGTA-TGATGTAAAAGGATA
                         * *     *  **  *    **   * gatae_Sp_040I09          ATCGTCTGAAAGG   (SEQ ID NO:37)
gatae_Sf_021N05_Contig3c ATTGAATTAGGAA   (SEQ ID NO:38)
                         **  *  *  *
```

Figure 7e

Gatae Flanking 5:

```
gatae_Sp_040I09            ATTGACTCAGAATCTACAGGAACGTGGATCTCTGTCTTCTCCTGGTTGTC
gatae_Sf_021N05_Contig4b   ATTGACTCAGAAACCACAGGAACGTGGATATCTGTCTTGCCCTGGTTGTC
                           *********** * ************* *** ******** gatae_Sp_040I09            TCCACTTCCAGGACTCCCCTTTTCTCCTTCAGTTCCCTCTTCGAATTCTC
gatae_Sf_021N05_Contig4b   TTCACTTCCAGGACTCCCCTTTTCTTCTTCACTTCCCTCTTCGAATTCTC
                           * ******************** * **************** gatae_Sp_040I09            TATCAAAGCTGCTTTCAGCGTCGTCGTCGCTGTGATCGTCTCTTGCTACT
gatae_Sf_021N05_Contig4b   TTTCAG--------------CGTCGTCGCTGTGGTCGTCTCTTGCTACT
                           * *                ********* ************ gatae_Sp_040I09            CTCCCGCTGTCAATGATCACCTCACGATGACTCTCAATGTCCACTTCGCT
gatae_Sf_021N05_Contig4b   CTCCCGCTGTCAATGATCACCTCACGATGACTTTCAATGTCCACTTCGCT
                           ****************************** *************** gatae_Sp_040I09            TGGACGTCGTTCAATCACCTTGTTGTTGTTATT---ATTGTTGTTGTTAT
gatae_Sf_021N05_Contig4b   TGAACGTCGTTCAATCACCTTGTTGTTGTTGTTGTTATTGTTGTTATTAT
                            **********************    ******* ** gatae_Sp_040I09            CTGAATGTGAGTTTTTGGTTGGTGTTGATTGATAAGGTGAGGCAGGCTTG
gatae_Sf_021N05_Contig4b   CTGAATGTGAATTTTTGGTAGGTGTTGAGTGATAAGGTGAGACAGGCTTG
                           ******** **** **** ******** ***** gatae_Sp_040I09            ACGGGTCCAGCTTCGACCGAGCTTGCCCAAACTCTAGCACTCTGTTCCAT
gatae_Sf_021N05_Contig4b   ACGGGTCCAGCTTCGACCGAGCTTGCCCAAACTCTAGCACTCTGTTCCAT
                           ************************************************** gatae_Sp_040I09            GAATTGAACAATTCGACGAAAAACGGGACATCTATATCAAAATCAAA-CA
gatae_Sf_021N05_Contig4b   GAATTGAGAAATTCGACGAAAAACGGGACATCTAT--CAAAATCAAAACA
                           *****  ********************** ****** gatae_Sp_040I09            GTACCAACCGCGAGTAAAAGTATGGAAAGTAGAAAATGAATGGAAAAAAT
gatae_Sf_021N05_Contig4b   GTACCAACCGCGAGTAAAAGTATAGAAAGTAGAAAATGAATGGAAAAAAG
                           ********************* *********************** gatae_Sp_040I09            AGTCCAAAGGAGTTGTTACTCTCGACTATCAAGATTAACGAGGGTAAAAC
gatae_Sf_021N05_Contig4b   AGTCCAAAGGAATTGTTACTCTCGACTATCAAGATTAACGAGGGTAAAAC
                           ********* ************************************ gatae_Sp_040I09            AAGGATAGCGGTTGCGATGTTTCACAAACAAACTCGACGTCCTATCTCTG
gatae_Sf_021N05_Contig4b   ATGGATAGCGGTTGCGATGTTTCACAAACAAACTCGACGTCCTATCTCTG
                           * *********************************************** gatae_Sp_040I09            CTGCAGGATAAAACACAACTGATATGATAACGAATCCCAAGCTCACTACC
gatae_Sf_021N05_Contig4b   CTGTAGGATAAAACACAACTGATATGATAACGAGTCACAAGCTCACTACC
                           * *************************  ************ gatae_Sp_040I09            AGTTTGCACCCGTAGAGCTTACCGTAGAAGCAGGAGCTTTGCTGGACTGA
gatae_Sf_021N05_Contig4b   AGTTTGCACCCGTAGAGCTTACCGTGGAAGCAGGAGCTTTGCTGGACTGA
                           *********************** ********************** gatae_Sp_040I09            TAGTGGTTCAAAGTAAACTTTGC-CAGGCTGTTAGAGTTGCCTTTACGAG
gatae_Sf_021N05_Contig4b   TAGTGGTTCAAAGTAAACTTTGTTCAGGCTGTTAGAGTTGCCTTTACGAG
                           ******************** ************************* gatae_Sp_040I09            CTCTGATTGGTGTGCTTACTCAAGCGAATTAGCGACGTGTGTTGAAGTAG
gatae_Sf_021N05_Contig4b   CTCTGATTGGTGTGCTTACTCAAGCGAATTAGCGACGTGTGTTGAAGTAG
                           **************************************************
```

Figure 7f

```
gatae_Sp_040I09           CTGGCAGTGACGTATTGGCAGGAGAGTGGGGTGCAGTGGTGGGCTTTAGG
gatae_Sf_021N05_Contig4b  CTGGCGGTGACGTATCGG---GAGAGTAGGGTGCAACGATGGATTATAGG
                          *** *****     **** ****  *  ***  * **** gatae_Sp_040I09           GGTGGGGTAGTAATAGTGCTGGTGGTAACAGAGAGAGAGAGAGAGAGAGA
gatae_Sf_021N05_Contig4b  GGTGGGGTAGTAGTAGCGCTGGTTGTAACAGAGACA--------------
                          ********** * **** ******** * gatae_Sp_040I09           GAGAGAGAGAGGGGGGGGTGAAGAAAGGGTTGTTTTAGAAGATTTCTAAA
gatae_Sf_021N05_Contig4b  CAGAGAGAGGGGGTGGGGTGAAGAAAGGGAT----------TTTTTACA
                          ****** * *************** *           *  * gatae_Sp_040I09           AGATTTCAAACTCA-GGGATATAGTGCCTGTAAAAAGTGCACTCAATGGA
gatae_Sf_021N05_Contig4b  AGATTTCAAACTCAAGGGATATAGTGCCTGTAAAAAGTGCACTCAATGGA
                          ************ ********************************* gatae_Sp_040I09           CTGCTTCAAAAATACAGTCCAAAA------TGAAGTAG--GCC-------
gatae_Sf_021N05_Contig4b  CGGCTTCAAAAACACTGTCCAAAAATATTTTAAATAGTAGCAGGGGTAA
                          * ********  ********      *   *  ** gatae_Sp_040I09           TAGTGTACGAAGTAAATAGTTTGGTATTGGTATACAAATTATTAATCTTT
gatae_Sf_021N05_Contig4b  TAGTGTACGTTGTAAATAGTTTGGTATTGGTCTTGAAGTTATTAATCTTT
                          *******  ***************** *   ********** gatae_Sp_040I09           TGG--------TAGGTATCATGATCATTGACCAAAAGCACTATTTTCGTC
gatae_Sf_021N05_Contig4b  TGGAGTTTTGGTGGGTATCATGATCATTGACTAAAAGCAATATTTTCGTC
                          ***         * *************** ** ******** gatae_Sp_040I09           ATCCAGATACCCACAATTTGAAGTATCACTTGATAACTCCATCAATATCT
gatae_Sf_021N05_Contig4b  ATCCAGATACCCACAATTTGAAATATCACTTGATAAATCAACTAATAGCT
                          ******************** *********   ** gatae_Sp_040I09           GATTGGAATATGATTGGCACAGTCATTCGTAAGAAAGTTAATAATGTGTA
gatae_Sf_021N05_Contig4b  GATTGGAATATGATTGGCACAGTGATTCGTAAGAAAATTAATAATGTGCA
                          ********************* ******** ********* * gatae_Sp_040I09           TTAGCTGAAGATTTCACATAGAATGGAAA---------------------
gatae_Sf_021N05_Contig4b  TTAGCAAAAGATTCCACACAGAATGGGAATTGGGAAGAGGGAAAGGCATT
                          ***  **  *** gatae_Sp_040I09           ----------------GAGGGGAAAGATTGTCACTGGTATATGGTAGAGT
gatae_Sf_021N05_Contig4b  GGGCGTGGCTCTAGTAGAGGGGTAAGATTATAACTGGTATGTGGTAGAGT
                                          ****** * ***** * ******* ******* gatae_Sp_040I09           CCAGTGAGGGGTGTGTTGGATGGATGTGGACGAATGCTCATTTGCTACTG
gatae_Sf_021N05_Contig4b  CCAGTGAGGGGTGTGTTGGGTGGGTGTGGGTGAATGGTCACTTGCTACTG
                          ***************** * ***  * * ******** gatae_Sp_040I09           ACGTCCTTC---TGACCATGGTTCAAATAAACCAAGAAGTCAATAAACGC
gatae_Sf_021N05_Contig4b  ATGTCCTTCAGCTGACCGTGGTTCAAATAAACCAAGAAGTCAATAAACGC
                          * *****   * ****************************** gatae_Sp_040I09           GACCAAACTAGTCATCTGTAATAACAACGTATAGAGAACAAAGAAATACT
gatae_Sf_021N05_Contig4b  GAACAAACTAGTCATCTGTAATAACAACGATAGAGAACAA---------
                           ********************** ******* gatae_Sp_040I09           GTCACGGTCACATGTTAAAAGGAGAAACGTTCATTAATATGTGATTGTTT
gatae_Sf_021N05_Contig4b  -----GATCACATGTTAAAAGGAGAAACGTTAATTAAAATGTGATTGTTT
                               * ********************** ***** ************
```

Figure 7g

```
gatae_Sp_040I09              GGATGATTGATGTACATAATGCTATTTACAATATAATAAC-----TCTTG
gatae_Sf_021N05_Contig4b     GGATGATTGATGTACATAG-GCTATTAGTATTACAACAACGTTATTCTGG
                             ****************  **     *       *** * gatae_Sp_040I09              GACATTGTACATACAACAACTGCACATCTTACTCAGCTAAATTAGTCATT
gatae_Sf_021N05_Contig4b     GACATTGTACATACA---ACTGCACATCTTTCTCAGCTAAAGTATTCATT
                             *************   ******** ******  ***** gatae_Sp_040I09              AACACATTAA-CAAATTAATAATCATAATTTCCCCCGATTCTGTTAAAAT
gatae_Sf_021N05_Contig4b     AACACATTAATCAAATTAATCATAAT--TTTCCCCTGATTCTGTTAAAAT
                             ******** *****    *** ************ gatae_Sp_040I09              TTGACTTTCCGTCATTCTTACTCAGTGTTACCTATAACCTACTGGTAAAT
gatae_Sf_021N05_Contig4b     TTTACTTTTCGTCATTCTGACCCTGTGTTACCTATATCCTACTGGAATGA
                              * ****   * ********** ****** * gatae_Sp_040I09              GTCAACTGTACGATTATACCTGTTTAAAGTTTCGTGTTATGGACTAAGCC
gatae_Sf_021N05_Contig4b     GTCCA-TATACAATTATACCTGTTTACAGTTTCATGTTATGGACTAAGCC
                             ***  *  *  ********* ** ************** gatae_Sp_040I09              TG---AGCGTTGTAATTTTTTTTCTTCAGGTTTCTGGAAGAGATGAGGAA
gatae_Sf_021N05_Contig4b     TGCTGAGCGTTGTGAATCATTT---TCAGGTTTGTGGGAGAGGTGAGGGA
                                ****** *   *    **** * *** *** * gatae_Sp_040I09              TACGAATGCCAGAATTAGCCATGATACTTGATAATACAACGTAGTTTTGA
gatae_Sf_021N05_Contig4b     TAAGAATGCCAGAGTAAGCCATGATACTT---------------------
                              ******** * ************* gatae_Sp_040I09              TTACCTCATAAAGTGAATTAACATTATAACTTAGCCGATGAACGTTTGCT
gatae_Sf_021N05_Contig4b     ------CATAAAAT--ATTAACATTATAACTTAGCCGATGAACGCTTGCC
                                   ****** *  ************************** ** gatae_Sp_040I09              ACCACATAACACACGGAACAGATTAAATATCCCTGGAAAAGACACTGCAT
gatae_Sf_021N05_Contig4b     ATCAAATAATTCACTAAACAGATTAATAATCCTAGGAATAGACACTGCAT
                             *   * ********   ** ********* gatae_Sp_040I09              CAAGACGGAAAATAATTTG-------CCGGGTTTCATTTTCCATCGTCAT
gatae_Sf_021N05_Contig4b     CAAG-TAATAAATAATTTGGACATTGCCGGGTTTCGTTTTCCATCGTCAT
                             **       *****         ***** ************ gatae_Sp_040I09              TTTTTTTTT-CTGGGAAACTCTTCAGGAACAAATAGATA-----------
gatae_Sf_021N05_Contig4b     TTTTTTTTTTCTGGGAAACTCTTCAGGAACAAATAGAGACGATAGTGCAC
                             *******  *************************** * gatae_Sp_040I09              -----TTTTACTCCAA----GACAGTTTTCTGTTCAGTTGGACTAACGTA
gatae_Sf_021N05_Contig4b     AATATTTCTACTCCAATTAAGACAATTTTCTGTTCAGTTGGACTAACGTA
                                   ****     ************************* gatae_Sp_040I09              AGTGCGCGCTTAATATAGATCCTTGGTTATAACAT-TGGTGCTTCT----
gatae_Sf_021N05_Contig4b     AGTGCGCGCTTAATGTAGATCCTTGGTTATAACACGTAGTAGGTCCATGG
                             ************ *****************   * gatae_Sp_040I09              --------------TCTGTTCTGTGGTAAAAACTGAACTGAGAACCAACA
gatae_Sf_021N05_Contig4b     TTATAACATGGGTGCTTGTTATGTGGTAAAAACCGAACTGAGAAACAAAA
                                           * ** ******  ********  *  * gatae_Sp_040I09              TTAAAGGATGTGGGTGACAGGAGAGATTTCAAAAAGGTGCGAATGATTTA
gatae_Sf_021N05_Contig4b     TTAAAGGATGTGGGTGACAAGAGACAATTCGAAAAGGTGCGAATGATTGA
                             *******************  ****   ** ****************** *
```

Figure 7h

```
gatae_Sp_040I09         TGAGGTTGATGTAGCTTCCGTGGAAGATGTAGAGATCATGTGACGAAAAG
gatae_Sf_021N05_Contig4b TGAGGTTGATGTAGCTTCCGTGGAAGATGTAGAGATCATGTGACGAAAAG
                        ************************************************** gatae_Sp_040I09         ATGGATTGTGAGTCAAACAATGATGTCAAACAGCCCGGTGCTCATGGGGT
gatae_Sf_021N05_Contig4b ATGGATTGTGAGTCAAACAATGATGTCAAACAGCTTGGTGTTCATGGGAT
                        ********************************  **** * gatae_Sp_040I09         GACACGACATGACTGGTGCGCTGAATGTGCTG---GATGTGCTGCTCAAA
gatae_Sf_021N05_Contig4b GACACGACATGACTGGTGCGCTGGATATGCTGCTGGATGCGCTGTTCAAA
                        *********************  ***     *** gatae_Sp_040I09         GACCACACGAAGATATATTGAGAGGAAACATAAGACATGTAAGATAAGGA
gatae_Sf_021N05_Contig4b GACCTCACGAAGATAT--TGAAAGGAAAC--GATGCTTGTAAGCTAAGGA
                        ** ******   * *******     *  **** **** gatae_Sp_040I09         TGTTGGTGATGACGATAATGATGATGACGACGATCGTGTTCCTCGGATCG
gatae_Sf_021N05_Contig4b TGTTGGTGATGA---------TGATGACGACGATCGTGTTCCTCGAATCA
                        **********         ******************** * gatae_Sp_040I09         AAT--AAAGAGAGACTTTCAAGAGTTGTGAAGCGC-ATTGATCTTTTGAT
gatae_Sf_021N05_Contig4b AATTAAAAGAGAGACTTTCAAGAGTTGTGAAGTGTTATTGATCTTTTGGT
                        *   ************************ *  ************ * gatae_Sp_040I09         ATATTTTTTAAAAAGATATTGAAATTATTAAAAAGCAAAAAAGAGAAAG
gatae_Sf_021N05_Contig4b AGATTTTTTAAAAAGATATTGAAATTATTAAGAAGCAAAAAAGAGAG-G
                        * ***** **************** ************ * gatae_Sp_040I09         ACAAAGAGAGGGGGGAAATAAGAGATGATGAGGACAAT----GTGATTGC
gatae_Sf_021N05_Contig4b AAAGAGAGAGAAAA-AAATGAGAAGTGATGAGGACAATAAGTGTGATTGC
                        *  ****    * *********** ***** gatae_Sp_040I09         GATGGTTGTTGATTGTCACGATAGAAGATCCAAAGATTGGTGAAAAAAAT
gatae_Sf_021N05_Contig4b GAGGGTTGTTGATGGTCACGATAGAAGATCCAAAGATTGGTGAAAGTAAT
                         ****** *************************** * gatae_Sp_040I09         TAAC-TTTGAATAGTCGTGATATCATTATTATCTTAGTGATACACGCAAT
gatae_Sf_021N05_Contig4b TAAAATTTGAATAGTCGTGATATCATTATTATCTT-GTGATACACGCAAT
                        *  ************************** ************ gatae_Sp_040I09         GAAAATAATAACAAAAGCAAAGTTACACCAGAGTTGAACAT-----GTGA
gatae_Sf_021N05_Contig4b GAGAATGATAACAAAGTAAAGTTAAACCAAAGATGAACATAACTTGTGA
                         * ******  *** *   ****     ** gatae_Sp_040I09         CGTCGTAGAATGATTGAGAATCAAAGAAAGGACAAAGTAACCATAAATCT
gatae_Sf_021N05_Contig4b CGTCATAGAATGATTGAGAAACAAAGAAAGGACAACGTAACCGTAAATCT
                        ** *********** ********** ** ***** gatae_Sp_040I09         TTTACTCTTTACAGAATCAATCTTGACAAAGAAATTGGGATTTTGTTTCT
gatae_Sf_021N05_Contig4b TTTACACTTTACAGAATCAAACTTG---AAGAAATAGGGATTCCGTTTAC
                        *** **********     ****   ** gatae_Sp_040I09         CTCGTTATCAAGGCTAAATATTTTGCTTACGTTTATTTGTCAAATTAAAC
gatae_Sf_021N05_Contig4b CTCGTATTCAAGGCTAAATATTTTGCTTACTTCTATTTGTCAAATTAAAC
                        *** **********************  * **************** gatae_Sp_040I09         CCC-----------GTGGGTACACCAACT-AGAGAACAGACATATTG-
gatae_Sf_021N05_Contig4b CCCAGGGGTACTGGTAGTGGGTACACCAACTTAGATAACATACATAATGT
                        ***             ***  **********  *** ***  *****  **
```

Figure 7i

```
gatae_Sp_040I09            ------------------------------AATCTCGTCATGGAGGTG
gatae_Sf_021N05_Contig4b   GACGATATTAATGTAGCATTAATACTTCCATAAATCTTGTCATGGAGGTG
                                                         ***  ********** gatae_Sp_040I09            AAAGTTATTGGTCCATGTTCAGACCTTTACGCTTGACATTGATGGTGTCT
gatae_Sf_021N05_Contig4b   AAAGTTATTGGTCCATGTTTAGACCTTTACGCTTGACATTGATGGTGTTT
                           ***************** *************************** * gatae_Sp_040I09            TCAAAGGTGAATCCTACCAGTAAAAGTGATTGCGACGCTTTACAAGGAAC
gatae_Sf_021N05_Contig4b   TCAAAGGTGAATCCTACCAGTAAAAATGATTGCAACGCTTTACAAGGAAC
                           ***********************  **  ******* gatae_Sp_040I09            AACCCAAGCGGGCCTATTACGATACCCCCTCCCTCCCCTTCACATCAGAA
gatae_Sf_021N05_Contig4b   CTCCCAAGCGGACCTATTACGATACCCCCTCCCTCCCCTTCACATCAGAA
                             ****** ************************************ gatae_Sp_040I09            TAAAACTTGTAGCAATATAACGAAGTGCACCACTGCAAATTTGGAGATCG
gatae_Sf_021N05_Contig4b   TAAAACTTGTAGCAATACAACGACGAGCATCACTGCACATTTGGAGATCG
                           *************** *** * * ** ********** gatae_Sp_040I09            GGATGCATCTCT   (SEQ ID NO:39)
gatae_Sf_021N05_Contig4b   GTATGCATCCCT   (SEQ ID NO:40)
                           * ******* **

Gatae Flanking 6:

gatae_Sp_040I09            CTGGTTAGGAGGAACCAAACAATGAAGGGACAAACGACATTTCAAGAGAT
gatae_Sf_021N05_Contig4d   CTGGTTAGGAGGATACAAAGATTGAAGGGGCAAACTAGAT----------
                           ***********  ** * *****     * gatae_Sp_040I09            TGGTCTACAGACCTCAAGTGAAGAATCTCCCTGGAAC--GAGGTCTATGC
gatae_Sf_021N05_Contig4d   -------------------AAGTATTTCCCTGGAAAAGGGGGCCTATGC
                                              *  ********    *  **** gatae_Sp_040I09            TAACAACAATTAGGAAGCGACACCACAATCACACCAGAATTAAATTCGTA
gatae_Sf_021N05_Contig4d   TAACGACATTTAGGAAGTGACAACA-----------GAATTAAATTCGTA
                           ** * ******   *           **** **** gatae_Sp_040I09            CCTTTTGTTAGCCCTCTTTTTATTCCAATTCTCATATAGAGA-GTCTCTA
gatae_Sf_021N05_Contig4d   CCCTTCGATAATCCTATT---ATTACAATTCTCATATAGAGACGTCTCTA
                             *    *     * *************** ***** gatae_Sp_040I09            GAAGCTTAGTGTAATGATAGAGTGCATGGTCGGTTAGAAGTATTTTAGTA
gatae_Sf_021N05_Contig4d   GAAGATTTGTGTTAAGATAGAGTG----GTGGGCTAGAAGTGTTATAGTA
                           **   **** * ******      ***  ***** gatae_Sp_040I09            ATCTACATAGGCCTTTACTTTACATCAGT------------------AT
gatae_Sf_021N05_Contig4d   ATCTACATAGGCCTATACTTTACACCAATCTTACTTCTCCTTGGTTTTAT
                           ************ ****  *                    ** gatae_Sp_040I09            CTATTGAAGTCATACATTAATGGCTCTTTGAAACGTTTTCAGGTA-----
gatae_Sf_021N05_Contig4d   CTAATGAAGTCATACATTGATGGCTCTTTGAAATGTTTTCAGGTACAGTA
                           * ********** ********** ******* *** gatae_Sp_040I09            ATGGAAGTAGAGTTTGCCTTTTCATTGTTTAAA-CCAAATGTTATCATGT
gatae_Sf_021N05_Contig4d   ATGGAAGTAGAGTTTGCCTTTTCATTGATAAAAACCAAATGTTATCATGA
                           ************************** *  *** ***************
```

Figure 7j

```
gatae_Sp_040I09          TGATTGTCATATAAGCATATACACGAGACAAGACATTAAATATGAGACTA
gatae_Sf_021N05_Contig4d TGATTGTCATACTAGCCTATACACGAAACACGAAATTAAATATGAGACTT
                         *********  *  ******  *   *********** gatae_Sp_040I09          TCATCATGATGTGTCTCTTCATGAATGGAATCATTATTATGTTGTCATCA
gatae_Sf_021N05_Contig4d TCGTCATGATGTATATCTTCGTGAATGTA---ATTATTATGTTGTCATCA
                          ******* *  *** **    *************** gatae_Sp_040I09          ACATTTAATATTGACTTCGATAGAGATACAATGCTGGCAATTGG------
gatae_Sf_021N05_Contig4d GAACTTACGATCGAGTTCGAGAGAAATATAAAGCTGGCAATTAGAAGTGC
                         *  *      * *  *   ******* * gatae_Sp_040I09          TCACACCATACATTTGCAGCGTTGCCGTCATTTAC--GTAGTAGGTCCAT
gatae_Sf_021N05_Contig4d TCACACCATACATTTGCAGCGTTGCCGTCATTTAAAGGTACTATGTCCCA
                         ********************************  *  ** gatae_Sp_040I09          GTTTAAACTAACTTGAATTACTTCGATGAACCTCAAATTGGAGTCCTTTT
gatae_Sf_021N05_Contig4d CTTTAAACTAACTTGAATTACTTCGATGAACCTCAAATTGGCATCCTTTT
                          **************************************  **** gatae_Sp_040I09          ATTTTTAAAAGGTGAAACAAACAACTCTTATTCTATATACCTGGTACATG
gatae_Sf_021N05_Contig4d AT----AAAAGATGAAACAAACAACTCTTATGCTATATACATGGTACATG
                             * *************** **** ****** gatae_Sp_040I09          ATTGTAGCAAGGTGTGGGCAAGGGAGATGAAGAGAGCCTGTGTTTACTCG
gatae_Sf_021N05_Contig4d ATTGTAGCAAGGTGTGGGAAAGGAAGATGATGAGAGCCTGTGTTTACTCG
                         ****************** * **  *  ************** gatae_Sp_040I09          AGACAGAGGGAGTCATGGCTGACCTGTCGGGTTCTGATCTGGCTTGGCTC
gatae_Sf_021N05_Contig4d AGACAGAGGGATTCATGGCTGACCTGTCGGGTTATGATCTGGCTTGGCTC
                         *********  **************** ************** gatae_Sp_040I09          ATGATGATGGCTGTATTGAGCGTTCATCTATCATGTTGGTTTGTTGTTCA
gatae_Sf_021N05_Contig4d ATCATGATGGCTGCATTGAGCGTTCATCTATCATATTGGTTTTTTGTTCA
                          ****** **************** ***** **** gatae_Sp_040I09          TTGTGTGATGACATCGCTACCACATACAGACTCACTCCCTTGACACTGTA
gatae_Sf_021N05_Contig4d TTGTGTGATGACATCGCTACCACATACATACTCACTCCCTTGACACTGCA
                         **************************  ****************** * gatae_Sp_040I09          ACATGACATGGGGGCAACAAATTACCCCTCCGTGGCTTCTACCA------
gatae_Sf_021N05_Contig4d ACATGACATGGGGGCAACAAATTACCCCTCCGTGGCTTCTACCATGAACA
                         ******************************************** gatae_Sp_040I09          ACAGTGGTTGGTATAGGATTGGAAGACAACCCAGGTGCGATGAGTACTG-
gatae_Sf_021N05_Contig4d ACAGTGGTTGGTATAGGATTGGAAGACAATCCAGGTGCGATGAGTGCTGG
                         ***************************  ********* * gatae_Sp_040I09          ------CTCTATAGGGTCATCATGGTCATCATG-------GTATCTTGTT
gatae_Sf_021N05_Contig4d TAACTACTCTACAGGGTCATCATGGTCATCATGATTCATGGTATCTTGTT
                               *** *****************       ******* gatae_Sp_040I09          GCCATAGTGATGAAATGAAAGTCTACGTATGGACCCATAAT-----ATGA
gatae_Sf_021N05_Contig4d GCCATGGTGATGGAATGAAAGTCTACGTATGGACCCATAATCAGGCATGA
                         *** ** ************************     ** gatae_Sp_040I09          TACTGGTTCAA-TAATCGGAATTGTA--
gatae_Sf_021N05_Contig4d AACTGGTTCAAATAATTGCAATTGTAAA
                         ********** **** * *******
```

Figure 7k gatae_Sp_040I09            CTTTTAAACAAG  (SEQ ID NO:41)
gatae_Sf_021N05_Contig4d   CTTGTAAACAAG  (SEQ ID NO:42)
                           * ******

Figure 71

Otx Alignments

<u>Otx Active 1:</u>

```
otx_Sp_006F13            TTCTCTTTGAACGCATCTTCTGGACATCATGTCTACTGATTTCAATGAGA
otx_Sf_048I10_Contig1a   TTCTCTTT-AATGCATCTTCTGGACATCATGTCTACTGATTTCAATGAGA
                         ******  ************************************** otx_Sp_006F13            CCTTATTGTAATTAGCTCCAAGAACGAGTCATTGGGAGAATAGGAAAACA
otx_Sf_048I10_Contig1a   TCTTATTGTAATTAGCTCCGAGAACGAGTCATTGGGAGAATGGGAAAACA
                          **************** ***************** ***** otx_Sp_006F13            TACGAATTCGAAGATCAGCGGATTGAGTGTTTCAATCGCGTTAGCATCCG
otx_Sf_048I10_Contig1a   TACGAATTCGGAGATCAGCGGATTGAGTGTTTCAATCGCGTTAGCATCCG
                         ******** ************************************* otx_Sp_006F13            CTCTTTAAAAAATAGAGGAGGTATTTCGAGTCTTACCCTTCTACTGGTGG
otx_Sf_048I10_Contig1a   CTCTTTTAAAAATAGAGGCGGTATTTCGAGCCTTACCCGACTACTGGTGG
                         **** *******  ******  **  ******** otx_Sp_006F13            TCGTACTCCAACGCCATTAGGCCGATAGAGCTCGCTGAGAAGGGA-AAAA
otx_Sf_048I10_Contig1a   TCGTACTCCAACGCCACTAGGCCGATAGAGCTCGCTGAGAAGGGGGAAAA
                         ************** ***********************  ** otx_Sp_006F13            ACCATGCACCGCACAAAACACTTAGCATCATCAGTATTGGCAGATATGAG
otx_Sf_048I10_Contig1a   ACCATGAACCGCACAAAACACTTAGCATCATCAGTATTGGCAGATATGAG
                         **** ***************************************** otx_Sp_006F13            TCACGTGACCAAACACTGTGAGACCGTCTGTGATTGGCCAATAGGAACCC
otx_Sf_048I10_Contig1a   TCACGTGACCAAACACTGTGAGACCGTCTGTGATTGGTCAATAGGAACCC
                         *********************************** ********* otx_Sp_006F13            AGTGAGAATGAAAGGAAGCCGGTCAAAGAATGGCTCTTGTACTTCTCAAA
otx_Sf_048I10_Contig1a   AGTGAGAATGAAAGGAAGCCGGTCAAAGAATGGCTCTTGTACTTCTCAAA
                         ************************************************** otx_Sp_006F13            GCGTGACGTCGTCATATTCACTAAACTTATCTCTATCTCTCTCTCTCTCT
otx_Sf_048I10_Contig1a   GCGTGACGTCGTCATATTCACTAAACTTATCTCT----CTCTCTCTCTCT
                         ********************************    ********** otx_Sp_006F13            CCTCTGTTCGGGATTTTTACCGTCAATTTCTGTCAGGCGGTGGTATGTAT
otx_Sf_048I10_Contig1a   CCTCTGTTCGGGATTTTTACCGTCAATTTCTGTCAGGCGGTGGTATGTAT
                         ************************************************** otx_Sp_006F13            AAACGC  (SEQ ID NO:43)
otx_Sf_048I10_Contig1a   AAACGC  (SEQ ID NO:44)
                         ******
```

<u>Otx Active 2:</u>

```
otx_Sp_006F13            TCTTGTTCTCTCTATACCTTATACCATCTTCAAGAAGAATAGTAATCGCC
otx_Sf_048I10_Contig1d   CATTGTTCTTTCTATACCCTATACCATCTTCAAGAAGAATAGTAATCGCC
                          ****  ***** **************************** otx_Sp_006F13            CACATGCATGCATTCTTTTGTTCCTCTTTAAATTATAGTCCAGGGCCATA
otx_Sf_048I10_Contig1d   CACATGCATGCATTCTTTTGTTCCTCTTTAAATTAAGGTCCAGGGCTATA
                         ***********************************  ********* ***
```

Figure 8

```
otx_Sp_006F13           CCGTCCCATTACGGAACACCCCATCGTTAAAAACTCGACAAACAGAAGAA
otx_Sf_048I10_Contig1d  CCGTCCCATTACGGAACACCCCATCGTTAAAAACTCGACACACGGAAGAA
                        **************************************  ****** otx_Sp_006F13           AAAATCGATTTGTTCGGGGCCAAATATATAGAACGGTGGGTTTGAGGTTG
otx_Sf_048I10_Contig1d  AAAATCGATTTGTTCGGGGCCAAA----TAGAACGGTGGGTTTGAGGTTG
                        **********************    ******************** otx_Sp_006F13           GGGTCCAGGGGACAGAAGGGAAGGTATTGTGACGAGTGAGGTAAAGAATA
otx_Sf_048I10_Contig1d  GGGTCCAGGGAACAGAAGGGAAGGTATTGTGACGAGTGAAGTAAAGAATA
                        ******** ************************* ******* otx_Sp_006F13           ACTCTTAAACCAGGATGGTCGAGTACTAATCAACCAACGCCATACCGTGA
otx_Sf_048I10_Contig1d  ACTCTTAA-CCAGGATGGTCGAGTGCTAATCAACCAACGCCATACCGTGA
                        ******  ********** *********************** otx_Sp_006F13           CATAAGCCATCTCTGCACCCCTATTCACCAAATATCGATCCACATTGCCT
otx_Sf_048I10_Contig1d  CATAAGCCATCTCTGCACCCCTATTCACAAAATATCGATCCCCATTGCCT
                        ************************** ******** ***** otx_Sp_006F13           TCTTCACCACCCCTTTCACCCGCAGTGCACCATGTGGAGTCACAAAAGAT
otx_Sf_048I10_Contig1d  TCTTTACCACCCCTTTCACCCGCAATGCACCATGTGGAGTCACAAAAGAT
                        ** *************** *********************** otx_Sp_006F13           CCTTTGCAATCTCTTAAAATGAAAGTTATCTGTACCTCCCTCATGAATCT
otx_Sf_048I10_Contig1d  CCTTTGCAATCTTT--AAATGAAAGTTATCTGTACCTCCCTCATGACTCT
                        ************ *  *************************** * otx_Sp_006F13           CGTAGCTTTGTTGAAGTGTAGCTGTGTC    (SEQ ID NO:45)
otx_Sf_048I10_Contig1d  CGTAGCTTTGTTGAAGTG--------TC    (SEQ ID NO:46)
                        ******************        **

Otx Flanking 1:

otx_Sp_006F13           TTCCGCCCGTACCGCCCCAACATCACCACCACCTTCAGAACAAGATGAAC
otx_Sf_048I10_Contig1c  TTCCGCCCGTACCGCCCCAACATCACCATCACCTTCAGAACAAGATGAAC
                        **************************  ****************** otx_Sp_006F13           GCACTCGGCTCTCCGTACTCCGTCAACGGGCGATCGCTGGCGTCGCCGAA
otx_Sf_048I10_Contig1c  GCACTCGGCTCTCCCTACTCCGTCAACGGGCGTTCGCTGGCGTCGCCGAA
                        ************ ************* *************** otx_Sp_006F13           CGTTGAGCTCATGCATCCCGCTATGTCATATACAAGTAAGTCATACTCTC
otx_Sf_048I10_Contig1c  CGTTGAACTCATGCATCCCGCTACGTTATATACAAGTAAGTCATACTCTC
                        **** ***********  ************************ otx_Sp_006F13           TTAATTTGTTCCTTCTGG---------GAATTTTGTATCCCCC-------
otx_Sf_048I10_Contig1c  TTAATTAGTTCCTTCTGGCCTTTCTGGGAATTTTGTTTTGCCTGCTTTAG
                        **** *******         ******* *  ** otx_Sp_006F13           --------CTTCCCAAATATAGACTAAATGTCTACTCTTATTATAAATAT
otx_Sf_048I10_Contig1c  CTTTTATTCCTCCCAAATATAGAATGAATGTCTACTCTAATTATAAATAT
                                * ************ *  ********** ******** otx_Sp_006F13           CATAGGATTTACACGACAGTAAAGTTTACTTTTAATTTTACTACTAGTAC
otx_Sf_048I10_Contig1c  CAGAGGATGTACATG----TACA--CGACAGTCAAATTTACAG--AGTAC
                        ** ***** **** *    ** *   ** * ** *****     *****
```

Figure 8a

```
otx_Sp_006F13        GAAGAGCGCAAGCACAATTGGCATATATAGGCCTAT----CATCTTTCAA
otx_Sf_048I10_Contig1c   GAAGTACGAATGC-CGAAGAGCGTATATAGGCATAATTGGCATTATCGAA
                     **   * ** * *    *****      ***  *  ** otx_Sp_006F13        TTTCTTTT-ACAAAATTACACATCGCTT----ATGTACAAGAATCATTAT
otx_Sf_048I10_Contig1c   TTTCTTTTTACAAAATTACACATCGTTTTAATATGTAAAAGAACCATTAT
                     ****** ***********     ***  * **** otx_Sp_006F13        TT-CGACTATATGAATACTTAAAATCAGAAATATTTGAACAAGTGAACTA
otx_Sf_048I10_Contig1c   TTTCGACTGTATGA---------ATCAAAAATATTAGAACAAGTGAACTA
                      * *          *** ************ otx_Sp_006F13        GATTAAATTATTTATAAAATTATATATTCAGTAATGAAGCGATAACATTT
otx_Sf_048I10_Contig1c   GATAAAATTATTTAAAGATATATATTTTCAGTAATGGCGCGATTACATTT
                     * ******** *  *** ***** *  * **** otx_Sp_006F13        ACGTATCATGCGGGTATTGGAACCAAACAAAATGCACTGCGGTTAGTTCA
otx_Sf_048I10_Contig1c   ACGTATCTTGTAGGTATTGGAACAAAACAAAATGCACTGCGGTTAGTTCA
                     *****   ********  ************************ otx_Sp_006F13        TGTTATGGTATTTATGAATCGTTTAAGATTTCAACGAGATAATGTTTATC
otx_Sf_048I10_Contig1c   TGTGATGATATTAATGCATCGTTTAAGATTTCAACGGGATAATATTGTTC
                     * * ** * **************** **   ** otx_Sp_006F13        TAGATTAAATATCTGCATATATGAAAAAACATATATCTATATCTGCATTG
otx_Sf_048I10_Contig1c   TAGAATAAATATCTACATATTTGAAAATATATATATCTATATCTGCATTG
                     ** ***** * **    ***************** otx_Sp_006F13        AGAATTATCCTATGTGAAATAGTTGTGGAAGTGTTGGCAAGAGTGACGAT
otx_Sf_048I10_Contig1c   AGAATTATCCTATGTGAAATAGTTGTGGAAGTGTTGGTAAAAGTGACGAT
                     ***********************************  ******** otx_Sp_006F13        AAAC-TAAAGTAGTGTCAATGACAGCGGCACCTCTGTAGTGAAATAACTC
otx_Sf_048I10_Contig1c   AAAAATACAGTGGTGTCAATGACAGCGAAAGCTCTGAAGTGAAATAACCC
                     *   * *************  * *** *********  * otx_Sp_006F13        TTAGGGAGTAAGTATGTATTCATGGTATATTACTAATTAAATAATTAACG
otx_Sf_048I10_Contig1c   TTAGGGAGTGAGTTTGTATACATGGTAT--TAATAATTAAATAATTAACG
                     ******* * ***  **   ***************** otx_Sp_006F13        GTATTATTGCATTGTGTCACCCTGCTACATTGGAATAAGACCATTGATAA
otx_Sf_048I10_Contig1c   GTATCATTGCATTGTGTCATCCTACTACATTGGTATGAGACTCTTGATAA
                     ** ********** *  *******   ** ***** otx_Sp_006F13        GTTATATGACAGGTACATGGTGTTCCGTGAGGATAGTACAACGACGATAA
otx_Sf_048I10_Contig1c   GTTATGTTACAGGTGCATGGTGTTCTGTGAGGATAGTACTAAGACGATAA
                     ***** * **** ****** **********  * ******** otx_Sp_006F13        TTATAATAATTACCATTGGAAAGTTAGGAACTTTCCATTACTAATCATGT
otx_Sf_048I10_Contig1c   TTATAATGATCACCATTGGAAAGTAAGGAACTTTTCATTACTAT---TGC
                     *****  *********** ***** **** otx_Sp_006F13        CTGGACATTTTTTTAAAATTAACTAGAGTTTTTCCAAACGCAATCAGAC
otx_Sf_048I10_Contig1c   CTTGACATTTTTAC--AAATTAACTAGGCTTTTTCCCAACGTTATCAGAC
                      *****    ******* ***   ***** otx_Sp_006F13        ACGAATAATCTGTTTAAATGATTTTTAATTCAGTTCAATTTTGAATTCAA
otx_Sf_048I10_Contig1c   ACGAATACTCCGTTTAAATGATTTTCAATTCATTTCAATTTTAAATTCAA
                     ******* ** **************  ***** ********* *******
```

Figure 8b

```
otx_Sp_006F13         TGGTTCAGCATACATATTGCCATTCGTTTTTTTAAAACAATTTTTAGAGC
otx_Sf_048I10_Contig1c TGGTACAGCATATATACTTCCATTTGTTTTTT-AAAACAGTTTTTAGAGC
                      **  *** *  * ***  **  ** ******** otx_Sp_006F13         AGTTAAAAGATATTTACAGGAAAATGAGATTAATTTTAAAGCATAGTGGA
otx_Sf_048I10_Contig1c AGTTAACATATATTTACAGGAGAATGAGAGTAATTTTAAAGCATAGTGGA
                      ****** * ********** *** ***************** otx_Sp_006F13         ATCATACATGGAAGAAGGTGCACTCTCACAAATAAAAGAAAAACATTGGA
otx_Sf_048I10_Contig1c ATCATACATGGGATAAGGTGCACTCT---------AAAAAAAAATTGGA
                      *********** * ************         * *** **** otx_Sp_006F13         CAAAATATACCTATTAATAAAAATGGAGCATGCATGTA---TGTTTGATA
otx_Sf_048I10_Contig1c TAAAA-ATATCCATTAATAAAAATGGAGCATGCATGTACTATGTTTGTTG
                      **  * * *************************   **** * otx_Sp_006F13         ATATTATAACCATTATTGGGTATATACTAGCCAATTTCGGGTACATCTTA
otx_Sf_048I10_Contig1c ATATCATACCCATTATTGCGTAT----TACATCTTACCCAATATAACCAA
                      **  * ******           *  *    *  *  * otx_Sp_006F13         CCCAATATAACCAAGAAACATGCACGTACTATTTTAATCCAACTCTTTCT
otx_Sf_048I10_Contig1c CTTA-CATGTACAAAAAACGTTCCCGT-TTAGCCAAATT-ATTTTTTCT
                      *  *     *  ****  *  *      *   *  * ***** otx_Sp_006F13         ATAGTGTGTAAAAAGCCTGTGAAGCGAGGTTCCCGTGTAGGGTATATCCT
otx_Sf_048I10_Contig1c AGAGTGTGCCAAA-GCTTGTGAAGCAAAGTTCTCGTGTTGGGTACATTCT
                      * ****  *   ****  *  ** *   ** otx_Sp_006F13         GAAGGTTAACAATTGATTTTAAAATGTATCTGATAAACATATAGTCAATA
otx_Sf_048I10_Contig1c GAGGGTTAACAACATATTTTAAAATGTATCTGATAAACATATAGTCAATA
                       ****    ********************************* otx_Sp_006F13         AAATAGATGATCGTGAATTAGGGCAGTTCCCACAATTTTGTTTGTGATGA
otx_Sf_048I10_Contig1c AAATAGATGATCGTGA---AGGGCAGTTCCCACATTTTTGTTTGTGATGA
                      **************   **********  ************ otx_Sp_006F13         AGATCTACATCGGTATCTACAAGAAGCAATGCACTGCTGTGTACATATAG
otx_Sf_048I10_Contig1c AGATCTACATCGGTATCTACAAGAAGCAATGCACTGCTGTGTACATATAG
                      ************************************************** otx_Sp_006F13         CATCTTGTGTTGATTCAAATCATTAACATTAAGACGCTTAAAGTCTGTAA
otx_Sf_048I10_Contig1c CATCTTGTGTTGATTCAAATCATTAACATTAAGACGCTTAAATTCTGTAA
                      **************************************** ***** otx_Sp_006F13         GGTGTATA------GAAGGACATCTAGTTCGGCGGAGCACGCTATAAACT
otx_Sf_048I10_Contig1c GGTGTATAATTATAGAAGGACATCTCGTTCGGCAGAACGCGCTA--AACT
                      ******      *******  **   * **  ** otx_Sp_006F13         CCTCCACGAATTGCGGTAGATCTTTGGGAGATTTTAAGTGATCGAACTAC
otx_Sf_048I10_Contig1c CCTCCACGAATTGCGGTAGATCTTTGGGGGATTTTAAGTGATCGAACTAC
                      **************************  ****************** otx_Sp_006F13         TAGATTAGTGATAGAAATTATCTATGAGTTTAATCCAATGGGCGTAGTAT
otx_Sf_048I10_Contig1c TAAATTAGTGATAGATAGTATTT-TGAGTTTAATCCAAGGGGGGAAGTCG
                       ********  * *   *********** *  * * otx_Sp_006F13         CGATGAGATATTGATACTATGTT-GTCTAATTGATGTTTGTCGATGAGCA
otx_Sf_048I10_Contig1c CGGGGGAATAATGATTTTATGTTTATCCAATTGAAATTTTTCGAGGAGGA
                      **    * ***  ***  ******  ** ******   ****  *** *
```

Figure 8c

```
otx_Sp_006F13          -------------TCTTACATTTTGAAGAAACCGCTTAAAATAGCCCGAT
otx_Sf_048I10_Contig1c AGAAAGGGGAGCTTTTTACTTTTAGAAGAAACCGCTTAAA--AGCTCGAT
                                    * ** * ************** * **** otx_Sp_006F13          CTGAATATATTCTGGCAAAATACCTCACAATTATATTTATAAGAAAATGT
otx_Sf_048I10_Contig1c ATGAATAAATTCTCGCAAAATTTTTCCCAA------CTATAAGGGAATTT
                       **** * ***  *        ** * * otx_Sp_006F13          GTTAATGCTACTACATTCCAACTTGATAAGTCATATTTGTTTAATAGATA
otx_Sf_048I10_Contig1c GTTTATGCTACTCCATTCCGACTAGATAGGTCATATTTTTAAAATAGATT
                       * **** ** * *** ****** *  ******* otx_Sp_006F13          GTACAATTGCTTAAGATCAGTGGCAGACATACATATTTAAACTTAGTGTA
otx_Sf_048I10_Contig1c GTACAATTGCCCGAGATCAGTGACAGAAAAACATATTTAAACTTTTTGTA
                       ********  ***** ** * ************ ** otx_Sp_006F13          AAATTTAGTTTTTCTTTTCTTCTTATCGTCAGGAGTAGGATTTCTATGAG
otx_Sf_048I10_Contig1c AA------TGTTTTTTTTTTTTTA--------------------------
                       **       * *   *** otx_Sp_006F13          TATTTTCTTAAAATTAAAAATCTTAGAATCCATTTAAAGTCTAACGTAGA
otx_Sf_048I10_Contig1c --------------------------ATCCATTTTAAGTCTAACGTAGA
                                                 ***** ************ otx_Sp_006F13          TGGTGGTTAAAAGAGGCAACATTACAAATTATTCTAATGTTTTGTTCATC
otx_Sf_048I10_Contig1c TTCTAGTTGAAAGCGGCACCATTACAA----TTCTAATTTGTTGTTCATC
                       *  * *  * ***    ***** * ******** otx_Sp_006F13          CTTAAAATATAATTTTGTATGTTGTTAAATCATTATTGTT--------GT
otx_Sf_048I10_Contig1c CTTGAAATTTAATTATGTACCTCGTTAAATCATTGCTGTTTTATTGCCGT
                       *  * ** * ********* otx_Sp_006F13          CTTTATTCTTGCTAGTTCCTGTATGCCTGTAGCTTAGAATCTTTAATCAT
otx_Sf_048I10_Contig1c CTTTATTCTTGCTAGTTCATAATTGCCTGTAGCTTGGAATCTTTAATCAT
                       ****************** *  ********** ************ otx_Sp_006F13          A--AAAATAAGTCAAAAA-TAGATTTGGAAGAAATAAAGTATTTGAAGCT
otx_Sf_048I10_Contig1c ATAAAAACAGTTCAAAAAATAAATTTGGAAGAAATAGAATATTTGATGCT
                       *  **** * *****  ************** *  **** * otx_Sp_006F13          CTAATTTCATTTCGGAAACAATGAATATTAAATCAAGGTGTTAAATTTAT
otx_Sf_048I10_Contig1c CTCATTGCATTTTGGAAACGGTGAATATTACATTAAGGTCTTACATTT--
                        * *** **** * ********  * *** * **** otx_Sp_006F13          TTTCCTCCTATTTACATCAACCCTTAGACAAGAAATTGACGCTAATTAAA
otx_Sf_048I10_Contig1c TTCCCTTTCGTTTACATCAACCATCAGACAAGAAATTGACGCTGATTAAG
                        *        ******** * ***************** * otx_Sp_006F13          CTTACTGCCCTCTTATTATGCTTATTTGAAAT-----TTCCATAATCTCC
otx_Sf_048I10_Contig1c CTAACTGCCCTCTTATCATACTTATTTAAGACCCACCTTTCATAATCTCC
                        *********   ****          ********* otx_Sp_006F13          GTTCGTTAATTTGCTTCCGCGTTATATATTTCATAGTGGAAATAATTAAT
otx_Sf_048I10_Contig1c GTTCATTAATTTGCTTTCTCGTTAGATATTTTATGGTGGACACAATTAAT
                       ** *********  * **  *   ***** * ****** otx_Sp_006F13          CTACATATTTTACA--GTTGTTCCTCGTCTTAATTTCATTGGTTTTGCTA
otx_Sf_048I10_Contig1c CTACAGATTATACATTATTGTTCTTCGCCGCAATTGCATCGGTTTTGCGA
                       ***** *** ****  ******* ***     **** *** *******  *
```

Figure 8d

```
otx_Sp_006F13        TCTCATCTCATGGTTTTGATAGTCAAGACTTTAAATTAACTTATTAATCT
otx_Sf_048I10_Contig1c  TCTCATCCCATGGTTTTGATATTCAAGACTTTAAATTAACTGATTAATCT
                     ***** ********* ************  ******* otx_Sp_006F13        AGTTGTTAAAAATATAAGCTT------TTTTAACGAGTGATCGGATGCAG
otx_Sf_048I10_Contig1c  AGTTAT-GAAAATATAAGCTACATGTATTTTAATGAGTGATCGGATGCAG
                     ****  * **********        ** ************ otx_Sp_006F13        TCATCACAAGGCAACGTAAACATAGGTATAAATGCCAGCAAACGCTATGG
otx_Sf_048I10_Contig1c  TCACCACAACACAACATCTACATAGGTACA--TGTCAGCGAACGCTATGG
                     * *  ** *  ********* *     ****** otx_Sp_006F13        GCGAGTGAAGCAGTTTGCTAATATCTTGGTATGATTTCTTATCATTATT
otx_Sf_048I10_Contig1c  GCTAGTGAAGCAGTTTGCTAATATATTTGATATGATTCCTTATTAGTTTT
                      *****************   ** *** * * ** otx_Sp_006F13        TTTACATCAGTGAATGTGTGTCAATATAATCACTGTTTCCTTATGATAAA
otx_Sf_048I10_Contig1c  TCCCTATCAGTGAATGTGTGTCAGGATTATCACTGTTTTGTTATAATACA
                     *   ***************  ********** * **  * * otx_Sp_006F13        CGTTAATAAGATTATTATGGAACAAACGAGTTCAGTTTTAATTCTTGTAC
otx_Sf_048I10_Contig1c  CGTTAACAAGATTATTCTCGAACAAATGAGTTCAGTTTTAATTCGTGAAC
                     **** ******* * **** **************   * otx_Sp_006F13        CTTTGATTTAACTGCTATGTGATTTTTACTATAAGTACTACTACTACTAC
otx_Sf_048I10_Contig1c  CTTTAATCTAACTGCTGTGTGATTTTTACTATCATTACTACTACTACTAC
                     **  ****** *************  * ************** otx_Sp_006F13        TACTATTAGTAGTACTATACTACTACTTCTGCTACTACTACTACTACTAC
otx_Sf_048I10_Contig1c  TACTA-------------CTACTACTTCTACTACTTCTACAACTACTAC
                     ***             ******  *   ***** otx_Sp_006F13        TACTACCTCTGCTACCACTACTTCTACTACTATACTAATAGTACTATACT
otx_Sf_048I10_Contig1c  C------------------------------------------------- otx_Sp_006F13        ACTACAACTACTTCTTCTAATACATGTACTACTTATACGACAACTGTATA
otx_Sf_048I10_Contig1c  ---------------TCTAATACATGTACTACTTA----------TATA
                                    ****************          ** otx_Sp_006F13        TTACATTTGTCTGACTTATGATTTATTTTTGTTGATGGTCAATATCTAA
otx_Sf_048I10_Contig1c  TTACTATTGTCTGACTTATGATTACATTTTTGTTAATGGTCAATATCTAT
                     **  *************** * ****** ************ otx_Sp_006F13        AAAAAAGCTTCATGAAATTGTGTTATAAATTACTATAAACACAATCGCAG
otx_Sf_048I10_Contig1c  TTTTTAAAT-CATCAAATTGTTTCATAAATTACTATCATCACAATCGCAG
                      *  * *  *  ******* *  ********* *  ********** otx_Sp_006F13        TGATCTTTTTAAAGACGGCAATCAAAGCTATTACTAATTCAATCAATTTA
otx_Sf_048I10_Contig1c  TGATCTGTTTAAAGTCGGCAATCAAAGCTATTACTGATTCAATCAATTTA
                     **** *** **************** ************ otx_Sp_006F13        TATTTATTGGAATGCCACCTGGAGCTAAACTTGTTTTCTGGTACTAATGC
otx_Sf_048I10_Contig1c  TATTTATTGGAATGCCACCTAGAGCTAAACTTGTTTTCTGGCACTAATGC
                     ****************** **************** ****** otx_Sp_006F13        TAAGTCCTGGATAAGGGCCATTGTTTCCGTAAACATTCTCTCACATCATC
otx_Sf_048I10_Contig1c  TAAGTCCTGGATAAGGGCCATTGTTTCCGTAAACATTCTCTCACATTATC
                     ********************************************** ***
```

Figure 8e

```
otx_Sp_006F13           ACGAAAGAATACAGGGGCAATGGCATCAGTGCTT
otx_Sf_048I10_Contig1c  ACGAACGAATATAGGGGCAATGGCATCAGTGCTC
                        *** * ******************* otx_Sp_006F13           GGTCCTGTCT  (SEQ ID NO:47)
otx_Sf_048I10_Contig1c  GGTCCTGTCC  (SEQ ID NO:48)
                        *********

Otx Flanking 2:

otx_Sp_006F13           CCTTTGGCCGCAGTTGGAAATATCGTGGAGCATCGATCTGATAGGAGCAA
otx_Sf_048I10_Contig1e  CCTTTGGCCGCAGTTGGAAATATCATGGAACATCGATCTGATAGGAGCAA
                        **********************  ***************** otx_Sp_006F13           TTATTTTAACAACACGACTCCCACTGTAATAGAGGAGAAGAGTAGTGTCC
otx_Sf_048I10_Contig1e  ---TTTTAACAACACGACTCCCACTGTAATAGAGTAGAAGAGTAGTGTCC
                           ****************************** ************ otx_Sp_006F13           TGCAATCGAAGTCAAATAACATTTATTGTTCGTATTAAAAATGTAAATCA
otx_Sf_048I10_Contig1e  TGCAATCGAAGTCAAATAACACTTATTGTTCGTA----AAATGGAAATCA
                        ******************* ********     * **** otx_Sp_006F13           ACAACCCCCTGACAAACAAACATGCGTTCAAATTAATTCAACAAGACCGT
otx_Sf_048I10_Contig1e  ACAACCCC-TGACAAACAAACATGCGTTCACATTAATTCAATAAGACCGT
                        ****** **************** ******* ****** otx_Sp_006F13           TGATATTCGAATCTTTTTAAGTATTTGTTTTAAA-TGACTCAAGAGAATC
otx_Sf_048I10_Contig1e  TAATATTCAAATCTTTCTTAGTTTTTTTTACAAAATGACTTAAGAGAATC
                        * **** ***** * * *   * *** ******* otx_Sp_006F13           TTTATTTTAAAAGAAAATCAACGTCAGAGCTTGATAAGTTACAATAGCTG
otx_Sf_048I10_Contig1e  TTTAT----AAAAAAAATCAACGTCAGAGTTTGATAAGTTACGATAGCTG
                        ***    * ************** ******** ***** otx_Sp_006F13           GGGAAACCATTACCTTTGACGGA----AAAAAGCCATATTTACAAATAAT
otx_Sf_048I10_Contig1e  GGGAAACTCTTAAGTTTGAAGAAGAAAAAAAAGCCATGTTTACAAATAAT
                        ***** * ***** *  *      ******** ********** otx_Sp_006F13           CATGAACGATGAAGAGCAAAGTTTAGTAAAT-------------ATTAGC
otx_Sf_048I10_Contig1e  CATGAACGATAAAGAGCAAAGTTGAGTAAATCATTAAGCTTAATATTCGC
                        ******** ******** ***             * ** otx_Sp_006F13           CGAAAGATATTAGATCAGTGGGAAATTGTCATGATAATTTTTTTTAAAAT
otx_Sf_048I10_Contig1e  TGAAAGATATTAAATGAATGGGAAATTGTCATGATGAAAAATAT-GTATT
                         *********  * ***************** * *  * *    * * otx_Sp_006F13           ATTCATTCAACTTTATACATATTTTAAATAAATG
otx_Sf_048I10_Contig1e  CTACATACAACTCTATACAAATTTTCAAGAAATA
                         * * * ** *  **** otx_Sp_006F13           GAAATTAGCTTGT  (SEQ ID NO:49)
otx_Sf_048I10_Contig1e  GAAATTAGCTTGT  (SEQ ID NO:50)
                        *************
```

Figure 8f

Otx Flanking_3:

```
otx_Sp_006F13           CACTAATTATTTATAAGTTTACTA---TAAATAGAACAACTTATAAAGAA
otx_Sf_048I10_Contig2a  ---TACTTATTTATAGGTTTACTAATGTGAATGGAACAAATTATAAATCA
                            ***** *****  * * ** ***** * otx_Sp_006F13           AACTATTTTGATTGTTTACA-ATTTTGTTAAAGAGAAA--AAAATGCGTT
otx_Sf_048I10_Contig2a  AATTATTTTGTACGTTTACATGTTTCAATGCGCTTGTTCCGAGATGCCTC
                         ***  *** *   *              * **** * otx_Sp_006F13           TGTAACGAGATGCGGAGATACA--TTGTTCGCATCAGTTCGATGGTGTTT
otx_Sf_048I10_Contig2a  TGTTATATCCATTGTACACACCATTCAATCTCATTAGT-CAATGGTGTAT
                        *** *      *  * **   *    * *** * ******* * otx_Sp_006F13           TTATAGTTCGTATCTT----TAATATTGGACCTGGTAATTCCTTAATTCG
otx_Sf_048I10_Contig2a  TTCTAGTTCGTTTCTTAAAATAACATTGGACCTGGCAATTCCTTAATTCT
                         ****     * ********* *********** otx_Sp_006F13           AAGATGGTTGAAAGA------TATACATGTATCCCTTTCACTGTC-TTAT
otx_Sf_048I10_Contig2a  AAGATGATTGAAATACTAACATGTGCATGTATTCCGTTCACTGTCATTGT
                        **** **** *      *  *****  *******  * otx_Sp_006F13           CA-TTGCGTTTAATAATTAATAAAGTCCAACAATTATGGACATAATTCA-
otx_Sf_048I10_Contig2a  GAATTGTGATTCATAAACAAGGAACTCCAACGATTATGGACAGATTTCAT
                         * *** *       ** ******** * **** otx_Sp_006F13           ----CATAACTATATTTAAAAG-GTGTCTGAACCACGATTTTAACGGAGC
otx_Sf_048I10_Contig2a  TATTCATAATATTATATACAAGAGTATCTGTGCCACGATTTTAATAAAGC
                            ***  * *    ********   * otx_Sp_006F13           CAGGTTACACTATATACAAATAATCGAAACGAGTGAGATTAGTTTAACCG
otx_Sf_048I10_Contig2a  CAGGTTACAATATACA-AAACAATCAAAACGAGTGAGATGAGTTTAACCC
                        ******* *  * *  ******** ****** otx_Sp_006F13           CTCTAATCGTTATAAAATCGACACGTTATATCGAATGCACGCGTCAAGAT
otx_Sf_048I10_Contig2a  CTCT--TCGTTAAAAAATCGAAATGTTTTATTGAATGCACGTGTCAAGAT
                        **  ** ****** * * * ******* ***** otx_Sp_006F13           TAGAGAACTTTAATCTCATGATGGCGATTATGAGCTTTCTAATCTGATCT
otx_Sf_048I10_Contig2a  TAGAGAATTTTAATCTCATGATGGCGATTATGAGCTTTCTAATCTGATCC
                        ***** *************************************** otx_Sp_006F13           CATTCCATGTCCTAAGTCGGATTAACATTGGTTTGATCTGCCTGATCTGT
otx_Sf_048I10_Contig2a  CATTCTGTTTTCTAAGTCGGATTAACATTGGTTTGATCTGCCTGATCTGT
                        *****  * * ************************************** otx_Sp_006F13           CATCAGCTCCAAGTAACGGAGGTTTGTATTTAGAACCAGCTCCTTTCTAT
otx_Sf_048I10_Contig2a  CATCAGCTCCAAGTAACGGAGGCTTGTGTTTAGAACCAGCTCCTTCTCAT
                        ********************  ************** * ** otx_Sp_006F13           CCCTGCTTAACTCAATGAATGTAGATTATTGAAAGTAATAGTACTACTGT
otx_Sf_048I10_Contig2a  CTCTGCTTAATTCAATGCATGTAGATTATTGAAAGTATTAGTA---CTGT
                        * ****** ** ***************    ** otx_Sp_006F13           TCATTCGTTTTGAATCACTAACAAAAGACAAACACGCTTGTACAAGTCAT
otx_Sf_048I10_Contig2a  TCATTCGTTTTGAATCACCAA-AAAAGACGAACACGCTTGTACAATTCAT
                        ****************  ***** *********** ** otx_Sp_006F13           GTAGGCTTGATAATGATATTAAATACAAAATAAATAGAGTGACTATACAT
otx_Sf_048I10_Contig2a  GTAGGCTTGATACTGATATTGAGTACAAAATAAACAGAGTGACTA--CAT
                        ************ ******* * *********** **********  ***
```

Figure 8g

```
otx_Sp_006F13              TAACTGAAAGTTCAATGACTGCATAAAATACGCTGCTTATGAAACATAAC
otx_Sf_048I10_Contig2a     TAAACGAAAGTTCAACG----------------CTTGTATAACATAAT
                           *  ******* *                 ***  *  ******* otx_Sp_006F13              TTGTCGTTATTATATAAAAAAAAAGATTTGATAGCATGAATCCCTTGAA
otx_Sf_048I10_Contig2a     ATTACGTTGCT-TATGAAACAAACCTTTTTCTTATCAT-----------
                             *  ****  * * * *       *   * otx_Sp_006F13              GTTGATCAAAAAAAGGCTTGATAGCATGAATCCCTTGAAGTTGAAGGTTC
otx_Sf_048I10_Contig2a     ------TAAAAAAAGGTTTGATAGAATGAATCCCTTGAAG------GTTC
                                 ******* *** *********        ** otx_Sp_006F13              TACTGTTTTCAAGAAAAACAGTCTT-TGATCACGCTATTTGCTCTCTTTG
otx_Sf_048I10_Contig2a     TATTGTTTCCAAGAGAAACAAAAATGTGATTATGCTCTGTGCTCTCTTTG
                            * * ***       * **** * *  ******* otx_Sp_006F13              GTTATATAC--GAATATAGTCCAGATATATATTTTGGAATCCCTGCAAGA
otx_Sf_048I10_Contig2a     GTTATATACACGTATATATTCCAGATTTCTATTTTGGAATCCCTGCAAGA
                           *********   * *** **** *  ******************** otx_Sp_006F13              TTGTGTAAGTTTTTGA----------------------------------
otx_Sf_048I10_Contig2a     TTGAGTAAGTTCTGGAGGGATTTTCGAAAGAAGATGGGATATGATTAAAT
                           * ******  * ** otx_Sp_006F13              -TTTTTGTCCTGATGACACAGTAATAGTGCCGACTCTTCTAATGTTTTGT
otx_Sf_048I10_Contig2a     ATTTTTTTCCTGATGGAACAATAATAGTGCCGACTCTTCTTATGTTT-GT
                            *** ****  * **************** ** otx_Sp_006F13              ATCCGGTGACGCCATCACGCGGTCTTTTCCTGGAACATTGAACATCGTGT
otx_Sf_048I10_Contig2a     ATCCGGTGACGCCATCACGTGGCCTTTTAATGAAAAATTGAACATCGTTA
                           *****************    **    * *********** otx_Sp_006F13              TTTACTAATAAACAAACGCCGGATCCAGGAATCAATT-CTTCTGAAATAG
otx_Sf_048I10_Contig2a     TTTATTAATAGACAAACGTTGAATCCAGGAATCAATTTCTTCTGAAATT-
                           ** * *****  *  ************ ******** otx_Sp_006F13              TAATTATAAATTTCGAACTT-CCTATTGTCATTATGATAAATTTACACAA
otx_Sf_048I10_Contig2a     TAACTATAGATTTCGAACTTTCCTATTATCATAATCATAAATTCGCACAA
                           *  ******* **    *****  *** otx_Sp_006F13              AAACCAAACAGGGGATAGATAGTTTA-----TCGAGAAGGGGATTGATTG
otx_Sf_048I10_Contig2a     AATCCAAACGGGGGATAGATAGTTTAATTCATTGGGAAGGGAATTCATTG
                            ** **************      *  **** *  **** otx_Sp_006F13              ATATCCGTCCCTACTATTAATATCAAGAATGCGAGATGGATGATATCTTT
otx_Sf_048I10_Contig2a     ATATCCGACCCTACTGTTGATATCAAGAATGCGGGATGGATGATATCTTT
                           ***** ***  ************ ************** otx_Sp_006F13              CCAGACGACACCCTTCTTGACATCCCCCCTCTAAGGAGGATTCGGGTGTCA
otx_Sf_048I10_Contig2a     ACAGACGACACCCTTCTTGACATCCCC-TCTAAGGAGGATTCGGGTGTCA
                            ************************  ****************** otx_Sp_006F13              TCTCACTTCAGATGAGGGCGTTCCCACTGGGAGAGGTAGCCAGATCTGAC
otx_Sf_048I10_Contig2a     TCTCACTTCAGATGAGGACGTTCCCACTGGGAGGGGTAGCCAGATCTGAG
                           *************** *********** ************ otx_Sp_006F13              ACAGAATGATGAAGTGTGTAGCCCCT-CCTGGTATCGAGATACCGCACGT
otx_Sf_048I10_Contig2a     ACAGA-TGGTGCAGTGTTAAGCCCCTTCCTGGTATGGAAATACCGCACAG
                           *****  ** ** ****  *******  ******* ** ********
```

Figure 8h

```
otx_Sp_006F13            CATCGGCCAGGATGCGACTCGGCCGTGCAGCCAGGTTTCGATGTCGACAC
otx_Sf_048I10_Contig2a   CGTCGCCCAGGATGCGACTAGGCAGTGCACCCGGGTTTCGATGTCGACAC
                         * * ********* * ***  ***************** otx_Sp_006F13            GCACCGTGCATGATGAAAGCGCGGGAAGCGACACGTCCTCGCAGACGGTA
otx_Sf_048I10_Contig2a   TCACCGTG----ATGAAAGCGCGGGAAGCGACACGTCCTCGCAGACGGTA
                          *****    ************************************ otx_Sp_006F13            ACGGCCCTCGAGTTGAGAGGGGATTTCAAGGAGGAGGAGTGGATATGCAA
otx_Sf_048I10_Contig2a   ACGGCCCTCGAGTTGAGAGGGGATTTCAAGGAGGAGGAGTGGATATGCAA
                         ************************************************** otx_Sp_006F13            GAGCCCCCAGGGAGCATGATAGAACGGGAGATAACTCACACAGTTGACGC
otx_Sf_048I10_Contig2a   GAGCCCCCAGGGAGCATGATAGAACGGGAGATAACTCACACAGTTGACGC
                         ************************************************** otx_Sp_006F13            AAGAACAAGATACCTGGTAAACGGTGTCATCTGCGATTTCACTTCT-GTG
otx_Sf_048I10_Contig2a   AAGAACAAGATACTTGGTAAACGGTGTCATCTGCGATTTCACTTTTTGTG
                         *********** **************************** * *** otx_Sp_006F13            ATCCTTGAGGAGATGGGTCGACATGTAGATGGACACGAAGAGATCTCTCC
otx_Sf_048I10_Contig2a   ATCCTTGAGGAGATGGGTCGACATGTAGATCGACACGGAGAGCGCTCTCC
                         **************************** ** ** * ****** otx_Sp_006F13            TTGCTCGACCTCTAGCCAAAGTGCGACTTGTTCAAAGATAATTTATGTAA
otx_Sf_048I10_Contig2a   TTGCTCGACCTCTAGCCAAAGTGCGACTTGTTCAAAGATAATTTATGTAA
                         ************************************************** otx_Sp_006F13            AACGGAATAATGCAAATTGTGTGATTACTTAACTGACAAATA-AAATGGG
otx_Sf_048I10_Contig2a   TAAGGAATTATGCAAATTGTCTGATTACTGTACTGACAATTAGAAAAGAG
                          * *** *******  ****  ****  *** * * otx_Sp_006F13            CAGATATCCATGACAAATGTTGACATTGGAGT---------TAATACAAA
otx_Sf_048I10_Contig2a   AAGATATCCATGAAAAATGTTGACATTGGAGTAAGGCTACACAATACAAA
                          ********** **************         ***** otx_Sp_006F13            TACT-AATTTAATGCTCAGTTCACATGATAATTTGCTCCTTTCGAAACAT
otx_Sf_048I10_Contig2a   TATTTAACTAAATGCCCAGTTCACATAATATTTTTCGCCTATCGAAACAT
                         ** * ** * *** ****** * *** * * ****** otx_Sp_006F13            GTCTTGTTTTTGTTGACTGTAATTAGACAAT-AATCAACTGATGAAAAAA
otx_Sf_048I10_Contig2a   GTCTTGTTTTTCTTGACTGTAATTAGACAATTAGTCATCTGAGGAAAAAA
                         ********* **************** * *  ***** otx_Sp_006F13            AAAATT-CAAATAAGTGATTAAGAACACTGAATTT---ATACCTAATAAT
otx_Sf_048I10_Contig2a   ATGCTTTCAAATGAGATATTAAGAACACTGAATTTCATACACCTAACAAT
                         *   *   ****************    * **** * otx_Sp_006F13            ACAGGAAAAATAT---------------TTTATTTTATGGATTATTACA
otx_Sf_048I10_Contig2a   AAAAAAAAATTATCTAACCTTTAACACAATTCATTTTATGGATTATTACA
                         * *  ** *                 *************** otx_Sp_006F13            CTCGTTGTTTGTGTATACGAAGAAGTCTCTCTTTTAGATTT---------
otx_Sf_048I10_Contig2a   CTCGTCGTTTGTCACTACGAAGAAGCCTGTCTTTTAGATTTACTTCCAGA
                         *** **    *****  ************ otx_Sp_006F13            ---CCTTAGTTCCAAAGCAAAGGTAAGGCGTATTATTTGTTAGTGTTTAG
otx_Sf_048I10_Contig2a   GTTCCTTAATCCTAAAACAAAGGCAAGGCTTATTTTCTTTTAGAGTTTAG
                            ***** * *** ****** ***** **** **  * **** ******
```

Figure 8i

```
otx_Sp_006F13           CTTCTCAAGATCATACTTCGGAATTGACGATGTGTCAAAACCAAGAGAAA
otx_Sf_048I10_Contig2a  CTTCTAAAGATCAAACTTCGGAATCGACAATTTGTCAAAACCAAGAGAAA
                        *** *** ****** *   *************** otx_Sp_006F13           GAAATTACTGAACATTATCAACAATTACATTAATGTCTAATAATCTATCT
otx_Sf_048I10_Contig2a  GAAATTACTGAACATTCCCAACACGTACATTATTGTCTAATAATCTATCT
                        **************    *    ***** ************* otx_Sp_006F13           TACTATAAATATGCTTTACAAATAGTTGTTGTTTCTCTTTGAATAACAAA
otx_Sf_048I10_Contig2a  TACTATAATTATGCTTTTAAAATAGTTGTTGTTTCTCT-------ACATA
                        ******  ***  **************        * * otx_Sp_006F13           CACACAAAAACCCTTTTTGGGACATAAGATATCAATTAATCAATCAATTG
otx_Sf_048I10_Contig2a  CACACAAGGCCCCTATTTTGGTCATAAGATAT------------------
                        *****   *  ******** otx_Sp_006F13           ATCATTTCAAATTTATTTCAACAAAGCAATTGCAAAAATATAAAAGACAT
otx_Sf_048I10_Contig2a  -------------------------------------------------- otx_Sp_006F13           TCATAGAACTAAACATTGTCACATAAAAGAATAGAATACAATGTACATAC
otx_Sf_048I10_Contig2a  -------------------------------------------------- otx_Sp_006F13           ATTAGTACAACAATATAAAAGCTGCTTGGCAGGTATCAGCCAGAGTTGAG
otx_Sf_048I10_Contig2a  ---------------------------------------------GTTGA-
                                                                     ***** otx_Sp_006F13           AAAGGAGTTATGAGTGGCCGACCTAAATATGTATAATTGAAAGATAAATA
otx_Sf_048I10_Contig2a  -------------------------------------------------- otx_Sp_006F13           TAAGTGCCAGATTACAGGGGGGATACGACACCAGAGTCGACCAGAAAGCT
otx_Sf_048I10_Contig2a  ----------------------------------AGTTGACCAGAAAGCC
                                                          * ******** otx_Sp_006F13           TTTCTTTACCTTAATTTCTTTTCAATTATAGAGACAAAT-AATCAAAAGT
otx_Sf_048I10_Contig2a  TTTGGTTATCTAAATTTCTTTTCAGTTATGGAGACAAATGAAACAAAAGT
                        *  *   *******    ****   ****** otx_Sp_006F13           GTGCTATCGATATTTCAGAGGATTTAAATGTCTCAGAGTGTGAAAACCTT
otx_Sf_048I10_Contig2a  GTGCCATCGATATTTCGGAGGAATTCAATGTCTAAAAGTATGGAAACCTT
                        ** *******  *   ****    * * ******* otx_Sp_006F13           GTGATATTTATAGCTTTATGATGATAGGAAATCAATTATCGTCTAATTTA
otx_Sf_048I10_Contig2a  GTGATTCTTATAGCTTTATGATAATAGGAAATCAATTATCGTCTAATTTA
                        ***  *********** ************************* otx_Sp_006F13           TTTATCATTATTTTGATGAAGATCTTTGGCACAAAATTGAT---GTGTTC
otx_Sf_048I10_Contig2a  TTTATAATT----TGACGAAGATCCTTGGCACACAATTAATAATGTGTTC
                        *** *    * *** ****     ****** otx_Sp_006F13           TC--------CTTTCTCTTCCGACTAATTTAGTAAACCGTCTTGAAGTT
otx_Sf_048I10_Contig2a  GCGTTTTTATACTTTCTCATCAAACTAATTTAATGAACCGTCTTGAATAT
                        *       *****  ********* * ************  * otx_Sp_006F13           TTAAAAGCTTTTGAAATCCAAGATT  (SEQ ID NO:51)
otx_Sf_048I10_Contig2a  TTAAAGGAATT-GTGATTCAAGATT  (SEQ ID NO:52)
                        ***** *  **  ** * *******
```

Figure 8j

Wnt8 Alignments

Wnt8 Active_1:

```
wnt8_Sp_041A08           GACTCACAAACTGTATCTCATACACGAGTGAAAACTGAAAACAAAGAATA
wnt8_Sf_012H20_Contig1b  GACTCACAAACTGTATCTCATACACGAGTGAACACTGAAAACAAAGAATA
                         ******************************  ************** wnt8_Sp_041A08           CTTGACACTGGATA-AATTTTGTTTTT-ACATTTTCTGCGTTCAAATGTA
wnt8_Sf_012H20_Contig1b  CTTGACGCTGAATATAATTTTGTTTTTTACAATTTATACTTTCAAATGTA
                         **** * * ******** * *** * * ********* wnt8_Sp_041A08           TTTTCCTTAAAATTCACATGAACATACCTGGCAAGTTTCAACAAATTGAT
wnt8_Sf_012H20_Contig1b  TTTTCCTTAAAATCCACATGAACATACTTGGCAAGTTCCAACAAATTAAT
                         *********** ********* ***** ***** wnt8_Sp_041A08           TAGAAAAATAAAAAAGTGAAAATTGTTAACAATAACAATTCACTCCGAAT
wnt8_Sf_012H20_Contig1b  TAAAAAAATTAGGAAGTGAAAATTGTTGACAATAACAATTCACTCTAAAT
                          **** *    ********** *************  * wnt8_Sp_041A08           -ACCAATTGGATATTACAAAAAAGTCAATAATATATTAATTACAATATATAC
wnt8_Sf_012H20_Contig1b  TACCCACTGGATATTACAAAATAGTCTTTTATATTAATTACAATATATAC
                          *** * *********** **  * ********************* wnt8_Sp_041A08           AAAAATACATACATCTATATCAAATTCGCCATACAGAATCTCGACAAAAA
wnt8_Sf_012H20_Contig1b  AAAAATACATACATCTATATCAAAT-GCCATACAAAAATTCAATAAGAA
                         *********************** ****   **  * wnt8_Sp_041A08           TATTATGAAAATAACATTGCCCTCAA
wnt8_Sf_012H20_Contig1b  TATTACAAGATATTAATAACTTTTAA
                         *****  *     ** *   *  ** wnt8_Sp_041A08           A----TAACCCA     (SEQ ID NO:53)
wnt8_Sf_012H20_Contig1b  AATCATCGCCCT     (SEQ ID NO:54)
                         *    *  ***
```

Wnt8 Active_2:

```
wnt8_Sp_041A08           AGGAACCCCCCACTTGGAATTCCATATCACGGTGTTAAATACTAACTCTA
wnt8_Sf_012H20_Contig3c  AGGAACCCCC-ACTTGGAATTCCATATCACGGTGTTGAATACTAACTCAA
                         ********  *********************** ********* * wnt8_Sp_041A08           CACAAAGCAGCTTTTTTCCCACGAGTAATTCCATTCCGAAAAGAAAGGTT
wnt8_Sf_012H20_Contig3c  TACAAAGCAGCTTTTTTCCCACGTGTAATTCCGTGCCCAAAAGAAAGGTT
                          ******************** ****** *  ********* wnt8_Sp_041A08           CATTTTAACCACGATTTTGT-CGCTCTTCCAAACAGACCTTTGGATTTAG
wnt8_Sf_012H20_Contig3c  CATTTTAACCACGATTTTTTTCGCCATTCGAAACAAACCATTGGATTTAG
                         ****************** * *  ***  * *********** wnt8_Sp_041A08           GAGACCTTAATGGAACTTCTATTGATTTCCTAAACTATAGCCTTTGTACG
wnt8_Sf_012H20_Contig3c  GAGACCTTAATGGAACTTCTATTGATTTCCAAAACTATAGCCTTTGTACG
                         **************************** ***************** wnt8_Sp_041A08           CAGGAAGATTACGGTGTGCAGGAGAGGGTACAAAAGGGGTTCACATGGG
wnt8_Sf_012H20_Contig3c  CTGGAAGATTACAGTGTCCGGGAGAGGGTGCAAAGGGGGTTCTCAGGGG
                         * **********  ****  * *******  **** ****** **  ***
```

Figure 9

```
wnt8_Sp_041A08          TGCGTGAAAGAGGTGCAATAGACAAGATCCTCCTTCTAAAAGCGTAAACC
wnt8_Sf_012H20_Contig3c  TGCGTGAAAGAGGTGCAATAGA--AGATCC--CTTATGAAAGCGTAAACC
                        ******************** **  * * ************ wnt8_Sp_041A08          TCTTAACACAAGCCGGCTAATCGCGGGGACAACACGGTAACTAAAAAGCA
wnt8_Sf_012H20_Contig3c  TCTTAACACAAGCCGGCTAATCGCGAGGACAACACGGGAACTA---AGCA
                        *********************** ****** *    ** wnt8_Sp_041A08          AAGTTGTTTCTTAGAG    (SEQ ID NO:55)
wnt8_Sf_012H20_Contig3c  AAGTTGTTTCTTAGAG    (SEQ ID NO:56)
                        ****************

Wnt8 Active 3:

wnt8_Sp_041A08          AGATGTGTATCAATTACTATCTCCTGCTGTGAGGCTAACAAAAGTTGAGA
wnt8_Sf_012H20_Contig4b  CGATGTGTATCAATTACTATCTCCAGCTGTGAGGCAATCACAATTTGAGA
                         ********************* ******** *    ****** wnt8_Sp_041A08          GCTGACCAGACACTTGTTGACGATTCGAACTTCTCAAAAGCTAATGAAGT
wnt8_Sf_012H20_Contig4b  ACTGACGAGACACTTGTTGACGATTCGAACTTCCAAGAAGGTAATGAAGT
                        ***** * ************************* *  *  ****** wnt8_Sp_041A08          TTATCA-GAGTTGTAGCTCTTATAAATTACATCGACACACCTTTGACTTG
wnt8_Sf_012H20_Contig4b  TTCTCCTGAGTTGTAGCTCTTATAAATGACAACGACACACCTTTATCTTG
                           ****************** * **********  ** wnt8_Sp_041A08          TCTCCTCATCAAAAAGAGCATAAATGATACCTTGACATGACAGCTGGAT
wnt8_Sf_012H20_Contig4b  TCTTCTCATTAAAAA-GAGCATAAATGATACCTTGACATGACAGCTCGAT
                        * * *  ************************** * wnt8_Sp_041A08          GACGGCTTGCCATTGGAGCGGCGAGCATAATAAGGCATGAGTGGTCCAAT
wnt8_Sf_012H20_Contig4b  GAAGGCTTGCCATTGGAGCGGTGAGCATAATAAGGCATGAGTGGGCCAAT
                         ************** ****************** *** wnt8_Sp_041A08          GAGAATGCAGCTCATGTTCGCATGAATAGATCCGTGGGATGATCAAAGCA
wnt8_Sf_012H20_Contig4b  GAGAATGCAGCTTATGTTCGCATGAATAGAGCCGTGGGATGATCAAAGCA
                        ********** ************* ***************** wnt8_Sp_041A08          ATAGGCGCATCG-------CTATTGTTTTGGCGGCTAAATTGGGGGCACT
wnt8_Sf_012H20_Contig4b  ATAGGCGCATCGGCCATCGCTATTGTTTTGGCGGTTAAATTGGGGGCACT
                        **********       *********** ************* wnt8_Sp_041A08          TTTGTTCGCATCGTCTGCTCTTTGCAAGGACGCGCTCTCGTGAGCAAGAG
wnt8_Sf_012H20_Contig4b  TTTGTTCGCATCGTCTGCTCTTTGCAAGGACGCGCTCTCGTGAGCAATAG
                        ********************************************* wnt8_Sp_041A08          AAGAATAGATCGCCCACCGAGCTTTCAATTTGCAGGAACAAAAGG-GGAT
wnt8_Sf_012H20_Contig4b  AAGAATAGATCGCCCACCGCGCTTTCAATTTGCAGGAACAAAAGGAGGAT
                        *****************  *******************   ** wnt8_Sp_041A08          TTCAGGCTTTCTCAAAGTTTGGGTAGCGTTTCTTTAAACTTCCTTTTTTC
wnt8_Sf_012H20_Contig4b  TTCAGGCTTTCTAAAAGTTTGGGTAGCGTTTCTTTAAACTTCCCTTTTTC
                        ********** ************************** **** wnt8_Sp_041A08          AAACTGGAACCTAAAGTGACCTCGAGGCGGTAGCTGGTTTGAAAAGGAAG
wnt8_Sf_012H20_Contig4b  AGACTGAAATCTAAAGTGACCTCGAGGCAGTAGCTGGTTTGAAAAGGAAG
                        * **** ** ****************** *********************
```

Figure 9a

```
wnt8_Sp_041A08             GAGTAAGCGAACAAAAAGATGATGAAGCGTAAGAGCATGCATTTAGACAG
wnt8_Sf_012H20_Contig4b    GAGAAAGGGAACAAAACGATGATGAAGCGTAAGAGCATGCATTTAGACAG
                           * * ****** ******************************* wnt8_Sp_041A08             ATATTCAATCACTAATAATAGTTTAAGATTAAAGATTAAACTCTGGATAG
wnt8_Sf_012H20_Contig4b    ATATTCAATCACT--TAATAGTTTAAGAT-AAAGATTAAACTCTCGATAG
                           ***********  ********* ********** *** wnt8_Sp_041A08             AGCTTTCTGACGAGAG-------------
wnt8_Sf_012H20_Contig4b    AGCTTTCTGAAGAGAGAGGGGAGAAAGAG
                           ******** *** wnt8_Sp_041A08             TTGTATGCAGT    (SEQ ID NO:57)
wnt8_Sf_012H20_Contig4b    TTGTATACAGT    (SEQ ID NO:58)
                           ****** ****

Wnt8_Flanking 1:

wnt8_Sp_041A08             TACATGTTATTGAAAACTGTCATATTCCAATAACCGTTCCCTTTATAAAT
wnt8_Sf_012H20_Contig1a    TACGTGTTAGTGATTACTATCATATTCCAACAACCATCCACTCCATTAAT
                           * * *   * ********  *   **  * *** wnt8_Sp_041A08             ATAATCGCT----CGTGATGTAATTA--CGACAAACCCCGATGACCAATT
wnt8_Sf_012H20_Contig1a    ACAATCGCTTACGCGTAATGTAATTATACGACAAACTCCGATGATCAATT
                           * *****    * ******  ****  *** *** wnt8_Sp_041A08             TATGTGCAAAAGGCGTAAAGGTGTCT-----TCATTTAATTCATTTTCT-
wnt8_Sf_012H20_Contig1a    TCTGTGCAAAAGGCTTAAAGACGTCTAGACTTCATTAAATTCACTTGCCG
                           * ********** *        **   * wnt8_Sp_041A08             ATCAGTGG----GTCCAGAAATTCCACCGCGTACGTTGTCTCTTGACATT
wnt8_Sf_012H20_Contig1a    ATCGGTGGAAGGGTCCAGAAAT-CCATCGCAT-TATTATATTCCACCGA-
                           *     ****** * *** *   **  *   *    * wnt8_Sp_041A08             TAGCAGACGTGGTGTTTTATAGTGTACGACTACATAACGGCGTTCAATCA
wnt8_Sf_012H20_Contig1a    -AGCAGACGTGGTGTTTCACCGATTACGACTGTATAACGGCGTTCGGTCA
                            ***************** *   ***** ********* ** wnt8_Sp_041A08             ACATCTTCAAGGCTAAGACAGGGGCTAAGATTTGGACCAAGCATTACTTC
wnt8_Sf_012H20_Contig1a    ACATCCTCAAGGCCA-----------AGATTTGGACCAAACATTACTTT
                           *** ***** *           *********** ***** wnt8_Sp_041A08             GTTTCGTCACATGGGTTATAATTAAAGAGCACTAAAAGGTGCATTGACAT
wnt8_Sf_012H20_Contig1a    GTTTCATCA-----------TTAAAGACCACTAAAAGGTGCACTAACAT
                           *** *           ***** ************ * **** wnt8_Sp_041A08             TGTCGATACCCGGGGTCGATACCCTATATACCTCGCACTATGTACAGA--
wnt8_Sf_012H20_Contig1a    TGACGATACC------------CTACATGTCTCGCAC-ATGTACAGTAA
                            ***            *   *** ****** wnt8_Sp_041A08             --TGTAGGCTTACTTTGGTCCTAAGCTGCACCCGCTATGCAGCAGTGATC
wnt8_Sf_012H20_Contig1a    GTTGTAGGCTTACTTTGGTCCTAAGCTGCACCCACAATGCAGCAATGATT
                             ****************************** * ******* ** wnt8_Sp_041A08             AGATATCATCCTCCTAACTCGAATATAACGGTGATCACCAGTAGTGTACT
wnt8_Sf_012H20_Contig1a    AGCTCTCATCCTCCTAACTAGAAAATAATGGTGATCTCCAGGAATGTAAT
                           ** * ************** ***  **** ******  ***  ***  *
```

Figure 9b

| | |
|---|---|
| wnt8_Sp_041A08 | TTCTTCCCTCTCATTAGCACTCTGTACCAGTCAGCAGGTGTAGGATACTC |
| wnt8_Sf_012H20_Contig1a | TTCTTCCCTCTCATTAGCAATCTGCACCAGTCTGCA--TGGAGGAGACTC |
| | ****************** **** ******* *** ** **** **** |
| wnt8_Sp_041A08 | AATGTTAAATACACATTTTAAGTGG-----TGGTGGCGGACTAAAAGCAA |
| wnt8_Sf_012H20_Contig1a | AATGGAAAATTCACCTTTTAAGTGGCAACCTGATGGCTAACTAAAAGCAA |
| | **** **** *** **********     ** **** ************ |
| wnt8_Sp_041A08 | ATGGTGTTGATTTAGCAATTACCATTGATGATGCAGAATAACATCGTCAA |
| wnt8_Sf_012H20_Contig1a | ATGGTGTTGATCTTGCAATTACCATTGATGACGCAGAATAACATCGTCAA |
| | *********** * ***************** ***************** |
| wnt8_Sp_041A08 | TTATTTTGAAATATATTACTTATATGCGATCGATTTT-AAATGGGTTCTG |
| wnt8_Sf_012H20_Contig1a | TTATTTTGAAACATATTTCTTACA--CGATCGATTTTTAAATGGATTCTA |
| | *********** ***** **** *   ************ ****** **** |
| wnt8_Sp_041A08 | GGGACCTGGTCGAACCATCTGCAAGAATATATCAAGAAAAATACCATCAT |
| wnt8_Sf_012H20_Contig1a | AGGACCTGGCCGAACCATCAGCAAGAG------ATGAGAAATGGTTTGCA |
| | ******** ********* ******       * ** ****   * |
| wnt8_Sp_041A08 | GGCAAATAACACAGACATAATACCGCGTGAGTCCAAAAAAAAGTACACAC |
| wnt8_Sf_012H20_Contig1a | ACCAAACCTCAAGAACATATCA-------AGAACAAAATAAGATATTCTT |
| | ****   **   ***** *       ** ***** **   ** * |
| wnt8_Sp_041A08 | TAGAAAATTGGTAATTATTTTTAAAATCATCTATGAACAGTAAATTATTA |
| wnt8_Sf_012H20_Contig1a | ------ATTCATAAGTGC----AAAATAACACGTG----GTATATGATAA |
| |       ***  *** *      ***** *    **       *** ** ** * |
| wnt8_Sp_041A08 | CACATCTTATGAAAGAGTGTTTTATCCCGAATCATTTAGTATCATTTTGT |
| wnt8_Sf_012H20_Contig1a | CG-ATCTCAAAGATGGAT-CGTTATGCTAA------CGGAGCCATCCTCC |
| | *  **** *   *  * *  * **** *        *  *** * |
| wnt8_Sp_041A08 | GTGGTTCGTGTTCACGCTTGGATGAATGTAGGAGGCATTGTTTACGAGAG |
| wnt8_Sf_012H20_Contig1a | TCTCTTTCT-CTCTCGTCGTCCTGGTTATCATGCTCAGTGTATACCTTAA |
| | ** * ** **     ** * *         ** *** ***     * |
| wnt8_Sp_041A08 | AGAGTGTAAAAATCGACTTGCGCTAAAGTTGCTTATCTGATGTTTGAATA |
| wnt8_Sf_012H20_Contig1a | AGGGCAATCCAACC--CTTGTATTAAGTTGATTTGTATGAAAGCAGAAAA |
| | ** *       ** * ****    ***  *   ** * ***     *** * |
| wnt8_Sp_041A08 | AAACAATGGGGATTTGGGTATTAATTCGGTCTTTACAGATCCAA--ATAA |
| wnt8_Sf_012H20_Contig1a | ATAACAGAAGTAGGATGGCAAAAGTTTGAAATGAATCGGACCAATAGTAA |
| | * *     *  **  * ****   *    * *  *   * ****   *** |
| wnt8_Sp_041A08 | CATCCCTAACAAAATCAACAATGCCA---CACATATCAAATATGAATATC |
| wnt8_Sf_012H20_Contig1a | GGAAGTTATGAATGTTTGAAATGTGAGATCACTAAGTCTATGCGAATCTC |
| | **  **  *     ****  ***   *     ** **** ** |
| wnt8_Sp_041A08 | AAATATCAACAAACATTTGTGCGCGTGTGTGCATGAGTGTGACTTTGCTT |
| wnt8_Sf_012H20_Contig1a | AAATTGGTAGTTTGGTCAGTGGATTGTGACGTAGAACAAGGACTAGTCTC |
| | ****  *   *   ***      * * *    ****  ** |
| wnt8_Sp_041A08 | CTGCAAAAAGCATATGCAATACATTTCAGTTGATACATTCAATTCATTCT |
| wnt8_Sf_012H20_Contig1a | CCATTTGCCGTGTACAAAAATATCATTAATTTCTGTTTTTCTCGTAAGTT |
| | *      * **   **      * **   *    **       *  * |
| wnt8_Sp_041A08 | CTCACTCCGCTAATCCCAACATATAATAATACATACTGTAGGCATTACTT |
| wnt8_Sf_012H20_Contig1a | CCTTCTCCCTTGAGGC--ACTACTAAAAATATAT--TATAGATAGCATAT |
| | *  ****  *  * **  *** **** ** * *** * * * |

Figure 9c

```
wnt8_Sp_041A08      TGGCGCAAGTCGATTTTAGCACTCTTCTTCTTCTTATTCTTCTTCTTCCA
wnt8_Sf_012H20_Contig1a  TAGTATAGGTCCTCTAAAAAGAATAGACCCTCCTGAGCCATGATCTTTTG
                         *  *    * ***    *  *            **   * *  **** wnt8_Sp_041A08      GTTAAGTGCAGCTTCAAGGTGATGAAGATAATCGCACTGGTTGCGAACAA
wnt8_Sf_012H20_Contig1a  AAAAATTGAAATTTTTAGTCATTTTATAATAT-------GTTG-GAACAG
                            *            *   *          *** wnt8_Sp_041A08      TGCCATCCAAGCGCGAACACATACCACACAAAAATGATACCAAATGATTT
wnt8_Sf_012H20_Contig1a  ----ATGAGAAAGTATTCCGACACTACATCACATTGACTTTAC-CGCTTC
                             **   *   *    *  *  *  * *  ***   *  * ** wnt8_Sp_041A08      GTGATAAAACACTCTTTCATAATAATAATTTACTGTTCATAGATGATTTT
wnt8_Sf_012H20_Contig1a  AT------ACGTATAGTGATTGCAACCTTCAAACATTCATAACTT-TTTC
                         *       **    *           *  *   ******  *  *** wnt8_Sp_041A08      AAAAATAATTAGCAATTTTCTAGGTGTAAACTTTGTTTTGACTCACACGG
wnt8_Sf_012H20_Contig1a  ATATTTAGTCAGATTTAATTGAAACTTGAA--TCAGTTTGCTTCTC-TGA
                         * *    **      *    *  **  *    **   *   * wnt8_Sp_041A08      TATATCAGATAGATCCTAATACTAGCTGAGTCTTCATCCTCTCTTTCTCT
wnt8_Sf_012H20_Contig1a  TTTTTCTGCTTT-CTTTAAGAGTAGTTGTCTATTTGGGTTGGATATCCCT
                         *     *    *** * *   * **       *   * wnt8_Sp_041A08      TTTGTCGTCCGGGTAATGATGTGTATATAGTGTATTATGTATAGACG---
wnt8_Sf_012H20_Contig1a  TCAAGGAGACGAGTAATGAAATAGATTTTTTCAGATAACTTTGGACGTTT
                         *         ****    *    *  *       **  *  * **** wnt8_Sp_041A08      --AAAATAGATTCCATTCCAGTTATTCAT--ACCACATTCTAAGCGATCG
wnt8_Sf_012H20_Contig1a  GTAAAGTATTACAAAATTTGTTTATACATGTACCAGAATCCAAGCGATCG
                           *         *   * *    ** *  **** *   ******* wnt8_Sp_041A08      GAATGAAATTAAACAGTTTTCTTTTTTGGT-CTCGTTTATGAAAGGTGCA
wnt8_Sf_012H20_Contig1a  GAATGAAATGAAACAGTTTTCTTTTTTTATTCCCGTTTATGAAAGGTGCA
                         ******  *****************    *  * ******************* wnt8_Sp_041A08      A---GCCTTTTAACATGCACAGTAGACCTGTTTACTACTTTTTATGCAAA
wnt8_Sf_012H20_Contig1a  ATCAGCCTTTTCACATGCACAATCGACCTGTTTACTACTTGTTATGCAAA
                         *    *****  ******* *  ******************  ******* wnt8_Sp_041A08      CTTCTCGAAGAAAAGTTTCCCTTGACAACACAAAAGCTTGCCAAACATAG
wnt8_Sf_012H20_Contig1a  CTTTTTGAAAAAAATTTCCCCTTGACACCCCAAAAGCTTGGCAAACATAG
                         ***  * *    ********* * ******** ******* wnt8_Sp_041A08      CAACAGTTAGTGTATGCAAAGGGAATTACATCTATAGAAATCTCATTATG
wnt8_Sf_012H20_Contig1a  CAACAGTTAGCGTATGCAAAGTGAATTATATCTATAGAAATGCCATTAAA
                         ********  ***** **  ********   *** wnt8_Sp_041A08      TATAGCAAGTGAATCTAAAACATGTTGTTAGTAACTAGGGATTAAGGATT
wnt8_Sf_012H20_Contig1a  TATAACTAGTGAATCTAATACAC------------AGGGATTAAGGAGA
                         ****  * ********  *              ************ wnt8_Sp_041A08      AAATTATTTCCTATTAAAAAAGGTGTATTTGTCATTGGTAAAAGTACAAT
wnt8_Sf_012H20_Contig1a  ACATGCATAATTTTAAACATATTTATGCATGTCATTGGTAAAAGTACAAT
                         * **  *    *  *  * *         ******************* wnt8_Sp_041A08      CGTCTTTTACTGTTTTGTTGGTCTAATGTATATTCAGGCTTTTGGTTAAC
wnt8_Sf_012H20_Contig1a  CGTCTTGAACTATTT-GTAGGTCCACGGTAAATTCAGGCTTTTGGTTAAC
                         ****** *** ***  ** *****      * ****************** 
```

Figure 9d

```
wnt8_Sp_041A08              CGAGTCAGTCTTTTGTTCGACAAGAAAATGCTGTTTTCGAGTCTATAAAG
wnt8_Sf_012H20_Contig1a     CAATTCGGTCTTTTGTTCGAG--------------TTTGAA-----AGAG
                            *  *   *********               **      * ** wnt8_Sp_041A08              AGTAAGACCGCTTTAAAGGACGTTCTGCCACTGGCATGTTGACTGTAAGG
wnt8_Sf_012H20_Contig1a     AATAAGAACGCTTTAAGGGACGTCCTGCCACTGGTTTGTTGACTCTAAGG
                            * ***  **** ** ****    **** *** wnt8_Sp_041A08              TTCTTGAGCTTG----GTGTGTCT-TTTTATAGGGAAACAATGTTTACTG
wnt8_Sf_012H20_Contig1a     TTTTTGAGCTTGCATGGTGTGTCTGTTTTTAGGGAAACAATGTTTACTG
                             *****    ****   **************** wnt8_Sp_041A08              GTTGACACCCTGAAAGGTGCTTCTACTGAAAAGGATCAGATCACTTCTTG
wnt8_Sf_012H20_Contig1a     GTTGGCACTTTGAAAGGTGCTTTTACTGAAAAGGATACGATCACTTTTTG
                            **  *  ********* ***********  * ***** wnt8_Sp_041A08              TAAACTTCTCGGGATACCATTTTTTTTGACAGAGAAGAGATATAATGAAT
wnt8_Sf_012H20_Contig1a     TAAACTTTTCCGGGAACCATTTGTT--------------ATTTATTGAAT
                            *****    ***                 ***** wnt8_Sp_041A08              GAAGATGCTATAAGCTTAAGTTCAACTGATTAACACAACAATAAGTGTGA
wnt8_Sf_012H20_Contig1a     TGAGAGG--GTAAGCTTA-GTTCAACGGATTAACACAACAATTATTGTGG
                            *** *    ******* *** *************  * **** wnt8_Sp_041A08              CACCCCAACCCGCCCCCTTCTATATCTCTGTATGTCTCATTTCTTTCCGC
wnt8_Sf_012H20_Contig1a     ------AACCCCCCCCCCTCTCTCTCTCT---------------------
                                  *** *  * * *****  * wnt8_Sp_041A08              TATGTCGCTCTCTCTCACTGTCTGACTCACCCTCTCTCACCCTCTCCCCT
wnt8_Sf_012H20_Contig1a     -------CTCTCTCTCTGTATGTCTCATTCTGTCCC-------CTCAT
                                   *******  *     **  *      *  *  * wnt8_Sp_041A08              GTCTCCACTTCTCTCTCTGTAATATGTCTCATTTATGTCGCTCTCTCTCT
wnt8_Sf_012H20_Contig1a     GTCTCCCCTTCTCTCTCTGT---ATGTCTCATTC-TGCCCCTGTCTCCCC
                            **** *********   ******   *   **  * wnt8_Sp_041A08              CTCTCATTGTCTTTCTCTGTCTAACTCACCCTCTCCCCTGTCTCCACTTC
wnt8_Sf_012H20_Contig1a     TTCTC--------TCTCTGTATGTCTCATTCTGTCCTCTGTCTCGACCCC
                            **          ***** *    **   ******    * wnt8_Sp_041A08              TCTCTCTCTGTAATATGTCTCATTTATGTCGCTCTCTCTCACCGTCTTTC
wnt8_Sf_012H20_Contig1a     T---------------------------------------TCTCTC
                            *                                        * wnt8_Sp_041A08              TCTGTCTAACTCATCCTCTCCCCTGTCTCCACTTCTCTCTCTGTAATATG
wnt8_Sf_012H20_Contig1a     TCTGTAAGTCTCATTCTGTCCCCTGTCTCCCCTTCTCTCTCTG---TATG
                            ***          **********  ********   ** wnt8_Sp_041A08              TCTCATTTATGTTGCTCTCTCTCTCACTGTCTTTCTCTGTCTAACTCACC
wnt8_Sf_012H20_Contig1a     TCTCATT-------------------------------------------
                            ******* wnt8_Sp_041A08              CTCTCCCCTGTCTCCACTTCTCTCTCTATAATATGTCTCATTTATGTCGC
wnt8_Sf_012H20_Contig1a     CTGTCCTCTGT--------------------ATGTCTCATT-------
                             * **                    ******** wnt8_Sp_041A08              TCTCTCTCTCACTGTCTTTCTCTGTCTAACTCACCCTCTCCCTTGTCT
wnt8_Sf_012H20_Contig1a     ----------------CTCTCTCTTTATATCTCATTCTGTCCCCTGTCT
                                            ** *****  **  **** ** **** *****
```

Figure 9e

```
wnt8_Sp_041A08          CCACTTCTCTCTCTGTAATATGTCTCATTTATGTCGCTCTCTCTCACTGT
wnt8_Sf_012H20_Contig1a  CCCTTTCTCTCTCTGT---ATGTCTCATT---------------------
                           ********   ******** wnt8_Sp_041A08          CTTTCTCTGTCTAACTCACCCTCTCCCCTGTCTCCACTTCTCTCTCTGTA
wnt8_Sf_012H20_Contig1a  --------------------CTGTCCTCTGT-------------------
                                               * **** wnt8_Sp_041A08          ATATGTCTCATTTATGTCGCTCTCTCTCTCAGTGTCTTTCTCTGTCTAAC
wnt8_Sf_012H20_Contig1a  --ATGTCTCATT---------CTCTCTCTTTATATCTCATTCTG------
                          ********         ******  * *    ** wnt8_Sp_041A08          TCACCCTCTCCCCTGTCTCCACTTCTTTCTCTGTAATATGTCTCATTTAT
wnt8_Sf_012H20_Contig1a  ---------CCCCTGTCTCC-CTTCTCTCTG---TATGTCTCATT---
                                  *********  * **    ********* wnt8_Sp_041A08          GTCGCTCTCTCTCACTGTCTTTCTCTGTCTAACTCACTCTCTCCCCTGTC
wnt8_Sf_012H20_Contig1a  ---------------CTGTC---CTCTGTATGTCTCATTCTCTCTCTT---
                                        ***   **** *  ** ****  * * wnt8_Sp_041A08          TCCACTTCTCTCTGTAATATGTCTCATTTATGTCGCTCTCTCTCACTGTC
wnt8_Sf_012H20_Contig1a  -----------------TATATCTCATTC-TGTCGTCCACTCTCTTTATC
                                          * ***  *** * *****  * ** wnt8_Sp_041A08          TTTCTCTGTCTAACTCACCCTCTCCCCTGTCTCCACTTCTCTCTCTGTAA
wnt8_Sf_012H20_Contig1a  TCCTTCT--CTTACTCTTCTTTACATATGACTGCA----------GCAA
                         *  *   ****  *   *    **          * ** wnt8_Sp_041A08          TATGTCTCATTTATGTCGCTCTCTCTCACTGTCTTTCTCTGTCTAACTCC
wnt8_Sf_012H20_Contig1a  TGAATGATGTCTATAAAA-------------------------AA----
                         *    *  * * wnt8_Sp_041A08          CCCTCTCCCCTGTCTCCACTTCTCTCTCTGTATGACTCATTATGTTGCCC
wnt8_Sf_012H20_Contig1a  --------------------------TATAAAAATGATGATGAAGATG
                                                    * **   * *   *   * wnt8_Sp_041A08          CCGCTCTTTATCTCTATATCTTACTCTCTCTCTCTTGCTTACTCTTCT
wnt8_Sf_012H20_Contig1a  GTGATGGTGATGAC--------------------CCTGATTATAAAGTT
                          *  *  **  *                       *  *       * wnt8_Sp_041A08          TTACATAACTATTACTGCATCAATTTGTTTA
wnt8_Sf_012H20_Contig1a  TTACACAACA-----TACGT---TTTAGTTT
                         ***  *         * * *   * wnt8_Sp_041A08          AATTATATACG    (SEQ ID NO:59)
wnt8_Sf_012H20_Contig1a  AATCACACACG    (SEQ ID NO:60)
                         ***   * * ***

Wnt8_Flanking_2:

wnt8_Sp_041A08          ATTATGATCACATTAA--TTTTGTCAACTTTATTGATAATAAAAACACGT
wnt8_Sf_012H20_Contig1c  TCAATTAACTTATTAACATTTTGATAACGTTAATAATGATGCAAATTATC
                         ** * *   ***  *  *  * * *     *** wnt8_Sp_041A08          ATTTTGGGTAGATTAGTGCAA-GTTTAGTTGTCCCGTATATAAATCAACA
wnt8_Sf_012H20_Contig1c  ATCTT-----TATCGATACAACATACATTTGTTTTG---GTAGAGTAGTG
                         **  **      **  * ***  *  * * **** *    ** *   *   * *
```

Figure 9f

```
wnt8_Sp_041A08              TAAAGCTTAAGAATA--TTATAATCATC-CAGTTTCTATTACAAAGTAAG
wnt8_Sf_012H20_Contig1c     CAAGTTTCGTTGTTTCCTTGAAATTATCATAGTTTCAATTTCAAAATAGA
                            **    *     *    *  *  **  * ** wnt8_Sp_041A08              TTAGAGAGTCCTTTTAAAAGAGAGAGAGACTGTATTTATACAAGGCTGGT
wnt8_Sf_012H20_Contig1c     TTAGAAAATCCTTTTGAAAGAGAGAGA--CTA-AAATATACAAA----GT
                            ***  ***  *******   *  ***** wnt8_Sp_041A08              GTTCTGTACACAGTCTTAATGTGAGTAGTCATAGCATAGACAAAGCATCC
wnt8_Sf_012H20_Contig1c     GTTCTGTATACAGTCTTAATGAGAGCAGTCTTAAAATAGACAAAGCGTCC
                            ****** ********  *  **** *  ******** * wnt8_Sp_041A08              AACTTAGTGGACATTAAAAAGTTCATCTTCCTCAGAGTTCAAAGATATTT
wnt8_Sf_012H20_Contig1c     AACTTGGTGGACATTAAAGAGTTC------CTCAGAGTTCAAAGACCTTC
                            *** ******** *      *********** wnt8_Sp_041A08              GGG-ACCTACAGCCTCGATCCAACGGGCTGGCACGTCCGCCTGGTCACAG
wnt8_Sf_012H20_Contig1c     GGGGACCTACAGCATCGAGCCGACGGGCTGACACGTCCGCCTGGTAACAG
                            * *****   ****** ********* ** wnt8_Sp_041A08              TTCGCCGAC        (SEQ ID NO:61)
wnt8_Sf_012H20_Contig1c     T-CGCCGAC        (SEQ ID NO:62)
                            * *******

Wnt8_Flanking_3:
wnt8_Sp_041A08              AAACGAAGTTGCAGTTGCAGCTGGACGTAATGACGACTTGAGTCTTACGG
wnt8_Sf_012H20_Contig2a     AAACGAAGTTGCAGTTGCAGCTGGATGTGATGACGACTTCAGTCTTACGA
                            ***********************  ******* ******* wnt8_Sp_041A08              ATCACCATCCCGCAGCTCCTACACAGTCTGCTACAGCTCTGCTTCACCCA
wnt8_Sf_012H20_Contig2a     ATCACCATCCCGCAGCTCCTACACAGTCTGCTACAACTCTGTTTCACCCA
                            ********************************* * ***** wnt8_Sp_041A08              TCGGAACGATGAAGGCGACGTCGAATCCTTGGTCAATGATGACGATGATG
wnt8_Sf_012H20_Contig2a     TCGGAAGGATGAAGGCGACGTCGAGTCCTTGGTCAAAGATGACGATGATG
                            **** ************* ******* *********** wnt8_Sp_041A08              ATACCTCGGTGACATCCTCTCGCACCATGCACTCCCTGCCCGCAGTCCCG
wnt8_Sf_012H20_Contig2a     ATGCCTCGGTGACATCTTCTCGCACCATGCACTCCCTGCCGGCAGTTCCG
                             ********* ******************* * * wnt8_Sp_041A08              GTGACACCGATGGTGAGGTTGGCACGGCAGTAGTCGGGGGACTGGTCCAG
wnt8_Sf_012H20_Contig2a     GTGACACCGATGGTGAGGTTGGCACGGCAGTAGTCGGGGGACTGGTCCAG
                            ************************************************** wnt8_Sp_041A08              GAAAACGAGGTCGCGACGGTTGTGCGATGCGCTCACTACGGCTTGAGGGA
wnt8_Sf_012H20_Contig2a     GAAAACGAGGTCGCGACGGTTGTGCGATACGGTCATGACGGCACGAGGGA
                            **************************  *  **  *** wnt8_Sp_041A08              AGCGATCTTCAGCGCTGTTGCCGTCGATGAGTTTCCCACGAACGAAGTCG
wnt8_Sf_012H20_Contig2a     AGCGATCTTCAGCACGGTTGCCGTCGATGAGTTTACCGCTGACGAAGTCG
                            *************   * **************      ********* wnt8_Sp_041A08              ACGCGTACGGCCTGGAAGTACTTGCGCTTGATCTCGTCCCCGATGACACG
wnt8_Sf_012H20_Contig2a     ACGCGTACGGCCTTGAAGTACTTCCGCTTGATCTCGTCCCCGATGACACG
                            ************* ********* **************************
```

Figure 9g

| | |
|---|---|
| wnt8_Sp_041A08<br>wnt8_Sf_012H20_Contig2a | GAAGTTTGCGACGTGGTTCCAGCAGGTCTGTAGAGAGCAGGAGCCGGAGA<br>GAAGGTTGCGACGTGGTTCCAGCAGGTCTGGAGGGAGCAGGAGCCGGAGA<br>**** ************************* ** ***************** |
| wnt8_Sp_041A08<br>wnt8_Sf_012H20_Contig2a | CGCCATGACACTTACAGGTTCGTTGGAGGGTCTGTTTGACAGCCTGTCAA<br>CGCCGTGACACTTACAAGTTCGCTGAAGTGTCTGTTTGACAGCCTGTCAA<br>**** *********** ***** ** ** ********************* |
| wnt8_Sp_041A08<br>wnt8_Sf_012H20_Contig2a | CAATAAGAAGAAATAAACAGTTAGTCAAATTGAATACGAAT-------TA<br>CAATAAGCAGAAAGAAACAGTTTACAAAAATAAACAAGACTAAGTTTTTA<br>******* ***** ********   *** * ** * ** *        ** |
| wnt8_Sp_041A08<br>wnt8_Sf_012H20_Contig2a | TACATCATTAAGCGTCAATAAACTAAGA----CTAAGATTTTGTTTAAC<br>AAAACTAGCAACAGTTAACATCATAAAAACAACAAAAAACAGAATTTATG<br> *  *   ** ** **  *    *** *      * **  *     **** |
| wnt8_Sp_041A08<br>wnt8_Sf_012H20_Contig2a | TAGCAACAGTAAACATATTCCCCCCTTTTTCCCCC---ATTCCACAAGGT<br>CAAATACACTGAATTGGCTGATGATTATGCCCTCTGAGAGTTTAAAGGGA<br> *   *** * **    *      * * ** *     *  *   *  ** |
| wnt8_Sp_041A08<br>wnt8_Sf_012H20_Contig2a | TCC------TTTATT----------AAACAATGTC----GCTCACAATGT<br>TCCGGTAACTTTGTCTCAGATTCTGAAACAAAATTCTGGATTTAGCTCAT<br>***      *** **          ******  *        * *    * |
| wnt8_Sp_041A08<br>wnt8_Sf_012H20_Contig2a | -ATACAAGGAAAGATATACACATGCAGA--ATTTAAAAA-----TGATAT<br>GATGCAATGATAATCATAAACCTTTAGGTCAGTCAGGAACCCCATGACTT<br> ** *** **  *   *** ** *  ** *  * **   ***   *** * |
| wnt8_Sp_041A08<br>wnt8_Sf_012H20_Contig2a | TC-----TTGGCCATTCAAAATATGATAAGAACATACAT--TTATATATA<br>TTACAAGCTGATCGCCTGTCTGATTATCAAGATATTTATGATTGGAATTA<br>*       **  *       ** ** *   *  **  **   **   ** |
| wnt8_Sp_041A08<br>wnt8_Sf_012H20_Contig2a | TATATATAAGTTACAAATTGC-----AATTTTTTAAACATCACAGATTTA<br>CAAATTTTGAAAACCGTTCGCCTGATGGTTTTCATAACACTATAG-TCTA<br> * ** *       **    * **        ****  **** * ** ** |
| wnt8_Sp_041A08<br>wnt8_Sf_012H20_Contig2a | CTCGGCAAAATAAATTTAGAAGAAATGAACAATACATAATTCATA-----<br>TTAGGGAAAACGAGTATGGTAAAACCGGTCAATCAAAGATTTTTACTTTT<br> * ** ****  *  *   * * ** *  *   **** *  ***  ** |
| wnt8_Sp_041A08<br>wnt8_Sf_012H20_Contig2a | --------------AAACAACTAAAATTATGGTTATTTTA-------ATA<br>TTGAGGCACTTCTTGATCATTTTGAAGCGCAATTTTTTTAGGGCTTCATT<br>               *  **   *  **    ** *****          ** |
| wnt8_Sp_041A08<br>wnt8_Sf_012H20_Contig2a | AAGAAAAAAAAGGTTATACGCAAATAGTATGAATTGGCTGGTA------A<br>ATTACACCATATCACAGACACTAATAACATGTAGGGCCGTGTATCTCAGA<br> *  *  *  *    * ** ****  ***  *  *  ***         * |
| wnt8_Sp_041A08<br>wnt8_Sf_012H20_Contig2a | TTATGCACTTTGAGAGTCTGACTTTCATAAAGTCTTACC-----------<br>TTTAACACTGTTAAACGATCCCTTTAATAAAGTATTACCCCAACTATCAC<br>**  **** * *    * **** ******* *****  |
| wnt8_Sp_041A08<br>wnt8_Sf_012H20_Contig2a | --------ATTTCAAAATT--AAAAACG-AGTTATCACTTGATATTTGTG<br>CTGATTATATCTCACCATTTCAAAATTGCAGTAATCAATTGATATTCGTG<br>        ** ***   ***  *  *** **** ******** *** |
| wnt8_Sp_041A08<br>wnt8_Sf_012H20_Contig2a | AAAATGCTTCACTCTTGGACAATTTTGAGAATGAATTTCATGAAGTTATG<br>AAAATACTTCACTCTTGGTCAATTTTGAGGAGGAATTTCATGAAGTTATG<br>***** ************ ********** * ***************** |

Figure 9h

```
wnt8_Sp_041A08           CTAACAGTTGAATTAACTTCTTTTTTT--TAAGAAGAGAGAAA---TAGA
wnt8_Sf_012H20_Contig2a  CTAACAGTTAAATGATTTTTATTTTGTAATATAAAGAAATAGACCATAAA
                         ******* * *  ** *  ** *   * wnt8_Sp_041A08           ------------------------------CCACTGGTG---ATTCGATATC
wnt8_Sf_012H20_Contig2a  GGAATGTAAAATATTGTTCTATCGTGTCCCACTAGTGTTAATTCGATGTT
                                                       *** *   ******* * wnt8_Sp_041A08           CTGGGAATAAGAATTGCACTTCGACGTCACTTTTGGTACTCACCTTTCTG
wnt8_Sf_012H20_Contig2a  CTGAGAATAAGATTCGCATTTCGACGTCACTTTCGGTACTCACCTTTCTG
                         * ****** * * ********** ************** wnt8_Sp_041A08           CC  (SEQ ID NO:63)
wnt8_Sf_012H20_Contig2a  CC  (SEQ ID NO:64)
                         **

Wnt8_Flanking_4:

wnt8_Sp_041A08           CTGAAAAATATCACAGAAATTAAATAAGTTATAGATTGAACTTGAAGCTG
wnt8_Sf_012H20_Contig2c  CTGAAAAATAACATAGAAA-----TAAGTTATAGATTGAACTTGTAGATG
                         ********  ***     ****************** * ** wnt8_Sp_041A08           AATTAACAACGCTAATCATTAAGCAAACAAAAGTATTGAAC---------
wnt8_Sf_012H20_Contig2c  AAATTACAACGATTATCATGAAGCAAAAAAAGTACTGAACCTGGTATTG
                         ** * ****** * *** *** *** *** wnt8_Sp_041A08           -AACAAATATATTCCTTGCATCAAACACAATCGAGTTTGTGAAACAAAAA
wnt8_Sf_012H20_Contig2c  AAAAATAGATATTCCTGGCCTAAAACGCGGTC-AATTTATGAAACAAAAA
                         ** * * ******  *  **** *    ** * * ******** wnt8_Sp_041A08           ATCGATGCAGTGGGTGCAGAAATTCTCGACCTTTCTAGTCGTGTATTTAG
wnt8_Sf_012H20_Contig2c  AT-GATGCAGTGGGTGCAGAAATTCTTGGCGTTTCTA-------CTCAA
                          *********************  * * ******         * * wnt8_Sp_041A08           TATATTTTCAGGAC-TGTGAATAAAAAACGACTGTGCTAATTATATACCA
wnt8_Sf_012H20_Contig2c  CATGCATCTAGGATGCATGAGTCTAAAGTTCTTGTGCTTA------ACCA
                         **    * **   * *  *   **** *      **** wnt8_Sp_041A08           CAAAGTATGGACTGATTGTCGAAAATGAAGGGGTTTCTTAATAAATGACT
wnt8_Sf_012H20_Contig2c  CAAAATGTGGACCGAATGTCGAGAAATTAAGGGTGTCTAAATAAATGACA
                         **** * ***  ****  *  ** * ********** wnt8_Sp_041A08           GATCTGTTATCCATAGATGATAATAATAATGATAATAAGGATTAACACGA
wnt8_Sf_012H20_Contig2c  GATCTAATATTCATAGAGGAC-----TAATCA-------------ACTA
                         *** * ****       **** *               ** * wnt8_Sp_041A08           TCACAACTATTTACGAAAAATCAACCTGAGGAATTTTCAATAACCTCGCA
wnt8_Sf_012H20_Contig2c  CTTTGATTGTTGGCGTGAAAGGAA--AGACAAAT----GATAA-------
                         *   *    *   **** wnt8_Sp_041A08           CTGGGTCACGTTTTGTATTTAGCGAACATTACAATGACGCAATTATTACG
wnt8_Sf_012H20_Contig2c  ------------------TAACGATGAACACGAT--CGCAACTACT---
                                             *  *   ***  * wnt8_Sp_041A08           TTATCCGAACATGATGCTATGAGACATACAGTACGATATCGGAATCGCCA
wnt8_Sf_012H20_Contig2c  ---TTCGAAATTG--------------------GGTAATGGAATTGCTC
                            * **** **                       * ** ***** **
```

Figure 9i

```
wnt8_Sp_041A08           TTGATGTGTTGATTATTCATTTATAATTTAAACAATTGAAAAAAAATCTT
wnt8_Sf_012H20_Contig2c  TTGAATTGATAGTTAAATGTTGTTGATTAACTTTATTT--------TTTT
                         **   *  *     * *** *    ***          * ** wnt8_Sp_041A08           TAAAAAACCTCTCCAAAAAAAAAAAACGTA  (SEQ ID NO:65)
wnt8_Sf_012H20_Contig2c  TAAAGATAAACT--ATAACAAAAAAACGTA  (SEQ ID NO:66)
                         **** *    **  * * ** **********
```

Wnt8_Flanking 5:

```
wnt8_Sp_041A08           TGAAAGAAGAGAAAGAAAACACAGGGTTAAATTATATGCAACTCAGTCAT
wnt8_Sf_012H20_Contig2e  TGA----AGAGAAAGTAACACCCTTTGTTAGATTTAATGCAAC----TCAT
                         *    ****   *    ** * ****    ** wnt8_Sp_041A08           GGCGGGGGATAACTCGATAAAGTTAAACATACTAGATAAAAACAGAATTG
wnt8_Sf_012H20_Contig2e  AACGGGGGATATCACGACAAAGTAAGACATACTAAATAAAAACAGAATTA
                         * ******** * *  ** *  *****  *********** wnt8_Sp_041A08           CAGTGTATTCATATCAATATTCACAATACCATATATTACATTCATAAATA
wnt8_Sf_012H20_Contig2e  AAGTGTATTCATATCAATATTCACAATACCATATTTTACATTCATATATA
                          ******************************  ****** * wnt8_Sp_041A08           TTTTCTTTTAT--AACAAGTTGATGCGAACTATTTTGTCATATTTCGTTT
wnt8_Sf_012H20_Contig2e  TTTTCTTTTTTTTAACAAGCTGATGCGAACTTTTTAA--ATATTTCGTTA
                         ********* *  **** *******  *   ********* wnt8_Sp_041A08           AGACTTGCATATTTCTGTAGGACTTTTTAACATTTTAACATCCGCTGTAC
wnt8_Sf_012H20_Contig2e  AGACTTGTATATTTCTGTAGAGCTTGT-AAAATCATGACATCCGCATTAC
                         ***** ********  *  *    * ***** * wnt8_Sp_041A08           GCATTCCTATTTCATACATACCTACCTCTGAATTTTAAAGATAACCTATA
wnt8_Sf_012H20_Contig2e  ACATCCCTATTTCATACATACCTTCCTCTAA--TTTAAT-----TTTTTG
                          * ************** *     ***     *  * wnt8_Sp_041A08           ATTATTT-AGAAAATTACACAATGAAATATAAAACTTTAATAGGTCATTG
wnt8_Sf_012H20_Contig2e  ATTATTTTAGAAGATAATGCAATGAAAGATAAA-CTTTGATAGGACATTG
                         *****      ******      ** wnt8_Sp_041A08           TTGTTGAACATCGTGTGCTCGATCTCCGAAGTGAAAATACCCCCCCCCCC
wnt8_Sf_012H20_Contig2e  TTGTAAAGAATCTTTTGACTTGCACCCAATAAATGAACATCGCGTGCTTG
                         ****   * ***  *            **     * *  *  * wnt8_Sp_041A08           CCCATCTGAATTAACATCATATTTTATTTTCAGGGGCGGAATCATGATC
wnt8_Sf_012H20_Contig2e  ATCTTGTAATTACAAACTAG--------TCCAAAAAAAAAATCTT----
                          *  * *  ***  *  *             *        ** * wnt8_Sp_041A08           AGGGACAAAGGGCACACAATTTCGATAAT   (SEQ ID NO:67)
wnt8_Sf_012H20_Contig2e  -GGAACCAGCGGGATTTGAACCTGAGATC   (SEQ ID NO:68)
                          ** ** * **  *   ** *
```

Wnt8_Flanking 6:

```
wnt8_Sp_041A08           TGCAAAGGGAGAAAAAGAAAGAGATTTAAAGGTCAGCATGTATGTCATTA
wnt8_Sf_012H20_Contig3b  TGGAAAGGGAGAACAAGAATGAGAAATATCGGTCAGCATTTCTTGCATTA
                          ****** *   *   ****** *  *  ***** wnt8_Sp_041A08           CT-----------TAAAGTTTCAAACAATGTATCCACGTTCCTCGATAA
wnt8_Sf_012H20_Contig3b  CTATAGTCTATACATGTAGTTTCAAACAATGTATCCATGTTTCTCGATAA
                         **                 ******************* ***  *******
```

Figure 9j

```
wnt8_Sp_041A08           TTGATTAAGATATTATATAAG--TGTTATATAGAATGATTACGATATTTG
wnt8_Sf_012H20_Contig3b  TAAACAAGGTCATGTAAAAAGATGGTCTTCAGAATAATAATGTTATTTG
                         *  *  *** *  *       ** * *  ***  * * ****** wnt8_Sp_041A08           TCATTCTTTTACCAAATAGCCTGGATTTGTTTTACTTCTTTTTTTAAATA
wnt8_Sf_012H20_Contig3b  ACATTCTTGTAACAAATAG----------------TTCTGTTCTT-----
                          *****  *****                  ** wnt8_Sp_041A08           GGACATTTCTGATAGTGAGATATCACCCAAAAATGTAGCAAACGATTCCA
wnt8_Sf_012H20_Contig3b  ---CATTT------GTGAAATATCA-----------GCAAAAGAATTAA
                            ***       **           *  *  * wnt8_Sp_041A08           ACGAATACAGAGTATACGCAAACAAAAATATATAAGCCTCCATATAAGAG
wnt8_Sf_012H20_Contig3b  ACGGGCAC----TATA----------------------------------
                         *      **** wnt8_Sp_041A08           GGAAAAGAAGAAAAGGAGTAAACTGTCATAGACCGGAAATTAAACATAAA
wnt8_Sf_012H20_Contig3b  -------------------------------------------------- wnt8_Sp_041A08           GTCAACATTAAACAGAAAACAGAAGATTGTCTTTTAGGAGAAATTTCGAT
wnt8_Sf_012H20_Contig3b  -------------------------------TTCCGGAGGATTTGCAAC
                                                           ** * ** * wnt8_Sp_041A08           ATTCCCAGCAGGGGCGTAGATTATTACTGCGCTTTTGAGAAGGCTCAAGA
wnt8_Sf_012H20_Contig3b  ATTCCTAGTAGGGGCGTACATTACTACTGCACTTTCGAGAAGGTTCAAGA
                         ***  *******  **  ***  *** wnt8_Sp_041A08           AGAGTATCTTAAATGCACTCTTAGTAAACTGAG---AATACATCGTGCCT
wnt8_Sf_012H20_Contig3b  AAAGGACATTAAATGCTCTCTTAGTAAACTGAATTAAATACATCGTGCGT
                         * ** *  ****** *********     **********  * wnt8_Sp_041A08           AATATC----AATAGACATGAACACAATGTAGG-TCTAAT----------
wnt8_Sf_012H20_Contig3b  AACATATAGGAATAGACATGAACACAAAGTAGGATTTAATTGGAATGTGT
                                  *************** *** * **** wnt8_Sp_041A08           AACATTTGTTCTCCTATATTAGTAAGGTCTGGCTGACTTATTTTCTTCCA
wnt8_Sf_012H20_Contig3b  AACATTTGTAAGCCTAGATTATTAGTGCCTGGTTGACTTGTTTCCTTCTC
                         *******      ** *  * ** ** *  **** wnt8_Sp_041A08           CAATTTTGCAGACACTATTCTCTCTTTCTGTATGTACTACCTGGTTTCGT
wnt8_Sf_012H20_Contig3b  TAATTTTGCAGACA-TATTTTTTCTTTCTTTCTGTACTACATG-------
                          *********** ** *  ******  * **** wnt8_Sp_041A08           CGCTTAAATATCCATTCCAGATTTGTAAAGGCCGTATTAACAAAAAAGGT
wnt8_Sf_012H20_Contig3b  --------TATCTGGTT-AGATCTGTCA---TCGGATAGAATAAGTGGA-
                                 ****  * ** * *     *  ** * wnt8_Sp_041A08           CCCTTCCTATGCATACACAAACTCTGACAAAATTTGCTTTAAAAACACGT
wnt8_Sf_012H20_Contig3b  ----GCCAAGACACATCTTGTGTCGTATAAAAGT-ACTTTAAATATATAT
                               *           * **  *****  *  * wnt8_Sp_041A08           TCAAGTTTGTCATTAACTACATATTAATTCGAACCAAGGCTTGTAACTAT
wnt8_Sf_012H20_Contig3b  ATATATATAGCAGTCCCTACATATTACTT---------------AAATAT
                          *  *  ** * ********                   * wnt8_Sp_041A08           ATAGCAGGCAAACGTATTACTGACATTTTTAGAAGAATGTGATTTCCTTA
wnt8_Sf_012H20_Contig3b  TCAAAAG---AATGT------GATTTCGTTGAAACA---------CACTA
                          *  **   ** **      ** *  ** *  ** *          * **
```

Figure 9k

```
wnt8_Sp_041A08              GGA     (SEQ ID NO:69)
wnt8_Sf_012H20_Contig3b     TGA     (SEQ ID NO:70)
                            **
```

Wnt8 Flanking 7:

```
wnt8_Sp_041A08              GTCACCGGCTAATTAAAGTTGAGAG---------TTTGTGGTCTGATTAT
wnt8_Sf_012H20_Contig3d     GTCACCGGCTAATTAAAGTTGAGAGCGATGACAGTTTGTGGTCTGATTAT
                            ***********************         ************** wnt8_Sp_041A08              ATTGATACTCGGGTTCTAAAGGCCCATTACGGTTTTTAATTAAGAGGGAG
wnt8_Sf_012H20_Contig3d     ATTGATACTCG--TTCTAAAGGCCCATTACGGTTATTAATTAAGAGGGAG
                            *********  ****************** ************ wnt8_Sp_041A08              AGTAAAAAGCAGTAAGGGATGATACGTGCTTGAACAAGTTATCTTAAGAT
wnt8_Sf_012H20_Contig3d     GGTAAAAAGCAGGAAGGGATGATACGTGCTTGAACAAGTTATGTTGGGAT
                             ********** * ****************************  * * *** wnt8_Sp_041A08              GAATCAGAATGTTGTGCTTTTGAAAGCCTTGACGTCATC-----------
wnt8_Sf_012H20_Contig3d     A------AATGTTATGCTTTTGAAAGCCTTTACGTCATCCTGGTCATGGG
                                   **** ************* ****** wnt8_Sp_041A08              ATGGGAGGGGATTGCAAACACTGACAGGAAAC--CCTATTTCCGCATGAA
wnt8_Sf_012H20_Contig3d     ATGGGACGGGAATATTAACAATGACAAGAAAAAACGGGGTTTCGCATGAA
                            **** **  *    ** ***  *    *    ****** wnt8_Sp_041A08              AATCGAAAGAGAAAG---AAACTTTCAGC---------TTTATTACTTTT
wnt8_Sf_012H20_Contig3d     AATCGAAAAGGGCCTCTTAAATATTTAGTAATGAATAATTCATTAGTAAT
                            ********   *      *             **** * * wnt8_Sp_041A08              TAGAAATCC-CAAATTACCGAGTAATTAAAAGG----GGTGA--TATTGA
wnt8_Sf_012H20_Contig3d     GAATAATTCATTACTTGACAAAGAATGAGGAGGATTGGGTGAATTGTTGA
                             *   ***  *  **  *  *  *** *  *    ***  * **** wnt8_Sp_041A08              ACGATTTGCAAAGTAA-----------------
wnt8_Sf_012H20_Contig3d     ATTGTATGTTAATTAAGTTTTTTTTTAATTTAA
                            *   *  **   *    * wnt8_Sp_041A08              AGTGTTTTTCTTACC     (SEQ ID NO:71)
wnt8_Sf_012H20_Contig3d     AGTATTTTCCTTACC     (SEQ ID NO:72)
                            *** **** ******
```

Wnt8 Flanking 8:

```
wnt8_Sp_041A08              TTAAAAGACTTGGAGTGTACGATTAAGAGCTTTCTAAGTATCTAATACCT
wnt8_Sf_012H20_Contig4c     TTAAAAGACTTGGAGTGTACGATTAAGAGCTTTCTAAGTATCTAATACCT
                            ************************************************** wnt8_Sp_041A08              CCGTTTCTTTCACAGCAAATGGGACGCTTTATTGTCCGATAAGAAAACAC
wnt8_Sf_012H20_Contig4c     CCGTTTCTTTCATACCAAATGGGACGCTTTATTGTCTGATAAGAAAACAC
                            ************ * ****************** ************ wnt8_Sp_041A08              TCCTTTACAAATTACCATTTGTAAAAAGGGTAATTTGTCGATATCTTACT
wnt8_Sf_012H20_Contig4c     TCCTTTACAAATTACCATTTGTAAATAGGGTAATTTGTCGATACCTCACT
                            ************************* ***************** ** ***
```

Figure 9I

| | |
|---|---|
| wnt8_Sp_041A08 | CTGCTCGGTTGAATATTGTAAGAGGAATTTATTGATGAAGGCCTGCTTGA |
| wnt8_Sf_012H20_Contig4c | CGGCTCGGCTGAGTATCCCAAGATGA----ATTGATGAAGGC-TGCTTGA |
| | * ****** *** ***    **** **      ************ ******* |
| | |
| wnt8_Sp_041A08 | CACTTGTGTTCATCGTGTGCTGTGCTATTCGTAAACTTATCGATATGAGA |
| wnt8_Sf_012H20_Contig4c | CACTTGTGTTCAATGTATGCTACGCTATTTGTAAACTTATCGATATGAAA |
| | ************  ** ****  ****** ******************** * |
| | |
| wnt8_Sp_041A08 | GACTTAATATTAAGACTTGTAGGTGTATAACACGGTGCCCATTTTTGTAA |
| wnt8_Sf_012H20_Contig4c | GACTTACTATTAAGACTGGTAGGTGTATAA-----------------AA |
| | ****** ************ *************                 ** |
| | |
| wnt8_Sp_041A08 | TCATAGTTCCTCAATCCACATTTTGTTTATTCATAACTGCATCCATACTA |
| wnt8_Sf_012H20_Contig4c | TAAGAGTT--TGAGAAAGCATTTTGTTT-----TAAATGGAATTGAAGT- |
| | * * ****  * *       ********** *** ** *       * * |
| | |
| wnt8_Sp_041A08 | CAAAGTTTGTATACGCGCCTATTGATAATGTGCCATATTCGTCATCATTT |
| wnt8_Sf_012H20_Contig4c | -GAAATTTCAGTTTGAACTTATT-----------TATTCATGA------ |
| | ** ***    *  *  * ****           ***** * * |
| | |
| wnt8_Sp_041A08 | TATTCGAGTTGCATCGTATCCCGTTAAATGTCCCCGTTATGATCGTTCTA |
| wnt8_Sf_012H20_Contig4c | ------AGTTG----------------TCTCTCAGCTAAGAA------A |
| | *****                 * ** * ** **          * |
| | |
| wnt8_Sp_041A08 | TGGACAATTCAACAGTTTGAGAAAGATTTGTTGTTGGAATTCAGTGAAAT |
| wnt8_Sf_012H20_Contig4c | TGAACAAT-------------AGGTTTTGTTTTTGTGGTGGTATGATGT |
| | ** *****             * ******* ***   *    *** * |
| | |
| wnt8_Sp_041A08 | TTCAGTTTAAACATATTTATTCATGAAGCTGTCTCTCAGCTAGAAGAAAA |
| wnt8_Sf_012H20_Contig4c | GATAATTATTACAAATG-ATTAATGACAACATTTCACAT---GGTTTTAA |
| | * **   *** **  *** ****    * ** **    *      ** |
| | |
| wnt8_Sp_041A08 | AGAATATTGTTGGTATGATGGGATAATGATTACAAAATTATTAATGACGA |
| wnt8_Sf_012H20_Contig4c | ATAATAAACCTGAAA----GTGCTATTGAATCCTGAACCATTATTAGTGC |
| | * ****    ** *    * * ** *** * *  **  **** *   * |
| | |
| wnt8_Sp_041A08 | AATTTCACATGGTTTTAAATATTAAGTGTATAAGTGCTATTGTGTATACC |
| wnt8_Sf_012H20_Contig4c | GATTAAATAATAAACATAATGCTGCA---GCCAATGCTAAAATACAGACA |
| | ***  *  *    ***  *         * *****   *  * ** |
| | |
| wnt8_Sp_041A08 | GTATTGTATAATCGTATAACAAAAAACTCGCATTAATGGAAGTAAAATCG |
| wnt8_Sf_012H20_Contig4c | GTAGAGAATA-TCATATAATAAAA--CTTACATTAATGGAAGTAAAATTA |
| | ***   *  *** ** ***** ****  ** ****************** |
| | |
| wnt8_Sp_041A08 | TAATGTT----AGAATATGAAGAATATAAAGTATACATATTTTAAGAAG |
| wnt8_Sf_012H20_Contig4c | TAATTTTGTGTAGAATATGAAGAATATGAAATAT--ATATTTTAAGAAG |
| | **** **    *************** ** ***  ************* |
| | |
| wnt8_Sp_041A08 | TTGGCCGTGAAGGCAGGTAGAAAATCATAACTGATTTGTCAATACATAAA |
| wnt8_Sf_012H20_Contig4c | TTTGCCGTGAAGACTGGTAAAAAATCATAACGGATATTTCAATTTAAACA |
| | ** ********* * **** *********** ***  * ***** * * * |
| | |
| wnt8_Sp_041A08 | AA-CAAGCAGGATAAGAATAATATTGAAATATATAGAAGGGAATCGTT-- |
| wnt8_Sf_012H20_Contig4c | AATCAAGCGGAGTAAGAATAATATTGAAATATACAGAAGGGGTTCGTTTA |
| | ** *****  *  ************************ *******    ***** |
| | |
| wnt8_Sp_041A08 | -GCAAAAATACCAGACCGATTATCCCAAAGCATTTTAAAATT-CAACTAA |
| wnt8_Sf_012H20_Contig4c | TGAATAAATACCAAACCGATTATTCCAAAGCACTTTAAAATTTCAACCAA |
| |  * * ******** ******** ******** ********** **** ** |

Figure 9m wnt8_Sp_041A08           TTATTGTAAAGT   (SEQ ID NO:73)
wnt8_Sf_012H20_Contig4c  TTAGTGTAAAGT   (SEQ ID NO:74)
                         * ******

Figure 9n

Endo16 alignments

Endo16 Active_1:

```
endo16_Sp_Yuh_1994              TTGTAAAATTATTATATTTCTTACCTGTGGGCATTGACCGCGCCACGGCC
endo16_Sp_baylor_contig653345   TTGTAAAATTATTATATTTCTTACCTGTGGGCATTGACCGCGCCACGGCC
                                ************************************************** endo16_Sp_Yuh_1994              AAAACCGCGAACAGCAAAATATTTAACCTCATCATCGTCTCAAAAATTAG
endo16_Sp_baylor_contig653345   AAAACCGCGAACAGCAAAATATTTAACCTCCTCATCGTCTCAAAAATTAG
                                **************************** ***************** endo16_Sp_Yuh_1994              CAATATTATGACCTGTCCTCGACCAGTCTTTCTCTATTTAACCCTCCGCT
endo16_Sp_baylor_contig653345   CAATATTATGACCTGTCCTCGACCAGTCTTTCTCTATTTAACCCTCCGCT
                                ************************************************** endo16_Sp_Yuh_1994              CTTGATGAGGGGGGTAAAGTTACACCCCTTTGTCTTTGATAGCACAATCA
endo16_Sp_baylor_contig653345   CTTGATGAGGGGGGTAAAGTTACACCCCTTTGTCTTTGATAGCACAATC-
                                ************************************************* endo16_Sp_Yuh_1994              GGAGACGAAACTCAAACAGTTTAACCCGGGGATGTGATAACTTTGAGATG
endo16_Sp_baylor_contig653345   -----CAAAACTCAAACAGTTTAACCTGGG-ATGCGATAACTTTGAAATG
                                     * ****************** * * ******* * endo16_Sp_Yuh_1994              ATGTAATCACTTGGTAGTTTAATCACTTAATCCTACGCGATGATAATGGT
endo16_Sp_baylor_contig653345   ATGTAATCTCTTGGTAGCTTGATCACTTAATCCTCCGCGATGATAATGGC
                                ****** ****  *********** ************ endo16_Sp_Yuh_1994              ATGATCATTTTGGTCAATATTTTTGAGACGTTGCGATTTACGACGTTTCT
endo16_Sp_baylor_contig653345   GTGATCATTTTGGTCAATATTTTTGAGACGTTGCGATTTACGACGTT-CT
                                 ******************************************** endo16_Sp_Yuh_1994              TAGAAGTAAGGGCGATTTAAGAGGAAATTACGCTTTTGTTACATTGTTTG
endo16_Sp_baylor_contig653345   TAGAAGTAAGGGCGATTTAAGAGGAA-TTACGCTTTTGTTACATGGTTTG
                                ************************ ************ *** endo16_Sp_Yuh_1994              ATGAAGTTTAAATGCATTTGTCAGATGTTTGTGTTTACGGGCATTAAATC
endo16_Sp_baylor_contig653345   ATGAAGTTTAA-TGCATTTGTCAGATGTTTGTGTTTACGGGCATTAAATC
                                ********* ************************************ endo16_Sp_Yuh_1994              TTGCGTGGAAACAAAGGACGTTCAGTTCCAGGTATATTCGGGGTTTTATC
endo16_Sp_baylor_contig653345   TTTCGTGGAAACAAAGAACGTTCAGTTCCAGGTATATTCGGGGTTTTATC
                                 ********* ******************************* endo16_Sp_Yuh_1994              TCATCGGAATCGACTGAAAAACATCCAAAATTAATTTGAAAAACCAACAA
endo16_Sp_baylor_contig653345   TCATCGGAATCGACTGAAAAACATCCGAAATTAATTTGAAAAACCAACAA
                                ************************ ********************* endo16_Sp_Yuh_1994              AGTTAAAGTCTTTATTCATGATAACATTTCTGAATTAGAAGTGCCCTCTT
endo16_Sp_baylor_contig653345   AGTTAAAGTCTTTATTCATGATAACGTTTCTGAATTAGAAGTGCCCTCTT
                                *********************** ********************** endo16_Sp_Yuh_1994              CATTTGTTATTTGATATACAAAAACAACTCCGAATTGGAAATCCAAACCC
endo16_Sp_baylor_contig653345   CATTTGTTATTTGATATACAAAAACAACCCCGAATTGGAAATCCAAACCC
                                **************************** *********************
```

Figure 10

```
endo16_Sp_Yuh_1994              CTTCTCCATAAGCCACGTTTTGAGTGTGG
endo16_Sp_baylor_contig653345   -TTCTCCATAAGCCACGTTTTGAGTGTGA
                                 **************************** endo16_Sp_Yuh_1994              GTGTACATTAG   (SEQ ID NO:75)
endo16_Sp_baylor_contig653345   GTGTACATTAG   (SEQ ID NO:76)
                                ***********
```

Endo16 Active 2:

```
endo16_Sp_Yuh_1994       TTGTAAAATTATTATATTTCTTACCTGTGGGCATTGACCGCGCCACGGCC
endo16_Sp_BAC_127I21     TTGTAAAATTATTATATTTCTTACCTGTGGGCATTGACCGCGCCACGGCC
                         ************************************************** endo16_Sp_Yuh_1994       AAAACCGCGAACAGCAAAATATTTAACCTCATCATCGTCTCAAAAATTAG
endo16_Sp_BAC_127I21     AAAACCGCGAACAGCAAAATATTTAACCTCCTCATCGTCTCAAAAATTAG
                         **************************** ***************** endo16_Sp_Yuh_1994       CAATATTATGACCTGTCCTCGACCAGTCTTTCTCTATTTAACCCTCCGCT
endo16_Sp_BAC_127I21     CAATATTATGACCTGTCCTCGACCAGTCTTTCTCTATTTAACCCTCCGCT
                         ************************************************** endo16_Sp_Yuh_1994       CTTGATGAGGGGGTAAAGTTACACCCCTTTGTCTTTGATAGCACAATCA
endo16_Sp_BAC_127I21     CTTGATGAGGGGGTAAAGTTACACCCCTTTGTCTTTGATAGCACAATC-
                         ************************************************ endo16_Sp_Yuh_1994       GGAGACGAAACTCAAACAGTTTAACCCGGGGATGTGATAACTTTGAGATG
endo16_Sp_BAC_127I21     -----CAAAACTCAAACAGTTTAACCTGGG-ATGCGATAACTTTGAAATG
                              * ****************** * * ****** * endo16_Sp_Yuh_1994       ATGTAATCACTTGGTAGTTTAATCACTTAATCCTACGCGATGATAATGGT
endo16_Sp_BAC_127I21     ATGTAATCTCTTGGTAGCTTGATCACTTAATCCTCCGCGATGATAATGGC
                         ****** ****  *********** ************ endo16_Sp_Yuh_1994       ATGATCATTTTGGTCAATATTTTTGAGACGTTGCGATTTACGACGTTTCT
endo16_Sp_BAC_127I21     GTGATCATTTTGGTCAATATTTTTGAGACGTTGCGATTTACGACGTT-CT
                          ******************************************** endo16_Sp_Yuh_1994       TAGAAGTAAGGGCGATTTAAGAGGAAATTACGCTTTTGTTACATTGTTTG
endo16_Sp_BAC_127I21     TAGAAGTAAGGGCGATTTAAGAGGAA-TTACGCTTTTGTTACATGGTTTG
                         ************************ ************* *** endo16_Sp_Yuh_1994       ATGAAGTTTAAATGCATTTGTCAGATGTTTGTGTTTACGGGCATTAAATC
endo16_Sp_BAC_127I21     ATGAAGTTTAA-TGCATTTGTCAGATGTTTGTGTTTACGGGCATTAAATC
                         ********* ************************************ endo16_Sp_Yuh_1994       TTGCGTGGAAACAAAGGACGTTCAGTTCCAGGTATATTCGGGGTTTTATC
endo16_Sp_BAC_127I21     TTTCGTGGAAACAAAGAACGTTCAGTTCCAGGTATATTCGGGGTTTTATC
                          ********* ******************************* endo16_Sp_Yuh_1994       TCATCGGAATCGACTGAAAAACATCCAAAATTAATTTGAAAAACCAACAA
endo16_Sp_BAC_127I21     TCATCGGAATCGACTGAAAAACATCCGAAATTAATTTGAAAAACCAACAA
                         ************************ ********************* endo16_Sp_Yuh_1994       AGTTAAAGTCTTTATTCATGATAACATTTCTGAATTAGAAGTGCCCTCTT
endo16_Sp_BAC_127I21     AGTTAAAGTCTTTATTCATGATAACGTTTCTGAATTAGAAGTGCCCTCTT
                         ************************* ************************
```

Figure 10a

```
endo16_Sp_Yuh_1994           CATTTGTTATTTGATATACAAAAACAACTCCGAATTGGAAATCCAAACCC
endo16_Sp_BAC_127I21         CATTTGTTATTTGATATACAAAAACAACCCCGAATTGGAAATCCAAACCC
                             **************************  ****************** endo16_Sp_Yuh_1994           CTTCTCCATAAGCCACGTTTTGAGTGTGG
endo16_Sp_BAC_127I21         -TTCTCCATAAGCCACGTTTTGAGTGTGA
                              *************************** endo16_Sp_Yuh_1994           GTGTACATTAG    (SEQ ID NO:77)
endo16_Sp_BAC_127I21         GTGTACATTAG    (SEQ ID NO:78)
                             ***********
```

Endo16 Flanking 1:

```
endo16_Sp_Yuh_1994           TCGGATATCGTGACATTAATTTTATAATATATCATGACATTTTTGCTGCA
endo16_Sp_haplotype_SdrFH5   TCGGATATCGTGACATTAATTT-ATGATATATGATGACATTTTTGCTTCA
                             ********************  **** ********** endo16_Sp_Yuh_1994           TATTTTGCGGTACCGGAAGATGGTGATTTTAACATGGGGATAAAGATATT
endo16_Sp_haplotype_SdrFH5   TATTTTGCGGTACCGGAAGATGGTGAGTTTAACATGAGGATAAAGATATT
                             ************************ ***** ********** endo16_Sp_Yuh_1994           GCATCAAGATTTGCACAAGCTCTTATTCTAATATCCACCCTTGCCCCCCC
endo16_Sp_haplotype_SdrFH5   GCATCAAGATTTGCGCAAGCTCTTGTTCTAATATACACATTG---CCCCC
                             ************ ***** ***** *  *    ***** endo16_Sp_Yuh_1994           CCCCCATCTGCTCCCC-TCTCACTCCCTGTTTCTTTCTTCGTCGTCGTTC
endo16_Sp_haplotype_SdrFH5   CCCCCATCTGCTCCCCCTCTCACTCCCTGTTTCTT-CTTCTTCTTC-TTC
                             ************** **************    * endo16_Sp_Yuh_1994           TTCTTATTCGTCTTCTCCTTTTCCCCTTTGTACATATCCCTTTCTTTATC
endo16_Sp_haplotype_SdrFH5   TTCTTCTTCTTCTTCTTCTTCTTCTTCTTCTTCTACTTCTTCTTTTTCTT
                             *** * **** * *   ** * *   * * * * *** * endo16_Sp_Yuh_1994           CTCTCTCTCTCTCTCCCCCGTTTCCATCTACACCTCCCTCTGTTTCTG
endo16_Sp_haplotype_SdrFH5   CTTCCTCCTCCTATTTTATTCTTCTTCTTTTTAGTCTTCTTCTTCTTCTT
                              *   **  * *   *   * * *     ** *  * ** endo16_Sp_Yuh_1994           TTTCTGTATCTCACTCTTGTTTCTTACACTGACCCAGTTCGCACTCCCTC
endo16_Sp_haplotype_SdrFH5   CCTCT---TCTTCTTCTTGTTCTTCTCCTT----------CTTCTTCTT
                             * *   *   *******  *  * *            *   ** endo16_Sp_Yuh_1994           TTTATTTTCCTTCACCCACACTCGATCTCTCTCTCTCCTGCTCTATATC
endo16_Sp_haplotype_SdrFH5   CTTGTTCTTCTTGTTCTTGTTCTTGTTCTTCTTCT-TCTTCTTCTTAATC
                               ***  *   *   ** * *   * ** *  *   * endo16_Sp_Yuh_1994           TCTCTGTATATCTGTCTCTATGTGTGTGGGTGTGTGTGTGTGTGTGTG
endo16_Sp_haplotype_SdrFH5   GTCTTCTCCCTTTCCCCTT----------------TGTACATACATGTA
                              * *  * * *    *  *                ***  *  *** endo16_Sp_Yuh_1994           TGTGCGTGCTCTCACCTCAGCATTCTTGTGGGGTTTTAATGTGCGCTTCA
endo16_Sp_haplotype_SdrFH5   TATCCTTTTCGTTATCCTCTCTCTCTCCCCCGTTTCCA--------TTTA
                             *  *    * *    * *     *  * *     *            * endo16_Sp_Yuh_1994           CATACCCCTTGTGAGGCATTTTACTTTGTGGGGTAATTTTTCAGGACCCC
endo16_Sp_haplotype_SdrFH5   CATCTCCCTC------TGTTTC--------------TGTTTCTGTATCTC
                             ***  ****       ** ***                * **** *  * *
```

Figure 10b

```
endo16_Sp_Yuh_1994          ACAGAGTAAAGTCTTTCAAATGACTGTATATTCGGTGTCCTATGCTGCGG
endo16_Sp_haplotype_SdrFH5  AC---------TCTTT-------------------TTTCTTACACTG--A
                                     ***                   *       *** endo16_Sp_Yuh_1994          GGCATTAGAAGTGGTACCCCATAAATGACTTTTTGTGA-GCGTGTGCTAA
endo16_Sp_haplotype_SdrFH5  CCCATTCG------CACTCCCTCTTTCTCTTTCCTTCACACACACACTCG
                             *  *  *         *   * ****   * * *           ** endo16_Sp_Yuh_1994          AACTTGCACACTTTTTTATGGGTAACATCGTAAGCACACCGCCGGGTTGT
endo16_Sp_haplotype_SdrFH5  ATCTCTCTCTCTCT----------------------CTCCTGCTCTT
                              * **   * * ** * *                      * **  *   * endo16_Sp_Yuh_1994          TATCGCCAGGTTGTACATACCCCACTAGTAGGGGACCACAAGGTATATCT
endo16_Sp_haplotype_SdrFH5  TATCTGTGTGT-GTGTGTGTCTCTCTA---------------TGTGTGT
                            **       **    * * ***                    * * * * endo16_Sp_Yuh_1994          GGAACGCACAGAAATACCCCACAATCAGGTGCCCCACAAAGGCCCTGATG
endo16_Sp_haplotype_SdrFH5  GGGGGG---AGGGGTGTGT---------GTATCTCTCTCACTCTCTAA--
                            **    *   **  *            **   *   * *  ***  * endo16_Sp_Yuh_1994          TGAGAATGCGTGTGTGCGCGTGTGTTTGTGTGTGTGTCTCTCTCTCTCTC
endo16_Sp_haplotype_SdrFH5  -----GTATCTATCTCCTTCCCCATTC-TCTCTTTCTCCCACTCTCAGTC
                                 *   * * *         **  *  * *  ** *  *** endo16_Sp_Yuh_1994          TCTCTCTCTCACTCTCTAAGTATATCTATCTCCTTCCCCATTTTCTCTTT
endo16_Sp_haplotype_SdrFH5  TCTCACACACACCCTCTGAGTAT--CTACCTCCTTCCCCATTTTCTCTT-
                            ****  *  *  *   *  ********************* endo16_Sp_Yuh_1994          CCCCCTCTGAAATATTGATAAAAAGAATACATAATTTGGGTTTTCTGTTG
endo16_Sp_haplotype_SdrFH5  CGCCCTCTCAAATATTGATAAAAAGAATACATAATTTGGGTTTTTTGTTG
                            * **** *******************************  *** endo16_Sp_Yuh_1994          TACGCAGAAAAACCCCTAAATGTCGTATTCTTTCACAAATATTCGACTTC
endo16_Sp_haplotype_SdrFH5  TACGCCAACAAA------AAAATTGCATTCTTTCATATATATTCGACTTC
                            *****  * *        * * ********  * * *********** endo16_Sp_Yuh_1994          GAACTCATTT-----------CCTTGCAGAAATGTGTCTCTAATCACATC
endo16_Sp_haplotype_SdrFH5  AAACACATTTGTTTTGAAATTCTTGCAGAAATGCGTCTCAAATGACATT
                             * *           ******** * * * ** endo16_Sp_Yuh_1994          CTCCTAATACATTTATGATACAATTTTATTTTAGGGAAAATGTTGTCGTC
endo16_Sp_haplotype_SdrFH5  CTCTTTATACATT-ATAATACAATTT------AAGCGAAATTTTGTCGTC
                            *** * *****  ********       * *  **  ***** endo16_Sp_Yuh_1994          AAAATGTATGGGGCTCCCAACGCTTCA----AAGGGGCTTTAAAGTTATC
endo16_Sp_haplotype_SdrFH5  AAA-TGTATGAGGCTCCCAACGCTTCAGCTAGAGGGGCTTTAAAGTTAT-
                            * ** **********        *************** endo16_Sp_Yuh_1994          ATATGAATGTAACCTAAACCTTCTGAAA-ATAATCATGATATTGGGCACT
endo16_Sp_haplotype_SdrFH5  --ATGAATGTAACCTAAACCTTCTGAATTACGGTCATGGTATTGGGCACT
                              ***********************   *    *     ** ********** endo16_Sp_Yuh_1994          GCTGGGATGATTTTA   (SEQ ID NO:79)
endo16_Sp_haplotype_SdrFH5  GCTGTGATCATTTTA   (SEQ ID NO:80)
                            ****  *** * ******
```

Figure 10c

<u>Endo16 Flanking 2:</u>

```
endo16_Sp_Yuh_1994          TCGGATATCGTGACATTAATTTTATAATATATCATGACATTTTTGCTGCA
endo16_Sp_haplotype_SpuFH5  TCGGATATCGTGACATTAATTT-ATAATATATCATGACATTTTTGCTGCA
                            ******************** ************************* endo16_Sp_Yuh_1994          TATTTTGCGGTACCGGAAGATGGTGATTTTAACATGGGGATAAAGATATT
endo16_Sp_haplotype_SpuFH5  TATTTTGCGGTACCGGAAGATGGTGATTTTAACATGGGGATAAAGATATT
                            ************************************************** endo16_Sp_Yuh_1994          GCATCAAGATTTGCACAAGCTCTTATTCTAATATCCACCCTTGCCCCCCC
endo16_Sp_haplotype_SpuFH5  GCATCAAGATTTGCACAAGCTCTTATTCTAATATCCACCTTG--CCCCCC
                            *************************************** *  ****** endo16_Sp_Yuh_1994          CCCCCATCTGCTCCCCTCTCACTCCCTGTTTCTTTCTTCGTCGTCGTTCT
endo16_Sp_haplotype_SpuFH5  CCCCCATCTGCTCCCCTCTCACTCCCTGTTTCTT-CTTCGTCGTC-TTCT
                            ******************************** ***** ** endo16_Sp_Yuh_1994          TCTTATTCGTCTTCTCCTTTTCCCCTTTGTACATATCCCTTTCTTTATCC
endo16_Sp_haplotype_SpuFH5  TCTTATTCGTCTTCTCCTTTTCCCCTTTGTACATATCCCTTTCTTTATCC
                            ************************************************** endo16_Sp_Yuh_1994          TCTCTCTCTCTCTCCCCCGTTTCCATCTACACCTCCCTCTGTTTCTGT
endo16_Sp_haplotype_SpuFH5  TCTCTCTCTCTCTC--CCCCGTTTCCATCTACACCTCCCTCTGTTTCTGT
                            ************  ******************************** endo16_Sp_Yuh_1994          TTCTGTATCTCACTCTTGTTTCTTACACTGACCCAGTTCGCACTCCCTCT
endo16_Sp_haplotype_SpuFH5  TTCTGTATCTCACTCTTTTTTCTTACACTGACCCAGTTCGCACTCCCTCT
                            *************** ****************************** endo16_Sp_Yuh_1994          TTATTTTCCTTCACCCACACTCGATCTCTCTCTCTCCTGCTCTATATCT
endo16_Sp_haplotype_SpuFH5  TTATTTTCCTTCACCCACACTCGATCTCTCTCTCTCCTGCTCTATATCT
                            ************************************************** endo16_Sp_Yuh_1994          CTCTGTATATCTGTCTCTATGTGTGTGTGGGTGTGTGTGTGTGTGTGTGT
endo16_Sp_haplotype_SpuFH5  CTCTGTATATCTGTCTCTATGTGTGTGTGGGTGTGTGTGTGTGTGTGTGT
                            ************************************************** endo16_Sp_Yuh_1994          GTGCGTGCTCTCACCTCAGCATTCTTGTGGGGTTTTAATGTGCGCTTCAC
endo16_Sp_haplotype_SpuFH5  GTGTG---------------------------------------------
                            *** * endo16_Sp_Yuh_1994          ATACCCCTTGTGAGGCATTTTACTTTGTGGGGTAATTTTTCAGGACCCCA
endo16_Sp_haplotype_SpuFH5  -------------------------------------------------- endo16_Sp_Yuh_1994          CAGAGTAAAGTCTTTCAAATGACTGTATATTCGGTGTCCTATGCTGCGGG
endo16_Sp_haplotype_SpuFH5  -------------------------------------------------- endo16_Sp_Yuh_1994          GCATTAGAAGTGGTACCCCATAAATGACTTTTTGTGAGCGTGTGCTAAAA
endo16_Sp_haplotype_SpuFH5  -----------------------------------CGTGTG---------
                                                               ****** endo16_Sp_Yuh_1994          CTTGCACACTTTTTTATGGGTAACATCGTAAGCACACCGCCGGGTTGTTA
endo16_Sp_haplotype_SpuFH5  -------------------------------------------------- endo16_Sp_Yuh_1994          TCGCCAGGTTGTACATACCCCACTAGTAGGGGACCACAAGGTATATCTGG
endo16_Sp_haplotype_SpuFH5  --------------------------------------------------
```

Figure 10d

```
endo16_Sp_Yuh_1994           AACGCACAGAAATACCCCACAATCAGGTGCCCCACAAAGGCCCTGATGTG
endo16_Sp_haplotype_SpuFH5   -------------------------------------------------- endo16_Sp_Yuh_1994           AGAATGCGTGTGTGCGCGTGTGTTTGTGTGTGTCTCTCTCTCTCTC
endo16_Sp_haplotype_SpuFH5   ----TGCGCGTGTGCGTGTGT----GTGTGTGTCTCTCTCTCTCTC
                                 ***** **        ******************** endo16_Sp_Yuh_1994           TCTCTCTCACTCTCTAAGTATATCTATCTCCTTCCCCATTTTCTCTTTCC
endo16_Sp_haplotype_SpuFH5   TCTCTCTCACTCTCTAAGTATATCTATCTCCTTCCCCATTTTCTCTTTCC
                             ************************************************** endo16_Sp_Yuh_1994           CCCTCTGAAATATTGATAAAAAGAATACATAATTTGGGTTTTCTGTTGTA
endo16_Sp_haplotype_SpuFH5   CCCTCTCAAATTTTGATAAAAAGAATACATAATTTGGGTTTTCTGTTGTA
                             ****  ************************************ endo16_Sp_Yuh_1994           CGCAGAAAAACCCCTAAATGTCGTATTCTTTCACAAATATTCGACTTCGA
endo16_Sp_haplotype_SpuFH5   CGCAGAAAA---CCTAAATGTCGTATTCTTTCACAAATATTCGACTTCGA
                             *******   ************************************ endo16_Sp_Yuh_1994           ACTCATTTCCTTGCAGAAATGTGTCTCTAATCACATCCTCCTAATACATT
endo16_Sp_haplotype_SpuFH5   ACACATT-CCTTGCAGAAATGTGTCTCTAATCACATCCTCCTAATACATT
                               **************************************** endo16_Sp_Yuh_1994           TATGATACAATTTTATTTTAGGGAAAATGTTGTCGTCAAAATGTATGGGG
endo16_Sp_haplotype_SpuFH5   -ATGATACAATTTTATTT-AAGGAAAATGTTGTCGTCAAA-TGTATGGGG
                              ***************** * ****************** ****** endo16_Sp_Yuh_1994           CTCCCAACGCTTCAAAGGGGCTTTAAAGTTATCATATGAATGTAACCTAA
endo16_Sp_haplotype_SpuFH5   CTCCCAACGCTTCAAAGGGGCTTTAAAGTTATCATATGAATGTAACCTAA
                             ************************************************** endo16_Sp_Yuh_1994           ACCTTCTGAAAATAATCATGATATTGGGCACT
endo16_Sp_haplotype_SpuFH5   ACCTTCTGAAAATAATCATGATATTGGGCACT
                             ******************************** endo16_Sp_Yuh_1994           GCTGGGATGATTTTAT    (SEQ ID NO:81)
endo16_Sp_haplotype_SpuFH5   GCTGGGATGATTTTAT    (SEQ ID NO:82)
                             ****************

Endo16 Flanking 3:

endo16_Sp_Yuh_1994           TCGGATATCGTGACATTAATTTTATAATATATCATGACATTTTGCTGCA
endo16_Sp_haplotype_SdrFH9   TCGGATATCGTGACATTAATTT-ATAATATATGATGACATTTTGCTTCA
                             ******************** ***** ********* endo16_Sp_Yuh_1994           TATTTTGCGGTACCGGAAGATGGTGATTTTAACATGGGGATAAAGATATT
endo16_Sp_haplotype_SdrFH9   TATTTTGCCGTACCGGAAGATAGAGATGTTAACATGGGGATAAAGATATT
                             ****** ********** *  * ******************* endo16_Sp_Yuh_1994           GCATCAAGATTTGCACAAGCTCTTATTCTAATATCCACCCTTGCCCCCCC
endo16_Sp_haplotype_SdrFH9   GCATCAAGATTTGCACAAGCTCTTGTTCTAATATCCACCTTGCCCCCCCC
                             ********************** ********** ***** endo16_Sp_Yuh_1994           CCCCCATCTGCTCCCCTCTCACTCCCTGTTTCTTTCTTCGTCGTCGTTCT
endo16_Sp_haplotype_SdrFH9   CCCCCATCTACTCCCCTCTCACTCCCTGTTTCTT-CTTCTTCGTC-TTCT
                             ********* ************************ **** ****  ****
```

Figure 10e

```
endo16_Sp_Yuh_1994          TCTTATTCGTCTTCTCCTTTTCCCCTTTGTACATATCCCTTTCTTTATCC
endo16_Sp_haplotype_SdrFH9  TCTTATTCGTCTTCTCCTTTTCCCCTTTGTACATTTTTATGTCATTTTCT
                            **********************************  *   *     ** endo16_Sp_Yuh_1994          TC--TCTCTCTCTCTCCCCCGTTTCCATCTACACCTCCCTCTGTTTCT
endo16_Sp_haplotype_SdrFH9  TTATCCTCTCTCTCTCCCTCGTTTCCATGTACACCTTCCTCTGTTTCT
                             *   **************  ****  **  *********** endo16_Sp_Yuh_1994          GTTTCTGTATCTCACTCTTGTTTCTTACACTGACCCAGTTCGCACTCCCT
endo16_Sp_haplotype_SdrFH9  GTTTCTGTATCTCACTCTTTTTTCTTACACTGACCCAGTTCGCACTCCCT
                            *****************   ************************** endo16_Sp_Yuh_1994          CTTTATTTTTCCTTCACCCACACTCGATCTCTCTCTCTC----CTGCTCT
endo16_Sp_haplotype_SdrFH9  CTTTATTTTTCCTTCACCCACACTCGATCTCTCTCTCTCTCCTGCTCT
                            *************************************    **** endo16_Sp_Yuh_1994          ATATCTCTCTGTATATCTGTCTCTATGTGTGTGTGGGTGTGTGTGTGT
endo16_Sp_haplotype_SdrFH9  ATATCTCTCTGTATATCTCTCTCTATGTGTGTGTGGGTGTGTGTGTGT
                            ****************  **************************** endo16_Sp_Yuh_1994          GTGTGTGTGCGTGCTCTCACCTCAGCATTCTTGTGGGGTTTTAATGTGCG
endo16_Sp_haplotype_SdrFH9  GTGTGTGTGCGCGC------------------------------------
                            ********* endo16_Sp_Yuh_1994          CTTCACATACCCCTTGTGAGGCATTTTACTTTGTGGGGTAATTTTTCAGG
endo16_Sp_haplotype_SdrFH9  -------------------------------------------------- endo16_Sp_Yuh_1994          ACCCCACAGAGTAAAGTCTTTCAAATGACTGTATATTCGGTGTCCTATGC
endo16_Sp_haplotype_SdrFH9  -------------------------------------------------- endo16_Sp_Yuh_1994          TGCGGGGCATTAGAAGTGGTACCCCATAAATGACTTTTTGTGAGCGTGTG
endo16_Sp_haplotype_SdrFH9  -------------------------------------------------- endo16_Sp_Yuh_1994          CTAAAACTTGCACACTTTTTTATGGGTAACATCGTAAGCACACCGCCGGG
endo16_Sp_haplotype_SdrFH9  -------------------------------------------------- endo16_Sp_Yuh_1994          TTGTTATCGCCAGGTTGTACATACCCCACTAGTAGGGGACCACAAGGTAT
endo16_Sp_haplotype_SdrFH9  -------------------------------------------------- endo16_Sp_Yuh_1994          ATCTGGAACGCACAGAAATACCCCACAATCAGGTGCCCCACAAAGGCCCT
endo16_Sp_haplotype_SdrFH9  -------------------------------------------------- endo16_Sp_Yuh_1994          GATGTGAGAATGCGTGTGTGCGCGTGTGTTTGTGTGTGTGTCTCTCTCTC
endo16_Sp_haplotype_SdrFH9  ----------GCGTGTGTGTGTGTGTGTGTGTGTGTGTCTCTCTCTC
                                      *********  *  ****  ******************* endo16_Sp_Yuh_1994          TCTCTCTCTCTCACTCTCTAAGTATATCTATCTCCTTCCCCATTTTCT
endo16_Sp_haplotype_SdrFH9  TCTCTCTC------ACTCTCTAAGTATATCTATCTCCTTCCCCATTTTCT
                            ******      ********************************** endo16_Sp_Yuh_1994          CTTTCCCCCTCTGAAATATTGATAAAAAGAATACATAATTTGGGTTTTCT
endo16_Sp_haplotype_SdrFH9  CTTTCCCCCTCTCAAATATTGATAAAAAGAATACATAATTTGGGTTTTCT
                            ************ *************************************
```

Figure 10f

```
endo16_Sp_Yuh_1994          GTTGTACGCAGAAAAACCCCTAAATGTCGTATTCTTTCACAAATATTCGA
endo16_Sp_haplotype_SdrFH9   GTTGTACGCAGAAAA---CCTAAATGTCGTATTCCTTCACAAATATTCGA
                             *************   ************ ************* endo16_Sp_Yuh_1994          CTTCGAACTCATTTCCTTGCAGAAATGTGTCTCTAATCACATCCTCCTAA
endo16_Sp_haplotype_SdrFH9   CTTCGAACACATT-CCTTGCAGAAATGTGTCTCTAATCACATCCTCCTAA
                             ******   ********************************* endo16_Sp_Yuh_1994          TACATTTATGATACAATTTTATTTTAGGGAAAATGTTGTCGTCAAAATGT
endo16_Sp_haplotype_SdrFH9   TACATT-ATGATACAATTTTATTT-AAGGAAAATGTTGTCGTCAAA-TGT
                             ****  ************  **************** * endo16_Sp_Yuh_1994          ATGGGGCTCCCAACGCTTCAAAGGGGCTTTAAAGTTATCATATGAATGTA
endo16_Sp_haplotype_SdrFH9   ATGGGGCTCCCAACGCTTCAAAGGGGCTTTAAAGTTATCATATGAATGTA
                             ************************************************** endo16_Sp_Yuh_1994          ACCTAAACCTTCTGAAA-ATAATCATGATATTGGGCACTGCTGGGATGAT
endo16_Sp_haplotype_SdrFH9   ACCTAAACCTTCTGAATTACGGTCATGATATTGGGCACTGCTGGGATGAT
                             ****************   *   *************************** endo16_Sp_Yuh_1994          TTTA    (SEQ ID NO:83)
endo16_Sp_haplotype_SdrFH9   TTTA    (SEQ ID NO:84)
                             ****
```

Endo16 Flanking 4:

```
endo16_Sp_Yuh_1994          TCGGATATCGTGACATTAATTTTATAATATATCATGACATTTTTGCTGCA
endo16_Sp_haplotype_SdrFH11  TCGGATATCGTGACATTAATTT-ATAATATATGATGACATTTTTGCTTCA
                             ********************  ****  ********* endo16_Sp_Yuh_1994          TATTTTGCGGTACCGGAAGATGGTGATTTTAACATGGGGATAAAGATATT
endo16_Sp_haplotype_SdrFH11  TATTTTGCCGTACCGGAAGATGGTGATGTTAACATGGGAATAAAGATATT
                             ******  *************  *  ****** * endo16_Sp_Yuh_1994          GCATCAAGATTTGCACAAGCTCTTATTCTAATATCCACCCTTGCCCCCCC
endo16_Sp_haplotype_SdrFH11  GCATCAAGATTTGCACAAGCTCTTGTTCTAATATCCACCT-----CCCCC
                             ********************** ***********     *** endo16_Sp_Yuh_1994          CCCCCATCTGCTCCCCTCTCACTCCCTGTTTCTTTCTTCGTCGTCGTTCT
endo16_Sp_haplotype_SdrFH11  CCCCCATCTGCTCCCCTCTCACTCCCTGTTTCTT-CTTCTTCGTC-TTCT
                             ********************************  * ** endo16_Sp_Yuh_1994          TCTTATTCGTCTTCTCCTTTTCCCCTTTGTACATAT--CCCTTTCTTTAT
endo16_Sp_haplotype_SdrFH11  TCTTATTCGTCTTCTCCTTTTCCCCTTTGTACATATATCATTTTATTTAT
                             **********************************    *  ***** endo16_Sp_Yuh_1994          CCTCTCTCTCTCTCTCT--CCCCCGTTTCCATCTACACCTCCCTCTGTTT
endo16_Sp_haplotype_SdrFH11  CCTCTCTCTCTCTCTCTCTCCCTCATTTCCATTTACACCTTCCTCTGTTT
                             ***************   * * **** *** ******* endo16_Sp_Yuh_1994          CTGTTTCTGTATCTCACTCTTGTTTCTTACACTGACCCAGTTCGCACTCC
endo16_Sp_haplotype_SdrFH11  CTGTTTCTGTATCTCACTCTT-TTTCTTACACTGACCCAGTTCGCACTCC
                             ******************* ************************** endo16_Sp_Yuh_1994          CTCTTTATTTTTCCTTCACCCACACTCGATCTCTCTCTCCTGCTCTAT
endo16_Sp_haplotype_SdrFH11  CTCTTTATTTTTCCTTCACCCACACTCTCTCTCTCTCTCTCTCTCTCT
                             ***************************  ***********   **** *
```

Figure 10g

```
endo16_Sp_Yuh_1994              ATCTCTCTGTATATCTGTCTCTATGTGTGTGTGGGTGTGTGTGTGTGT
endo16_Sp_haplotype_SdrFH11     CTCCTGCTCTATATCTCTCTGTATATCTGTCTCTATGTGTGTGTGAGTGT
                                   ***** * *** * *** *   ******** ** endo16_Sp_Yuh_1994              GTGTGTGCGTGCTCTCACCTCAGCATTCTTGTGGGGTTTTAATGTGCGCT
endo16_Sp_haplotype_SdrFH11     GTGTGTGTGTG----------------TGTGTG-------TGTGCGT-
                                ***** *                **** *       ****** endo16_Sp_Yuh_1994              TCACATACCCCTTGTGAGGCATTTTACTTTGTGGGGTAATTTTTCAGGAC
endo16_Sp_haplotype_SdrFH11     ------------------GTGTCTCTCTCTCT--------CTCTCA----
                                                   *  *  ** * *          * *** endo16_Sp_Yuh_1994              CCCACAGAGTAAAGTCTTTCAAATGACTGTATATTCGGTGTCCTATGCTG
endo16_Sp_haplotype_SdrFH11     ---------------CTCTC---TAAGTATATATCTCCTTCCCTATTCT-
                                                    * * *****   * *** endo16_Sp_Yuh_1994              CGGGGCATTAGAAGTGGTACCCCATAAATGACTTTTTGTGAGCGTGTGCT
endo16_Sp_haplotype_SdrFH11     ------------------------------CTCTTTCT-----------
                                                               * * endo16_Sp_Yuh_1994              AAAACTTGCACACTTTTTTATGGGTAACATCGTAAGCACACCGCCGGGTT
endo16_Sp_haplotype_SdrFH11     ----CCCGCTCTCTCTCTCTT-----------------------------
                                    *    **  * * endo16_Sp_Yuh_1994              GTTATCGCCAGGTTGTACATACCCCACTAGTAGGGGACCACAAGGTATAT
endo16_Sp_haplotype_SdrFH11     ------------------TCTCTCACT---------CTCTAAGTATAT
                                                   *  * ****         * * * ****** endo16_Sp_Yuh_1994              CTGGAACGCACAGAAATACCCCACAATCAGGTGCCCCACAAAGGCCCTGA
endo16_Sp_haplotype_SdrFH11     CTA-----------------------------------------------
                                ** endo16_Sp_Yuh_1994              TGTGAGAATGCGTGTGTGCGCGTGTGTTTGTGTGTGTGTCTCTCTCTCTC
endo16_Sp_haplotype_SdrFH11     --------------------------------------TCTCCTTCCCCA
                                                                      **   * endo16_Sp_Yuh_1994              TCTCTCTCTCTCACTCTCTAAGTATATCTATCTCCTTCCCCATTTTCTCT
endo16_Sp_haplotype_SdrFH11     TTTTT-----------------------TCTTTCCCCCTTTTCTCT
                                * * *                         ** ****** endo16_Sp_Yuh_1994              TTCCCCCTCTGAAATATTGATAAAAAGAATACATAATTTGGGTTTTCTGT
endo16_Sp_haplotype_SdrFH11     TTCCCCCTCTCAAATATTGATAAAAGGAATACATAATTTGGGTTTTCTGT
                                ******** ************* ****************** endo16_Sp_Yuh_1994              TGTACGCAGAAAAACCCCTAAATGTCGTATTCTTTCACAAATATTCGACT
endo16_Sp_haplotype_SdrFH11     TGTACGCAGAAAA---TCTAAATGTCGTAATCCTTCGCAAATATTCGACT
                                ***********   *********  ** ********* endo16_Sp_Yuh_1994              TCGAACTCATTTCCTTGCAGAAATGTGTCTCTAATCACATCCTCCTAATA
endo16_Sp_haplotype_SdrFH11     TCGAACACATT-CCTTGCAGAAATGTGTCTCAAATCACATCCTCCTAATA
                                ****   **************  *************** endo16_Sp_Yuh_1994              CATTTATGATACAATTTTATTTTAGGGAAAATGTTGTCGTCAAAATGTAT
endo16_Sp_haplotype_SdrFH11     CATT-ATGATACAATTTTATTT-AAGGAAAATGTTGTCGTCAAA-TGTAT
                                **  ************   **************** *** endo16_Sp_Yuh_1994              GGGGCTCCCAACGCTTCAAAGGGGCTTTAAAGTTATCATATGAATGTAAC
endo16_Sp_haplotype_SdrFH11     GGGGCTCCCAACGCTTCAAAGGGGCTTTAAAGTTATCATATGAATGTAAC
                                **************************************************
```

Figure 10h

```
endo16_Sp_Yuh_1994              CTAAACCTTCTGAAA-ATAATCATGATATTGGGCACTGCTGGGATGATTT
endo16_Sp_haplotype_SdrFH11     CTAAACCTTCTGAATTACGGTCATGATATTGGGCACTGCTGGGATGATTT
                                *************  *  ******************************** endo16_Sp_Yuh_1994              TA   (SEQ ID NO:85)
endo16_Sp_haplotype_SdrFH11     TA   (SEQ ID NO:86)
                                **
```

Endo16 Flanking 5:

```
endo16_Sp_Yuh_1994              TCGGATATCGTGACATTAATTTTATAATATATCATGACATTTTTGCTGCA
endo16_Sp_haplotype_SdrFH23     TCGGATATCGTGACATTAATTT-ATAATATATGATGACATTTTTGCTTCA
                                ******************** **** ********** endo16_Sp_Yuh_1994              TATTTTGCGGTACCGGAAGATGGTGATTTTAACATGGGGATAAAGATATT
endo16_Sp_haplotype_SdrFH23     TATTTTGCCGTACCGGAAGATAGAGAT----ACATGGGAATAAAGATATT
                                ****** **********  * *    ** ********* endo16_Sp_Yuh_1994              GCATCAAGATTTGCACAAGCTCTTATTCTAATATCCACCCTTGCCCCCCC
endo16_Sp_haplotype_SdrFH23     GCATCAAGAGTTGCACAAGCTCTTGTTCTAATATCTACCTTGCCCCCCCC
                                ******* ********** ****** * * ******* endo16_Sp_Yuh_1994              CCCCCATCTGCTCCCCTCTCACTCCCTGTTTCTTTCTTCGTCGTCGTTCT
endo16_Sp_haplotype_SdrFH23     CCCCCATCTGCTCCCCTCTCACTCCCTGTGTCTT-CTTCTTCGTC-TTCT
                                ***************************   * ** endo16_Sp_Yuh_1994              TCTTATTCGTCTTCTCCTTTTCCCCTTTGTACATAT--CCCTTTCTTTAT
endo16_Sp_haplotype_SdrFH23     TCTTATTCGTCTTCTCCTTTTCCCCTTTGTACATATATCATTTTCTTTAT
                                ************************************  *  ********* endo16_Sp_Yuh_1994              CCTCTCTCTCTCTCTCCCCCGTTTCCATCTACACCTCCCTCTGTTTCT
endo16_Sp_haplotype_SdrFH23     CCTCTCTCTCTCTCCCTC----GTTTCCATTTACACCTTCCTCTGTTTCT
                                ************      ***** *** ********** endo16_Sp_Yuh_1994              GTTTCTGTATCTCACTCTTGTTTCTTACACTGACCCAGTTCGCACTCCCT
endo16_Sp_haplotype_SdrFH23     GTTTCTGTATCTCACTCTT-TTTCTTACACTGACCCAGTTCGCACTCCCT
                                ***************** **************************** endo16_Sp_Yuh_1994              CTTTATTTTTCCTTCACCCACACTCGATCTCTCTCTCTCCTGCTCTATAT
endo16_Sp_haplotype_SdrFH23     CTTTATTTTTCCTTCACCCACACTCGATCTCTCTCTC--CTGCTCTATAT
                                ***********************************  ********* endo16_Sp_Yuh_1994              CTCTCTGTATATCTGTCTCTATGTGTGTGTGGGTGTGTGTGTGTGTGTGT
endo16_Sp_haplotype_SdrFH23     CTCTCTGTATATCTGTCTCTATGTGTGTGTGGGTGTATGTGTGTGTGT
                                ********************************** ********** endo16_Sp_Yuh_1994              GTGTGCGTGCTCTCACCTCAGCATTCTTGTGGGGTTTTAATGTGCGCTTC
endo16_Sp_haplotype_SdrFH23     CTCT-----CTCTCTCTCTCTCTC--------------------------
                                * *      ***** *     * *** endo16_Sp_Yuh_1994              ACATACCCCTTGTGAGGCATTTTACTTTGTGGGGTAATTTTTCAGGACCC
endo16_Sp_haplotype_SdrFH23     ----------------------------------------TCTCTC----
                                                                        *  * ** endo16_Sp_Yuh_1994              CACAGAGTAAAGTCTTTCAAATGACTGTATATTCGGTGTCCTATGCTGCG
endo16_Sp_haplotype_SdrFH23     -----------TCTCTC---------------------------------
                                           *** **
```

Figure 10i

```
endo16_Sp_Yuh_1994           GGGCATTAGAAGTGGTACCCCATAAATGACTTTTTGTGAGCGTGTGCTAA
endo16_Sp_haplotype_SdrFH23  -----------------------------TCTCT----------------
                                                          * * * endo16_Sp_Yuh_1994           AACTTGCACACTTTTTTATGGGTAACATCGTAAGCACACCGCCGGGTTGT
endo16_Sp_haplotype_SdrFH23  --CTCTCACACTCTCT--------------AAGTA------------T
                                 ****  *                 ***  *           * endo16_Sp_Yuh_1994           TATCGCCAGGTTGTACATACCCCACTAGTAGGGGACCACAAGGTATATCT
endo16_Sp_haplotype_SdrFH23  TATCTCC---TTCCACATTCTCTCTT------------------------
                             **       ** * *   * endo16_Sp_Yuh_1994           GGAACGCACAGAAATACCCCACAATCAGGTGCCCCACAAAGGCCCTGATG
endo16_Sp_haplotype_SdrFH23  -------------------------------------------------- endo16_Sp_Yuh_1994           TGAGAATGCGTGTGTGCGCGTGTGTTTGTGTGTGTGTCTCTCTCTCTCTC
endo16_Sp_haplotype_SdrFH23  ----------------------------------TCTCCCGCTCTCTCTC
                                                                * **  * ******** endo16_Sp_Yuh_1994           TCTCTCTCTCACTCTCTAAGTATATCTATCTCCTTCCCCATTTTCTCTTT
endo16_Sp_haplotype_SdrFH23  TCTCACACACACTCTCTGAGTAT--CTACCTCCTTCCCCATTTTTTCTTC
                             ****  *  * ******      *  **************  ** endo16_Sp_Yuh_1994           CCCCCTCTGAAATATTGATAAAAAGAATACATAATTTGGGTTTTCTGTTG
endo16_Sp_haplotype_SdrFH23  CCCCCTCTCAAATATTGATTAAAAGAATACATAATTTGGGTTTTTTGTTG
                             ******  ******  ********************  *** endo16_Sp_Yuh_1994           TACGCAGAAAAACCCCTAAATGTCGTATTCTTTCACAAATATTCGACTTC
endo16_Sp_haplotype_SdrFH23  TACGCCAAAAAACA---AAATTGTGTATTCTTTCATAAATATTCGACTTC
                             ***  **         *******  *********** endo16_Sp_Yuh_1994           GAACTCATTT----------CCTTGCAGAAATGTGTCTCTAATCACATC
endo16_Sp_haplotype_SdrFH23  AAACACATTTGTTTTGAAAATTCTTGCAGAAATGCGTCTCAAATGACATC
                               * *          ******** ** * ***** endo16_Sp_Yuh_1994           CTCCTAATACATTTATGATACAATTTTATTTTAGGGAAAATGTTGTCGTC
endo16_Sp_haplotype_SdrFH23  TTCTTTATACATT-ATGATACAATTT------AAGCGAAATGTTTTCGTC
                              **  *  *****  ********        * *  ***** *** endo16_Sp_Yuh_1994           AAAATGTATGGGGCTCCCAACGCTTCAAAGGGGCTTTAAAGTTATCATAT
endo16_Sp_haplotype_SdrFH23  AAAGC-TATGGGGCTCCTAACGCCTCAGAGGGTCTT-AAAGTTATCATTT
                             *   ****** *      *********  * endo16_Sp_Yuh_1994           GAATGTAACCTAAACCTTCTGAAA-ATAATCATGATATTGGGCACTGCTG
endo16_Sp_haplotype_SdrFH23  GAATGTAACCTAAACTTTCTGAATTACGGTCATGGTTTTGGGCACTGCTG
                             *************  *****   *     *****  *   ************** endo16_Sp_Yuh_1994           GGATGATTTTA   (SEQ ID NO:87)
endo16_Sp_haplotype_SdrFH23  GGATGATTTTA   (SEQ ID NO:88)
                             ***********

Endo16_Flanking_6:

endo16_Sp_Yuh_1994           TCGGATATCGTGACATTAATTTTATAATATATCATGACATTTTTGCTGCA
endo16_Sp_haplotype_SdrFH27  TCGGATATCGTGACATTAATTT-ATAATATATGATGACATTTTTGCTTCA
                             **********************  ********  *************  **
```

Figure 10j

```
endo16_Sp_Yuh_1994        TATTTTGCGGTACCGGAAGATGGTGATTTTAACATGGGGATAAAGATATT
endo16_Sp_haplotype_SdrFH27  TATTTTGCGGTACCGGAAGATGGTGATTTTAACATGGGGATAAAGATATT
                          ************************************************** endo16_Sp_Yuh_1994        GCATCAAGATTTGCACAAGCTCTTATTCTAATATCCACCCTTGCCCCCCC
endo16_Sp_haplotype_SdrFH27  GCATCAAGATTTGCACAAGCTCTTGTTCTAATATCCACCTTG--CCCCCC
                          ********************** ************ *   ****** endo16_Sp_Yuh_1994        CCCCCATCTGCTCCCCTCTCACTCCCTGTTTCTTTCTTCGTCGTCGTTCT
endo16_Sp_haplotype_SdrFH27  CCCCCATCTGCTCCCCTCTCACTCCCTGTTTCTT-CTTCTTCGTC-TTCT
                          ********************************  * ** endo16_Sp_Yuh_1994        TCTTATTCGTCTTCTCCTTTTCCCCTTTGTACATATCCC--TTTCTTTAT
endo16_Sp_haplotype_SdrFH27  TCTTATTCGTCTTCTCCTTTTCCCCTTTGTACATATATCATTTTCTTTAT
                          ************************************ *  ********* endo16_Sp_Yuh_1994        CCTCTCTCTCTCTCTCCCCCGTTTCCATCTACACCTCCCTCTGTTTCT
endo16_Sp_haplotype_SdrFH27  CCTCTCTCTCTCTCCCTC----GTTTCCATTTACACCTCCCTCTGTTTCT
                          ************ *     ***** ***************** endo16_Sp_Yuh_1994        GTTTCTGTATCTCACTCTTGTTTCTTACACTGACCCAGTTCGCACTCCCT
endo16_Sp_haplotype_SdrFH27  GT------ATCTCACTCTTTTTTCTTACACTGACCCAGTTCGCACTCCCT
                                 ****** **************************** endo16_Sp_Yuh_1994        CTTTATTTTTCCTTCACCCACACTCGATCTCTCTCTCT--CCTGCTCTAT
endo16_Sp_haplotype_SdrFH27  CTTTATTTTTCCTTCACCCACACTCGATCTCTCTCTCTCTCCTGCTCTAT
                          ************************************  ******** endo16_Sp_Yuh_1994        ATCTCTCTGTATATCTGTCTCTATGTGTGTGTGGGTGTGTGTGTGTGTGT
endo16_Sp_haplotype_SdrFH27  ATCTCTCTGTATATCTGTCTCTATGTGTGTGTGGGTGTGTGTGTGCGTGT
                          ******************************************* ** endo16_Sp_Yuh_1994        GTGTGTGCGTGCTCTCACCTCAGCATTCTTGTGGGGTTTTAATGTGCGCT
endo16_Sp_haplotype_SdrFH27  GTGTGGGTGTG---------------------------------------
                          ***** * *** endo16_Sp_Yuh_1994        TCACATACCCCTTGTGAGGCATTTTACTTTGTGGGGTAATTTTTCAGGAC
endo16_Sp_haplotype_SdrFH27  -------------------------------------------------- endo16_Sp_Yuh_1994        CCCACAGAGTAAAGTCTTTCAAATGACTGTATATTCGGTGTCCTATGCTG
endo16_Sp_haplotype_SdrFH27  -------------------------------------------------- endo16_Sp_Yuh_1994        CGGGGCATTAGAAGTGGTACCCCATAAATGACTTTTTGTGAGCGTGTGCT
endo16_Sp_haplotype_SdrFH27  -----------------------------------TGTGTGCGTGTG--
                                                             ** ***** endo16_Sp_Yuh_1994        AAAACTTGCACACTTTTTTATGGGTAACATCGTAAGCACACCGCCGGGTT
endo16_Sp_haplotype_SdrFH27  -------------------------------------------------- endo16_Sp_Yuh_1994        GTTATCGCCAGGTTGTACATACCCCACTAGTAGGGGACCACAAGGTATAT
endo16_Sp_haplotype_SdrFH27  -------------------------------------------------- endo16_Sp_Yuh_1994        CTGGAACGCACAGAAATACCCCACAATCAGGTGCCCCACAAAGGCCCTGA
endo16_Sp_haplotype_SdrFH27  --------------------------------------------------
```

Figure 10k

| | |
|---|---|
| endo16_Sp_Yuh_1994 | TGTGAGAATGCGTGTGTGCGCGTGTGTTTGTGTGTGTGTCTCTCTCTCTC |
| endo16_Sp_haplotype_SdrFH27 | TGTGGGTGTGTGTGTGTGTGTGTGTGTGTCTCTCTCTCTCTCTCTCTCTC |
| | **** * ** ******* * ****** * * * * * ************ |
| endo16_Sp_Yuh_1994 | TCTCTCTCTCTCACTCTCTAAGTATATCTATCTCCTTCCCCATTTTCTCT |
| endo16_Sp_haplotype_SdrFH27 | TCTCTCTCTCTCACTCTCTAAGTATATCTATCTCCTTCCCCATTTTCTCT |
| | ************************************************** |
| endo16_Sp_Yuh_1994 | TTCCCCCTCTGAAATATTGATAAAAAGAATACATAATTTGGGTTTTCTGT |
| endo16_Sp_haplotype_SdrFH27 | TTCCCCCTCTCAAATATTGATAAAAAGAATACATAATTTGGGCTTTCTGT |
| | ********** ****************************** ******* |
| endo16_Sp_Yuh_1994 | TGTACGCAGAAAAACCCCTAAATGTCGTATTCTTTCACAAATATTCGACT |
| endo16_Sp_haplotype_SdrFH27 | TGTACGCAGAAAA---CCAAAATGTCGTATTCCTTCACAAATATTCGACT |
| | *************   ** ************ ***************** |
| endo16_Sp_Yuh_1994 | TCGAACTCATTTCCTTGCAGAAATGTGTCTCTAATCACATCCTCCTAATA |
| endo16_Sp_haplotype_SdrFH27 | TCGAACACATT-CCTTGCAGAAATGTGTCTCTAATCACATCCTCCTAATA |
| | ****** **** ************************************* |
| endo16_Sp_Yuh_1994 | CATTTATGATACAATTTTATTTTAGGGAAAATGTTGTCGTCAAAATGTAT |
| endo16_Sp_haplotype_SdrFH27 | CATT-ATGATACAATTTTATTT-AAGGAAAATGTTGTCGTCAAA-TGTAT |
| | **** ***************** * ******************** ***** |
| endo16_Sp_Yuh_1994 | GGGGCTCCCAACGCTTCAAAGGGGCTTTAAAGTTATCATATGAATGTAAC |
| endo16_Sp_haplotype_SdrFH27 | GGGGCTCCCAACGCTTCAAAGGAGCTTTAAAGTTATCATATGAATGTAAC |
| | ********************** *************************** |
| endo16_Sp_Yuh_1994 | CTAAACCTTCTGAAA-ATAATCATGATATTGGGCACTGCTGGGATGATTT |
| endo16_Sp_haplotype_SdrFH27 | CTAAACCTTCTGAATTACGGTCATGATATTGGGCACTGCTGGGATGATTT |
| | **************  *      ***************************|
| endo16_Sp_Yuh_1994 | TA (SEQ ID NO:89) |
| endo16_Sp_haplotype_SdrFH27 | TA (SEQ ID NO:90) |
| | ** |

Endo16 Flanking 7:

| | |
|---|---|
| endo16_Sp_Yuh_1994 | TCGGATATCGTGACATTAATTTTATAATATATCATGACATTTTTGCTGCA |
| endo16_Sp_haplotype_SdrFH28 | TCGGATATCGTGACATTAATTT-ATGATATATGATGACATTTTTGCTTCA |
| | ********************** ** ****** ************** ** |
| endo16_Sp_Yuh_1994 | TATTTTGCGGTACCGGAAGATGGTGATTTTAACATGGGGATAAAGATATT |
| endo16_Sp_haplotype_SdrFH28 | TATTTTGCCGTACCGGAAGATAGAGATGTTAACATGGGGATAAAGATATT |
| | ******** ************ * *** ********************** |
| endo16_Sp_Yuh_1994 | GCATCAAGATTTGCACAAGCTCTTATTCTAATATCCACCCTTGCCCCCCC |
| endo16_Sp_haplotype_SdrFH28 | GCATCAAGATTTGCACAAGCTCTTGTTCTAATATCCACC--TGCCCCCCC |
| | ************************ **************  ********* |
| endo16_Sp_Yuh_1994 | CCCCCATCTGCTCCCCTCTCACTCCCTGTT--TCTTTCTTCGTCGTCGTT |
| endo16_Sp_haplotype_SdrFH28 | CCCCAATCTGCTCCCCTCTCACTCCCTGTTTATCCTTCTTCTTCTAC-TT |
| | **** ************************  ** ****** ** * ** |
| endo16_Sp_Yuh_1994 | CTTCTTATTCGTCTTCTCCTTTTCCCCTTTGTACATATCCCTTTCTTTAT |
| endo16_Sp_haplotype_SdrFH28 | CTTCTTCTTCTACTTCTTCTTCTTCTTCTTCTACTT-----CTTCTTTTT |
| | ****** *** ***** *** * * ** *** *        ****** * |

Figure 101

```
endo16_Sp_Yuh_1994          CCTCTCTCTCTCTCTCTCCCCCGTTTCCATCTACACCTCCCTCTGTTTCT
endo16_Sp_haplotype_SdrFH28 CTTCTTCCTCCTCCTATTTTTCTTCTTCTTCTTCTCCTCCTTCTTCTTCT
                             * *  *   ** *      * *  * * *** * *** * **** endo16_Sp_Yuh_1994          GTTTCTGTATCTCACTCTTGTTTCTTACACTGACCCAGTTCGCACTCCCT
endo16_Sp_haplotype_SdrFH28 TTTTCTTCTTCTTCTTCTTCTTCTTCTCCTTCTTCTTCTTCTT-CTTCTT
                             ***  *  **    *   *   *  *  *    * * endo16_Sp_Yuh_1994          CTTTATTTTTCCTTCACCCACACTCGATCTCTCTCTCTCCTGCTCTATAT
endo16_Sp_haplotype_SdrFH28 CTTC-TTCTTCTTCTTCTTTTTCTTAATCGTCTTCTCCCTTTCCC-----
                             *   *   *     *  **** * * * * endo16_Sp_Yuh_1994          CTCTCTGTATATCTGTCTCTATGTGTGTGTGGGTGTGTGTGTGTGTGTGT
endo16_Sp_haplotype_SdrFH28 --CTTTGTACATATATCCCTTT-CGT--------------------TAT
                                 *    *  **                      * * endo16_Sp_Yuh_1994          GTGTGCGTGCTCTCACCTCAGCATTCTTGTGGGGTTTTAATGTGCGCTTC
endo16_Sp_haplotype_SdrFH28 CCTTCCTCTCTCTCCTCCG------------TTTCCATCTACACCTC
                             *  *  *** **  *            *   *  *  ** endo16_Sp_Yuh_1994          ACATACCCCTTGTGAGGCATTTTACTTTGTGGGGTAATTTTTCAGGACCC
endo16_Sp_haplotype_SdrFH28 ------CCTCTGT------TTCTG---------------TTTCTGTATCT
                                    *       ** *                **** * * * endo16_Sp_Yuh_1994          CACAGAGTAAAGTCTTTCAAATGACTGTATATTCGGTGTCCTATGCTGCG
endo16_Sp_haplotype_SdrFH28 CAC---------TCTTT-------------------TTTCTTACACTGA-
                             *         ***                    *    *** endo16_Sp_Yuh_1994          GGGCATTAGAAGTGGTACCCCATAAATGACTTTTTGTGAGCGTGTGCTAA
endo16_Sp_haplotype_SdrFH28 ------CCCAGTTTGCACTCCCTCTTT-ATTTTTCCTTCACCCACACTCT
                                   *  *       *  * *   *  * ****  *  *   ** endo16_Sp_Yuh_1994          AACTTGCACACTTTTTTATGGGTAACATCGTAAGCACACCGCCGGGTTGT
endo16_Sp_haplotype_SdrFH28 CTCTCTCTCTCTCTCTC--------------------TCTCCTGCTCTA
                             **  * * **  * *                      * ** * * endo16_Sp_Yuh_1994          TATCGCCAGGTTGTACATACCCCACTAGTAGGGGACCACAAGGTATATCT
endo16_Sp_haplotype_SdrFH28 TATCTCT---CTGTATATATGTCTCTAT-------------GTGTGTGT
                             ****  *    ** *  * *               *  * endo16_Sp_Yuh_1994          GGAACGCACAGAAATACCCCACAATCAGGTGCCCCACAAAGGCCCTGATG
endo16_Sp_haplotype_SdrFH28 GGG---------------------TGTGTGT---------------GTG
                                                   *                   ** endo16_Sp_Yuh_1994          TGAGAATGCGTGTGTGCGCGTGTGTTTGTGTGTGTGTCTCTCTCTCTCTC
endo16_Sp_haplotype_SdrFH28 TGTGTGTGTGTGCGCGCGCGCGTGTGTGTGTGTGTGTGTCTCTCTC
                             ** *   *  * ***** *   *********  * ******** endo16_Sp_Yuh_1994          TCTCTCTCTCACTCTCTAAGTATATCTATCTCCTTCCCCATTTTCTCTTT
endo16_Sp_haplotype_SdrFH28 TCTCCCTCTCACTCTCTAAGTATATTTATCTCCTTCCCCATTTTCTCTTT
                             **  ************** ******************** endo16_Sp_Yuh_1994          CCCCCTCTGAAATATTGATAAAAAGAATACATAATTTGGGTTTTCTGTTG
endo16_Sp_haplotype_SdrFH28 CCCCCTCTCAAATATTGATAAAAAGAATGCATAATTTGGGTTTTCTGTTG
                             ******  **************  ****************** endo16_Sp_Yuh_1994          TACGCAGAAAAACCCCTAAATGTCGTATTCTTTCACAAATATTCGACTTC
endo16_Sp_haplotype_SdrFH28 TACGCAGAAAA---CCTAAATGTCGTATTCCTTCACAAATATTCGACTTC
                             ***********    ***************  *******************
```

Figure 10m

```
endo16_Sp_Yuh_1994         GAACTCATTTCCTTGCAGAAATGTGTCTCTAATCACATCCTCCTAATACA
endo16_Sp_haplotype_SdrFH28 GAACACATT-CCTTGCTGAAATGTGTCTCTAATCACATCCTCCTAATACA
                           **    ** ***************************** endo16_Sp_Yuh_1994         TTTATGATACAATTTTATTTTAGGGAAAATGTTGTCGTCAAAATGTATGG
endo16_Sp_haplotype_SdrFH28 TT-ATGATACAATTTTATTT-AAGGAAAATGTTGTCGTCAAA-TGTATGG
                            ************* ****************** **** endo16_Sp_Yuh_1994         GGCTCCCAACGCTTCAAAGGGGCTTTAAAGTTATCATATGAATGTAACCT
endo16_Sp_haplotype_SdrFH28 GGCTCCCAACGCTTCAAAGGGGCTTTAAAGTTATCATATGAATGTAACCC
                           ************************************************* endo16_Sp_Yuh_1994         AAACCTTCTGAAA-ATAATCATGATATTGGGCACT
endo16_Sp_haplotype_SdrFH28 AAACCTTCTGAATTACGGTCATGATATTGGGCACT
                           ************  *   ***************** endo16_Sp_Yuh_1994         GCTGGGATGATTTTA    (SEQ ID NO:91)
endo16_Sp_haplotype_SdrFH28 GCTGGGATGATTTTA    (SEQ ID NO:92)
                           ***************

Endo16 Flanking 8:

endo16_Sp_Yuh_1994         TCGGATATCGTGACATTAATTTTATAATATATCATGACATTTTTGCTGCA
endo16_Sp_haplotype_SdrFH29 TCGGATATCGTGACATTAATTT-ATGATATATAATGACATTTTTGCTTCA
                           ********************  **** ********** endo16_Sp_Yuh_1994         TATTTTGCGGTACCGGAAGATGGTGATTTTAACATGGGGATAAAGATATT
endo16_Sp_haplotype_SdrFH29 TATTTTGCGGTACCGGAAGATGGTGATTTTAACATGGGGATAAAGATATT
                           ************************************************** endo16_Sp_Yuh_1994         GCATCAAGATTTGCACAAGCTCTTATTCTAATATCCACCCTTGCCCCCCC
endo16_Sp_haplotype_SdrFH29 GCATCAAGATTTGCACAAGCTCTTGTTCTAATATCCACCTTG--CCCCCC
                           ********************** ************ *    ****** endo16_Sp_Yuh_1994         CCCCCATCTGCTCCCCTCTCACTCCCTGTTTCTTTCTTCGTCGTCGTTCT
endo16_Sp_haplotype_SdrFH29 CCCCCATCTGCTCCCCTCTCACTCCCTGTTTCTT-CTTCGTCGTC-TTCT
                           ******************************** ****** ** endo16_Sp_Yuh_1994         TCTTATTCGTCTTCTCCTTTTCCCCTTTGTACATA--TCCCTTTCTTTAT
endo16_Sp_haplotype_SdrFH29 TCTTATTCGTCTTCTCCTTTTCCCCTTTGTACATATATCATTTTCTTTAT
                           *********************************   ********* endo16_Sp_Yuh_1994         CCTCTCTCTCTCTCTCTCCCCCGTTTCCATCTACACCTCCCTCTGTTTCT
endo16_Sp_haplotype_SdrFH29 CCTCTCTCTCTCTCCCTC----GTTTCCATTTACACCTTCCTCTGTTTCT
                           ************  *    *****  ** ********* endo16_Sp_Yuh_1994         GTTTCTGTATCTCACTCTTGTTTCTTACACTGACCCAGTTCGCACTCCCT
endo16_Sp_haplotype_SdrFH29 GTTTCTGTATCTCACTCTTTTTTCTTACACTGACCCAGTTCGCACTCCCT
                           ***************** **************************** endo16_Sp_Yuh_1994         CTTTATTTTTCCTTCACCCACACTCGATCTCTCTCTC----TCCTGCTCT
endo16_Sp_haplotype_SdrFH29 CTTTATTTTTCCTTCACC-ACACTCGATCTCTCTCTCTCTCCTGCTCT
                           **************** **************      ***** endo16_Sp_Yuh_1994         ATATCTCTCTGTATATCTGTCTCTATGTGTGTGTGGGTGTGTGTGTGTGT
endo16_Sp_haplotype_SdrFH29 ATATCTCTCTGTATATCTGTCTCTATGTGTGTGTGGGTGTGTGTGTGTGT
                           **************************************************
```

Figure 10n

```
endo16_Sp_Yuh_1994           GTGTGTGTGCGTGCTCTCACCTCAGCATTCTTGTGGGGTTTTAATGTGCG
endo16_Sp_haplotype_SdrFH29  GTGTGCGCGCGTG------------------------------TGTGCG
                             ***** * ***                              **** endo16_Sp_Yuh_1994           CTTCACATACCCCTTGTGAGGCATTTTACTTTGTGGGTAATTTTTCAGG
endo16_Sp_haplotype_SdrFH29  --------------TGTG------------TGTG---------------
                                           **            ** endo16_Sp_Yuh_1994           ACCCCACAGAGTAAAGTCTTTCAAATGACTGTATATTCGGTGTCCTATGC
endo16_Sp_haplotype_SdrFH29  -------------------------------------------------- endo16_Sp_Yuh_1994           TGCGGGGCATTAGAAGTGGTACCCCATAAATGACTTTTTGTGAGCGTGTG
endo16_Sp_haplotype_SdrFH29  ----------------------------------TGTGTGTGTGTGTG
                                                               **** * ***** endo16_Sp_Yuh_1994           CTAAAACTTGCACACTTTTTTATGGGTAACATCGTAAGCACACCGCCGGG
endo16_Sp_haplotype_SdrFH29  -------------------------------------------------- endo16_Sp_Yuh_1994           TTGTTATCGCCAGGTTGTACATACCCCACTAGTAGGGGACCACAAGGTAT
endo16_Sp_haplotype_SdrFH29  -------------------------------------------------- endo16_Sp_Yuh_1994           ATCTGGAACGCACAGAAATACCCCACAATCAGGTGCCCCACAAAGGCCCT
endo16_Sp_haplotype_SdrFH29  -------------------------------------------------- endo16_Sp_Yuh_1994           GATGTGAGAATGCGTGTGTGCGCGTGTGTTTGTGTGTGTGTCTCTCTCTC
endo16_Sp_haplotype_SdrFH29  --TGTGTGCGCGCGTGTGTGTGCGTGTGTGTGTGTGTGTCTCTCTC
                               **** *  ****** *** ******* ******* endo16_Sp_Yuh_1994           TCTCTCTCTCTCACTCTCTAAGTATATCTATCTCCTTCCCCATTTTCT
endo16_Sp_haplotype_SdrFH29  TCTC---------ACTCTCTAAGTATATCT-------------------
                             **         ************** endo16_Sp_Yuh_1994           CTTTCCCCCTCTGAAATATTGATAAAAAGAATACATAATTTGGGTTTTCT
endo16_Sp_haplotype_SdrFH29  --TTCCCCCTCTCAAATATTGATAAAAAGAATACATAATTTGGGTTTTCT
                               ******* *********************************** endo16_Sp_Yuh_1994           GTTGTACGCAGAAAAACCCCTAAATGTCGTATTCTTTCACAAATATTCGA
endo16_Sp_haplotype_SdrFH29  GTTGTACGCAGAAAA---CCTAAATGTCGTATTCCTTCACAAATATTCGA
                             *************   ************ ************ endo16_Sp_Yuh_1994           CTTCGAACTCATTTCCTTGCAGAAATGTGTCTCTAATCACATCCTCCTAA
endo16_Sp_haplotype_SdrFH29  CTTCGAACACATT-CCTTGCAGAAATGTGTCTCTAATCACATCCTCCTAA
                             ******  ********************************** endo16_Sp_Yuh_1994           TACATTTATGATACAATTTTATTTTAGGGAAAATGTTGTCGTCAAAATGT
endo16_Sp_haplotype_SdrFH29  TACATT-ATGATACAATTTTATTT-AGGAAAATGTTGTCGTCAAA-TGT
                             ****  ************* ************** * endo16_Sp_Yuh_1994           ATGGGGCTCCCAACGCTTCAAAGGGGCTTTAAAGTTATCATATGAATGTA
endo16_Sp_haplotype_SdrFH29  ATGGGGCTCCCAACGCTTCAAAGGGGCTTTAAAGTTATCATATGAATGTA
                             ************************************************** endo16_Sp_Yuh_1994           ACCTAAACCTTCTGAAA-ATAATCATGATATTGGGCACTGCTGGGATGAT
endo16_Sp_haplotype_SdrFH29  ACCTAAACCTTCTGAATTACGGTCATGATATTGGGCACTGCTGGGATGAT
                             ****************  *    ***************************
```

Figure 10o

```
endo16_Sp_Yuh_1994            TTTA  (SEQ ID NO:93)
endo16_Sp_haplotype_SdrFH29   TTTA  (SEQ ID NO:94)
                              ****
```

Endo16 Flanking 9:

```
endo16_Sp_Yuh_1994            TCGGATATCGTGACATTAATTTTATAATATATCATGACATTTTTGCTGCA
endo16_Sp_haplotype_SdrFH30   TCGGATATCGTGACATTAATTT-ATGATATATGATGACATTTTTGCTTCA
                              ********************  **** ********** endo16_Sp_Yuh_1994            TATTTTGCGGTACCGGAAGATG------GTGATTTTAACATGGGGATAAA
endo16_Sp_haplotype_SdrFH30   TATTTCGCGGTACCGGAAAATACTAGTAGTGATTTTAACATGGGAATAAA
                              *** ********         **************  *** endo16_Sp_Yuh_1994            GATATTGCATCAAGATTTGCACAAGCTCTTATTCTAATATCCACCCT-TG
endo16_Sp_haplotype_SdrFH30   GATATTGCATCAAGATTTGCACGAGCTCTTGTTTCAATATCCACTTTGCC
                              ******************** **  ********* *    * endo16_Sp_Yuh_1994            CCCCCCCCCCCCATCTGCTCCCCTCTCACTCCCTGTTTCTTTCTTCGTCG
endo16_Sp_haplotype_SdrFH30   CCCCCCCCCCCCATCTGCTCCCCTCTCACTCCCTGTTTATCCTTC-----
                              **************************************  *    * endo16_Sp_Yuh_1994            TCGTTCTTCTTATTCGTCTTCTCCTTTTCCCCTTTGTACATATCCCTTTC
endo16_Sp_haplotype_SdrFH30   ---TTCTTCTACTTCTTCTTTTTCTTCTTCC-----------TCCTCCTA
                                 *****   * ****  *  *** *             *  * endo16_Sp_Yuh_1994            TTTATCCTCTCTCTCTCTCTCCCCCGTTTCCATCTACACCTCCCTCTG
endo16_Sp_haplotype_SdrFH30   TTTTTCTTCTTCTTCTTCTCCTCCTTCTTCTTCTTCTTCTTCTTCTT
                              *  *    *    ***   *  * ***  *  ** * *** endo16_Sp_Yuh_1994            TTTCTGTTTCTGTATCTCACTCTTGTTTCTTACACTGACCCAGTTCGCAC
endo16_Sp_haplotype_SdrFH30   CTTCTTCTTCTTCTTCTTCTTCTTCTTAA-----------TCGTCT
                              **    *  **   *  *                  *** endo16_Sp_Yuh_1994            TCCCTCTTTATTTTTCCTTCACCCACACTCGATCTCTCTCTCCTGCTC
endo16_Sp_haplotype_SdrFH30   TCTCCCTTTCCCCTTTGTACATATATCC-----CTTTCTTTATCCT----
                              ** * **       * **   *  *         * * **** endo16_Sp_Yuh_1994            TATATCTCTCTGTATATCTGTCTCTATGTGTGTGTGGGTGTGTGTGTGTG
endo16_Sp_haplotype_SdrFH30   ---ATCTCCCCCCCCCCCCGTTTCCATCTACACCTCCCTCTGTTTCTGTT
                                 ***** *     *    **  *      *   *** * *** endo16_Sp_Yuh_1994            TGTGTGTGTGCGTGCTCTCACCTCAGCATTCTTGTGGGGTTTTAATGTGC
endo16_Sp_haplotype_SdrFH30   TCTGTAT--------CTCAC-TCTTTTTTCTTACACTGACCCAGTTCGC
                              * *** *         ***      *****     *      *   *   ** endo16_Sp_Yuh_1994            GCTTCACATACCCCTTGTGAGGCATTTTACTTTGTGGGGTAATTTTTCAG
endo16_Sp_haplotype_SdrFH30   ACTCC----------------CTCTTTATTTT---------TCCTTCA-
                              ** *                  * ** *         *  **** endo16_Sp_Yuh_1994            GACCCCACAGAGTAAAGTCTTTCAAATGACTGTATATTCGGTGTCCTATG
endo16_Sp_haplotype_SdrFH30   ---CCCACA------------------------CTCGATCTCTCTCT
                                 ****                              **** * *** endo16_Sp_Yuh_1994            CTGCGGGGCATTAGAAGTGGTACCCCATAAATGACTTTTTGTGAGCGTGT
endo16_Sp_haplotype_SdrFH30   CTCC--------------TGCTCTATAT----CTCTCTGTATATCTGT
                              ** *               * * * ***   ** * ***     ***
```

Figure 10p

```
endo16_Sp_Yuh_1994         GCTAAAACTTGCACACTTTTTTATGGGTAACATCGTAAGCACACCGCCGG
endo16_Sp_haplotype_SdrFH30 ------------------CTCTATGTGTG----TGTGGGTGTG-------
                                             * **           **  * endo16_Sp_Yuh_1994         GTTGTTATCGCCAGGTTGTACATACCCCACTAGTAGGGGACCACAAGGTA
endo16_Sp_haplotype_SdrFH30 ----------------TGTGCGT----------------------GTG
                                           *** * *                          ** endo16_Sp_Yuh_1994         TATCTGGAACGCACAGAAATACCCCACAATCAGGTGCCCCACAAAGGCCC
endo16_Sp_haplotype_SdrFH30 TGCGTG--------------------------------------------
                           *  ** endo16_Sp_Yuh_1994         TGATGTGAGAATGCGTGTGTGCGCGTGTGTTTGTGTGTGTGTCTCTCTCT
endo16_Sp_haplotype_SdrFH30 ---TGTGTGTGTGCGCGCGCGCGTGTGTTTGTGTGTGTGTGTGTCT
                              ****  *   ** * * * ********************* * * *** endo16_Sp_Yuh_1994         CTCTCTCTCTCTCTCACTCTCTAAGTATATCTATCTCCTTCCCCATTTTC
endo16_Sp_haplotype_SdrFH30 CTCTCTCTCCCTCTCACTCTCTAAGTATATTTATCTCCTTCCCCATTTTC
                           *******  *************** **************** endo16_Sp_Yuh_1994         TCTTTCCCCCTCTGAAATATTGATAAAAAGAATACATAATTTGGGTTTTC
endo16_Sp_haplotype_SdrFH30 TCTTTCCCCCTCTCAAATATTGATAAAAAGAATACATAATTTGGGTTTTC
                           *********** ********************************** endo16_Sp_Yuh_1994         TGTTGTACGCAGAAAAACCCCTAAATGTCGTATTCTTTCACAAATATTCG
endo16_Sp_haplotype_SdrFH30 TGTTGTACGCAGAAAA---CCTAAATGTCGTATTCCTTCACAAATATTCG
                           **************   ************ *********** endo16_Sp_Yuh_1994         ACTTCGAACTCATTTCCTTGCAGAAATGTGTCTCTAATCACATCCTCCTA
endo16_Sp_haplotype_SdrFH30 ACTTCGAACACATT-CCTTGCAGAAATGTGTCTCTAATCACATCCTCCTA
                           *******   ******************************** endo16_Sp_Yuh_1994         ATACATTTATGATACAATTTTATTTTAGGGAAAATGTTGTCGTCAAAATG
endo16_Sp_haplotype_SdrFH30 ATACATT-ATGATACAATTTTATTT-AAGGAAAATGTTGTCGTCAAA-TG
                           *****  ************  *************** endo16_Sp_Yuh_1994         TATGGGGCTCCCAACGCTTCAAAGGGGCTTTAAAGTTATCATATGAATGT
endo16_Sp_haplotype_SdrFH30 TATGGGGCTCCCAACGCTTCAAAGGGGCTTTAAAGTTATCATATGAATGT
                           ************************************************** endo16_Sp_Yuh_1994         AACCTAAACCTTCTGAAA-ATAATCATGATATTGGGCACTGCTGGGATGA
endo16_Sp_haplotype_SdrFH30 AACCTAAACCTTCTGAATTACGGTCATGATATTGGGCACTGCTGGGATGA
                           *****************   *   ************************** endo16_Sp_Yuh_1994         TTTTA  (SEQ ID NO:95)
endo16_Sp_haplotype_SdrFH30 TTTTA  (SEQ ID NO:96)
                           *****
```

Figure 10q

METHOD FOR IDENTIFICATION OF CIS-REGULATORY MODULES VIA COMPUTATIONAL ANALYSIS OF SINGLE POLYNUCLEOTIDE POLYMORPHISMS (SNPS) AND INSERTIONS/DELETIONS (INDELS)

RELATED APPLICATION

This application claims the benefit of priority under 35 U.S.C. §119(e) of U.S. Ser. No. 60/634,196, filed Dec. 7, 2004, the contents of which are incorporated herein by reference in its entirety.

STATEMENT OF GOVERNMENT SUPPORT

This invention was made in part with government support under Grant No. IOB-0212869 awarded by the National Science Foundation. The government has certain rights in this invention.

BACKGROUND OF THE INVENTION

1. Field of the Invention

The present invention relates generally to gene regulatory networks and more specifically to identifying genomic sequences which function as cis-regulatory modules.

2. Background Information

In bilaterian animals, such as humans, all major life processes, both developmental and physiological, are controlled by large gene networks. The gene networks that control development are of particular importance, as well as of particular complexity. These networks define each bilaterian species and lade, and they determine the ultimate inherited capabilities of the organism, since by their hardwired architecture, they define all species-specific aspects of the body plan.

Whole genome analysis has demonstrated that the most important genes utilized in development are all shared across Bilateria. These genes are the genes encoding transcriptional factors and co-factors and elements of signaling systems. Differences in the repertoire of these genes, or of genomically encoded protein domains, cannot account for the differences in body plan amongst bilaterian animals: rather, the causal explanation for particular developmental pathways lies in the regulatory connections programmed in the genome.

But as detailed functional studies have revealed the internal structure of some cis-regulatory modules, it is less clear whether much of the sequence length that is included in the relatively conserved sequences must be located between, and not within, the known transcription factor target sites. It is unlikely that base pairs located between the transcription factor target sites of cis-regulatory modules have sequence dependent function, and the mechanism that constrains evolutionary change within cis-regulatory modules is incompletely understood.

SUMMARY OF THE INVENTION

The present invention relates to identification of cis-regulatory modules in genomes by comparing selected interspecific genome sequences using statistical targeting of putative patches, which patches contain suppressed indels and SNPs in regions within such patches when compared to flanking sequences.

In one embodiment, a method of identifying a cis-regulatory module is provided, including, determining sequence similarities significantly greater than random expectation on selected genome sequences from two or more closely related species in sequences that lie outside of protein coding regions, sorting the similarities for conserved patches of single nucleotide polymorphisms (SNPs) and insertion/deletions (indels), constructing a computational map of SNPs/indels, where the SNPs/indels have occurrence rates within the patches which are suppressed when compared to flanking sequences, computing a moving window snp/indel intensity parameter based on the patches, and moving the window across a query sequence, where a putative cis-regulatory module is identified if a region in the query sequence significantly matches the window parameter. In one aspect, the computational map is from one or more closely related primate species, including where the primate is an ape, monkey, or human. In a further aspect, the method includes comparing the cis-regulatory modules based on the primate derived computational map to select genome sequences from non-primates and predicting cis-regulatory modules in the non-primate sequences.

In one aspect, the flanking regions comprise large indels having a length of at least 6-10 nucleotides. In another aspect, the suppressed occurrence rate within the patches for SNPs exhibits a decrease in frequency of about 30% to about 50% when compared to flanking sequences.

In another aspect, the method includes calculating the ratio of indels of differing lengths in transcriptionally active sequences versus flanking sequences, wherein the length of the indels is about 1 to 5 nucleotides, about 6 to 10 nucleotides, about 11-15 nucleotides, about 16 to 20 nucleotides, or greater than about 21 nucleotides. In a related aspect, the ratio of indels of about 6 to 10 nucleotides is between about 0 to about 0.7.

In one aspect, the method includes identifying disease associations in the identified cis-regulatory modules.

In another aspect, determining sequence similarity includes using a computer algorithm to compare aligned sequences.

In one embodiment, a computational map generated by the method of the present invention is provided.

In another embodiment, a library of genomic target site clusters including putative cis-regulatory modules identified by the method of the present invention is provided.

In one embodiment, a computer readable medium is provided, having computer-executable instructions for performing the method of the present invention.

Exemplary methods and compositions according to this invention are described in greater detail below.

Figure 2:
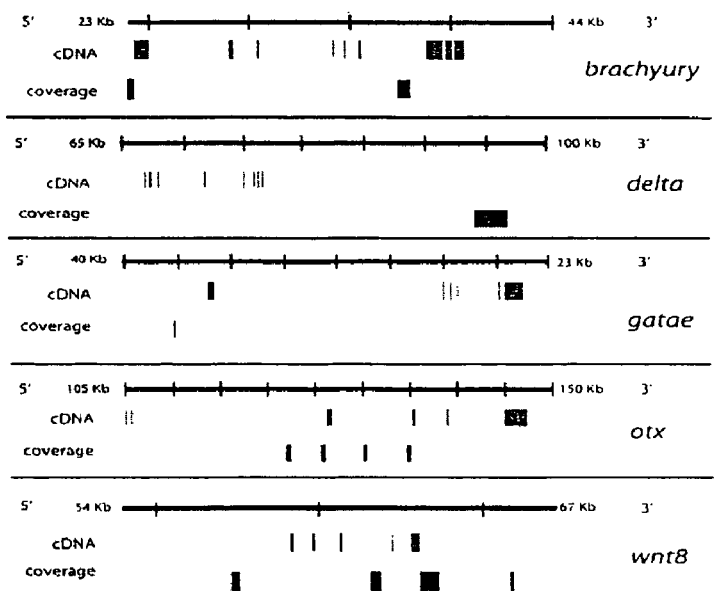

FIG. 2 illustrates the active and flanking regions converging from the *S. franciscanus* BAC sequence for the five genes mapped onto the *S. purpuratus* BAC clones with the *S. purpuratus* exon positions for reference. The genomic sequence in the *S. franciscanus* BAC is depicted in light gray for flanking regions and in dark gray for active regions. The coordinates of the *S. purpuratus* BAC are indicated in kb at the end of the black line representing the sequence. The orientation of the sequence with respect to the direction of transcription is indicated outboard of the number (5' and 3').

Figure 3:
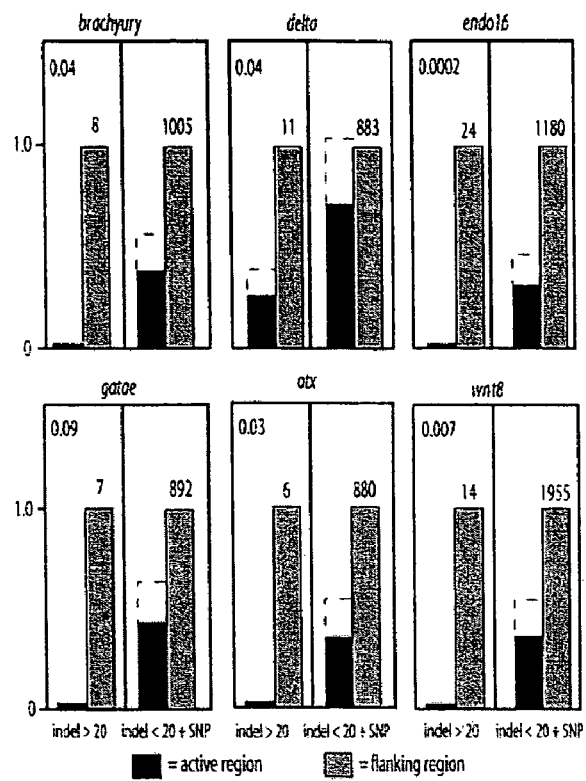

FIG. 3 shows the distribution of indels and SNPs for active cis-regulatory sequences (black) compared with adjacent inactive sequence (gray).

Figure 4:
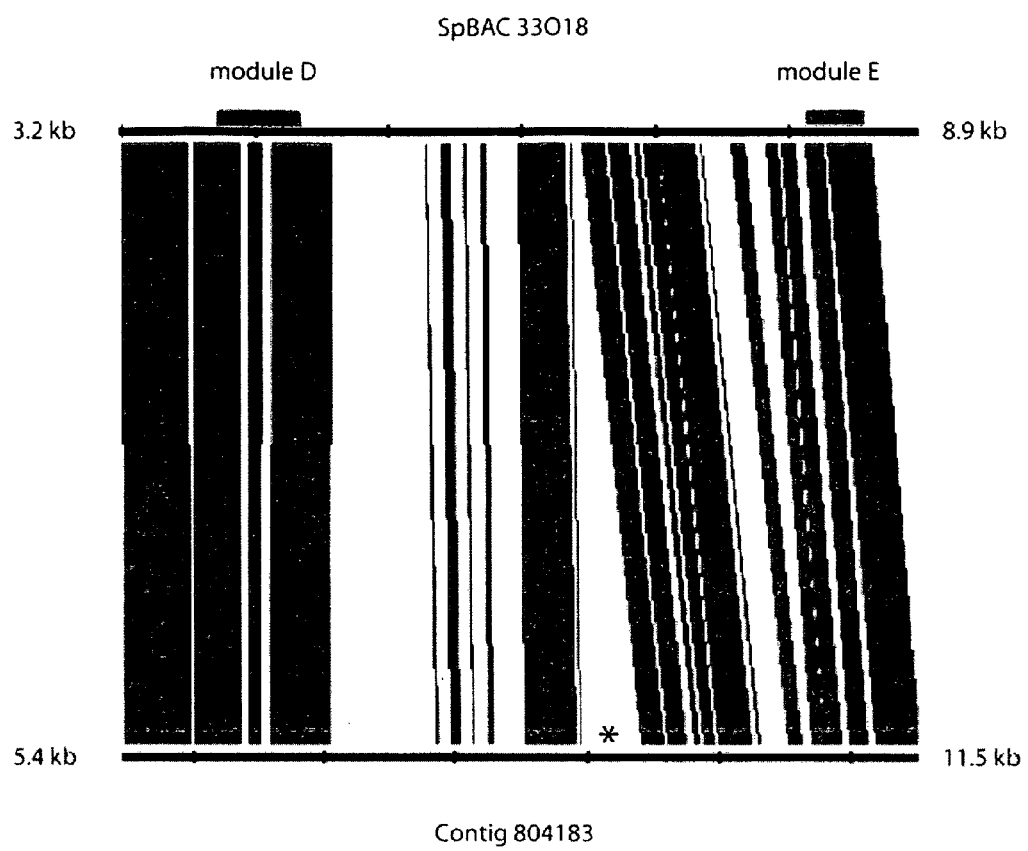

FIG. 4 illustrates the preliminary analysis of transcription factor, gcm. A PAIRCOMP analysis (window=20 bp; similarity=95%) of the SpBAC sequence and a contig obtained from the WGS assembly displayed in the region of the two cis-regulatory modules D and E shown in green. In addition to a surprising lack of sequence similarity in the region between the modules, there is a graphic example of either an insertion in the contig or a deletion in the BAC (asterisk).

FIGS. 5(*a-k*) show a sequence alignment for brachyury. The pairwise sequence alignments are used to calculate the proportion of base changes and gaps between either *S. purpuratus* and *S. franciscanus* or among a group of *S. purpuratus* individuals. The alignments are reformatted from a CLUSTALW output. In the interspecific comparisons, the *S. purpuratus* BAC sequence is the upper sequence; the lower sequence is the *S. franciscanus* one. The intraspecific comparisons for the endo16 gene use the originally published sequence as reference.

FIGS. 6(*a-o*) show a sequence alignment for delta. The pairwise sequence alignment calculations are the same as for FIG. 5.

FIGS. 7(*a-l*) show a sequence alignment for gatae. The pairwise sequence alignment calculations are the same as for FIG. 5.

FIGS. 8(*a-j*) show a sequence alignment for otx. The pairwise sequence alignment calculations are the same as for FIG. 5.

FIGS. 9(*a-n*) show a sequence alignment for wnt8. The pairwise sequence alignment calculations are the same as for FIG. 5.

FIGS. 10(*a-q*) show a sequence alignment for endo16. The pairwise sequence alignment calculations are the same as for FIG. 5.

DETAILED DESCRIPTION OF THE INVENTION

Before the present compositions, methods, and computational methodologies are described, it is to be understood that this invention is not limited to particular compositions, methods, and experimental conditions described, as such compositions and methods may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure. All publications mentioned herein are incorporated herein by reference in their entirety.

As used herein "cis-regulatory modules," including grammatical variations thereof, are the specific DNA sequences that directly regulate expression of a given gene.

As used herein "indel," including grammatical variations thereof, means insertion and/or deletion of nucleotide sequences.

As used herein "informative alignment," including grammatical variations thereof, means the appropriateness of the relative positioning of sequences that allows firm conclusions about the structure of conserved patterns to be drawn such that one region of sequence is favored over another. For example, regions with many insertions and deletions in the alignment are less informative.

As used herein, "genomic target site clusters," means sites along a given genome where transcription factors bind.

As used herein, "snp/indel intensity parameter" means the measure of SNP/indels used in a window to define similarity and statistical significance between aligned sequences. In a related aspect, such windows can be about 10 bp to about 20 bp, about 20 bp to about 30 bp, about 30 bp to about 40 bp, or about 40 bp to about 50 bp. In another related aspect, sequence similarity or homology is about 70%, about 75%, about 80%, about 85%, about 90%, or about 95%.

In one aspect, where the transcription factor target sites are not known in advance, the present disclosure provides an interspecific sequence comparison method for physically identifying putative cis regulatory modules in the intronic or intergenic DNA sequence of given animal genes. As has long seemed reasonable to assume on the grounds that they are functionally essential, these key regulatory units are evolutionarily conserved relative to flanking sequence.

The DNA of functional cis-regulatory modules displays extensive sequence conservation in comparison of genomes from closely species, as disclosed herein. Patches of sequence that are several hundred base pairs in length within these modules are often seen to be 80-95% identical, although the flanking sequences cannot even be aligned (e.g., due to a high number of indels).

In one aspect, percent sequence identity may be calculated using computer programs or direct sequence comparison. A plurality of homology search algorithms may be used to determine optimal alignment of sequences. These include the local homology algorithm of Smith & Waterman, Adv Appl Math (1981) 2:482, the homology alignment algorithm of Needleman & Wunsch, J Mol Biol (1970) 48:443, the similarity method of Pearson & Lipman, Proc Natl Acad Sci USA (1988) 85:2444, the PSI-Blast homology algorithm of Altschul et al., Nucleic Acids Res (1997) 25:3389-402, the computerized implementations of algorithms GAP, BESTFIT, FASTA, and TFASTA included in the Wisconsin Genetics Software Package, Genetics Computer Group, 575 Science Dr., Madison, Wis.), by Hidden Markov Models (HMM, Durbin, Eddy, Krogh & Mitchison, Cambridge University Press, 1998), or EMotif/EMatrix to identify sequence motifs (Nevill-Manning et al., Proc Natl Acad Sci USA (1998) 95(11):5865-71), or by visual inspection (see generally Ausubel et al., supra). Each of the above identified algorithms and the references are herein incorporated by reference in its entirety for all purposes. These algorithms are well known to one of ordinary skill in the art of molecular biology and bioinformatics. When using any of the aforementioned algorithms, the user will define parameters for "Window", gap penalty, and the like (e.g., the user can define the window-size, how window boundaries are determined, how gaps will be handled, and how absolute similarity and statistical significance will be indicated in program output). Practitioners of the art molecular biology with average skill will recognize these parameters (e.g., gap penalty is a scoring value to prevent large gaps from occurring in reported alignments).

Thus, as provided in the present disclosure, cis-regulatory modules can be detected computationally by interspecific comparison of the sequence surrounding a gene of interest, recognized as a block of sequence that has remained relatively similar between two or more species.

Such sequences may be excised by, for example, but not limited to, PCR and incorporated in an expression vector. Their function can be studied by direct gene transfer methods. In one aspect, for "closely related species," the appropriate evolutionary species distance is not so close such that unselected (i.e., "background") sequences have not had time to diverge, but the distance is not so far that the pattern of conservation has been lost by too much divergence. In a related aspect, the evolutionary distance may range from about 1 to about 5 million years, about 5 to about 10 million years, about 10 to about 20 million years, about 20 to about 30 million years, about 20 to about 50 million years, or about 50 to about 100 million years.

At the appropriate distance, cis-regulatory modules stand out from the immediately flanking background as patches of well conserved sequence that are usually several hundred base pairs in length and terminated at their boundaries by abrupt transitions to sequence that has diverged too greatly for facile computational alignment.

Cis-regulatory modules may be defined experimentally as DNA fragments that, as a whole, faithfully recreate given developmental patterns of expression in gene transfer experiments. They consist of the target sites for the transcription factors to which they respond, plus the sequence intervening between these sites.

Although interspecific sequence comparisons may reveal cis-regulatory modules as long contiguous patches of sequence that are relatively well conserved with respect to external sequences, it is not obvious why there would be deleterious effects of sequence change outside the specific base pairs that participate directly in chemical interactions with transcription factor amino acid side chains. In three dimensional analysis of DNA-transcription factor complexes, detailed mutational studies, and "selex" assays, only a few base pairs per interaction are seen to be partially or wholly constrained, and these elements are commonly confined to short sequences typically about 6 to about 8 base pairs in length. Furthermore, for well studied examples, there is direct evidence that the actual transcription factor target sites often occupy less than half of the module length. This evidence is of several kinds, including (i) oligonucleotides mapping of all specific sites of DNA-protein interaction (see, e.g., Yuh et al., Mech Dev (1994) 47:165-186), (ii) numerous reconstruction mutation studies in which modular sequences are altered without discernable effects on function except when constrained nucleotides within target sites are changed (e.g., see, Davidson, *Genomic Regulatory Systems: Development and Evolution,* 2001, Academic Publishing, San Diego, Calif.; Yuh et al., Science (1998) 279:1896-1902; Yuh et al., Development (2001) 128:617-628; and Kirchhammer and Davidson, Development (1996) 122:353-348), (iii) studies on regulatory modules of which the transacting factors are known and the sites of their interaction can be recognized in the sequence (see, e.g., Arnone and Davidson Development (1997) 124:1851-1864 and Davidson (2001)), and (iv) comparative studies on orthologous cis-regulatory modules from animals that are so distant from one another that only the transcription factor target sites are unchanged (see, e.g., Tümpel et al., Dev Biol (2002) 246:45-56; Shashikant et al., Proc Natl Acad Sci USA (1998) 95:15446-15451; Kim et al., Proc Natl Acad Sci USA (2000) 97:1655-1660; Ludwig et al., Development (1998) 125:949-958; Langeland and Carroll, Development (1993) 117:585-596; and Williams et al., Nature (1994) 368:299-305).

Though not to be bound by theory, this suggests that the target sites themselves are spaced by intervening sequences that have undergone a great deal of change during evolution. The evidence combines to exclude the idea that the observed patterns of cis-regulatory module conservation are due to functional nucleotide-by-nucleotide selection across the whole length of the module.

A mechanism that might account for what is observed is as follows. Again, not to be bound by theory, in the evolution of cis-regulatory modules, the occurrence of indels that are large enough to be likely to affect adjacent target sites might be selectively disfavored, whereas the occurrence (fixation) of single-nucleotide substitutions and small indels between transcription factor target sites is not constrained, although change within the sites themselves is, of course, constrained. It has been observed that for several cases the rate of indel accumulation in unselected sequence is sufficiently high to account for a large fraction of the total sequence change during divergence (see, e.g., Britten et al., Proc Natl Acad Sci USA (2003) 100:4661-4665; Britten, Proc Natl Acad Sci USA (2002) 99:13633-13635; and Fujiyama et al., Science (002) 295:131-134). Given these observations, the relative suppression within cis-regulatory modules of large indels but not of small indels or single-nucleotide changes gives the following predictions: (i) Comparison of two genomes just sufficiently distant so that nonselected sequence cannot usually be aligned will indeed reveal cis-regulatory modules as internally aligned, and thus apparently conserved patches of sequence, because the occurrence of large indels rapidly generates sequence that cannot easily be aligned, whereas, until it approaches saturation, the occurrence of single-nucleotide substitutions or small indels does not. (ii) Within these patches, the rate of occurrence of single nucleotide substitutions and of small (one or a few base pairs long) indels will be similar to the rate outside them after correcting for the fraction of the modules included in the actually constrained target site sequence. (iii) At greater evolutionary distance, as small changes accumulate, the apparent conservation of the module as a whole will disappear, because similarities of the unconstrained portions of the intramodular sequence will be lost, and only the transcription factor target sites themselves will be retained as conserved sequence elements.

That cis-regulatory modules can be effectively identified by detection of patchy interspecific sequence conservation consistent with prediction (i), is the starting point. Consistent [with prediction (iii)] is the observation that at great evolutionary distance, patchy sequence conservation of cis-regulatory modules can no longer be seen, even where gene transfer experiments reveal conserved target site function.

The requirements are (i) to ascertain sequence divergence within cis-regulatory modules that are already known experimentally to be functional, so that the comparison of sequences within and outside its boundaries is meaningful and (ii) that a species pair be used that is sufficiently close so that the genomic sequence can be unequivocally aligned both inside and outside selectively conserved features.

In one aspect, "selected genomic sequences" will be obtained for a sequenced target genome within which to search for the relevant cis-regulatory modules. For example, but not limited to, an insert that extends from the adjacent gene on the 5'-side of the gene of interest to the adjacent gene on the 3'-side, minus certain classes of sequence that are stripped out computationally, may serve as a selected genome sequence. In the case of clustered genes of the same family, e.g., Hox genes or some of the NK class homeodomain genes, certain sequences may not be excluded on the other side of the adjacent genes because of their associated functional consequences if deleted, but many genes of interest are unique, and are not found in paralogue clusters (i.e., homologous because of a gene duplication event).

The sequences stripped out are those exonic sequences encoding protein, direct simple sequences (mono-, di-, and tri-nucleotide repeats greater than 11 bp in length), and recognizable repetitive sequences. Repetitive sequences may be highly species-specific and in the absence of extensive genomic sequence data, may be difficult to recognize at the sequence level. However, one of skill in the art may modify this criterion to serve user specific requirements. For example, while BAC-end sequence resources deriving from various genome projects can provide a useable library of repeat elements for their associated species, only the higher frequency repeats are routinely identified. Again, this criterion may be modified by the user.

In a related aspect, for example, but not limited to, all sequence elements 500 bp long to all others within a genomic sequence are compared, looking for any sequence similarities significantly greater than random expectation. For example, the statistical significance of genome mapping may be determined by chi-square test of observed number of orthologs between genomic sequences and a randomly expected number, with respect to the smallest number of genes on these genomes. The random expectation can be calculated as a fraction of the number of orthologs on the genome of one of a first corresponding closely related species that would be expected to fall on the genome of a second species in the pair, assuming uniform distribution over all of the genes of the second closely related species. Alternatively, Hidden Markov Modeling may be used to determine the likelihood of an observation that is significantly greater than random expectation (i.e., a statistical model in which the system being modeled is assumed to be a Markov process with unknown parameters, and the challenge is to determine the hidden parameters from the observable parameters. The extracted model parameters can then be used to perform further analysis, for example for pattern recognition applications). Further, other means include Poisson metrics.

These similarities are then sorted for families of sequence elements ≧80% or 90% homologous. Thus, as data accumulates for each species, a log of both locally repeated sequence elements (e.g., within given genomic sequence) and globally interspersed repeated sequences (e.g., among genomes) is constructed. These may be flagged, or if identified clearly enough, stripped from the selected sequence. What remains of the selected sequence surrounding the gene of interest is then used as the search basis for putative/conserved patches. This will be the largely single copy sequences flanking the gene on either side, plus intronic sequences.

To annotate the sequences, sequencing may be searched preliminarily for sequenced genes identifiable by comparison with protein data banks (e.g., TRANSFAC transcription database, maintained at the GBF Brunschweig, Germany; GenBank, National Institutes of Health) and then analyzed by various annotation programs (e.g., modified Genotator; Sea Urchin Genome AnnotatoR (SUGAR); GLIMMERM, The Institute for Genomic Research (TIGR), and the like). Selected genome regions are identified then stripped.

In one embodiment, a method of identifying a cis-regulatory module is provided, including, determining sequence similarities significantly greater than random expectation on selected genome sequences from two or more closely related species in sequences that lie outside of protein coding regions, sorting the similarities for conserved patches of single nucleotide polymorphisms (SNPs) and insertion/deletions (indels), constructing a computational map of SNPs/indels, where the SNPs/indels have occurrence rates within the patches which are suppressed when compared to flanking sequences, computing a moving window snp/indel intensity parameter based on the patches, and moving the window across a query sequence, where a putative cis-regulatory module is identified if a region in the query sequence significantly matches the window parameter. In a related aspect, a computational map generated by the disclosed method is provided.

Nucleic acids so identified can be amplified from genomic DNA using established polymerase chain reaction (PCR) techniques (see K. Mullis et al. (1986) *Cold Spring Harbor Symp. Quant. Biol.* 51:260; K. H. Roux (1995) *PCR Methods Appl.* 4:S185) in accordance with the nucleic acid sequence information provided herein.

In another aspect, alignment/predictive algorithms include, but are not limited to, BLASTN (National Center for Biotechnology Information, hosted by the National Library of Medicine, Nation Institutes of Health, Bethesda, Md. FAMILY RELATIONS (FR) (see, FamilyJewels, Tools for Comparative Sequence Analysis, hosted by the California Institute of Technology, Pasadena, Calif.), CLUSTAL W (*Bioinformatics: A Practical Guide to the Analysis of Genes and Proteins*, (2001), 2nd ed., (Baxevanis and Guellette, eds.), Wiley-Interscience, New York, N.Y.), AMPS (Barton, Methods Enz (1990) 183:403-428), GENSCAN (Burge and Karlin, Curr Opin Struct Biol (1998) 8:346-354), PROCRUSTES (Gelfand et al., Proc Natl Acad Sci USA (1996) 93:9061-9066), GeneParser (Snyder and Stormo, in DNA and Protein Sequence Analysis, 1997, (Bishop and Rawlings, eds.), p 209-224, Oxford University Press, New York, N.Y.) and the like, or a combination thereof. In another aspect, comparing the putative cis-regulatory module to known cis-regulatory modules to further define SNP/indels occurrence rates is provided.

In one aspect, the decrease in frequency of SNPs is about 30% to about 50%. In a related aspect, the method includes calculating the ratio of SNPs in transcriptionally active sequences versus flanking sequences. In a further related aspect, the ratio determined is between about 0.1 to about 0.7.

In another aspect, the method includes calculating the ratio of indels of differing lengths in transcriptionally active sequences versus flanking sequences, where the length of the indels is about 1 to 5 nucleotides, about 6 to 10 nucleotides, about 11-15 nucleotides, about 16 to 20 nucleotides, or greater than about 21 nucleotides. In a related aspect, the ratio of indels of about 6 to 10 nucleotides is between about 0 to about 0.7.

In one aspect, genome wide computational maps of SNPs and indels may be constructed from the data generated by the disclosed method using closely related species, with reference to those species of interest (e.g., humans), to compute a moving window snp/indel intensity parameter as a function of position. For example, the basic idea is to slide a window across a query sequence and identify which region it matches best with each new position of the window. A query sequence is identified as a putative patch if it shows significant similarity to sequences identified in "selected genomic sequences." The program accepts a query sequence and a background alignment, and allows the user to define the window-size, how window boundaries are determined, how gaps will be handled, and how absolute similarity and statistical significance will be indicated in program output.

The unlikelyhood of the ratio given the local background can be computed, using, for example, a low order Markov model (see e.g., U.S. Pat. No. 6,772,069 and U.S. Pat. No. 6,470,277) for local background, in all regions of the genome, where unusual snp/indel ratio features of the appropriate size are stored as a look-up table that are accessed by comparing such features to the genes they are near. In a related aspect, computing a likelihood ratio via a first order Markov for the genome sequence is provided to represent the likelihood that a suppressed SNP/indel ratio will randomly occur in a sequence being analyzed.

Another aspect of the present invention pertains to expression vectors comprising a putative cis-module operably linked to at least one reporter gene sequence. "Operably linked" is intended to mean that the cis-module sequence is linked to a reporter gene sequence in a manner that allows expression of the reporter gene sequence. Reporter sequences are known in the art and are selected to determine transcriptional modulation in an appropriate host cell. (see, e.g., D. V. Goeddel (1990) Methods Enzymol. 185:3-7). It should be understood that the design of the expression vector may depend on such factors as the choice of the host cell to be transfected and/or the type of reporter desired to be expressed. Such reporter proteins include, but are not limited to, β-galactosidase, luciferase, chloramphenicol acetyltransferase, green fluorescent protein, secreted alkaline phosphatase, and the like.

Appropriate host cells for use with the present invention include bacteria, fungi, yeast, plant, insect, and animal cells, especially mammalian and human cells. Replication and inheritance systems include, but are not limited to, M13, ColE 1, SV40, baculovirus, lambda, adenovirus, CEN ARS, 2 μm ARS, and the like.

Vectors can contain one or more replication and inheritance systems for cloning or expression, one or more markers for selection in the host, e.g., antibiotic resistance, and one or more expression cassettes. The inserted sequences of interest can be synthesized by standard methods, isolated from natural sources, or prepared as hybrids. Ligation of the sequences of interest can be carried out using established methods.

In one aspect, the method further includes operably linking the putative patch region to a reporter sequence in a vector and determining whether the reporter sequence is expressed in a host comprising the vector.

In another aspect, a canonical approach is used to computationally identify target cis-regulatory modules. The stripped sequences or putative patches are subjected to two forms of a priori analysis. They are first analyzed for statistical features indicative of putative cis-regulatory modules, and likely target regions are identified and displayed on sequence coordinates. These are regions where short sequence motifs appear in clusters (i.e., multiply, within a set distance with respect either to individual motifs, and/or several motifs in combination).

In one embodiment, two algorithms can be used: one statistical, the other heuristic (using artificial neural networks, see, e.g., Hatzigeorgiou, et al., 1996. Functional site prediction on the DNA sequence by artificial neural networks. In *Proceedings of the IEEE International Joint Symposia on Intelligence and Systems*, pp. 12-17. IEEE Computer Society Press, Los Alamitos, Calif.) to identify motifs of multiple putative transcription factor binding sites clustering within shorter (user defined) lengths of sequence such that the rate of occurrence of the clusters falls outside of statistical expectations. Exact patterns or user defined degrees of variability in the putative binding sites can be used.

The putative patches can be compared to the equivalent genomic sequence of related species, and then other species. For example, relevant sequences surrounding genes of interest in rat can be compared to that surrounding the same gene in, for example, mice and then to that surrounding the orthologous gene in humans. In one aspect, computational maps are generated from one or more closely related primate or murine species. In a related aspect, the primate is an ape, monkey, or human. In a further related aspect, cis-regulatory modules based on the primate derived computational map are compared to select genome sequences from non-primates and used to predict cis-regulatory modules in the non-primate sequences or vice versa.

Such comparisons are carried out using FAMILY RELATIONS program, or the like, and the results compared to the statistically selected regions of the same sequence, with particular weight given to interspecific conserved elements that also have the desired statistical features. In one aspect, a library of putative cis-regulatory modules is provided, where the modules are identified by the method as described.

In another embodiment, oligonucleotides, or longer fragments derived from conserved patch sequences described herein may be used as targets in a library/microarray (e.g., biochip) system. The microarray, for example, can be used to identify genetic variants, mutations, and polymorphisms. This information may be used to determine gene function, to understand the genetic basis of a disease, to diagnose disease, and to develop and monitor the activities of therapeutic or prophylactic agents. Preparation and use of microarrays have been described in WO 95/11995 to Chee et al.; Lockhart et al., Nature Biotechnology (1996) 14:1675-1680; Schena et al., Proc Natl Acad Sci USA (1996) 93:10614-10619; U.S. Pat. No. 6,015,702 to Lal et al.; Worley et al., Microarray Biochip Technology, (Schena, ed.), Biotechniques Book, Natick, Mass., (2000) pp. 65-86; Rogers et al., Anal Biochem (1999) 266(1):23-30; Head et al., Mol Cell Probes (1999) 13(2):81-7; Watson et al., Biol Psychiatry (2000) 48(12):1147-56.

In one aspect, microarrays containing arrays of conserved patch sequences can be used to identify mutations or polymorphisms in a population, including but not limited to, deletions, insertions, and mismatches. For example, mutations can be identified by: (i) placing cis-regulatory module polynucleotides of the present invention onto a biochip; (ii) taking a test sample and adding the sample to the biochip; (iii) determining if the test samples hybridize to the cis-regulatory module polynucleotides attached to the chip under various hybridization conditions (see, e.g., Chechetkin et al., J Biomol Struct Dyn (2000) 18(1):83-101). Alternatively microarray sequencing can be performed (see, e.g., Diamandis, Clin Chem (2000) 46(10):1523-1525).

In another aspect, methods of the present invention can be used to generate a database of transcription target site clusters comprising low SNP/indel ratios.

In another embodiment, a conserved patch sequence or cis-regulatory module, or a complementary sequence, or fragment thereof, can be used as a probe which is useful for mapping naturally occurring genomic sequences. The sequences may be mapped to a particular chromosome, to a specific region of a chromosome, or contig, to human artificial chromosome constructions (HACs), yeast artificial chromosomes (YACs), bacterial artificial chromosomes (BACs), bacterial PI constructions, or single chromosome cDNA libraries (see, e.g., Price, Blood Rev (1993) 7:127-134 and Trask, Trends Genet (1991) 7:149-154).

The following examples are intended to illustrate but not limit the invention.

EXAMPLE 1

Methods

Genes and cis-Regulatory Modules.

The five cis-regulatory modules derive from three genes that encode transcription factors (gatae, brachyury, and otx) and two genes that encode signaling ligands (delta and wnt8). The endo16 gene, also included in the analysis, encodes a terminal differentiation protein of the endoderm. GenBank accession numbers for all six genes are listed in Table 2. The analysis of another transcription factor, gcm, can be seen in FIG. 4.

The sequences used to perform an intraspecific analysis of the endo16 gene of *S. purpuratus* were collected from several sources: (i) those determined in a previous study of the cis-regulatory modules controlling endo16 (Yuh et al. (1998) and Yuh et al. (2001)), (ii) a previously sequenced BAC insert, (iii) a contig from the whole-genome assembly shotgun assembly (GenBank Acc No. AAGJ00000000), and (iv) the sequence determined in other studies. Three active regions and nine flanking regions lying within the region 5' of the conserved A and B modules of endo16 were analyzed.

Primer Design and Sequencing from *S. franciscanus* BACs.

To obtain tracts of sequence from the genomic regions surrounding the relevant cis-regulatory modules in *S. franciscanus*, primers that lie outside the highly conserved protein coding regions were required. For each gene, alignments between the *S. purpuratus* and *L. variegatus* BAC inserts had been previously had been performed. To identify suitable conserved regions for primer design, BLASTN (Altschul et al., J Mol Biol (1990) 215:403-410) and additional FAMILY RELATIONS (FR) analyses were performed. For example, at a window size of 10 bp and a similarity of 90%, FR reveals tracts of conserved sequence easily seen in dot plots. Such highly conserved regions were taken as likely primer targets in the *S. franciscanus* sequence, because it is much less diverged from *S. purpuratus* than is *L. variegatus*. The FR routine produces a machine-readable XML file, which was used directly for computation of sets of PCR primer pairs, each of which lies in a conserved region. Primers were designed on the *S. purpuratus* sequence by using EPRIMER3, and primer pairs were selected to yield overlapping products for sequencing. Appropriate BAC inserts from *S. franciscanus* served as templates in standard PCRs. For sequencing reactions, the amplified products were gel-purified, and the PCR primers were used as sequencing primers in standard Applied Biosystems BIG DYE® (dyes designed for specialty applications that require optimal base calling adhacent to the primer and for sequencing short PCR product templates with rapid electrophoresis run modules) sequencing reactions, which were read on a 3730 DNA Sequencer (Applied Biosystems). Sequencing reads were assembled with the PHRED-PHRAP-CONSED package (see, e.g., Ewing and Green, Genome Res (1998) 8:186-194 and Ewing et al., Genome Res (1998) 8:175-185) and mapped onto the *S. purpuratus* sequence with CROSSMATCH (Gordon et al., Genome Res (1998) 8:195-202). The CROSSMATCH output was translated into XML and viewed in FAMILY RELATIONS. The assembled *S. franciscanus* sequences were primarily aligned to the *S. purpuratus* BAC sequences by using BLASTN to choose suitable regions for alignment with CLUSTTALW (Thompson et al., Nucleic Acids Res (1997) 24:4876-4882). Regions marked by long indels were examined by hand to confirm proper alignment. Identities, single base pair substitutions, and number and size gaps were tabulated from the CLUSTALW output. Approximately 30 kb of sequence was obtained by this method in the absence of any previously known tracts of *S. franciscanus* sequence. Primer-walking methods were used to fill in many of the sequence gaps and to obtain additional sequence. *S. franciscanus* genomic sequence data is as set forth in Table 3.

Sea Urchin Species.

Figure 1:
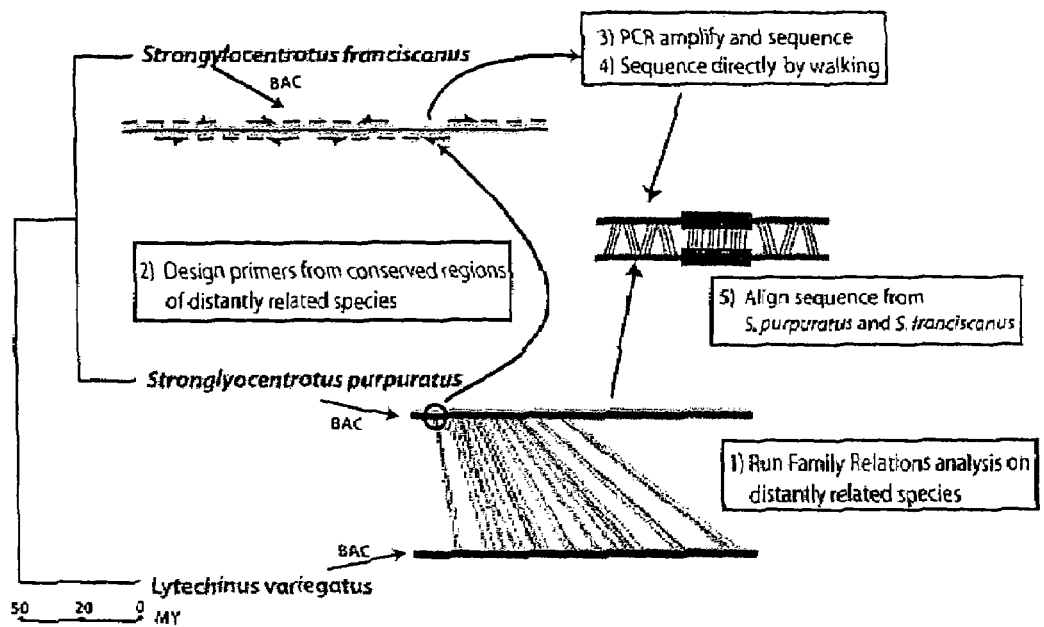
FIG. 1 shows sea urchin evolutionary distances and the sequencing method. The phylogenetic tree derived from several sources is depicted on the left side. The scale of divergence times in millions of years appears below the tree. To the right, the sequencing strategy is shown as a cartoon ("1"). A FAMILY RELATIONS comparison made between the BAC sequences of the more distantly related species, *S. purpuratus* (purple) and *L. variegatus* (green), is displayed as red lines ("2"). The conserved patches thus revealed are then used to design primers. An example of a conserved region thus used is circled, and an arrow points to the assortment of these primers used on the *S. franciscanus* BAC sequence (red) ("3" and "4"). Both standard PCR followed by sequencing and direct sequencing from the *S. franciscanus* BAC template were used with these primers ("5"). The resulting *S. fran-* ciscanus sequence was aligned with the *S. purpuratus* sequence, and the number of gaps and substitutions was tallied.

Extensive comparisons of genomic *S. purpuratus* vs. *L. variegatus* sequence around all genes included in this example revealed the conserved cis-regulatory modules to be flanked by sequence that is too divergent to be recognized. The family Toxopneustidae, to which Lytechinus belongs, is believed to have diverged from the Strongylotrotidae ~50 million years ago (Gonzales and Lessios, Mol Biol Evol (1999) 16:938-952; Littlewood et al., Philos Trans R Soc London B (2002) 347:213-234). To be able to align and compare not only the orthologous cis-regulatory modules but also the flanking, freely diverging sequence, a member of the genus *Strongylocentrotus* was used, *S. franciscanus* (Hall et al., J Mol Evol (1980) 16:95-110; Springer et al., Mol Biol Evol (1995) 12:219-230). The North Pacific radiation of the Strongylocentrotidae represented by *S. franciscanus* and *S. purpuratus*, which are today sympatric, is dated to ~18 million years ago (Gonzales (1999); Littlewood et al. (2002); Lee, Mol Biol Evol (2003) 20:1211-1221; and Biermann et al., Evol Dev (2003) 5:360-371). The adult forms of these two species are in all respects very similar, except for the brick-red pigmentation and the much larger size of *S. franciscanus*. The phylogenetic relation of all three species is summarized in the diagram of FIG. 1.

Five genes were chosen, of which cis-regulatory modules had been discovered and characterized in other studies. Although whole BAC sequences covering the respective gene regions of *L. variegatus* and *S. purpuratus* were available (see Table 1), it was necessary to obtain the desired *S. franciscanus* sequence de novo.

TABLE 1

Ordered and oriented BAC sequences for Sp and Lv BAC clones.

| Gene | Clone name | Accession number |
|---|---|---|
| Spdelta | 046A16 | AC131451 |
| Lvdelta | 129M22 | AC146987 |
| Spendo 16 | 127I21 | AC160519 |
| Lvendo 16 | 199M10 | AC160518 |
| Spgatae | 040I09 | AC146984 |
| Lvgatae | 032P20 | AC131496 |
| Spgcm | 033O18 | AC131382 |
| Lvgcm | 018J03 | AC131487 |
| Spotx | 006F13 | AC131452 |
| Lvotx | 229L05 | AC131493 |
| Spwnt8 | 041A08 | AC131383 |
| Spwnt8 | 099F11 | AC131454 |
| Lvwnt8 | 183H12 | AC131485 |

The starting point was to screen an *S. franciscanus* BAC library (Cameron et al., Proc Natl Acad Sci USA (2002)

97:9514-9518) so that genomic sequence in and around the test genes could be directly accessed. As summarized in FIG. 1 and detailed in Materials and Methods, the *S. franciscanus* sequence desired for example comparisons was obtained by two different approaches. Where the sequence similarity between *L. variegatus* and *S. purpuratus* genomes was very high (that is, in particularly conserved exons and in known and putative cis-regulatory modules), elements of these sequences in pairs of PCR primers that would be expected also to recognize the orthologous *S. franciscanus* sequence were included. The intervening DNA was thereby amplified from the *S. franciscanus* BAC and could be sequenced directly. Otherwise, the *S. franciscanus* sequence was obtained by "walking" directly on the BAC DNA, beginning with a conserved primer site. Maps of the *S. purpuratus* and *S. franciscanus* cis-regulatory and flanking sequences with respect to the exonic structure of each of the five genes are shown in FIG. 2.

Divergence Processes Within cis-Regulatory Modules and in the Flanking Sequence.

The intrageneric sequence comparisons that were obtained for the five cis-regulatory modules and their respective nearby external sequences are shown in Table 2 and FIG. 3 (sequence comparisons are available in FIGS. 5(*a-k*)-10(*a-q*)).

TABLE 2

The distribution of sequence features in the active and flanking regions of six genes.

| Gene | SNPs | Indels 1-5 | Indels 6-10 | Indels 11-15 | Indels 16-20 | Indels 21+ |
|---|---|---|---|---|---|---|
| brachyury | | | | | | |
| Active | 550.0 | 87.5 | 25.0 | 0.0 | 0.0 | 0.0 |
| Flanking | 1,498.6 | 162.9 | 32.2 | 8.5 | 3.4 | 13.6 |
| Ratio | 0.4 | 0.5 | 0.8 | 0.0 | 0.0 | 0.0 |
| delta | | | | | | |
| Active | 636.9 | 67.0 | 13.4 | 10.1 | 3.4 | 3.4 |
| Flanking | 880.3 | 111.6 | 18.6 | 15.1 | 1.2 | 12.8 |
| Ratio | 0.7 | 0.6 | 0.7 | 0.7 | 2.9 | 0.3 |
| gatae | | | | | | |
| Active | 657.0 | 33.4 | 22.3 | 0.0 | 0.0 | 0.0 |
| Flanking | 1,077.5 | 135.2 | 26.8 | 11.3 | 5.6 | 9.9 |
| Ratio | 0.6 | 0.2 | 0.8 | 0.0 | 0.0 | 0.0 |
| otx | | | | | | |
| Active | 287.3 | 62.8 | 9.0 | 0.0 | 0.0 | 0.0 |
| Flanking | 1,183.4 | 118.5 | 21.3 | 9.1 | 4.6 | 9.1 |
| Ratio | 0.2 | 0.5 | 0.4 | 0.0 | 0.0 | 0.0 |
| wnt8 | | | | | | |
| Active | 837.6 | 110.2 | 7.3 | 7.3 | 0.0 | 0.0 |
| Flanking | 2,249.1 | 165.4 | 40.7 | 21.6 | 10.2 | 17.8 |
| Ratio | 0.4 | 0.7 | 0.2 | 0.3 | 0.0 | 0.0 |
| endo16 | | | | | | |
| Active | 261.2 | 72.6 | 14.5 | 0.0 | 0.0 | 0.0 |
| Flanking | 927.6 | 117.7 | 23.2 | 13.9 | 11.1 | 22.2 |
| Ratio | 0.3 | 0.6 | 0.6 | 0.0 | 0.0 | 0.0 |
| Total | | | | | | |
| Active | 556.5 | 72.7 | 14.1 | 4.7 | 1.2 | 1.2 |
| Flanking | 1,271.3 | 133.0 | 26.7 | 13.7 | 6.4 | 14.9 |
| Ratio | 0.4 | 0.5 | 0.5 | 0.3 | 0.2 | 0.1 |

The data are arranged vertically to allow comparison of the active and flanking region values. The number in each category is normalized to the length of sequence examined. The third row for each gene is the number of features in the active region divided by the number of features in the flanking region.

Data from comparable analyses of sequence divergence in the cis-regulatory domains of the endo16 gene within the species *S. purpuratus*, has been recalculated in the same manner as that used for the *S. franciscanus-S. purpuratus* sequence comparisons obtained in this example. These results are also included in both FIG. 3 and Table 2. The endo16 gene resides in a rapidly evolving region of the genome; for example, unlike the case for all of the other genes in this study, none of the endo16 cis-regulatory modules that were identified experimentally (Yuh et al., Development (1996) 122:4045-4056; Yuh et al., Development (1996) 122: 1069-1082) display patchy sequence conservation between *S. purpuratus* and *L. variegatus* except for the proximal module A (Kirchhamer et al., Proc Natl Acad Sci USA (1996) 93:9322-9328), whereas module B is partially conserved.

Here, modules A and B were taken, for which every target site has been studied functionally in *S. purpuratus* (Yuh et al., 2001), and considered them as bona fide cis-regulatory modules; the upstream regions which contain the repressive modules F and E, part of D, and the distal booster module G (Yuh et al. ((1996)), are taken as the flanking sequence because it is entirely nonconserved to *L. variegatus*. This maneuver is a conservative one, for there could indeed be some conservation in these regions relative to true flanking sequence. Note, however, that the intraspecific divergence of these flanking regions among the 11 different individual genomes included in this example is equivalent in magnitude to the interspecific sequence divergence for the other five genes (Table 3).

TABLE 3

*S. franciscanus* sequence within and contiguous to cis-regulatory modules.

| Gene | BAC clone | Accession number |
|---|---|---|
| Sfbra | 24O17 | DQ088382 |
| Sfdelta | 35H4 | DQ088383 |
| Sfgatae | 21N5 | DQ088384 |
| Sfotx | 48I10 | DQ088385 |
| Sfwnt8 | 12H20 | DQ088386 |

This divergence was compared with that among three different alleles of modules A and B.

Comparison within vs. outside the cis-regulatory regions consistently yielded two revealing statistics. First, single base pair changes and small indels indeed occur frequently within the cis-regulatory module sequences (shown on the right side of each graph in FIG. 3). In contrast, as shown on the left side of the graphs, larger indels are almost totally suppressed inside the regulatory modules with respect to their rate of occurrence in the flanking sequence.

A simple Poisson metric shows that in five of the six cases (i.e., except for the gatae module), long indel suppression is highly improbable ($P<0.05$) on random expectation, using the rate of occurrence of the large indel class in the flanking sequence as the model expectation. Larger indels are lacking within the gatae regulatory module as well but are also sufficiently rare in the flanking sequence to obscure the inside/outside difference. Details are given for each gene in the legend of FIG. 3. These comparisons indicate that the patchy sequence conservation relative to flanking regions of the genome that is so useful for identification of cis-regulatory modules suggest two separate causes. An important qualitative difference is the near absence of large indels within conserved modules; in addition, there is typically an ≈30-50% decrease in the frequency of small changes within conserved modules, which could be due to restriction in change inside and immediately adjacent to target sites. Outside the modules, the much greater change in nearby sequence is due to not only accumulation of single-base changes and small indels but also the occurrence of large indels. Another gene in which evolution is proceeding at a particularly rapid rate is the gcm gene. Here, as illustrated in FIG. 4, there is a remarkable incidence of large indels, which distinguish two alleles recovered from different *S. purpuratus* genomes. However, these large indels again occur exclusively outside, not inside, the known cis-regulatory modules.

REFERENCES

Arnone, M. & Davidson, E. H. (1997) *Development* (Cambridge, U.K.) 124, 1851-1864.

Davidson, E. H. (2001) *Genomic Regulatory Systems: Development and Evolution* (Academic, San Diego).

Yuh, C.-H., Bolouri, H. & Davidson, E. H. (1998) *Science* 279, 1896-1902.

Yuh, C.-H., Bolouri, H. & Davidson, E. H. (2001) *Development* (Cambridge, U.K.) 128, 617-628.

Hall, T. J., Grula, J. W., Davidson, E. H. & Britten, R. J. (1980) *J. Mol. Evol.* 16, 95-110.

Altschul, S. F., Gish, W., Miller, W., Myers, E. W. & Lipman, D. J. (1990) *J. Mol. Biol.* 215, 403-410.

Rozen, S. & Skaletsky, H. (2000) in *Bioinformatics Methods and Protocols: Methods in Molecular Biology*, eds. Krawetz, S. & Misener, S. (Humana, Totowa, N.J.), pp. 365-386.

Ewing, B. & Green, P. (1998) *Genome Res.* 8, 186-194.

Ewing, B., Hillier, L., Wendl, M. & Green, P. (1998) *Genome Res.* 8, 175-185.

Gordon, D., Abajian, C. & Green, P. (1998) *Genome Res.* 8, 195-202.

Thompson, J. D., Gibson, T. J., Plewniak, F., Jeanmougin, F. & Higgins, D. G. (1997) *Nucleic Acids Res.* 24, 4876-4882.

Yuh, C.-H., Ransick, A., Martinez, P., Britten, R. J. & Davidson, E. H. (1994) *Mech. Dev.* 47, 165-186.

Kirchhamer, C. V. & Davidson, E. H. (1996) *Development* (Cambridge, U.K.) 122, 333-348.

Tümpel, S., Maconochie, M., Wiedemann, L. M. & Krumlauf, R. (2002) *Dev. Biol.* 246, 45-56.

Shashikant, C. S., Kim, C. B., Borbely, M. A., Wang, W. C. H. & Ruddle, F. H. (1998) *Proc. Natl. Acad. Sci. USA* 95, 15446-15451.

Kim, C.-B., Amemiya, C., Bailey, W., Kawasaki, K., Mezey, J., Miller, W., Minoshima, S. Shimizu, N., Wagner, G. & Ruddle, F. (2000) *Proc. Natl. Acad. Sci. USA* 97, 1655-1660.

Ludwig, M. Z., Patel, N. H. & Kreitman, M. (1998) *Development* (Cambridge, U.K.) 125, 949-958.

Langeland, J. A. & Carroll, S. B. (1993) *Development* (Cambridge, U.K.) 117, 585-596.

Williams, J. A., Paddock, S. W., Vorwerk, K. & Carroll, S. B. (1994) *Nature* 368, 299-305.

Britten, R. J., Rowen, L., Williams, J. & Cameron, R. A. (2003) *Proc. Natl. Acad. Sci. USA* 100, 4661-4665.

Britten, R. (2002) *Proc. Natl. Acad. Sci. USA* 99, 13633-13635.

Fujiyama, A., Watanabe, H., Toyoda, A., Taylor, T. D., Itoh, T., Tsai, S.-F., Park, H.-S., Yaspo, M.-L., Lehrach, H., Chen, Z., et al. (2002) *Science* 295, 131-134.

Littlewood, D. T. J. & Smith, A. B. (1995) *Philos. Trans. R. Soc. London B* 347, 213-234.

Gonzalez, P. & Lessios, H. A. (1999) *Mol. Biol. Evol.* 16, 938-952.

Springer, M. S., Tusneem, N. A., Davidson, E. H. & Britten, R. J. (1995) *Mol. Biol. Evol.* 12, 219-230.

Lee, Y.-H. (2003) *Mol. Biol. Evol.* 20, 1211-1221.

Biermann, C. H., Kessing, B. D. & Palumbi, S. R. (2003) *Evol. Dev.* 5, 360-371.

Cameron, R. A., Mahairas, G., Rast, J. P., Martinez, P., Biondi, T. R., Swartzell, S., Wallace, J. C., Poustka, A. J., Livingston, B. T., Wray, G. A., et al. (2002) *Proc. Natl. Acad. Sci. USA* 97, 9514-9518.

Yuh, C.-H., Moore, J. G. & Davidson, E. H. (1996) *Development* (Cambridge, U.K.) 122, 4045-4056.

Yuh, C.-H. & Davidson, E. H. (1996) *Development* (Cambridge, U.K.) 122, 1069-1082.

Kirchhamer, C. V., Yuh, C.-H. & Davidson, E. H. (1996) *Proc. Natl. Acad. Sci. USA* 93, 9322-9328.

Cameron et al., (2005) Proc Natl Acad Sci USA 102, 11769-11774.

Although the invention has been described with reference to the above examples, it will be understood that modifications and variations are encompassed within the spirit and scope of the invention. Accordingly, the invention is limited only by the following claims.

---

What is claimed is:

1. A method of identifying a cis-regulatory module, comprising:
   a) determining, using a suitably programmed computer, sequence similarities significantly greater than random expectation on selected genome sequences from two or more species in sequences that lie outside of protein coding regions, wherein the evolutionary distance between the two or more species is selected from the group consisting of about 1 to 18 million years;
   b) sorting the similarities for conserved patches of single nucleotide polymorphisms (SNPs) and insertion/deletions (indels);
   c) constructing a computational map of SNPs/indels, which SNPs/indels have occurrence rates within the patches that are suppressed when compared to sequences which flank the patches, wherein a suppressed occurrence rate within the patches for SNPs exhibits a decrease in frequency of about 30% to 50% when compared to flanking sequences, and wherein the flanking sequences comprise large indels having a length of at least 6-10 nucleotides;
   d) computing a moving window SNPs/indels-intensity parameter based on the patches; and
   e) moving the window across a query sequence;
   f) selecting patches in the query sequence which significantly match the window SNPs/indels-intensity parameter; and
   g) operably linking a sequence comprising a patch selected in step (f) to a reporter sequence in a vector,
   wherein a cis-regulatory module is identified in a patch in the query sequence if the reporter sequence is expressed in a host comprising the vector, thereby identifying a cis-regulatory module.

2. The method of claim 1, wherein the selected genome sequences from the two or more species extend upstream from the adjacent gene on the 5' side of a protein coding region to the adjacent gene on the 3' side of a protein encoding region.

3. The method of claim 1, further comprising comparing the cis-regulatory module to known cis-regulatory modules to further define SNPs/indels occurrence rates.

4. The method of claim 1, further comprising calculating a ratio for indels of differing lengths in patches versus flanking sequences, wherein the length of the indels in the patches is about 1 to 5 nucleotides, and the length of the indels in the flanking sequences is about 6 to 10 nucleotides, about 11 to 15 nucleotides, about 16 to 20 nucleotides, or greater than about 21 nucleotides.

5. The method of claim 4, wherein a ratio of indels of about 6 to 10 nucleotides in the patches versus the flanking sequences is between about 0 to about 0.7.

6. The method of claim 1, further comprising annotating genes as a function of the identified cis-regulatory module.

7. The method of claim 1, further comprising computationally stripping exonic sequences and simple nucleotide repeats.

8. The method of claim 1, wherein the determining step further comprises computing a likelihood ratio via a first order Markov for the genome sequences to represent the likelihood that the suppressed SNPs/indels occurrence rates will randomly occur in the genome sequences.

9. The method of claim 1, further comprising identifying disease associations in the cis-regulatory module.

10. The method of claim 8, further comprising storing suppressed SNPs/indels occurrence rates as a look-up table for comparing the likelihood ratio to regions flanking protein coding regions.

11. The method of claim 1, wherein the genome sequences from two or more species can be aligned along their total lengths.

12. The method of claim 11, wherein the determining comprises applying a computer algorithm to compare aligned sequences.

13. The method of claim 12, wherein the computational map of SNPs/indels is from two or more primate species.

14. The method of claim 13, wherein the two or more primate species are selected from apes, monkeys, and humans.

15. The method of claim 13, further comprising comparing the cis-regulatory module based on the computational map derived from the two or more primate species to select genome sequences from non-primates and predicting cis-regulatory modules in the non-primate sequences.

16. A computer readable storage medium having computer-executable instructions for performing the computational steps in the method of claim 1.

* * * * *

SEQUENCE LISTING

<160> NUMBER OF SEQ ID NOS: 96

<210> SEQ ID NO 1
<211> LENGTH: 151
<212> TYPE: DNA
<213> ORGANISM: Strongylocentrotus purpuratus

<400> SEQUENCE: 1

```
agaagagaaa agccagggtg gtcgaagttt tgtcaataaa agcccaccaa aagtcctttt      60
cattcgtgat cgccgaataa acattcgcac ttgcgacgtg aaacgagact tacgccggag     120
agaaaaggag aaagtgacga aagcaccacc c                                    151
```

<210> SEQ ID NO 2
<211> LENGTH: 145

```
<212> TYPE: DNA
<213> ORGANISM: Strongylocentrotus franciscanus

<400> SEQUENCE: 2
aaaaagccag ggtggtcgaa gttttgtcaa taaaagcccc ccaaaagtcc ttttcattcg    60
tgatcaccga ataaacattc gcacttgcga cgtgaaacga gacttacgcc gaagagaaaa   120
ggagaaagtg acgaaagcac caccc                                        145

<210> SEQ ID NO 3
<211> LENGTH: 651
<212> TYPE: DNA
<213> ORGANISM: Strongylocentrotus purpuratus

<400> SEQUENCE: 3
cttgtcaagg aaaaaaagcc tttgatctcg catctcaccg ccaataatta gtaaacaata    60
gcggagcaca tggcctatct cagcttttat agtttggact ttctttgtcg atctcttata   120
atataaactg gttatcacgc cacgcgtagt aaaagacagg cataaaactg ggcggtcggt   180
tgcctgtatt ctgttctgtt cccaaacaca atgtcccgat tatccaacgg acctttttcag  240 gttgatttta caccggtcaa ttaaaacgaa atcattgtc aaccaaacaa agggggcggc    300
gggacttcaa aggaaaaggc gctttgaagt gaagaaagaa ataatagaa atgggattcc   360 ttctttctgt aaagccctta gatgagtcat ggtgaaataa aagatgtttt atgagatagt   420
ttggaagggg ttataatgtt tccaattccg ctctggagca cataatgtat ccgttggctt   480
ttatttttat ttttatttt gagggtggca ggccagatag actttgtttg aacttcccga    540 ttttatgaa tgaaatgaac ccggtaaaat gtgaataat tgatccattg cattcttga    600 gactggcctt gttacattg ccaaattcac gatgtgattg ccggtgagaa t            651

<210> SEQ ID NO 4
<211> LENGTH: 641
<212> TYPE: DNA
<213> ORGANISM: Strongylocentrotus franciscanus

<400> SEQUENCE: 4
cttgtcaaag aaaaacaagc ctttgatctc gcatcgcacc gccaataatt agtaaacaat    60
agcagcgcac atggtctatc tcagctttta gtttggac tttctttgtc gatctgttat    120
ataaacttgt tatcacgcca cgcgtagtaa aaagacaggc ataaaactag gcggttcgtt   180
gcgtgtattc tgatccagtg ccgaacacaa tgtcccgatt atccaacgaa ccttttcagg   240
ttgattttac accggtcaat taaaacgaaa atcattgtca accaaacaaa gggggcggc    300 gggacttcaa aggaacaggc gctttgaaga aagaaaataa tagaaatggg attccttctt   360
tctgtaaagc cctttatagat gagtcatagt ggaataaaag atattttacg agatagtttg   420
gaaggggtta atgtttccaa ttccgctc tagaggacat aatgtatccg ctggcttttca    480 ttttgattt gagggtggca ggccagatag actttgtttg aactccccga tttttatgaa    540
tgaaatgaac tcggtaaaag gtagaataat tgatccattg acattcttga gacttgcctt   600
gtttacattg ccaaattcac gatgtgattg ccgttgagaa t                      641

<210> SEQ ID NO 5
<211> LENGTH: 759
<212> TYPE: DNA
<213> ORGANISM: Strongylocentrotus purpuratus

<400> SEQUENCE: 5
```

```
gtaaggaagt tttaatttat tacattttt  aacttgttag attgctacca tcatgactat      60 gatttttat  cattttaaa  gagttagata ttacaagaat atatatttt  gaagcaatgc     120 gattacccca aaatgcgttt agacgttatt taatttttag gtgttatttg atgttatatg     180
aatgctctta ttacatctca tggacttgtc aataactttg aatcttttta aatgttacaa     240
cctagacaat aagggagtcg ttctatgcaa attcaaattg tagattacta tgaatgaagt     300
aattttctta accacatgtt gattagtttg ataatctgta tggtaatggt gttgacttgc     360
tacaatattc aaacactttg atgatgttga acaattttat gcggagatgg tcttgttttt     420
agcgcataga tggacgatag aggtgaaatt tcacgtgcat ttgatgagat gctttgatat     480
tttgtttaac actatttggt attttttcat aatgttattc gtaatcaatt ttttataat      540 tatgttgcat agaagcctac tgaagatagt gtatatttct ttattaatta agtttatgta     600
aagtcataac gaagtggcat cgaacttggg gaagttataa agaaaacgac ttgaaacttt     660
ttaaggcatt acctgatgtc tattttatg gaaaacgtct ccccacactt gtttggaact     720
ttcacagttt aaaagttgg  aaaatatggt tgatcttt                             759
```

```
<210> SEQ ID NO 6
<211> LENGTH: 824
<212> TYPE: DNA
<213> ORGANISM: Strongylocentrotus franciscanus
<220> FEATURE:
<221> NAME/KEY: misc_feature
<222> LOCATION: (687)..(687)
<223> OTHER INFORMATION: n is a, c, g, or t

<400> SEQUENCE: 6
```

```
gtaaggaagt tttgatttat tacatttttc aacttgttat gtagattgct aggattcttt      60
atcatttaaa gagtttaata ttaaacgaat atatatattt tttagcaata cgtttacccc     120
atattgcatt tagacattat ttgtggcatg ctgatgttcg ttaaactata atgttcttgt     180
taaatatctt ggacttgtca ctaacttgga atcttttcaa atgttacaac ctatagaaaa     240
ttaaggaggt cattctatgc gaatttaagt tgtagacgac tataaatgaa ataactttct     300
taaccaaatg ttgattagtt tgataatctg tatatatata tatatggtaa tggtgttgag     360
ttgccacaat attcaaacac tttgatgata ttaaacaatt tcatgcggag atagactcct     420
ttttaggctt ttagcgcata gatggacgat aatagtaaac tccatatttc taagagaaaa     480
tatattgttc acctttact  tggcacttta taacaagatg ctttgatatt ttgtttgaaa     540
atatttggta ctttttcata atgttatttg aaatcaaatt tcattgatta agtgaacttt     600
atgattatgt tgtatagaag cctactgtag aagcatatag tatatatttc tttattaatt     660
gatttaatgt aaagtaaaag aagtggnatg gaatttgggg gaagtgatta aaaatgattt     720 gaagtttta aggaataccc tgatgttaaa tttatggaaa aactctcccc acacttagtg     780
tgaaacttta aaaatttaaa aagttggaat ttggttgatt tttt                      824
```

```
<210> SEQ ID NO 7
<211> LENGTH: 1461
<212> TYPE: DNA
<213> ORGANISM: Strongylocentrotus purpuratus

<400> SEQUENCE: 7
```

```
ggggtaatga attacattat tttaaaaagt aatatatctc gttgttcgtt tctcaaattg      60
atgtccatca taataatata tcgacttta  cgtcataata gccaacattt gaaataggtg     120
aaatatgttc aggttactgt atcatcttta tcaatatcac ggtttgacaa tgcttttaca     180
```

```
aaagagtatt atatagacat tagataatgt aatacgattg gattggaaat taataaagca    240
tgaacaaaga catagtcgag cattaacaga tgatgataca aagggctac atccaaggca     300 catcttgaca tgcttgtagt ccagaaatat tgagttcata acacaagtc aaatagttac     360 ttagttacaa ggaatcgaga gggggtaatg ataaggagaa atggggtggg ctttccagt     420 atagcaaacg cctcaatgcg aaagacaaaa cgaaatgtag acacaaggta gatgtgcata    480
atcacttcat gtcgacttgc taccttatgc aattaaagtc tccgaaaaac tctcatctac    540
acgatttgca cgaacacgtc ccactctctc ttcaaatatt ctccgtcaaa aaagagcaac    600
aactgaatca acatcgaaaa cctgcccagg aatatcattt ctgaagatga ataacgtaaa    660
gctgttggtt tactttctgc tcgagaattt caagtgggga taaaaactga attgattttc    720
aagggatctt tcgaaatcaa taaaaatgtg tcttattatc tgtatcactg acactttaa    780 gacgggataa gggcaaattt aatcgaggtt aaattgatta ccgtatttc gttttcccaa    840 aagaagtatc ttgattttgt caaattaaat ttagggtcga tctgcgggga atttagtttg    900
ctttcaattg tggatgtctt ttcattaaac ttgttctgac acacttatat aatgaaacgt    960
ttttgctatg aatgaatgaa tgaatgaata aaaggtttta agttattatt tatgcttttt    1020
gtttcatatg attatttctt ccttatagct ttttaagaaa taaagtcact gatggcatta    1080
tttcttcttt ttaatgaaat aatgaacatg ttttgaaaat taatgtaaaa gagtgattta    1140
tttgaaggaa tatttaacat tacagatgat aaatggaagc atttaatata ggtaaacttt    1200
atcaaacatt ttaagttgct aagcgatatt tgttcatttt aagcaaaact tatgcctata    1260
atgttcgaaa ttatgacatc tgaagatctt ataatgatga tgtcccttg tcaaagtttc    1320 ctaaattcag aaaagtaaca gtccgtcaaa aggattttt ttaacttcat catcatttca    1380
tttccatatt ctcttcttcc gttagagttt tacgatcatc atactcatta atctctctgc    1440
tcttaactac caccttaac a                                               1461

<210> SEQ ID NO 8
<211> LENGTH: 1525
<212> TYPE: DNA
<213> ORGANISM: Strongylocentrotus franciscanus

<400> SEQUENCE: 8
gggggggggg ctaataaata aattatttgt aaaagtagta tatctcgttg ttttcgtatc     60
tcatgttatt gatgtccatc ataatttaga tcgactttca cgtcataacc caaacccgt    120 ttagactgtt agtaggtgac atatgttaaa tatttattgg ttactgtatc aatttatgaa    180
taacactgtt ttacagcaca tttacaaaat agtttagaca acagaaatg atagcacgat    240 tacacatcaa caaaacacga acaagaacat aatcgtgcat tcaaaggtga ttatatagaa    300
gggctacatc ctaggcatag tttgatatgc ttgtagtcca gaaacattga tttcatcaca    360
aatattacca agtcaaatgg tttacgtaca aggaatggag agggggtaat agtaaggagg    420
gatgtggtgg gggattttcca gtataacaaa cgtttcaatg cgaaagacaa aacgaaatgt    480
agagacaagg tagttgttca gaatcactcc atgtcgactt gctaccttat ggcattgagt    540
ctccgacaaa ctctcatcta cacgatttgc acgaacacgt tccactctct cttcaaatat    600
tcaccgtcaa aaaagagtag caactgaatc aacatcgaaa acctgcccag gaatatcact    660
tatgaagatg aataacgtaa agctgttagt ttattttaag ctcgagaatt tcaagtgggg    720
ataaaagttg aattgatttt caagggattt ttcaaaatca ataaaatgtg agttattatc    780
```

```
tgtatcactg acattttaa gacgggataa gggcaaattt aatcgaggtt aacttaatta      840
tccgtatttc gtcttcccaa aagaagcgtc ttcactcaaa ttaaatttag ggtcgatctg      900
cgggaaatag cttgctttca attttggatg tcttttcatt aaagttattt tgacacacta      960
taatttatta tgataaatat ttgctatgaa tgaaataacg aatgaagggt agaaattatt     1020
tgtgctcttt gttttatagt cagtcttct ttcttagctt tttaagaaat gaattcactg     1080
atggcatttt ttttttaat gaaatgatga tcatgttttg aaaattactt taaaaaagtg     1140
atttatctga cagaattaat caacattaca gatgatgaat ggaagtatta cataaaggta     1200
aactttatca atatttaa gttgctcaac gatagtgttc gttttaagca aaacttaggc     1260
ctatggatgt tagaaattgc gatatctgaa gatcgatgac gatgacgatg accctttgtc     1320
aaagtttcct aaattcagaa aagtaacggt ccgacaaaag gattttgttc aacctcatca     1380
tgattttgtt tccatattct cttcttccaa ctcttacgat catcaagcga atgttttaaa     1440
tgaataatcg tggtaaattt tcactcaaag actttactca tcaaactagt tttattccct     1500
ctcctctcaa ctatcaccac caaca                                          1525

<210> SEQ ID NO 9
<211> LENGTH: 343
<212> TYPE: DNA
<213> ORGANISM: Strongylocentrotus purpuratus

<400> SEQUENCE: 9
acgaaaaaga gaaatttcac tttgcttatg ttatgctcat actgtatagg cgacttctgg       60
aaactttttg atcgatagaa aacatttcaa aatgaaatca gtacaaaatg aaataatact      120
tttgatactg acttcaatat gaaaaataaa aaaggccttg gaattacaac attttcatt      180 ttttgctatt tattaatgtt gcatccatca ttttaaaagt taaatgtatc ccattttgaa      240
tacgctcttg ctccttggcc ctgtttaatg ttaacccgtg catttccga gtcttggaat      300 atacccatta cattgtattc ttatctttat gttctttctc aga                       343

<210> SEQ ID NO 10
<211> LENGTH: 350
<212> TYPE: DNA
<213> ORGANISM: Strongylocentrotus franciscanus

<400> SEQUENCE: 10
acgaataaga gaaatttcac tatacttatg ttgtgcttat actgtatagg cgactttgga       60 aacttttga tcgatagaaa atattccaaa atgaaatcag aacttaatga aataacactt      120
ttggaactga cttccatata aacaattaaa aaggccttgg atttacaaca ttttaaatg      180 ttgtacttt gctatataaa tgttgcatcc agcattttaa aagttaaaaa tgtatcccat      240
tttgtatacg ttattacacc cttgcctctc tttaatgtta atccgttgat tcatcgagtc      300
ttggaatata cccattacat gttattctta tctctatatt ctttttcaga                350

<210> SEQ ID NO 11
<211> LENGTH: 540
<212> TYPE: DNA
<213> ORGANISM: Strongylocentrotus purpuratus

<400> SEQUENCE: 11
agtaagtata aacatatttc ataatcaata tatcatttca aaactcttat taagttctgt       60
tttcccttct ctttctcaaa gtcttatccg atcaatatta cccattacct agaaaatatt      120
tgtatgtttc aagactagta ttggaaaaat gttaataaat gtctttcaca cagctataaa      180
```

```
acaaacgttt agttctattg ttatgtcaaa gttcttgaat agatttgtat atatttctta      240
atgtgtatat tgttattatc attgtatgtt atctacatga cattgtctga caatagtaat      300
cggtctttaa attacaagag caatttacat gtaagaagaa agtcaacgtc gttaaaatcg      360
ttttgggaat cgcgatgata tattttatca cctgacgaag tgtagcagct gcacacgaac      420
cgtcgtgatc ttttagatcc cttgttgacc gtacattgcg agacaaacga atgtcactag      480
cgatattatt ttcgataaat tttcttattt cctgttcatt ttattttatt ttcaagtaga      540
```

```
<210> SEQ ID NO 12
<211> LENGTH: 430
<212> TYPE: DNA
<213> ORGANISM: Strongylocentrotus franciscanus

<400> SEQUENCE: 12
```

```
agtaagtata aacataatcc ataatcaata tattatttca aaacccttaa gttctatctt       60 ccctttctctt tctcaaagtc ttatctgatc aattacctag aaaatatttg tatgttgaaa     120
cttgaaagtg ttgaaaaatg ttaataagtg tgtttcacgc agctataaaa cagacgttta     180
gttcgattgt tatatcaaag ttcttgaata gctttatatt tattttgtaa tgtgtatatt     240
gttattatcg ttgtatgaaa tctacatgaa atcgtcttat catatagagt gataataatc     300
ggtctttaaa ttacaagtgc aagttacatg tagaagaaag ccaacatgga ttaaatcttt     360
ttgggggaat tgcgatgatt ctaattatat atccttattt cctgtttcat ttttattccc     420
tttatgagga                                                              430
```

```
<210> SEQ ID NO 13
<211> LENGTH: 41
<212> TYPE: DNA
<213> ORGANISM: Strongylocentrotus purpuratus

<400> SEQUENCE: 13
tgtaagtatt cgaggttttc tctcacaatc actaaataga t                            41
```

```
<210> SEQ ID NO 14
<211> LENGTH: 41
<212> TYPE: DNA
<213> ORGANISM: Strongylocentrotus franciscanus

<400> SEQUENCE: 14
tgtaagtatt cgaggttcat tctcacaatc atcaaatgga t                            41
```

```
<210> SEQ ID NO 15
<211> LENGTH: 1093
<212> TYPE: DNA
<213> ORGANISM: Strongylocentrotus purpuratus

<400> SEQUENCE: 15
```

```
ctgctaataa caaggtaatc aaaccgcatt aataatgcaa ggcgctctac atcaaacgaa       60
atcttattgg ggagacccctt tccgatttct ataactcgaa cgagcacatt aaacggcgac    120
gctttgtaga attgatgatg acacagatac agacgtatgg gacagtgatt gcggtccaca    180
gaccacccta ttagcaacca aactaaagcc cgtgtaacaa taagagata tcgttaaatt      240 aacgccataa attccagtcg gaaaccaatg ctgtatatgg ggggtattgg taaataaggt    300
gtgacgtcaa cgcaagctgt cataaaaagc gctagccttt tgacacatta aatgagtggt    360
ttgatttcag aattgaaata catttttttat tggaacgagc agtgggatt tggtagaaaa    420
```

```
aatatcaaac gaaaacattc cccagtgaac tctgacttac atttgaatgt attcgacgac    480 accatttttaa aaatgcttac tttgtactct agataaaccg ataattgttt agatccaaat   540 atccttttcga ccatcccccc aaattcgaga cagtcatgat cgcaccactc cctctcattt   600
ctcaaagtct gaatctcttt gttttgtgat tattttgtgt atgtcatccg attatttact   660
atttcttgat gagaaagtaa gggtattacg gtattacaaa acatgcaca aacattaaaa   720 tcatacccctt ttactccttt gaaactcacc tttgaattca atttttcaaa attcatcttt   780
ataaaaactt gaaataatt gaatgtttgg cagtatcact tgataacaac agctgaatcg   840
atttgttttg tcggtgtcaa ttttataatt gtgaagaaaa agtactagtt tgtttaaatg   900
attttgtcgt ctggctctta ccagcacaaa tatatatttg gcgaaaattg tcattctcgt   960
ataggcctat attactttgt agttgttgaa ttttgaata gttagatttt caccccataa  1020
cctaactact tgattaatgt ttaagttcgt tgagcgggga atcatatagc atcccacaat  1080
aacaacgcaa atc                                                     1093

<210> SEQ ID NO 16
<211> LENGTH: 1188
<212> TYPE: DNA
<213> ORGANISM: Strongylocentrotus franciscanus

<400> SEQUENCE: 16
ctgctaataa caaggcaatc aaaccgcact aataatgcaa ggcgctctac atcaaacgaa     60
atcttatggg gagagccttt ccgttttctt taactcaaac gagcacatta aacggcgtcg    120
ctttatagaa ttgatgatga cacagataca cacgtatggg actgtcattg cggtgcacgg    180
accaccctat tagcaacgaa actataggcc gtgtaacaat gaagagctat cgtaaaatta    240
acgccataaa ttccagtcgg aaaccaatgc tttatatggg cggtattggt aaataagaat    300
gtgacgtcaa cgcgagctgt cataaaaaaa cgctagcctt ttgacacttt aaatgagtgg    360
tttgatttca caattgaaag attgttttttt tattggaacg agcagcgatt tgggtagaaa    420
aaaatatcaa acgaaaacat tcgccggtga acttttgactt acattagaat gtattcgacg    480
aaaccattct aaaaatgctt acttttttact ctaaaaaaaa aagaagataa ttgtttagat    540
ccaagtctcc tttcgtccct tcccccaaat tcaggacaga catgatcgcg ccactccctc    600
tcaattctcc aagtctggac ctcttttgttt gttttttttt tttttaatgt taaccgatca    660
tttcttattt cttgaagaaa aagtaaaaaa caaaaactct tactaaaatt tctcggaata    720
tgattaatgg ttttttttta ttttaaaaca ttataacaaa accatgcaca aactttcaaa    780
atcatacccc gcttactcct ttgaaagtcg actttgaatt catttttttt taatgcatac    840
atcatctgtt atgttaatga accagtagaa tgaatcaata tttggcagta atataatcat    900
ttaacagcag ctgaattgat ttgttttttc agtgtcaatt ttgttaatgg ttaaaacaat    960
tcaagtacta gtttgttttt aaatgaattt gtcgtattgc tctttttacca acaaaaatat  1020 atatttggcg aaaaatgtcg attccgtgtg tggtaggcct ataactttgt agttgttgaa  1080
attttgaaca gattgaattt tactcacatc cttaaactcc ttgcattatc aaagtttaag  1140
ttcgttgaga ggggaatcct atagcatccc acaataacaa cgcaaatc              1188

<210> SEQ ID NO 17
<211> LENGTH: 730
<212> TYPE: DNA
<213> ORGANISM: Strongylocentrotus purpuratus

<400> SEQUENCE: 17
```

```
tgggtccagg gggtgtttca caaagatcct aacttgaact tatctctaag ttggactaat      60
caattatgga aagccgttgg cattgatgaa atatttttgt aaaagttatc ttaaaaggca     120
taaaatgttg attcgaatca ttcatatttt ctattatgaa ggagatttca tgttcttgac    180
gtgaaattta taagagtctt aagatacttg aattttcgct tttgaatata ttttattttta   240 aggctgcaaa tggctctcca aaatgttgaa gtctcaagag ttaagttcga tttaggatct    300
ttgtgaaaca cccccagtat tagtaatgaa tttagtagat tgtgacccct gctattgaat    360
aattacgctc gaacatgact tgtaacatca atgttcccag ttttatcata aagtaatgtc    420
aatgacaagc acctcgcgct gtacgaacat ctcttcaaaa ttaatttctt cgttttccat    480
ctttaaaaaa aaaaccctt tcatcttacc ctaatattct ttatttaggc cctatacgtg     540
ttttccttct atatcttgta ttgttgagca tttggatttt attaatgttg tgtttttgat    600
tcataaaata taaacaagca aggatgtgta atttcatat ttttgttggt gcattatcgg     660
tacatttggg gaagattgat tgttgtact tacagttaaa gtcaaattat tttgtttctt     720
ttttgattta                                                            730

<210> SEQ ID NO 18
<211> LENGTH: 536
<212> TYPE: DNA
<213> ORGANISM: Strongylocentrotus franciscanus

<400> SEQUENCE: 18
tgggtccaga cttcgtaaag aatttggtag attgggacct ctgatgtaac cacatttata    60
aaatcatatt ctcatttact ctgaaatact tgttccttga tcatgtaaca tcaatgttca   120
tagtttcatc ataaagtaac gtcaaattat cgaattataa agaataaatt gttgctgcaa   180
atttcttaat ttcttcaaa tgtaatttga tttaaattgt cacttttgca ctgcaatcag    240 atttcagga tgccatgaaa cagatatatc gttacaaaga agtctataaa atacgcttca    300
tctcatcaat gacaacgacc tcaaactgta caatataat cgctctgaaa cagattcttc    360
gttttccata tgtcttttaa cgcgtttatc ttaccccact aatctttata cctttgtttt    420 ccttatttt ctgttattgt tgaacatttg gagtttactc attttgtata tttgggaaag    480
attgatttgt tacactttag ttattgttaa gttattttttg tttctctttc gattta        536

<210> SEQ ID NO 19
<211> LENGTH: 933
<212> TYPE: DNA
<213> ORGANISM: Strongylocentrotus purpuratus

<400> SEQUENCE: 19
tttgatcaat tggcagaata caataaacct ctgggaataa ctaaggttat ttttttaggg   60
tgaagtttcc tttaaattca tattggcaag gtatttactt cgagcatgaa agatgattat  120 tgaacccttta taaacccga acgctattaa acaaccagct taaaaagtga tctgagactg   180
aaacctccat gaagatgagt atatgtcaac cgcctggatt cgtctctctg cttggatatt   240
atttcaaatt taggcctacg acatgaatcg ttccaaaaaa gggccacaac ttagtgagga   300
gttatagtgc attgattata ttagtgcaat atcggcacgc ataaactttc aggacaagat  360
atttatatag ggctaaagtg atcccaaaca ttgtttatca aaatggcaac aataataaat   420
atctgacatt gttctaatac tattcaatgt ctctgaaaac aatatacatg gctagaaact   480
tagttgaaaa gttgaaatat gcaacatttt aatcgcactt cgaacctctc aatgtgttgc    540
```

```
caatttaaga attttaagcc ttatttcctt tttttgttaa ttcctggtat cgaacgcagt    600
atggttatgc acagagatgg gtacattgtg tgcagaaatg tttacccttt ctagtcattc    660
atccggtata atttttaag gctctgaatc gaacgttatt aagccaaaac aaaaaatgtg    720
gaagttttca tgaaagggtt taagagaaga aaaagtttg taaagagctt tctccttagt    780
ttgttttagg ggccatctac tatacaaacc tgatctcacc tgggctttat ttacacgatg    840
actaattcaa actttgtctc aggctcttct tctctttacg atgtatagcc tctttccttt    900
tattgttccc gggttctttg acgtaccatt tta                                 933
```

<210> SEQ ID NO 20
<211> LENGTH: 883
<212> TYPE: DNA
<213> ORGANISM: Strongylocentrotus franciscanus

<400> SEQUENCE: 20

```
tttgttcaat tggcaagaat ccaataaatt tttgagaata ataattgat ttcttggggt     60 gaggtttcat ttcaatttaa attggcaagg cttcttcg agcccgaaag atgattattg    120
aaacctaatg aaaatcaaaa cgctattaaa caaccagctt aataagtaat ctgaaactga    180
ttaatagacc tctataaaga tgactttatt tcaaccttct ggattcgtct ctctgcttag    240
attttatttc aaacttaggc atacgacatg aatcgataca aaaggggcc acaacttagt    300 gaggagttat ggcaccttga ggcaatattg gcaaacataa acctcctgga caggatattt    360
tatatatagg gctaaacaga tcacaatcat gttgttcttc aaattgacaa cactaataat    420
tatctgacat tgttctaata aaatgtaatg tctctgaaaa cattatacat ggctagaaac    480
tttgttggaa aattgaaaaa tgtcaaattt tgatccaatt ttgaacttct taatgtggta    540
ccaatctaat aattttaagt ttttttttt aattcctggt atctagggca gtatggttat    600
gcagcaatga tgggtgcagt gtgtgcagaa attttcaca ctctactcat gcatctggtt    660
tgatttctaa cgctctgaat catgaaaggg tttaagagaa agaaaaagt tttaaaagag    720 ctttctcctt cgtttgtttt acgggccatc tactatacaa accaagtctc acagggctt    780 tatttacccg gtgactaatt caaacttcgt ctaaatgttc ttctctttac gatgtagcct    840 tttcccttt attgttcccg ggtcccttg acgcacccat ttt                       883
```

<210> SEQ ID NO 21
<211> LENGTH: 2984
<212> TYPE: DNA
<213> ORGANISM: Strongylocentrotus purpuratus

<400> SEQUENCE: 21

```
catgccaaca tgaagatgca cacgggtgaa tctcaacgtg cacttagtgg aacgagattt     60
cggaaagaaa acaccaagaa ctcgtcaagc ttctgctttg attggaacag caggctttcc    120
tcaagttttt gttcaatcc ccttttcgca tctaataatc attctttgtc tgaacttcat    180
aaaatgtaga gtagtcttga gttggatgtg agatgagaaa ggagaaagat aagtaaaata    240
tgatatcatg agacatgaag aacaaaagaa aaaaggaag ggggttgggt taagtgttgg    300
tgagggcatt ggattaccag ataaaacttg cacgtacatc acatccactt caacaaaaca    360
tcaaccttcg gatgttgaat aggggatcgg agaaggtcga gtcctatccc atcaaaatac    420
taggaagtca catgacagac tgataaacaa gacagttatc caaatcattc catgagttca    480
agcagcgtgc aatcacgtgt taatgaagca tcaacatagt gatgccaacc acaaaaatta    540
tggcgcccct tatactatgt ctacagtgaa cacccgtttc cattattcaa tgaatctatg    600
```

-continued

```
ctatgagttc gtctttacca atgacactta gcaggatcca tctgaaaggt acaaatttaa    660
tcctcatata cacccacata ctaaatatta tagactttgg tgttgccttc ttagaattct    720
ttccccttca tagaaattgg taaatgcgaa caagcaatct ccgtttattg atcactattc    780
tgtgattgtc gtctgtctga ctcactcact cccacaccta gttcatgcag aagcgcgcaa    840
accataatat tagcacacct ttatttcaaa gcaaggaaac ttcctattaa gacttgtgca    900
tgctaatctg gacttcaatt catattattt cttttgtaa tcatggtaat gaccttagtt    960
atttgactcc ccgtaaaaat aatcgtacaa ttggtcgaaa atttgtgagc aggaaatggc   1020
cgatgacctg tgaatatggg tgacgaaagg aacgattaga atcaatgttc tttccacatg   1080
gtttgaacag gcgacctgac aatgaccgaa tgagtgagtt ccgattgaca aatgtatctt   1140
ttcagactat aattatagca ccattcatcc attgaaaaac aatgtaattc attttcccct   1200
tatgattttg tttagaaaca tatcatcatc atctttaatg ggagtgtgct cagtaaatga   1260
aaattgggag aaggtacaga gaatattttg aactattgtt aaagattttg cattattatg   1320
gacaataaca ttgaaaacaa tagggttttg gctgcacgct cttccatcgt attatttct   1380
gttttatct tttgaagtct agctgactaa atttcagaga atgagaaaga ccaacaacaa   1440
caaatcagta agaaaaatac catttgatta ttcaaacttg atctggtcaa catgaatacg   1500
cggctccttt actcgtttct tactatatat attcataata agtcatgtta tcagtactct   1560
tctttctaaa gccagtattg aatttgtttt cttggtcatt tgtattctca ttgcttcatc   1620
tggtttgttc ttctctgtga ttgtgttttg aaatcagaga tgcctgatct caaaatgaaa   1680
ttaaaatgag aagaattgat gaatagctat catgcacaat agattcgcgt gaagaataga   1740
tcgaagatta tgttacagcc aacttcgtga cgtcgaattg gcaacagctt tgtattaagc   1800
tgctatcgat cataagtcac atgatctagt ttaccttgac accggtagca tttcgtctgg   1860
ccgtcaaatt atgtcaacct caagacaacg atcgtttgca gacgaccttt aattacaatc   1920
gcttttgttc tcatgtattc atcgacattt actaatcgaa taatgagtat tccaatcgca   1980
agaggcctat gtaatgctat cttgagtagg ccaaatctgt aagcgatcaa acgcgaaatc   2040
agaagacaaa aagggtttgt ttttgtctaa ttttatgaaa gcattttttc ttatgtgatc   2100
gcttaacatg gttcccgcca aaaccaacgg gcgccaaaca gagtgaatct gatgatgcag   2160
ctgcaatgct tcacatctcc gacttgacta gatttctctc caaatcatcg gccatggtgg   2220
gatgatcaga acaatgcac agtcattcgt ccatctcagg aaactgagag aataaaaaaa   2280
aggggaaaag gggaagaagt gacaattggc atggatgata tgcagccaat gcatgacgac   2340
tcacaaaaga caccatttcc ctcatctcgc gtgctatctt tgctctgagg atgaaccta   2400
gtgatcaagc taccttgacg atgtgctgat tgtggtttgc attcatgctc ataaatagac   2460
gtcaaggtat tcatatcata tcacccgttc tctattcatt acaaaatctt ctctctaaac   2520
tgccaccaga gattaccatc ccgccctaac cgtataatta gctgccttt ccagcaagct   2580
ttatggcggc atggcgacaa agtgtaactt ccggcgcgag ccactcacaa aacgcgtgct   2640
aaacccttca aaacggacca aaccacgaac cccttttca aacctcgtgt agcttaagcc   2700
ggaaggacat gtcccatgga cttactgtat actacggttc ttctatgaaa agactggtat   2760
aacaaacata atttccattt tttttttctt cactacgtgc acgtcgatga cgacgaagat   2820
cagtttttat ttcacccatc cccgtgaatc aattaaagca aaccgacgag cttattcaa   2880
gctttcaata gaggcaatta aaggttcatt gtgcgcccat cgtcgttgat actcgagttt   2940
```

-continued taatgaagat tgaatttggg gttgattaaa cgagacgaga cgtg        2984

<210> SEQ ID NO 22
<211> LENGTH: 2986
<212> TYPE: DNA
<213> ORGANISM: Strongylocentrotus franciscanus

<400> SEQUENCE: 22
cataagtaca taaagatgca cgcgggtgaa tctcaacgtg cacttagtgg aacgagattt     60
tggaaagaaa acaccaagaa ctcgtcaagc gcttgctttg attggaacag gaggcttacc    120
tcaagttttc gtttcaatcc ccttttttgca tctactaata attctttgcc ttaaattcat    180
aaatcgtatt aggtatagtc ttgagctgga tgtgagatga gtaaggagaa agataagtaa    240
aatatgatat cataagacat gaagaacaaa acaaaagagg gaggggttga gttaggtgtt    300
ggtgagggca ttggattact agatagaact tgcacgtaca tcacatccac tttaataaaa    360
cattcaacct tacgatacga gaaggtcaag tcctatccca tcaaaatact aggaagtcat    420
gtgacagact gataaacaag acagttatcc aattcatttc atgagttcaa gcagcgtgca    480
atcacgtgtt aatgaagcat caacaaagtg atgccaacca caaaaattat ggcgccctac    540
catgtctaca gtgaacaccc atttcaatta ttcgatgaat ctatgctatg agttcgtctt    600
taccaatgac gtttagcttg cgacattaaa gttaatggaa acatgatcca ctgaaaggta    660
cagattcaat cctcatatac ccacatacta taaaatatag actttggtgt tgctttctta    720
gaattctttc cccttcatcg aaattggtaa atgaatgcgt gcgaacaagc aatctccgtt    780
tattgatcac tattttgtga ttgtcgtctg actcactcac tcccactcac tcccacacct    840
cagaagcgcg caaaccataa tattagccca cctttatttc aaagcaagga aacttcctat    900
taagatttgt ggatgctaat cttgacttca attcatatta tttctttttg taatcatggt    960
aatgacctta gttatttgac tccccgtaaa aataatcata caattggtcg aaaatttgtg   1020
agcaggaaat ggcagatgac ctgtgaatac gggcgacgaa aggaacaatt agaataaatg   1080
ttctttccac atggtctgaa caggcgacct gacaatgacc gaatgagtga gttccgattg   1140
acaaatgtat cttttcaaac tataattata gcaccattca tccattgaaa aacaaggtaa   1200
ttcattttcc ccttatgatt ttgtatagaa acatatcatc atcatcttga ataggagtgt   1260
gctcagtaaa tgagaattgg gagaaagtac agagagcatt ttgatactaa cattgcacac   1320
aataataggg tttgggcagc acgctgttcc atcgtactat tttctgtttt tatcttttga   1380
agtcaagctg agtaaatttt agagaatgag aaagataaac atcaacacca aaaaatctat   1440
gagaacaata ccatttgatt attcgaactt gatttgttca aaatgaatac gcgactcctt   1500
tactcgttta ttgctatata ttcataagta aacttgcata gtcattttat ccgtactctt   1560
ctttctaaag ccagtattca atttgttttc taggtcattg gtattctcat tgctcaatct   1620
gatttgttct tctctagtga ttttgttatg aaatcagaga tgcctgatcc caaattgaaa   1680
ttaaaatgag aagaattgat gaatagctat tatgcacaac agatttgcgt gaagaataga   1740
tcgaagatta tgttacagcc aacttcgtga cgtcgaattg caacagctt tgtaagctgc    1800
aatcgatcat aagttacatg atctagttca ccttgacacc ggtagcattt agtctggccg   1860
tcatcgcatg tcaacctcaa gacaacgatc gtttgcagac gacctttaat tacaatcact   1920
tttgttctca tgtattcatc gacatgtact aatcgaataa tgagtattcc aatcgcaaga   1980
tgcctatgta atgctatctt gagtaggcca aaactgtatc cgatgaaacg cgaaattaga   2040
tgacaaaagg ttttgttttt ttgtttaata ttatgaaagc atattttctt atgtgctcgc   2100

-continued

```
ttaacatggt tcccgccaaa accaacgggc gccaaacaga gggaatctga tgatgcagct    2160
gcaatgcttc acatctccga cttcactaga tttctctccg aaccatcggc catggtggga    2220
tgatcagaaa caatgcacaa tcattcgtcc atctcaggaa actgagagaa ttaaaaaaga    2280 aaaaagaag tgacaattcg catggatgca gtcgatgcat gacgactcac aaaagacact     2340
cattttcccc atctcgcgtg ctctctttta tatcaacagc catctttgct ctgaggatga    2400
acccttgtga tcaagctacc ttgacgatgt gctgattgtg gtttgcattc atactcataa    2460
atagacgtca aggtattcat atcatatcac ccgttctcta ttcattacaa aatcttctct    2520
ctaaactgcc accagagatt accatcccgc cctaaaccgt ataattagct gccttttcca    2580
gcaagcttta tggcggcatg gcgacaaagt gtaacttccg gcgcgagcca ctcacaaaac    2640
gcgtgctaaa cccttcaaaa cggtccaaac cacggacccc ttttcaaacc tctgtagctt    2700
aagccggaag gacatgtcct atggacatac tatataccac gggtcttcca tgaaaagact    2760
ggtaatataa caaacacaat ttccattttt ttttctacgt gcacgtcgat gacgacgaag    2820
atcagttttt atttcaccca ttcccgtgaa tcaattaaag caaaccgacg aggcttattc    2880
aagctttcaa tagaggcaat taaaggttca ttgtgcgcac atcgtcgttg atactcgcgt    2940
tttaatgaag attgaatttg gggttgatta acgagacga gacgtg                   2986
```

<210> SEQ ID NO 23
<211> LENGTH: 7776
<212> TYPE: DNA
<213> ORGANISM: Strongylocentrotus purpuratus

<400> SEQUENCE: 23

```
gggatgaaag ggagatgata attggccata tggtatgaca aatcaatcaa catcaccatc      60
cagaccaagt cggccatctg ggatggtctg agagggagac gggggcatct tcgatctcag     120
gtacatctag tggtgtaaaa ggagaagaaa agcccccatt gatgacgaat attgtaagta     180
ttttgtttaa gattccatgt ttaatcatgt tcatagttga ttgtttatat tacaagagtg     240
ctaacgaatc aagtatttgt ttaaaagaaa tttcatttag ggttgaaatc ttatagaata     300
gttaaattga gtgaatgtct tacctgacta gctcaagatc gaactgatct acatctgtac     360
aattaaaacc agaacaattt gcgacatgaa acgttcgcga tactggacca ctcaagagat     420
tcgcaacaaa atttggtttt aaatcacatt cccaaatgtt tgcagaaaac atgtggtaca     480
aagtcatttg tcgaaaggat ctaagatttc tttaaagaaa aagtaataaa taaacagaca     540
agactgtgat tgattacgtg attacaaaat aatgtttcaa gtattttttt gctattggtg     600
aatcgtcccg ttgctttccg atgtaaacta ggatcatgga acgaaatccg tttgattttg     660
atgcttttca caaaccagac catatctcca atagataatc ctaataacaa ctgaacatga     720
tatagcgatg ggatatttt catgcaggga tatcccatca ctataggtat aaggttcggc      780
ctggctcggt gtcttgtgat gcaacagtct tcatctttca gcgcttcgtg attacgatac     840
agggattaaa aagatagggga ctataaggga aggaggcaag caacaccaag gaaaatatct    900
agagcgaaca gatctagggg tcaagtccac acaatgcgtt attgaaatag ataggcctat     960
atggttcatg ttcggattga aacgagacta gagtgtcctc gtcgtatggt ctcagctcct    1020
ctgaaggctc tacataataa cgagaataat aatgtttata ttaatttggt ttaactagcc    1080
aggtaagact catcagcatc attgctattc tttccgaggg cgctgcaatt aatattaccc    1140
cggcaattac caggtaccca tttacacctg ggtggagagg ggcaaatgtg tattacaggc    1200
```

```
ttgtcaaagg acaatactgc cgggctagga ttcgaaccct cgatctttgg attgggagtc    1260
aagtgaatta agtactatac cacgatactt ccaccattct cacgattcac attcacaaga    1320
taatgtaggc ctacagtgtg attgaattgg attgaattga atttattttc ttctgcaaca    1380
tacacatcga attacatttc agcgatgcaa catataccaa aactgttttg tatacacagt    1440
ataataataa taaaaaatac gtcattgaaa caaaatgtaa atgatatcac actaccaata    1500
attattgaaa gcattgtcac ttgattttcc catgcatgtc gaaactgttc aaacatgaca    1560
ctacagtaca aagattcgcg aatcattgga tggatcagat aaaagagtgt tccccgaggc    1620
aatcatcatt gattgtcaca acaaagatca atattatgtg aaactatttc atcttattca    1680
taattctcat catcaaacgt tgaactgat atctgttttc agttcaaata atcgatgttg     1740
tacttcattc gaaaccgtat acatatagat gacatgattc atcactaaat acgaaaatga    1800
atccgcaaaa tatgttgaaa tatcaatcag ggagttggac catggacctg taacttgttg    1860
aaacaaagag gggtgctata tattctggaa ataaaactgt atcgacatta agcgatgatg    1920
gtttagtgct ggctaatcgt cgtgatactc ttcacactat cgacttcaag agaatccggc    1980
caggtccagt gttcgtaaac tgttgaaaag atccaccaaa tagacaacaa cctactatct    2040
ttccaatatt ttattttcat tttggtcttc acaaaccgat cgattttagc acggttgtac    2100
cggatttcta atttcccagg gatgtttatt tggaggaccc tggacaaagc cttttacgtc    2160
ataaacgtgg agaatgtgct gcaacaacac tagatatact aacacaatga tttcacacga    2220
gataatcata ttattttccc agactgtgag aattcaaata aagtacatac tcctaccatt    2280 tgttgcgat tagtatcttt ttcaagtttg tttgttcgtt tttatttccg aaatccataa     2340
tacatgcaag ttttaaaaac atgcacaata catttcaaat gataagttgt gtaaagtata    2400
gacaaacggt aggatagccc gtttcaggac cattttcaaa atggtcctgt tctttcagga    2460
ttaggactaa gtgattacaa tcaaccataa aattgcaggt atagttactg aaagcttgcc    2520
tcggaatcat atatggtcta gttggtatag gaccgtgaga gtttctcacc agactcctaa    2580
cactggttgt cgatggctcc tttgtttatg tcatggagag cgtgatctgt gagtggcctt    2640
ccctacttat cgatccaaag accaaaattt tcctgggaaa gcagtgattg attggagaga    2700
ttttgtcctt cgatcaactc gttggacgtg tcaaatcgtt gggatcccac gcacacacca    2760
acaacacgag gtgtcgtgtg gcccaccagc tggcgtgtgc tactggggtc aacatcaaga    2820
accccaagtt caattgcagg ggtcagagga tggatggggg aattagaact ggaccgtcat    2880
gttggtcctg tgcttgggat acacaatact cattaacctc attcgtgtat catgaacatt    2940
gggctcacag ggatatgtat acacataaaa taagacagca gttttttttcc tttcattttt    3000 acggtgttta atcaattata gtaaggccta tcgatccttc atcaaatgtt tcaacagtga    3060
gtcatacaaa ataatgagag ataaatgtca aaaactcgat catgattctt aatgaaaatc    3120
agctaatgtt gtttaatgtt gttaaatcaa catgatttca agcctgaatt aattaccata    3180
ctgattatct attcttaatc tataagaaaa tgaaagagaa ccatccaagc tgatgcgatg    3240
gtctaaccca tacaaagtta agaccatgtt cgagtagatg ggtgtaagtt gttacgtttg    3300
gatatcagcc aaaagtaacc cggcagcatt cccaaaacga gcaataaaca agaaaatatt    3360
gaaaacaaat aaattgaata catgacgatt ctgtataagt gtaataagtt tagtgtcaat    3420
acagtcccgg catgaaaccc atcatctatg tattacaagg atgcgcagca gatcgaccta    3480
cgtcataaat acaggacgaa actttcttca ttagagttgg tgttgacgat atagaatcga    3540
cagctcttta gcgcattgtc actttccacc aaaatcatgt ccttgtactt aggttgacca    3600
```

```
gatacacttg gctatgactc tcgccttata attgattttt ctatcttcac cactgttcac    3660
tcgatcgcta gggctatgcc cttggacgca gttatatgca taagtgtata ttgtgaggaa    3720
gtagtttaat ctattagtat tagttaaatg tattcctatg atggggttcc agtattcgtt    3780
atcagcctga cgacacctga ttttttctta taggtacatt tcgcttgaat taactatatt    3840
aatgtgatat aaaaatcgat attcataaac aacatcaaat cgtgttttga gatacgtgtt    3900
aatataatac aacttgaatc agtagattag gtagatgaga taagcgtatg tgctaatttt    3960
aaacggggtg gaggcggttg acgtctcgtg cccgaatatc aaattaaaat cgtaagtaat    4020
ttagtgaaat ccaaatcctg atataaaagt attttcatct aaacaaacaa acaaacaaaa    4080
caaaatgaaa aaaagtgaaa caaatttaag gtatgctgaa taggaacaaa agcatcaaca    4140
aagcaaatgc gaatattgtt taaaaacaaa attgtacata attatgatcg cattgcactc    4200
gacaaaatta gttcaatcaa aataaaaaca catgcaggag gaaaatgtag tgtagtggat    4260
atatacaata cctcgacaaa aaaggtaggc ctatattgta taaataaata aaaaataaat    4320
ttattaacta agttatcaac tttccagttt ccaaattcga gagcggggg ggggggggg     4380
gctgcaccct cttatgttct ccttgcacac ctatgatgat gatgatttag ttaagatgga    4440
attatgcgta ctttattgtt atgagctttt cttcttttcg tgatatttag tccttttttt    4500
taaagatatc attttattga aaagctaata atgtaatttg caagggtca ccacacgtgt     4560
ccagaaaaat agttcataat atatagttca ttctgtatga ctcaaaatcg acaatgggac    4620
tgatttaaaa tgtcagaata attgaacgtg acatggcagt accatgggag tctagactgt    4680
tggacaatca gtgaattaag agatgatgat tcggaaacct ctaaggtctt aagaacaggg    4740
tgtctcatga aaatgatcac aggagtcaat gttttttct tcacccaatc tctatcactt     4800
atatatagcg taagtaatac gaaacattac ttgagtgtga ataaaagaat gcattattct    4860
taatagagat attctaatgt tagaatatga tgattgtaaa atattcatga gtaaattaac    4920
gtccaggcca ctgttttaga aaagtctact taccctgtag acggagctac gcatttggtt    4980
tgggactacg cgtttgggac tagacgaaac gtaccgaaga aagaagtgag gaaataacca    5040
gtatcctacc accttaaccc cggtctaggg gacaaaatat gtagtccttg aagaataatc    5100
gaatagggaa tatcattaga tgtggagaga tgaattatct catttttccta acgagttgat    5160
ttcattttaa aacacaatgg tagggggctgg tgatttgaaa gaagcacgcg tggccattga   5220
gtgaggtgcg gggaaaatct atatctttc taattgtagg acgaacatgt gataattgaa     5280
attgccgatt tggtttactt atttctgagt gactggatta tatcgcattg aatggtgctg    5340
aaaataggca tgaccagggc atgattagtc agttcaaatt ttgtaccttg atgattatga    5400
ttagttttgg aattataatt gatatgttgg gtatacaatt tagttgcgtt tcactttggg    5460
aaataatttc ttttttgatt ttctcttctt tttactccca tataacccca tactgtccta    5520
cgtaattaat atatgcaaat gaattattat tgtcaaaata agtaatgttc ccgagctcct    5580
aacatagctc ttcattattc ccatcagtgt cactgatgtg tggtgtacaa tatctccatt    5640
cctgcgtgct gcccggtatt ttgatgtatg cacggttgtt cggaatacaa atttggcgac    5700
cacaatggct tactgcatct gggtcccatt ctcgcctggg taggtagtgg caagtacaga    5760
ttgatgtctc tctcgtgaac gttagcttcg tatatggggg agttgagaag ttttcacatc    5820
cacgagacca gagatcacga aaccattcta taaagtattc agcttcaccg tcgttcacat    5880
caccacttca tctgctttc tctcaaattc cgatatcaaa attttttgctc caaacagtca    5940
```

-continued

```
aacaaaaggc tagaaatctg aagtgtatcc accgagtctt cgtcacctcc acctctccat    6000
gtttgcacag ccaagacatc aatgcaagta attacattta aagcatcccg ctaaagaaaa    6060
caactcttcc gctttcgttt gtcgacaaac ttgactggac ccgtctcgat tgttcaaaca    6120
agagaatgga gaaattggtg aggggagggg agttcgtttg gccatcacat taactttgta    6180
tttgtattgt atcttatttg tactgctttc catcccgtct tcatccttt tctctgttcat    6240 taccaacaaa aggacagatt ttactaacca ttgatgaaag gaaagttatc ataattgcta    6300
aatattctat ctacaagaga gagaaggga aagagagaga gagagagaga gagagataga    6360
cacaaaaatc atataggcct tgtttgacaa atgaataatt tttttaaaga tagcaatcgt    6420
gattcctaag tatcttatca tttgattta tcttaacat ttctgaaatt taaatgttca    6480
tgaaggtttg ggactcctgt gatattatga taaacaaaat taaccctgg tgataacagt    6540 agtcatggac tctaaaacga ttgtatctct gtgggccggc aaagcctata tatgattatg    6600
gttattatct acacatcttc gattgtaaaa ataagctaaa atactgaatg ggatacatca    6660
ataaataaca cgtacttcta atactacttc tacttgcaag ataatggcgt tggtaaaaaa    6720
aaaaatgttg ttattaaaaa ggcgatctcc gaacatttgg cggttaacaa ctggggtggt    6780
gtcacttctt ggctgaagta attggctcgc gtgccattca ttaacagcga tggctggtgt    6840
gagttaggcc aattaaaaat ggaattagtg ataggagtgg tggtagggct gagaaggatc    6900
cccgctactt caagtcgacc atacaattca tggatattct ctccaaaagg atggagagga    6960 ttcgacccctt ctttgtcgcg ctcagtttaa cgtgattgtg gatatattga gttcgatgac    7020
atatttctaa cttgattaga aaacagttca atgtatcctt tcacgtcaac aggttaccaa    7080
cacaatagtg ataaacagta tttgcatgac agacatattt taatgttttg ttttttattt    7140
gaacaattag gtatgtgaga atctcagaaa cctatgacgg agtggaagct tctggttcac    7200
cgggatgcag gccaagcaca aaacagcagg gagaaaatgt ttgtggcata ctggcatccc    7260
atacacggtg ggacctcgtg catgtgttgc tgcgaagttg ccgacacata ctgaccaatt    7320
cgaatgtgta ctcatgttgt cgaagtgtat gttgcttgtg gaattgttta cctgttgctc    7380
gtgaccaagc gccataggtc ccctgtcata gccaacacta ataggtatc acttaattat    7440 tatcaagagc gtcattaaac attttttgcat gcaaatttga aattctgaac aacccttttg    7500
ggggcggttg gaggggacgg ttggagggga cggggaaaga aatcgactag gactaacttg    7560
aatgatggta catttttcg acaaaattaa tagccgcaat ggtcttgtga cgacagtgac    7620
ttgatacttg acaatattac tttaaagcct cacctcttct ctttgaataa aaaaggcgta    7680
catcttacca tggaattcct ccttcattt actgatggca tctcttttgt accggtcaga    7740
gaatctcctt tcctccggaa ggattaagta ttatac                             7776
```

<210> SEQ ID NO 24
<211> LENGTH: 7450
<212> TYPE: DNA
<213> ORGANISM: Strongylocentrotus franciscanus

<400> SEQUENCE: 24

```
gggcggagga tatgatattg accatatggt atgacaatca atcaacatca ccatccagac      60
caagccgacc atctgggatg gtctaagagg gagaaggggg catctttaat ctaaggtata     120
tctagtggtg ttaaggaga agaaaagccc catcgaggac gaatatttaa agtcttttgt     180
ttaagattcc atgtttgatc gatcgatact ggaccactca agagattcgc aacgaattct     240
ggttttacat cacatcctca aatgtttgca taaagcatgt ggtgcgaaat catttctcga     300
```

```
aaggatctga catttcatta agaaaagta gtaaataaac agaccacgta gattgtgatt      360
gattacgtgt ttacaaaata ctgtttcaag tatgttcttg caagtggtga atcgccccgt     420
tgctttccga tgtattttct tggatcatgg aacgaaatcc gtttgatttt gaagctaatc     480
acaaaccaga ccatctcttg cttccaatag atcattctaa tcataactga acatgatagt     540
gatgggatat ttttcatgcg gggatacaag gtataatgtt cggcctggct cggtgtcttg     600
tatgcaacag tcttcatctt tcagcgcttt gtgattatga tacagggatt aaaaagctag     660
ggactatggg agagaggcaa gcaacaccaa ggaaaatatc tagagcgaac agatctaggg     720
gtcaagtcca cacaaagcgt tattgaaata gataggactg tatggattga acaagacta     780
cagtgtcctc atcgtatata gtgtcagctc atctcaagga tctatataat aataagaata     840
ataatgtaga tactaatttt gtttaactag ccaggtaaga tgcatcagta tcaatgctgt     900
tctttcagag ggccctgcaa tttccaggta cccatttaca cctataggta gagggggca      960
aatgtgaatt aaaggcttgt caaaggacat tactgccggg ctgggattcg aaccctcaac    1020
ccttggattg agagtcaagt gaatgaacta ctataatata ccacgatacc tccactattt    1080
ttatgatgcc cattcgcaaa tgtaggccta ttgtgatgat catgtcactt cattttccca    1140
tgcatgtcaa aactattcaa acatgagact acagtacaaa gattcgcgaa tcattggatc    1200
agataaagca gtattggaat ggtggttgcc ccgaggcaat catcattgat tgtcacaata    1260
aagatcaata ttacgtgaaa ctatttcatc ttattcatat tctcatcatc aaacgtttga    1320
gctgatacct gttttcagtt caactaatcg attttgtact tcattcgaaa ctgtatgcat    1380
agatgacatg attcatcact aaatatggaa atgaatccgc aagaattgtt gaaatgtcaa    1440
tcagggagtt agacctagac cttgttgaaa ccatgggcct actaagacgg atgctatatc    1500
cttaattatt cacctgtatg tttctggaaa gcaaactgta tctacataaa gctccgatgg    1560
ttcagtgctg gccaatcatc gtgatattct tcacactgtc gacttcacga gaatccggcc    1620
agtcccggtg ttcgtaaact gttaaaaaga ttcaccaaat agacaacaac ctactatctt    1680
tccaatatct tatttttttc attttggtct tcacaaccga tcgattttag cacggttgta    1740
ccggatttct aatttcccag gtgagtttgt ttggaggacc ctggacatag ccttttacgt    1800
cataaacgtg aagaatgtgc tgcgacatag gcctttacat cacgagacat actaacgcaa    1860
tgatttcaca cgagataatc atattatttt accagagtgt gagaatttta ataaaagtac    1920
atactcctgc cattcgttg cgattagtat atttttcagg taaacattct gtttaggatt     1980
aagtgattac aatcaaccat aaaattgcac ttatagttac tgaaagcttg ccttgaatca    2040
tatacttggt ctagttgggt aggaccgtga gagtttctct tcagactcct accactgatt    2100
gtcgatggct cctttgttta tgtcatggag agcgtgatca gtgagtggcc ttccctatac    2160
ttatcgatcc aaagaccaaa attttcctgg gaaagcagtg attgattgga aaggttttgt    2220
ccttcgatca actcgttgga cgtgtcaaat cgttgggatc ccacgcacac accaacaaca    2280
cgaggtgtcg tgtggcccac cagctggcgt gtgctcccgg ggtcaacatc aaaaacccaa    2340
gttcaattcc aggggtcaga ggatggatgg gggaattaga actggaccgt cattttggtc    2400
ctgtgcttag gaaacacaat actcattaaa ctcattcctg tatcatattt attgtgctca    2460
ccggtctatg tatacaagta agctaaggca gaaggttttt tttcttccca ttttcatttt    2520
gcggtgttaa atcaattata gtaaggccta tcgatccgtc atcacatttg tcaacagtga    2580
gtcataacaa tgagagataa atgtcaaaaa ccagatcatg attcgtaatg aaaaatcagc    2640
```

```
tatgttgtta aatcaacatg atttcaagcc tgaattaatt accatactta ttatctaatc    2700
ttaatctaaa gacatgaaag aggaccaaga aggtgcaatg gtctaaccca tacaaagtta    2760
aaaccatgtt caattagatg gataaaagtt gttacgtttg atatcagtct aaaacgagca    2820
ataaacaaga aaacaatgaa aacaaataaa ttgaatacat gacgattctg tataagtgta    2880
agaaggatag tgtcaataca gtcccggtat gaataccatc atctgtttat tacaaggatg    2940
ccgaacagac ctacgtcata aacacaggac gaaactttct tcattagagt tggtgttgac    3000
gactcgaatc gacagctctt tagcgcattg tcactttcca ccaaaatcat gtccttgtac    3060
ttaggttgac cagatacact tggctatgac tctcgcctta taattgattt ttctatcttc    3120
accactgttc actcgatcgc tggggctata tgcccttgga cgcagttaga tgtataggtg    3180
tatattgtgt ggacgtagta attagcctat gagttaagcg tattcctatg ctggggttcc    3240
agtattcgtt gtcagtcaga cgacacacga attttcttc taggtacatt tcgcttgaat    3300
taactatatt aatgtaatac gaaaatcgat attcataaac aacataaaat tgtgttttga    3360
gatatgtgtt aatagaatac aactacagta gattaggtag atatgactgg ctgacgtctc    3420
gtgcccgaat atctaatcaa aatttttatgt aatttattga aatccaaatc ctgatataga    3480
aggattatca taaaaaaaca aacaaacaaa acaaacaaaa caaagtgaaa caaatttaag    3540
agatgctgaa taggaaaaaa gcctcaacaa agcaaaagcg aattgtttaa aaacgatact    3600
gtacataatt atgatcgcat tgcactcgac aaaattagta atacacacat gacatgtatt    3660
ttcatcatca cattcaaaat aaaacacagg aggggaatgt agaggatata aacaataccct   3720
caacaaacca aaagttgtat tgtatacaaa taaagttatt ttatttgtat acaatacaac    3780
ttttggtttg ttgaggtaac taacttatca actttccagt tgctgcccaa atatttaaaa    3840
tttcggggag gggggggggg ggggctgcac cctcttatat tctccttgca cgcctaggat    3900
gatgattatt tagttaagat gtacttatgc gtactttctt gttatgattt ttcttctttg    3960
cgtgatgttt agtccctata gttttaagat atcgctttat tcaaaagcta ataatgatct    4020
catttgcgaa gggtcatcac acgtgtccag gaaatatagt tcataatagt tcatttgaaa    4080
tgactttgt atgactcaaa atcaacaatg ggactgattc aaaatgttag aataattgaa    4140
agtgacatgg cagtaccatg ggagtctaga ctgttggaca atcagtgaat taagagatga    4200
tgattcggaa acctctaagg tcttaagaac agggtgtctc atgaaaatga aataggagt    4260
caatgttttt ttcttcaccc aatctctatc gcttattata gtgtaagtaa ctacgaaaca    4320
ttaattgttt gtgaagaaaa gaatatatta ttcttaataa agatattctt gtttctatga    4380
atatgatatg ttgaacaacg tcaaattaat acgtcgccca caagtttgca gtatctacaa    4440
ttgaacgata ttttgtatat atatctgtcg ggtctatatt gaatttgcgt gggtatatcc    4500
cataacaagt gttctggaat gcatgttatt gattgtaagg tgataatgtt agaatatgat    4560
gattgtaaaa tattcatgag tatatcaacg tccaggccat tgttttagaa aagtctactt    4620
accctataaa cggagctgcg cattgccgtg tttgggacct agacgaaacg taccgaagaa    4680
agaagtgagg aaataaccag tatcctaccg ccttaacccc ggtctagggg acaaaatata    4740
tagtccttga agacttaatc gaatagggaa tatcattaga tgtggagaga tgaattatct    4800
cattttccta acgagttgat ttcatattaa aacacaatgg tagccagggc aggtgatctg    4860
aaagaagcac gtcacctgca cgtgtggcca ttgagtgagg tgtgcaatgg ggaaatctag    4920
cttttctaat tgtaggacca acatgtgata attgaaattg ccaatttggt ttacttattt    4980
ctgagtgact ggattatact tcattgaatg atgatgaaaa tgaacatgac cagggcatga    5040
```

```
ttatgaacta attatgaact aatttcttct ttggttttc tctttttttt ccatccaact     5100
tcagactgtc ctacgtatac aatttatgtg tatacgcaaa tgaactataa ttgtcaaaat     5160
tagtaacgtt cctcagctcc taatatagct cttcattatg cccattgtca ctggtgtgtt     5220
gtgtacaata tctccattcc tgcgtgctgc ccggtatttt aattatgcat gcacagttgt     5280
attttggcga ctgcaatggc ttattgtatc tgggtcgcct gggtagggag tggcaaatac     5340
agattgatgt ctctctcttg agaaagttag cttcgtacgt ggggaagttg agcatgtgtc     5400
gcatccatca gattacgaaa ccattatata aagtattcat ctccaccgtc gttcacatca     5460
ccactccatc tgtttttctc tcaaattccg atatcaattt tttgcttcaa accgtcaaac     5520
aaaaggctag aaatctgaag tgtatccgag tcttcgtcac ttccacctct ccatgtttgc     5580
acaggcaaga catcaatgca agtaattaca tttaaagcat cccgctacag aaaacaactc     5640
ttccgctttc gtttgtcgac aaacttgacc aggcccgtct cgattgttca ataagagaa     5700
tggagacatt ggtgagggga ggggagttcg tttggacatc acattaactt tgtatttgta     5760
ctgaatctta tttgtattgc tttccatccc atcttcatcc tcttctttgt tcattatcaa     5820
cgaaagggca taattttacg agcctttgat gaaagggcaa ttatcataat tgctaattat     5880
tctaggccta tcatctacaa gtttagagag agaaaaaaaa aggataggga gagagataga     5940
gaaagagaaa gagagagaga gagagagaga gaggtaaaaa agagagagag agagacagag     6000
agatagagag agatagagaa agagatagag tgaaagaaag agagagagag agagagagag     6060
agacagagat agacacgaac atcagatagt tcgacaaatc aatgtttaaa ataatgaaa     6120
ttatagctat cgtgattcct gaatatctta tcatttgatt ttatctttga aatttctgaa     6180
atttaaatgt tcatgtaaat tttgggactc acgtgctatt atgatcacaa aattagctcc     6240
tggggataac ggtcggccat ggactctaaa tcggttgtat ctctgtgggt cggcatatac     6300
cctatatggt tattatctac aggtcttcga ttgtaaaata agctgaaata ctgaatggga     6360
tacatcgata aagaacacgt acttctaaaa caacttctac tgcaaaataa tggcgcgagt     6420
tggtaacaaa aaggttgtta ttaaaaaggc gatctccgaa acatttggcg gttaacaact     6480
ggggtggtgt cacttcttgg ctgaagtaat tggctcgcgt gccattcatt aacggcgatg     6540
gctggtgtga gttaggccaa tttaaaatga aattagttat aggagtggtg gtaggggtga     6600
gaaggatccc cgctacttca agtccaccat attaacacaa ttcatggact tctctccaaa     6660
aggatgggtc attcgaccct tctttgtcgc gttcagtttta gcgtgattgt ggataattat     6720
attgagttcg atgacatatt tccaacagta ttagaaaaag gttcaatgta tcattttcac     6780
gtcaacaggt taccgacaca actcataagc agtatttgca tgacatttca tttgaacaat     6840
taggtatgtg agagtgtgag acagtgagta gaaacctatg tcggagtgga agcttctggt     6900
tcaccgggat gcagccaagc acaaaacagc agggagaaaa tgtgtggcat cccatacacg     6960
atgggacctc gtgcgtgtgt tgctgcgaag ttgctgacac atactgagtg ccaatttgaa     7020
tgtttactca tgttgcttgt ggaattgttt acctgttgct cgtgaccaag cactaacttt     7080
gtaattaacc cttcaatggc ggtaggtccc ctgtcatata gcctatcact aaataggtat     7140
aacatttcta catgcaaatt tgaaattatg aggtacccctt ttttggggggg ggggagggc     7200
gggggtttcc tgaagaaaaa attgactagg cctaacttgg atgatagtac attttttcg     7260
acaaatagcc gcaaaggtcc agtgacgaca atgacttaat acttaacaat attactttac     7320
agcctcacct cttctctttt aattaaacgg cgtacatctt accatggaat tcctccttca     7380
```

```
tttactgat ggcatctctt ttgtaccggt cagagaattt cctttcctcc tgaaagatta      7440
agtattatac                                                           7450

<210> SEQ ID NO 25
<211> LENGTH: 226
<212> TYPE: DNA
<213> ORGANISM: Strongylocentrotus purpuratus

<400> SEQUENCE: 25
gctcaatact tagcttcaag caccaatcaa cagataactt attttcagta ttaacaaaaa      60
aagaaggaga aggggatgag ataaggcttg tagaggatca ggggtgggga atgacagggg     120
ggggggggta taaagaatga taataagcct ttgtagtcac ttattggact cgcatgcttg     180
attagcacgt ggccattgta acgaaggaca ttgtcttcta tacaca                   226

<210> SEQ ID NO 26
<211> LENGTH: 224
<212> TYPE: DNA
<213> ORGANISM: Strongylocentrotus franciscanus

<400> SEQUENCE: 26
gctcaatact tagcttcaag caccaatcaa cagataactt atttgcagta ttacaaaaag      60
aaggaaaagg gggtgagata aagcttgtag atgatcaggg gtggggaatg agatgggggg     120 gggggatgt caaaaatgat agtagcggtt tgtagtcagt tattggactc gcatgcttga     180
ttagcacgtg accattgtga cgaaggacat tgtctgatca cact                     224

<210> SEQ ID NO 27
<211> LENGTH: 640
<212> TYPE: DNA
<213> ORGANISM: Strongylocentrotus purpuratus

<400> SEQUENCE: 27
agattattag tcaccgcttg aagaacatcg ggaagagaat gcggcgctaa tcaaaaaggt      60
tgtaatccca agctaccctt ttattctagc atttgtccag gttcacccat taatctctta     120
ctaatccctt gtaactgtac aagatcgctt tcatagaagt acaaagcttt acaaagcaaa     180
gtgaattgtc tgcttgcgat ggcattcata aaacacagtt cacatgattc atacgatttg     240
ttttcagcag tttgcgccgg agtgttttct ttgtagtgct gtgattattt cgcggctcaa     300
gtgcggcgac aaacaacata cgtatttgct cgatgaacaa cgatacacgg gtagaagaac     360
aaaccaactt caaaatcaaa tttagcgaca aaagagaaaa aaggaggtgg gagaatgagt     420
gtatgtaagg atggtgccag tagaatgact acaaagctta ccgccaatct acgggtacac     480
gtgccaagat ttatgtttga gttcgtgtgc tttagcccgc cggtttgccg ctaaaacaaa     540
aacggatttt gctcaaagtt ccagaatatt gaatattgat ttagtgatgt aaaactaatt     600
tatcaaagta atggcttctg cgagtggtga atacaaatct                          640

<210> SEQ ID NO 28
<211> LENGTH: 638
<212> TYPE: DNA
<213> ORGANISM: Strongylocentrotus franciscanus

<400> SEQUENCE: 28
aaattattag tcaccgcctg gagaagttac taagaaaatg cggcgctgat caaaacgttc      60
taagggttgt aatcccaaac taccccttta ttctaacatt tgtccaggtt cgctcattaa     120
tctcttacta atcccttgta actgtacggg atcgcttaca taaagttaca aagcaaagtg     180
```

```
aattgtctgc tagcgatggc tttcatacaa gacaattcac atgattcata agatttgttt      240
tcagcagttt gcaccggagt gttttctttg tagtgctgtg attatttcgc ggctcaagtg      300
cggcgacaaa caacgcacgt atttgctcga ggaacaacga tacactggta gaggaccaaa      360
ctaacttcaa tatcaaattt agcgacaaaa agaaaaaaa ggaggtggga gaagaagtgt       420
atgtaaggat ggtgccagta tgatgactac aaagcttacc gccaatgtac gggtacacgt      480
gccaagattt atgtttgagt tcgtgtgctt tagcccgccg gtatgccgct aaaacaaaaa      540
ccgattttac tcaaagttcc tgaatattga atattgattt agtgatgtac aaccgattaa      600
tcaaaataat ggcttctgcg agtggtgaat acaaatcc                             638

<210> SEQ ID NO 29
<211> LENGTH: 260
<212> TYPE: DNA
<213> ORGANISM: Strongylocentrotus purpuratus

<400> SEQUENCE: 29
atgcatggtt gtataacgtt tgaacatgtg aaagtggagc gtccattaag ttggcataac       60
tctgccaatc aaatccttga cttggctttt cctcttatct cgaataaatg aatgaggaga      120
atgcgacaga tgcgtgttgg ttagataaga gaagcggaag atgacttcag aagatgtccc      180
atgcaaacca ttttcatctg ctcccatccc ctttgtcttc cctggctcc ttaaagggac       240 atgagatatt ttaaagggac                                                  260

<210> SEQ ID NO 30
<211> LENGTH: 261
<212> TYPE: DNA
<213> ORGANISM: Strongylocentrotus franciscanus

<400> SEQUENCE: 30
atgcatggtt gtataaagtt tgaacatgtg aaagcagagc gtccattaag ttggcataac       60
tctgccaatc aaatccttga cttggctttt cctcttatct cgaataaatg aatgaggaga      120
atgcgacaga tgcgtgttgg ttagataaga gaagcggaag atgacttcaa aagatgtccc      180
atgcaaacca ttttcatctg ctctcatccc cctttgtctt ctcctggctc cttaaaggga      240
cataagattt tttaaaggga c                                                261

<210> SEQ ID NO 31
<211> LENGTH: 1072
<212> TYPE: DNA
<213> ORGANISM: Strongylocentrotus purpuratus

<400> SEQUENCE: 31
cgcaagtcaa atatttgcac cggttttaag aacccgcctc ttcttcagct agtaacattt       60
accattgtct aatgactcg ctaaccattt gaggtactcg agtaaatcca gttcttagga      120
attcaatcaa aaatgattgt atgcgctggg agggcgggta ataaccctc aacaattctt      180 ttttttttctt ctactttttt tgagggtgtg tggataataa agtcattacg gacagttctt      240
aatatactca tttatgtacc taatgacaat cattaacagt tcagttatta aatgtaatgt      300
tcagtaagtt gaatatttaa tcaatatccg tttatccagg gttctaaact cactttctgc      360
acatggattt caattttcaag gtcgatatac ttacgccccc taaaattcta aatttggggg      420
ttccggagtc agtgaaatcc gagggcctga tatttcacaa ttattagtgt gaaataggtt      480
tttagtaatt ttttgatgaa aatgcggtcg ttatggcaaa acaatattgc atatcattaa      540
```

-continued

| | |
|---|---|
| ccattcaagt gaatatccga taaattctga aagatttgta actatggggg aaaattacaa | 600 |
| tttaacaaga gaatatctta gcggaatatt tatcgaaatt gttcaagttt tcttgaaagt | 660 |
| taggaaaggg cgtttcggtt aattttttaa ataatatttt tcttttttcat aaaagataaa | 720 |
| atttaaacta cactctttttt aatagcgttt gtaatgtttg taattcaaat gtgtacagtc | 780 |
| agaacgcgtt caaactttaa ggatattccc tggggggcccg tgtacgcata tctgaccact | 840 |
| gttggtgtct aactaaaata aaggaagtta atacagtggc acgggactcg aatccgagtc | 900 |
| agtagtgcgg aggcctttcc aactgaccat acaacctcta aaatccacca ggtatattcc | 960 |
| gtgtgattta actacttctg tattgagccg attcaacaag atggacagag aatccggtag | 1020 |
| gacactccga aagctgcatc gaatcgatac agcgcctcaa actttgaaaa gc | 1072 |

<210> SEQ ID NO 32
<211> LENGTH: 1091
<212> TYPE: DNA
<213> ORGANISM: Strongylocentrotus franciscanus

<400> SEQUENCE: 32

| | |
|---|---|
| gggggaatac atatttgcac cggatttttag aacccgcctc ttcttctgct aatatgggaa | 60 |
| catttaccat tgtcttaatg actcgctaac catttgaggt actcgagtat taactccagt | 120 |
| tcttaggaat tccatcagaa atatatgtct gtgcatggcc tgtgtgtggt gggaggagtg | 180 |
| gtaatataac ctcagcaaag tttgttttttt tgttttctgt ggataataaa gtcatgacgg | 240 |
| acagttctta atatactcat gtatgtactt aatgacaatc attaacagtt taatgttcaa | 300 |
| agttgaatat ttaaccaata tccgtttatc cagggttcta cattatttttc tgcacaggga | 360 |
| tttgaatttc aaggtcgata tacttacgcc ccctaaaatt ctaaatttgg gggttttgga | 420 |
| gttgaaatcc gagagcctga ttttttcacta tgtgcaatag gttttttaat ttttttttaat | 480 |
| gaaaatgcgg tcgttattgc aaaaacaaaa tagcctatca ttaaccttgc tacagtccaa | 540 |
| tgtctaaaac cattcaagtg aatatccgat aaagtctgaa ggattaatttt tgtaactatg | 600 |
| gggaaaatga aaatttatcg aaagaatata cctaagcgga atatttatca aaatttgtca | 660 |
| agttttcttg aaagttagga aatggcgttt cggttaattt ttctaataat gttttttcttg | 720 |
| ttcataaaaa atgaaaatta aactacatta ttttgaatag cgtttgtaat ttgtgtaatt | 780 |
| caaatgtgta cattcagaat gcgttcaaac tttaaggaca ttccctgggg tcccatgtac | 840 |
| gcctatctga cctcggttgg tgtctaacta aataaaggaa gtaagtacag tggcagggac | 900 |
| tcgaatccgg gtcagtagtg cggagaccta tccaactgac cacacaaccct ctaaaatccg | 960 |
| acaaatgtgg taatattccg tgtgatttaa cgacttctgt tttgagccga ttctacagaa | 1020 |
| gggacagaga atccggtagg tcactccgaa atctgcatgg aatcgataca gcgtctcaaa | 1080 |
| ctttaaaaag c | 1091 |

<210> SEQ ID NO 33
<211> LENGTH: 533
<212> TYPE: DNA
<213> ORGANISM: Strongylocentrotus purpuratus

<400> SEQUENCE: 33

| | |
|---|---|
| atgattgttt gaacaagatt ctaaacaagc catgaactac atatacaagg atatatttac | 60 |
| atgaggaagt ttatttcact taaacgtgtt cttactacct tgatgagtta aagggtacag | 120 |
| cactggttta tatgcttggc ttggttcctc ggatggaagc gcattctaaa tgctgaatct | 180 |
| gtcattctta atgttgtatc atacaatcaa acaactagaa gagattaatt ttttgcgcct | 240 |

```
tcagaagttc agctcactta aataccaaat atcagaataa ctgaaaaagt caattcaaat    300
gtccgttggg aagacggtca gactgccgtt gtgagtggcc gcataatcaa gtacgattac    360
aatgatcttg ttaatacgac aaatctagat agcagattca ttcgagtgat aacgaagatt    420
attataataa tgataatcat aataagaata atgataagag gaaaaggaag aagaagaaga    480
agtagaagaa aacgaagaaa gaaaagaaaa gaagaggaag aagaggaaga aga           533
```

<210> SEQ ID NO 34
<211> LENGTH: 576
<212> TYPE: DNA
<213> ORGANISM: Strongylocentrotus franciscanus

<400> SEQUENCE: 34

```
tgattggttt gacaagattc taaacaagcc atgaactaca tatacaagga tatatttaca    60
tgcggaagtt tatttcactt aaacgtgttc ttactacctt gatgatttaa aggatacagc    120
actggttcct atgcttgact tggttcctcg ggtcgaagag cattctataa atgctgaatc    180
tgccattctt aattttatat cgtacaatta acaactaga agagattatt atgaaatgtt     240
atataatggt agaggaggat tattctgtgc cttcagaagt tcagctcact taataccaac    300
tattagaatc actgaaaaag tcgactgaaa tgtccatgcg ggaagacggt gcagactgcc    360
gttgttagtg gtcgcattat cagcagttaa agaaagtacg attacaatga tcttgttagt    420
acgaaaaatc tagatagcag atggattcgg gtgataatga taattatcat attaatgata    480
agaagaagga aaagaagaaa aagaaaaaga agaagaggaa ggagaagaag aagaagtaga    540
agaagaagaa ggagaagaag aagaagaaga agaaga                              576
```

<210> SEQ ID NO 35
<211> LENGTH: 473
<212> TYPE: DNA
<213> ORGANISM: Strongylocentrotus purpuratus

<400> SEQUENCE: 35

```
aaaaattgat tagatcctca tttaaagtaa atgcatcttt cataattctt tcaaagtttt    60
ggaatttaaa cattatgata ttataattga tttacggccg aatcgtaaaa aatatgaatt    120
aagcattaat gattcctcga tttatattta attccatctg tcaaatttaa ggtacaaact    180
gaatctttat tataatttgt aattgtatat tttcttatag cgaaatggta ttaaaccaat    240
cgatcggtct cctataccac cgctgtgccg tgccataaca taaccaggtc ggaacctgaa    300
ttgtacatgt ttgtcggacg atgaacatta acatttttt tcgcctcttt aattcaggtg     360
aagggttatt attttattat aaaatccaca tattttccag acaaacagga catagaatag    420
catgtatctg caagattatt agtcaccgct tgaagaacat cgggaagaga atg           473
```

<210> SEQ ID NO 36
<211> LENGTH: 533
<212> TYPE: DNA
<213> ORGANISM: Strongylocentrotus franciscanus

<400> SEQUENCE: 36

```
aaaaattgat tcgatcctca ttaaaagtaa atatatcttt cattattctt tcaaagtttt    60
ggaatataaa cattatgtta ttattggttt actgtcaaat cgttaacaaa atataaatta    120
agcgctattt agacctcgat tcatatttta ttctctctgt caaaccttaa gtttgaaatt    180
gaatctttag tataaatttg tatttcttgc agcgaaatgg tataaccaat cgaccggtct    240
```

```
cataccaccg ctgtactgtg ccataacata accagatcgg aatctagatt gtatagaatg    300
tatgtgggac ggccgtgaac atgagtggtg gttattttg ttttacgtga ctgctaagaa    360
agcataaatg cttgttggta accaaccagc aacattttct ttgccttttc aatcatcagg    420
tgaaatgtaa ttattttta taaaatccat atattttcaa gacaaacagg acataatata    480
atatgtatcc gcaaaattat tagtcaccgc ctggagaagt tactaagaaa atg           533
```

<210> SEQ ID NO 37
<211> LENGTH: 878
<212> TYPE: DNA
<213> ORGANISM: Strongylocentrotus purpuratus

<400> SEQUENCE: 37

```
taacattgta acaattccaa tatattaata cttgcagtat ttccaagttt ttcccattta     60
tcattttaat ttcgttcatc ataattattt taaagtgaaa tatagaagat aacaagagag    120
tagagctaaa ttcttttcat taaattaatg cgataaaaac acccagacag cctatcgtat    180
atatgcacta ttagcgtctt atcacaatta ctacaagtga cattaaaatt agagtacgat    240
ttatcggtat gataaattgt gataaaatag atgatacgtc aacattttat cttgttaacc    300
gtttactgct aatttaatgg cattgatgtt gataaggtga cagtgcagta tagagcccac    360
tgactgactg gtctagtaag actccacaat agagctacac atatttcaaa gtttattacc    420
tttttaattt ctttctctgt tacggatttg accattttta ttctgatcca ctttcctttc    480
aacctggaat aaagtggtat aattcgtgta ggtcgatatt ttattgaaca atgaaaggga    540
tttaagtatc gaaattcgaa atttaataat ttcttttcag aaccctacca tattcagatg    600
aagattattt tacttaatat ccatttaagt ttttaactaa atgtgtaaat tcggcatcca    660
ttcacgaccg gtaatagcaa taaatatagg cctatatcat atttaaaaag taaaatttaa    720
tatatcaggg ccaagaacaa gagaacagat tatttctcca tcaaaatttc gttcgtaaaa    780
gtactgcacg gattcacctc accaaaaagc tcgatagttc tctgtcacaa ctcatgatat    840
tgtttgataa taattttgtc tcttcatcgt ctgaaagg                             878
```

<210> SEQ ID NO 38
<211> LENGTH: 824
<212> TYPE: DNA
<213> ORGANISM: Strongylocentrotus franciscanus

<400> SEQUENCE: 38

```
caacaattcc aatcaactaa tacttgcagt attttcaagc ttttcccatt tacactttta     60
agtgttcata ttttaaagtc aaatatagaa gagagtagag ctaaattcct aacattaaat    120
aatttaatgc gataaaaaca cacagacagc ctatcgtcac tatcaattat catcttatca    180
aaataactac aaatgacatt aaaatcagag tacgatttag cggtatgata aattgtgata    240
aaatagatta ttcgtcaaca ttttatcttg ttaaccgttt actgctaatt taatggcaat    300
agtgttgata aggtgaaaag tagacccgac tgacgggtct agagagactt cacatactga    360
catagacata ttttcaaagt ttatttcctt tttaattcct ttctctgcta cagatttgac    420
cattttattt tgatccactt cccttcaacc aggaatcaaa tggtaaaatt tgtgttaggt    480
tgatattaag caatgaaagg gatttagtat ctcaaattcg aaatgttaaa atttactctc    540
tttcttttca gaaccctacc atattcagat gaagattatt gtactcaata tccatttaa     600 ctaatgtgta gttcggcat tcattcacga ctggtaataa aaggcatata gcattttgg     660 aaagtaaaac tgaatgtatc agttagggcc aagaacatgt gaacatgctc atcggaaagg   720
```

```
aaatataccc gtattcacgt ctctgataga ttttactttc attaatttat ctacataatc    780
aggaatcagg atagtatgat gtaaaaggat aattgaatta ggaa                     824

<210> SEQ ID NO 39
<211> LENGTH: 3074
<212> TYPE: DNA
<213> ORGANISM: Strongylocentrotus purpuratus

<400> SEQUENCE: 39
attgactcag aatctacagg aacgtggatc tctgtcttct cctggttgtc tccacttcca     60
ggactcccct tttctccttc agttccctct tcgaattctc tatcaaagct gctttcagcg    120
tcgtcgtcgc tgtgatcgtc tcttgctact ctcccgctgt caatgatcac ctcacgatga    180
ctctcaatgt ccacttcgct tggacgtcgt tcaatcacct tgttgttgtt attattgttg    240
ttgttatctg aatgtgagtt tttggttggt gttgattgat aaggtgaggc aggcttgacg    300
ggtccagctt cgaccgagct tgcccaaact ctagcactct gttccatgaa ttgaacaatt    360
cgacgaaaaa cgggacatct atatcaaaat caaacagtac caaccgcgag taaaagtatg    420
gaaagtagaa aatgaatgga aaaaatagtc caaggagtt gttactctcg actatcaaga     480
ttaacgaggg taaaacaagg atagcggttg cgatgtttca caaacaaact cgacgtccta    540
tctctgctgc aggataaaac acaactgata tgataacgaa tcccaagctc actaccagtt    600
tgcacccgta gagcttaccg tagaagcagg agctttgctg gactgatagt ggttcaaagt    660
aaactttgcc aggctgttag agttgccttt acgagctctg attggtgtgc ttactcaagc    720
gaattagcga cgtgtgttga agtagctggc agtgacgtat tggcaggaga gtggggtgca    780
gtggtgggct ttaggggtgg ggtagtaata gtgctggtgg taacagagag agagagagag    840
agagagagag agagaggggg gggtgaagaa agggttgttt tagaagatttt ctaaaagatt    900 tcaaactcag ggatatagtg cctgtaaaaa gtgcactcaa tggactgctt caaaaatca    960 gtccaaaatg aagtaggcct agtgtacgaa gtaaatagtt tggtattggt atacaaatta   1020
ttaatctttt ggtaggtatc atgatcattg accaaaagca ctattttcgt catccagata   1080
cccacaattt gaagtatcac ttgataactc catcaatatc tgattggaat atgattggca   1140
cagtcattcg taagaaagtt aataatgtgt attagctgaa gatttcacat agaatggaaa   1200
gaggggaaag attgtcactg gtatatggta gagtccagtg aggggtgtgt tggatggatg   1260
tggacgaatg ctcatttgct actgacgtcc ttctgaccat ggttcaaata aaccaagaag   1320
tcaataaacg cgaccaaact agtcatctgt aataacaacg tatagagaac aaagaaatac   1380
tgtcacggtc acatgttaaa aggagaaacg ttcattaata tgtgattgtt tggatgattg   1440
atgtacataa tgctatttac aatataataa ctcttggaca ttgtacatac aacaactgca   1500
catcttactc agctaaatta gtcattaaca cattaacaaa ttaataatca aatttcccc    1560 cgattctgtt aaaatttgac tttccgtcat tcttactcag tgttacctat aacctactgg   1620
taaatgtcaa ctgtacgatt ataccctgttt aaagtttcgt gttatggact aagcctgagc   1680 gttgtaatttt tttttcttca ggtttctgga agagatgagg aatacgaatg ccagaattag   1740
ccatgatact tgataataca acgtagtttt gattacctca taaagtgaat taacattata   1800
acttagccga tgaacgtttg ctaccacata acacacggaa cagattaaat atccctggaa   1860
aagacactgc atcaagacgg aaaataattt gccgggtttc atttttccatc gtcatttttt   1920 ttttctggga aactcttcag gaacaaatag atattttact ccaagacagt tttctgttca   1980
```

```
gttggactaa cgtaagtgcg cgcttaatat agatccttgg ttataacatt ggtgcttctt    2040
ctgttctgtg gtaaaaactg aactgagaac caacattaaa ggatgtgggt gacaggagag    2100
atttcaaaaa ggtgcgaatg atttatgagg ttgatgtagc ttccgtggaa gatgtagaga    2160
tcatgtgacg aaaagatgga ttgtgagtca acaatgatg tcaaacagcc cggtgctcat     2220
ggggtgacac gacatgactg gtgcgctgaa tgtgctggat gtgctgctca aagaccacac    2280
gaagatatat tgagaggaaa cataagacat gtaagataag gatgttggtg atgacgataa    2340
tgatgatgac gacgatcgtg ttcctcggat cgaataaaga gagactttca agagttgtga    2400
agcgcattga tcttttgata tattttttta aaaagatatt gaaattatta aaaagcaaaa    2460
aagagaaaga caaagagagg ggggaaataa gagatgatga ggacaatgtg attgcgatgg    2520
ttgttgattg tcacgataga agatccaaag attggtgaaa aaaattaact ttgaatagtc    2580
gtgatatcat tattatctta gtgatacacg caatgaaaat aataacaaaa gcaaagttac    2640
accagagttg aacatgtgac gtcgtagaat gattgagaat caaagaaagg acaaagtaac    2700
cataaatctt ttactcttta cagaatcaat cttgacaaag aaattgggat tttgtttctc    2760
tcgttatcaa ggctaaatat tttgcttacg tttatttgtc aaattaaacc ccgtgggtac    2820
accaactaga gaacagacat attgaatctc gtcatggagg tgaaagttat tggtccatgt    2880
tcagaccttt acgcttgaca ttgatggtgt cttcaaggt gaatcctacc agtaaaagtg     2940
attgcgacgc tttacaagga acaacccaag cgggcctatt acgatacccc ctccctcccc    3000
ttcacatcag aataaaactt gtagcaatat aacgaagtgc accactgcaa atttggagat    3060
cgggatgcat ctct                                                     3074

<210> SEQ ID NO 40
<211> LENGTH: 3095
<212> TYPE: DNA
<213> ORGANISM: Strongylocentrotus franciscanus

<400> SEQUENCE: 40
attgactcag aaaccacagg aacgtggata tctgtcttgc cctggttgtc ttcacttcca      60
ggactcccct tttcttcttc acttccctct tcgaattctc tttcagcgtc gtcgctgtgg     120
tcgtctcttg ctactctccc gctgtcaatg atcacctcac gatgactttc aatgtccact     180
tcgcttgaac gtcgttcaat caccttgttg ttgttgttgt tattgttgtt attatctgaa     240
tgtgaatttt tggtaggtgt tgagtgataa ggtgagacag gcttgacggg tccagcttcg     300
accgagcttg cccaaactct agcactctgt tccatgaatt gagaaattcg acgaaaaacg     360
ggacatctat caaatcaaa acagtaccaa ccgcgagtaa agtatagaa agtagaaaat       420 gaatggaaaa aagagtccaa aggaattgtt actctcgact atcaagatta acgagggtaa     480
aacatggata gcggttgcga tgtttcacaa acaaactcga cgtcctatct ctgctgtagg     540
ataaaacaca actgatatga taacgagtca caagctcact accagtttgc acccgtagag     600
cttaccgtgg aagcaggagc tttgctggac tgatagtggt tcaaagtaaa ctttgttcag     660
gctgttagag ttgcctttac gagctctgat tggtgtgctt actcaagcga attagcgacg     720
tgtgttgaag tagctggcgg tgacgtatcg ggagagtagg gtgcaacgat ggattatagg     780
ggtggggtag tagtagcgct ggttgtaaca gagacacaga gagaggggt ggggtgaaga      840 aagggatttt ttacaagatt tcaaactcaa gggatatagt gcctgtaaaa agtgcactca     900
atggacggct tcaaaaacac tgtccaaaaa tatttttaaa tagtagcagg ggtaatagtg     960
tacgttgtaa atagtttggt attggtcttg aagttattaa tcttttggag ttttggtggg    1020
```

-continued

```
tatcatgatc attgactaaa agcaatattt tcgtcatcca gatacccaca atttgaaata   1080
tcacttgata aatcaactaa tagctgattg gaatatgatt ggcacagtga ttcgtaagaa   1140
aattaataat gtgcattagc aaaagattcc acacagaatg ggaattggga agagggaaag   1200
gcattgggcg tggctctagt agaggggtaa gattataact ggtatgtggt agagtccagt   1260
gaggggtgtg ttgggtgggt gtgggtgaat ggtcacttgc tactgatgtc cttcagctga   1320
ccgtggttca aataaaccaa gaagtcaata aacgcgaaca aactagtcat ctgtaataac   1380
aacgaataga gaacaagatc acatgttaaa aggagaaacg ttaattaaaa tgtgattgtt   1440
tggatgattg atgtacatag gctattagta ttacaacaac gttattctgg gacattgtac   1500
atacaactgc acatctttct cagctaaagt attcattaac acattaatca aattaatcat   1560
aattttcccc tgattctgtt aaaattttac ttttcgtcat tctgaccctg tgttacctat   1620
atcctactgg aatgatgctg agcgttgtga atcattttca ggtttgtggg agaggtgagg   1680
gataagaatg ccagagtaag ccatgatact tcataaaata ttaacattat aacttagccg   1740
atgaacgctt gccatcaaat aattcactaa acagattaat aatcctagga atagacactg   1800
catcaagtaa taaataattt ggacattgcc gggtttcgtt ttccatcgtc attttttttt   1860
ttctgggaaa ctcttcagga acaaatagag acgatagtgc acaatatttc tactccaatt   1920
aagacaattt tctgttcagt tggactaacg taagtgcgcg cttaatgtag atccttggtt   1980
ataacacgta gtaggtccat ggttataaca tgggtgcttg ttatgtggta aaaaccgaac   2040
tgagaaacaa aattaaagga tgtgggtgac aagagacaat tcgaaaaggt gcgaatgatt   2100
gatgaggttg atgtagcttc cgtggaagat gtagagatca tgtgacgaaa agatggattg   2160
tgagtcaaac aatgatgtca aacagcttgg tgttcatggg atgacacgac atgactggtg   2220
cgctggatat gctgctggat gcgctgttca aagacctcac gaagatattg aaaggaaacg   2280
atgcttgtaa gctaaggatg ttggtgatga tgatgacgac gatcgtgttc ctcgaatcaa   2340
attaaaagag agactttcaa gagttgtgaa gtgttattga tcttttggta gatttttttaa   2400 aaaagatatt gaaattatta agaagcaaaa agagaggaa agagagagaa aaaaatgaga   2460
agtgatgagg acaataagtg tgattgcgag ggttgttgat ggtcacgata aagatccaa   2520 agattggtga agtaattaa aatttgaata gtcgtgtatat cattattatc ttgtgataca   2580
cgcaatgaga atgataacaa aagtaaagtt aaaccaaaga tgaacataac ttgtgacgtc   2640
atagaatgat tgagaaacaa agaaaggaca acgtaaccgt aaatctttta cactttacag   2700
aatcaaactt gaagaaatag ggattccgtt tacctcgtat tcaaggctaa atattttgct   2760
tacttctatt tgtcaaatta aaccccaggg gtactggtag tgggtacacc aacttagata   2820
acatacataa tgtgacgata ttaatgtagc attaatactt ccataaatct tgtcatggag   2880
gtgaaagtta ttggtccatg tttagacctt tacgcttgac attgatgtg ttttcaaagg   2940 tgaatcctac cagtaaaaat gattgcaacg ctttacaagg aacctcccaa gcggacctat   3000
tacgataccc cctccctccc cttcacatca gaataaaact tgtagcaata caacgacgag   3060
catcactgca catttggaga tcggtatgca tccct             3095
```

<210> SEQ ID NO 41
<211> LENGTH: 1076
<212> TYPE: DNA
<213> ORGANISM: Strongylocentrotus purpuratus

<400> SEQUENCE: 41

```
ctggttagga ggaaccaaac aatgaaggga caaacgacat ttcaagagat tggtctacag      60
acctcaagtg aagaatctcc ctggaacgag gtctatgcta caacaatta ggaagcgaca     120 ccacaatcac accagaatta aattcgtacc ttttgttagc cctcttttta ttccaattct    180
catatagaga gtctctagaa gcttagtgta atgatagagt gcatggtcgg ttagaagtat    240
tttagtaatc tacataggcc tttactttac atcagtatct attgaagtca tacattaatg    300
gctctttgaa acgttttcag gtaatggaag tagagtttgc cttttcattg tttaaaccaa    360
atgttatcat gttgattgtc atataagcat atacacgaga caagacatta aatatgagac    420
tatcatcatg atgtgtctct tcatgaatgg aatcattatt atgttgtcat caacatttaa    480
tattgacttc gatagagata caatgctggc aattggtcac accatacatt tgcagcgttg    540
ccgtcattta cgtagtaggt ccatgtttaa actaacttga attacttcga tgaacctcaa    600
attggagtcc tttatttttt aaaaggtgaa acaaacaact cttattctat atacctggta    660
catgattgta gcaaggtgtg ggcaagggag atgaagagag cctgtgttta ctcgagacag    720
agggagtcat ggctgacctg tcgggttctg atctggcttg gctcatgatg atggctgtat    780
tgagcgttca tctatcatgt tggtttgttg ttcattgtgt gatgacatcg ctaccacata    840
cagactcact cccttgacac tgtaacatga catgggggca acaaattacc cctccgtggc    900
ttctaccaac agtggttggt ataggattgg aagacaaccc aggtgcgatg agtactgctc    960
tatagggtca tcatggtcat catggtatct tgttgccata gtgatgaaat gaaagtctac   1020
gtatggaccc ataatgatg actggttcaa taatcggaat tgtacttta aacaag         1076

<210> SEQ ID NO 42
<211> LENGTH: 1085
<212> TYPE: DNA
<213> ORGANISM: Strongylocentrotus franciscanus

<400> SEQUENCE: 42
ctggttagga ggatacaaag attgaagggg caaactagat aagtatttcc ctggaaaagg     60
gggcctatgc taacgacatt taggaagtga caacagaatt aatttcgtac ccttcgataa    120
tcctattatt acaattctca tatagagacg tctctagaag atttgtgtta agatagagtg    180
gtgggctaga agtgttatag taatctcat aggcctatac tttacaccaa tcttacttct     240
ccttggtttt atctaatgaa gtcatacatt gatggctctt tgaaatgttt tcaggtacag    300
taatggaagt agagtttgcc ttttcattga taaaaaccaa atgttatcat gatgattgtc    360
atactagcct atacacgaaa cacgaaatta aatatgagac tttcgtcatg atgtatatct    420
tcgtgaatgt aattattatg ttgtcatcag aacttacgat cgagttcgag agaaatataa    480
agctggcaat tagaagtgct cacaccatac atttgcagcg ttgccgtcat ttaaaggtac    540
tatgtcccac tttaaactaa cttgaattac ttcgatgaac ctcaaattgg catccttta    600 taaaagatga aacaaacaac tcttatgcta tatacatggt acatgattgt agcaaggtgt    660
gggaaaggaa gatgatgaga gcctgtgttt actcgagaca gagggattca tggctgacct    720
gtcgggttat gatctggctt ggctcatcat gatggctgca ttgagcgttc atctatcata    780
ttggtttttt gttcattgtg tgatgacatc gctaccacat acatactcac tcccttgaca    840
ctgcaacatg acatggggc aacaaattac ccctccgtgg cttctaccat gaacaacagt    900
ggttggtata ggattggaag acaatccagg tgcgatgagt gctggtaact actctacagg    960
gtcatcatgg tcatcatgat tcatggtatc ttgttgccat ggtgatggaa tgaaagtcta   1020
cgtatggacc cataatcagg catgaaactg gttcaaataa ttgcaattgt aaacttgtaa   1080
``` acaag 1085

<210> SEQ ID NO 43
<211> LENGTH: 505
<212> TYPE: DNA
<213> ORGANISM: Strongylocentrotus purpuratus

<400> SEQUENCE: 43

```
ttctctttga acgcatcttc tggacatcat gtctactgat ttcaatgaga ccttattgta    60
attagctcca agaacgagtc attgggagaa taggaaaaca tacgaattcg aagatcagcg   120
gattgagtgt ttcaatcgcg ttagcatccg ctctttaaaa aatagaggag gtatttcgag   180
tcttacccctt ctactggtgg tcgtactcca acgccattag gccgatagag ctcgctgaga   240
agggaaaaaa ccatgcaccg cacaaaacac ttagcatcat cagtattggc agatatgagt   300
cacgtgacca aacactgtga gaccgtctgt gattggccaa taggaaccca gtgagaatga   360
aaggaagccg gtcaaagaat ggctcttgta cttctcaaag cgtgacgtcg tcatattcac   420
taaacttatc tctatctctc tctctctctc ctctgttcgg gatttttacc gtcaatttct   480
gtcaggcggt ggtatgtata aacgc                                         505
```

<210> SEQ ID NO 44
<211> LENGTH: 501
<212> TYPE: DNA
<213> ORGANISM: Strongylocentrotus franciscanus

<400> SEQUENCE: 44

```
ttctctttaa tgcatcttct ggacatcatg tctactgatt tcaatgagat cttattgtaa    60
ttagctccga gaacgagtca ttgggagaat gggaaaacat acgaattcgg agatcagcgg   120
attgagtgtt tcaatcgcgt tagcatccgc tcttttaaaa atagaggcgg tatttcgagc   180
cttacccgac tactggtggt cgtactccaa cgccactagg ccgatagagc tcgctgagaa   240
gggggaaaaa ccatgaaccg cacaaaacac ttagcatcat cagtattggc agatatgagt   300
cacgtgacca aacactgtga gaccgtctgt gattggtcaa taggaaccca gtgagaatga   360
aaggaagccg gtcaaagaat ggctcttgta cttctcaaag cgtgacgtcg tcatattcac   420
taaacttatc tctctctctc tctctcctct gttcgggatt tttaccgtca atttctgtca   480
ggcggtggta tgtataaacg c                                             501
```

<210> SEQ ID NO 45
<211> LENGTH: 478
<212> TYPE: DNA
<213> ORGANISM: Strongylocentrotus purpuratus

<400> SEQUENCE: 45

```
tcttgttctc tctataccctt ataccatctt caagaagaat agtaatcgcc cacatgcatg    60
cattcttttg ttcctctttta aattatagtc cagggccata ccgtcccatt acggaacacc   120
ccatcgttaa aaactcgaca aacagaagaa aaaatcgatt tgttcggggc aaatatata    180
gaacggtggg tttgaggttg ggtccaggg acagaaggg aaggtattgt gacgagtgag    240
gtaaagaata actcttaaac caggatggtc gagtactaat caaccaacgc ataccgtga    300
cataagccat ctctgcaccc ctattcacca aatatcgatc cacattgcct tcttcaccac   360
cccctttcacc cgcagtgcac catgtggagt cacaaaagat cctttgcaat ctcttaaaat   420
gaaagttatc tgtacctccc tcatgaatct cgtagctttg ttgaagtgta gctgtgtc    478
```

<210> SEQ ID NO 46
<211> LENGTH: 463
<212> TYPE: DNA
<213> ORGANISM: Strongylocentrotus franciscanus

<400> SEQUENCE: 46

| | | | | | | |
|---|---|---|---|---|---|---|
| cattgttctt | tctataccct | ataccatctt | caagaagaat | agtaatcgcc | cacatgcatg | 60 |
| cattcttttg | ttcctctttta | aattaaggtc | cagggctata | ccgtcccatt | acggaacacc | 120 |
| ccatcgttaa | aaactcgaca | cacggaagaa | aaaatcgatt | tgttcggggc | caaatagaac | 180 |
| ggtgggtttg | aggttggggt | ccagggaaca | gaagggaagg | tattgtgacg | agtgaagtaa | 240 |
| agaataactc | ttaaccagga | tggtcgagtg | ctaatcaacc | aacgccatac | cgtgacataa | 300 |
| gccatctctg | caccccctatt | cacaaaatat | cgatccccat | tgccttcttt | accacccctt | 360 |
| tcacccgcaa | tgcaccatgt | ggagtcacaa | agatcctttt | gcaatcttta | aatgaaagtt | 420 |
| atctgtacct | ccctcatgac | tctcgtagct | tgttgaagt | gtc | | 463 |

<210> SEQ ID NO 47
<211> LENGTH: 3262
<212> TYPE: DNA
<213> ORGANISM: Strongylocentrotus purpuratus

<400> SEQUENCE: 47

| | | | | | | |
|---|---|---|---|---|---|---|
| ttccgcccgt | accgccccaa | catcaccacc | accttcagaa | caagatgaac | gcactcggct | 60 |
| ctccgtactc | cgtcaacggg | cgatcgctgg | cgtcgccgaa | cgttgagctc | atgcatcccg | 120 |
| ctatgtcata | tacaagtaag | tcatactctc | ttaatttgtt | ccttctggga | attttgtatc | 180 |
| cccccttccc | aaatatagac | taaatgtcta | ctcttattat | aaatatcata | ggatttacac | 240 |
| gacagtaaag | tttactttta | attttactac | tagtacgaag | agcgcaagca | caattggcat | 300 |
| ataggcct | atcatctttc | aatttctttt | acaaaattac | acatcgctta | tgtacaagaa | 360 |
| tcattatttc | gactatatga | aacttaaaa | tcagaaatat | ttgaacaagt | gaactagatt | 420 |
| aaattatta | taaaattata | tattcagtaa | tgaagcgata | acatttacgt | atcatgcggg | 480 |
| tattggaacc | aaacaaaatg | cactgcggtt | agttcatgtt | atggtattta | tgaatcgttt | 540 |
| aagatttcaa | cgagataatg | tttatctaga | ttaaatatct | gcatatatga | aaaacatat | 600 |
| atctatatct | gcattgagaa | ttatcctatg | tgaaatagtt | gtggaagtgt | tggcaagagt | 660 |
| gacgataaac | taaagtagtg | tcaatgacag | cggcacctct | gtagtgaaat | aactcttagg | 720 |
| gagtaagtat | gtattcatgg | tatattacta | attaaataat | taacggtatt | attgcattgt | 780 |
| gtcaccctgc | tacattggaa | taagaccatt | gataagttat | atgacaggta | catggtgttc | 840 |
| cgtgaggata | gtacaacgac | gataattata | ataattacca | ttggaaagtt | aggaactttc | 900 |
| cattactaat | catgtctgga | catttttttt | aaaattaact | agagttttc | caaacgcaat | 960 |
| cagacacgaa | taatctgttt | aaatgatttt | taattcagtt | caatttgaa | ttcaatggtt | 1020 |
| cagcatacat | attgccattc | gttttttaa | aacatttttt | agagcagtta | aaagatattt | 1080 |
| acaggaaaat | gagattaatt | ttaaagcata | gtggaatcat | acatggaaga | aggtgcactc | 1140 |
| tcacaaataa | aagaaaaaca | ttggacaaaa | tatacctatt | aataaaaatg | gagcatgcat | 1200 |
| gtatgtttga | taatattata | accattattg | ggtatatact | agccaatttc | gggtacatct | 1260 |
| tacccaatat | aaccaagaaa | catgcacgta | ctattttaat | ccaactcttt | ctatagtgtg | 1320 |
| taaaaagcct | gtgaagcgag | gttccgtgt | agggtatatc | ctgaaggtta | acaattgatt | 1380 |
| ttaaaatgta | tctgataaac | atatagtcaa | taaaatagat | gatcgtgaat | tagggcagtt | 1440 |

```
cccacaattt tgtttgtgat gaagatctac atcggtatct acaagaagca atgcactgct    1500
gtgtacatat agcatcttgt gttgattcaa atcattaaca ttaagacgct taaagtctgt    1560
aaggtgtata gaaggacatc tagttcggcg gagcacgcta taaactcctc cacgaattgc    1620
ggtagatctt tgggagattt taagtgatcg aactactaga ttagtgatag aaattatcta    1680
tgagtttaat ccaatgggcg tagtatcgat gagatattga tactatgttg tctaattgat    1740
gtttgtcgat gagcatctta cattttgaag aaaccgctta aaatagcccg atctgaatat    1800
attctggcaa ataccctcac aattatattt ataagaaaat gtgttaatgc tactacattc    1860
caacttgata agtcatattt gtttaataga tagtacaatt gcttaagatc agtggcagac    1920
atacatattt aaacttagtg taaaatttag ttttctttt cttcttatcg tcaggagtag    1980
gatttctatg agtattttct taaaattaaa aatcttagaa tccatttaaa gtctaacgta    2040
gatggtggtt aaaagaggca acattacaaa ttattctaat gttttgttca tccttaaaat    2100
ataattttgt atgttgttaa atcattattg ttgtctttat tcttgctagt tcctgtatgc    2160
ctgtagctta gaatctttaa tcataaaaat aagtcaaaaa tagatttgga agaaataaag    2220
tatttgaagc tctaatttca tttcggaaac aatgaatatt aaatcaaggt gttaaattta    2280
ttttcctcct atttacatca acccttagac aagaaattga cgctaattaa acttactgcc    2340
ctcttattat gcttatttga aatttccata atctccgttc gttaatttgc ttccgcgtta    2400
tatatttcat agtggaaata attaatctac atattttaca gttgttcctc gtcttaattt    2460
cattggtttt gctatctcat ctcatggttt tgatagtcaa gactttaaat taacttatta    2520
atctagttgt taaaaatata agcttttta acgagtgatc ggatgcagtc atcacaaggc    2580
aacgtaaaca taggtataaa tgccagcaaa cgctatgggc gagtgaagca gtttgctaat    2640
atctttggta tgattctta tcattatttt tacatcagtg aatgtgtgtc aatataatca    2700
ctgtttcctt atgataaacg ttaataagat tattatggaa caaacgagtt cagttttaat    2760
tcttgtacct ttgatttaac tgctatgtga ttttttactat aagtactact actactacta    2820
ctattagtag tactatacta ctacttctgc tactactact actactacta ctacctctgc    2880
taccactact tctactacta tactaatagt actatactac tacaactact tcttctaata    2940
catgtactac ttatacgaca actgtatatt acatttgtct gacttatgat ttattttttg    3000
ttgatggtca atatctaaaa aaaagcttca tgaaattgtg ttataaatta ctataaacac    3060
aatcgcagtg atcttttaa agacggcaat caaagctatt actaattcaa tcaatttata    3120
tttattggaa tgccacctgg agctaaactt gttttctggt actaatgcta agtcctggat    3180
aagggccatt gttccgtaa acattctctc acatcatcac gaaagaatac agggggcaatg    3240 gcatcagtgc ttggtcctgt ct                                              3262

<210> SEQ ID NO 48
<211> LENGTH: 3128
<212> TYPE: DNA
<213> ORGANISM: Strongylocentrotus franciscanus

<400> SEQUENCE: 48
ttccgcccgt accgccccaa catcaccatc accttcagaa caagatgaac gcactcggct      60
ctccctactc cgtcaacggg cgttcgctgg cgtcgccgaa cgttgaactc atgcatcccg     120
ctacgttata tacaagtaag tcatactctc ttaattagtt ccttctggcc tttctgggaa     180
ttttgttttg cctgctttag cttttattcc tcccaaatat agaatgaatg tctactctaa     240
```

```
ttataaatat cagaggatgt acatgtacac gacagtcaaa tttacagagt acgaagtacg    300
aatgccgaag agcgtatata ggcataattg gcattatcga atttcttttt acaaaattac    360
acatcgtttt aatatgtaaa agaaccatta ttttcgactg tatgaatcaa aatatattaga   420 acaagtgaac tagataaaat tatttaaaga tatatatttt cagtaatggc gcgattacat    480
ttacgtatct tgtaggtatt ggaacaaaac aaaatgcact gcggttagtt catgtgatga    540
tattaatgca tcgtttaaga tttcaacggg ataatattgt tctagaataa atatctacat    600
atttgaaaat atatatatct atatctgcat tgagaattat cctatgtgaa atagttgtgg    660
aagtgttggt aaaagtgacg ataaaaatac agtggtgtca atgacagcga aagctctgaa    720
gtgaaataac ccttagggag tgagtttgta tacatggtat taataattaa ataattaacg    780
gtatcattgc attgtgtcat cctactacat tggtatgaga ctcttgataa gttatgttac    840
aggtgcatgg tgttctgtga ggatagtact aagacgataa ttataatgat caccattgga    900
aagtaaggaa cttttcatta ctattgcctt gacattttta caaattaact aggctttttc    960
ccaacgttat cagacacgaa tactccgttt aaatgatttt caattcattt caattttaaa   1020
ttcaatggta cagcatatat acttccattt gttttttaaa acagttttta gagcagttaa   1080
catatattta caggagaatg agagtaattt taaagcatag tggaatcata catgggataa   1140
ggtgcactct aaaaaaaaat tggataaaaa tatccattaa taaaaatgga gcatgcatgt   1200
actatgtttg ttgatatcat acccattatt gcgtattaca tcttacccaa tataaccaac   1260
ttacatgtac aaaaaacgtt cccgtttagc caaattattt ttttctagag tgtgccaaag   1320
cttgtgaagc aaagttctcg tgttgggtac attctgaggg ttaacaacat attttaaaat   1380
gtatctgata aacatatagt caataaaata gatgatcgtg aagggcagtt cccacatttt   1440
tgtttgtgat gaagatctac atcggtatct acaagaagca atgcactgct gtgtacatat   1500
agcatcttgt gttgattcaa atcattaaca ttaagacgct taaattctgt aaggtgtata   1560
attatagaag gacatctcgt tcggcagaac gcgctaaact cctccacgaa ttgcggtaga   1620
tctttggggg atttttaagtg atcgaactac taaattagtg atagatagta ttttgagttt   1680
aatccaaggg gggaagtcgc ggggaataa tgattttatg tttatccaat tgaaattttt    1740
cgaggaggaa gaaaggggag cttttttactt ttagaagaaa ccgcttaaaa gctcgatatg   1800
aataaattct cgcaaaattt ttcccaacta taagggaatt tgtttatgct actccattcc    1860
gactagatag gtcatatttt taaaatagat tgtacaattg cccgagatca gtgacagaaa    1920
aacatattta aacttttgt aaatgttttt tttttttta atccattta agtctaacgt       1980 agattctagt tgaaagcggc accattacaa ttctaatttg ttgttcatcc ttgaaattta    2040
attatgtacc tcgttaaatc attgctgttt tattgccgtc tttattcttg ctagttcata    2100
attgcctgta gcttggaatc tttaatcata taaaaacagt tcaaaaaata aatttggaag    2160
aaatagaata tttgatgctc tcattgcatt ttggaaacgg tgaatattac attaaggtct    2220 tacattttc cctttcgttt acatcaacca tcagacaaga aattgacgct gattaagcta     2280
actgccctct tatcatactt atttaagacc cacctttcat aatctccgtt cattaatttg    2340
ctttctcgtt agatatttta tggtggacac aattaatcta cagattatac attattgttc    2400
ttcgccgcaa ttgcatcggt tttgcgatct catcccatgg ttttgatatt caagacttta    2460
aattaactga ttaatctagt tatgaaaata taagctacat gtatttaat gagtgatcgg     2520 atgcagtcac cacaacacaa catctacata ggtacatgtc agcgaacgct atgggctagt    2580
gaagcagttt gctaatatat ttgatatgat tccttattag tttttcccta tcagtgaatg    2640
```

```
tgtgtcagga ttatcactgt tttgttataa tacacgttaa caagattatt ctcgaacaaa      2700
tgagttcagt tttaattcgt gaacctttaa tctaactgct gtgtgatttt tactatcatt      2760
actactacta ctactactac tactacttct actacttcta caactactac ctctaataca      2820
tgtactactt atatattact attgtctgac ttatgattac attttttgtta atggtcaata     2880 tctattttt aaatcatcaa attgtttcat aaattactat catcacaatc gcagtgatct       2940
gtttaaagtc ggcaatcaaa gctattactg attcaatcaa tttatattta ttggaatgcc     3000
acctagagct aaacttgttt tctggcacta atgctaagtc ctggataagg gccattgttt     3060
ccgtaaacat tctctcacat tatcacgaac gaatataggg gcaatggcat cagtgctcgg    3120
tcctgtcc                                                              3128

<210> SEQ ID NO 49
<211> LENGTH: 479
<212> TYPE: DNA
<213> ORGANISM: Strongylocentrotus purpuratus

<400> SEQUENCE: 49
cctttggccg cagttggaaa tatcgtggag catcgatctg ataggagcaa ttattttaac      60
aacacgactc ccactgtaat agaggagaag agtagtgtcc tgcaatcgaa gtcaaataac     120
atttattgtt cgtattaaaa atgtaaatca acaaccccct gacaaacaaa catgcgttca     180
aattaattca acaagaccgt tgatattcga atcttttaaa gtatttgttt taaatgactc     240
aagagaatct ttatttaaaa agaaaatcaa cgtcagagct tgataagtta caatagctgg     300
ggaaaccatt acctttgacg gaaaaaagcc atatttacaa ataatcatga acgatgaaga     360
gcaaagttta gtaaatatta gccgaaagat attagatcag tgggaaattg tcatgataat     420
tttttttaaa atattcattc aactttatac atattttaaa taaatggaaa ttagcttgt      479

<210> SEQ ID NO 50
<211> LENGTH: 484
<212> TYPE: DNA
<213> ORGANISM: Strongylocentrotus franciscanus

<400> SEQUENCE: 50
cctttggccg cagttggaaa tatcatggaa catcgatctg ataggagcaa ttttaacaac      60
acgactccca ctgtaataga gtagaagagt agtgtcctgc aatcgaagtc aaataacact     120
tattgttcgt aaaatggaaa tcaacaaccc ctgacaaaca acatgcgtt cacattaatt      180 caataagacc gttaatattc aaatcttttct tagttttttt tacaaaatga cttaagagaa     240
tctttataaa aaaaatcaac gtcagagttt gataagttac gatagctggg gaaactctta     300
agtttgaaga agaaaaaaaa gccatgttta caaataatca tgaacgataa agagcaaagt     360
tgagtaaatc attaagctta atattcgctg aaagatatta aatgaatggg aaattgtcat     420
gatgaaaaat atgtattcta catacaactc tatacaaatt ttcaagaaat agaaattagc     480
ttgt                                                                  484

<210> SEQ ID NO 51
<211> LENGTH: 2845
<212> TYPE: DNA
<213> ORGANISM: Strongylocentrotus purpuratus

<400> SEQUENCE: 51
cactaattat ttataagttt actataaata gaacaactta taagaaaac tattttgatt       60
```

-continued

```
gtttacaatt tgttaaaga gaaaaaaatg cgtttgtaac gagatgcgga gatacattgt    120
tcgcatcagt tcgatggtgt ttttatagtt cgtatcttta atattggacc tggtaattcc    180
ttaattcgaa gatggttgaa agatatacat gtatcccttt cactgtctta tcattgcgtt    240
taataattaa taaagtccaa caattatgga cataattcac ataactatat ttaaaaggtg    300
tctgaaccac gattttaacg gagccaggtt acactatata caaataatcg aaacgagtga    360
gattagttta accgctctaa tcgttataaa atcgacacgt tatatcgaat gcacgcgtca    420
agattagaga actttaatct catgatggcg attatgagct ttctaatctg atctcattcc    480
atgtcctaag tcggattaac attggtttga tctgcctgat ctgtcatcag ctccaagtaa    540
cggaggtttg tatttagaac cagctccttt ctatccctgc ttaactcaat gaatgtagat    600
tattgaaagt aatagtacta ctgttcattc gttttgaatc actaacaaaa gacaaacacg    660
cttgtacaag tcatgtaggc ttgataatga tattaaatac aaaataaata gagtgactat    720
acattaactg aaagttcaat gactgcataa aatacgctgc ttatgaaaca taacttgtcg    780
ttattatata aaaaaaaaag atttgatagc atgaatccct tgaagttgat caaaaaaagg    840
cttgatagca tgaatccctt gaagttgaag gttctactgt tttcaagaaa acagtctttt    900
gatcacgcta tttgctctct ttggttatat acgaatatag tccagatata tattttggaa    960
tccctgcaag attgtgtaag ttttttgattt ttgtcctgat gacacagtaa tagtgccgac   1020
tcttctaatg ttttgtatcc ggtgacgcca tcacgcggtc ttttcctgga acattgaaca   1080
tcgtgtttta ctaataaaca aacgccggat ccaggaatca attcttctga aatagtaatt   1140
ataaatttcg aacttcctat tgtcattatg ataaatttac acaaaaacca aacagggat    1200 agatagttta tcgagaaggg gattgattga tatccgtccc tactattaat atcaagaatg   1260
cgagatggat gatatctttc cagacgacac ccttcttgac atcccctct aaggaggatt    1320 cgggtgtcat ctcacttcag atgagggcgt tcccactggg agaggtagcc agatctgaca   1380
cagaatgatg aagtgtgtag cccctcctgg tatcgagata ccgcacgtca tcggccagga   1440
tgcgactcgg ccgtgcagcc aggtttcgat gtcgacacgc accgtgcatg atgaaagcgc   1500
gggaagcgac acgtcctcgc agacggtaac ggccctcgag ttgagagggg atttcaagga   1560
ggaggagtgg atatgcaaga gcccccaggg agcatgatag aacgggagat aactcacaca   1620
gttgacgcaa gaacaagata cctggtaaac ggtgtcatct gcgatttcac ttctgtgatc   1680
cttgaggaga tgggtcgaca tgtagatgga cacgaagaga tctctccttg ctcgacctct   1740
agccaaagtg cgacttgttc aaagataatt tatgtaaaac ggaataatgc aaattgtgtg   1800
attacttaac tgacaaataa aatgggcaga tatccatgac aaatgttgac attggagtta   1860
atacaaatac taatttaatg ctcagttcac atgataattt gctcctttcg aaacatgtct   1920
tgtttttgtt gactgtaatt agacaataat caactgatga aaaaaaaaat tcaaataagt   1980
gattaagaac actgaattta tacctaataa tacaggaaaa atatttatt ttatggatta    2040 ttacactcgt tgtttgtgta tacgaagaag tctctctttt agatttcctt agttccaaag   2100
caaaggtaag gcgtattatt tgttagtgtt tagcttctca agatcatact tcggaattga   2160
cgatgtgtca aaaccaagag aaagaaatta ctgaacatta tcaacaatta cattaatgtc   2220
taataatcta tcttactata aatatgcttt acaaatagtt gttgtttctc tttgaataac   2280
aaacacacaa aaacccttttt tgggacataa gatatcaatt aatcaatcaa ttgatcattt   2340
caaatttatt tcaacaaagc aattgcaaaa atataaaaga cattcataga actaaacatt   2400
gtcacataaa agaatagaat acaatgtaca tacattagta caacaatata aaagctgctt   2460
```

```
ggcaggtatc agccagagtt gagaaaggag ttatgagtgg ccgacctaaa tatgtataat    2520
tgaaagataa atataagtgc cagattacag gggggatacg acaccagagt cgaccagaaa    2580
gcttttcttt accttaattt cttttcaatt atagagacaa ataatcaaaa gtgtgctatc    2640
gatatttcag aggatttaaa tgtctcagag tgtgaaaacc ttgtgatatt tatagcttta    2700
tgatgatagg aaatcaatta tcgtctaatt tatttatcat tattttgatg aagatctttg    2760
gcacaaaatt gatgtgttct cctttctctt ccgactaatt tagtaaaccg tcttgaagtt    2820
ttaaaagctt tgaaatcca  agatt                                          2845

<210> SEQ ID NO 52
<211> LENGTH: 2652
<212> TYPE: DNA
<213> ORGANISM: Strongylocentrotus franciscanus

<400> SEQUENCE: 52
tacttattta taggtttact aatgtgaatg gaacaaatta taaatcaaat tattttgtac      60
gtttacatgt ttcaatgcgc ttgttccgag atgcctctgt tatatccatt gtacacacca    120
ttcaatctca ttagtcaatg gtgtatttct agttcgtttc ttaaaataac attggacctg    180
gcaattcctt aattctaaga tgattgaaat actaacatgt gcatgtattc cgttcactgt    240
cattgtgaat tgtgattcat aaacaaggaa ctccaacgat tatggacaga tttcattatt    300
cataatatta tatacaagag tatctgtgcc acgattttaa taaagccagg ttacaatata    360
caaaacaatc aaaacgagtg agatgagttt aacccctctt cgttaaaaaa tcgaaatgtt    420
ttattgaatg cacgtgtcaa gattagagaa ttttaatctc atgatggcga ttatgagctt    480
tctaatctga tcccattctg ttttctaagt cggattaaca ttggtttgat ctgcctgatc    540
tgtcatcagc tccaagtaac ggaggcttgt gtttagaacc agctccttct catctctgct    600
taattcaatg catgtagatt attgaaagta ttagtactgt tcattcgttt tgaatcacca    660
aaaaagacga acacgcttgt acaattcatg taggcttgat actgatattg agtacaaaat    720
aaacagagtg actacattaa acgaaagttc aacgcttgta taacataata ttacgttgct    780
tatgaaacaa accttttttct tatcattaaa aaaggtttg atagaatgaa tcccttgaag    840
gttctattgt ttccaagaga aacaaaaatg tgattatgct ctgtgctctc tttggttata    900
tacacgtata tattccagat ttctattttg gaatccctgc aagattgagt aagttctgga    960
gggattttcg aaagaagatg ggatatgatt aaatattttt ttcctgatgg aacaataata    1020
gtgccgactc ttcttatgtt tgtatccggt gacgccatca cgtggccttt taatgaaaaa    1080
ttgaacatcg ttatttatta atagacaaac gttgaatcca ggaatcaatt tcttctgaaa    1140
tttaactata gatttcgaac tttcctatta tcataatcat aaattcgcac aaaatccaaa    1200
cgggggatag atagtttaat tcattgggaa gggaattcat tgatatccga ccctactgtt    1260
gatatcaaga atgcgggatg gatgatatct ttacagacga caccttctt  gacatcccct    1320 ctaaggagga ttcgggtgtc atctcacttc agatgaggac gttcccactg ggagggtag    1380 ccagatctga gacagatggt gcagtgttaa gccccttcct ggtatggaaa taccgcacag    1440
cgtcgcccag gatgcgacta ggcagtgcac ccgggtttcg atgtcgacac tcaccgtgat    1500
gaaagcgcgg gaagcgacac gtcctcgcag acggtaacgg ccctcgagtt gagagggat    1560 ttcaaggagg aggagtggat atgcaagagc ccccagggag catgatagaa cgggagataa    1620
ctcacacagt tgacgcaaga acaagatact tggtaaacgg tgtcatctgc gatttcactt    1680
```

-continued

```
tttgtgatcc ttgaggagat gggtcgacat gtagatcgac acggagagcg ctctccttgc    1740
tcgacctcta gccaaagtgc gacttgttca aagataattt atgtaataag gaattatgca    1800
aattgtctga ttactgtact gacaattaga aaagagaaga tatccatgaa aaatgttgac    1860
attggagtaa ggctacacaa tacaaatatt taactaaatg cccagttcac ataatatttt    1920
tcgcctatcg aaacatgtct tgttttctt gactgtaatt agacaattag tcatctgagg     1980
aaaaaaatgc tttcaaatga gatattaaga acactgaatt tcatacacct aacaataaaa    2040
aaaaattatc taacctttaa cacaattcat tttatggatt attacactcg tcgtttgtca    2100
ctacgaagaa gcctgtcttt tagatttact tccagagttc cttaatccta aaacaaaggc    2160
aaggcttatt ttcttttaga gtttagcttc taaagatcaa acttcggaat cgacaatttg    2220
tcaaaaccaa gagaaagaaa ttactgaaca ttcccaacac gtacattatt gtctaataat    2280
ctatcttact ataattatgc ttttaaaata gttgttgttt ctctacatac acacaaggcc    2340
cctattttgg tcataagata tgttgaagtt gaccagaaag cctttggtta tctaaatttc    2400
ttttcagtta tggagacaaa tgaaacaaaa gtgtgccatc gatatttcgg aggaattcaa    2460
tgtctaaaag tatggaaacc ttgtgattct tatagcttta tgataatagg aaatcaatta    2520
tcgtctaatt tatttataat ttgacgaaga tccttggcac acaattaata atgtgttcgc    2580
gtttttatac tttctcatca aactaattta atgaaccgtc ttgaatattt aaaggaattg    2640
tgattcaaga tt                                                        2652
```

<210> SEQ ID NO 53
<211> LENGTH: 331
<212> TYPE: DNA
<213> ORGANISM: Strongylocentrotus purpuratus

<400> SEQUENCE: 53

```
gactcacaaa ctgtatctca tacacgagtg aaaactgaaa acaaagaata cttgacactg     60
gataaatttt gttttacat tttctgcgtt caaatgtatt ttccttaaaa ttcacatgaa     120
catacctggc aagtttcaac aaattgatta gaaaaataaa aaagtgaaaa ttgttaacaa    180
taacaattca ctccgaatac caattggata ttacaaaaaa gtcaataata ttaattacaa    240
tatatacaaa aatacataca tctatatcaa attcgccata cagaatctcg acaaaaatat    300
tatgaaaata acattgccct caaataaccc a                                   331
```

<210> SEQ ID NO 54
<211> LENGTH: 337
<212> TYPE: DNA
<213> ORGANISM: Strongylocentrotus franciscanus

<400> SEQUENCE: 54

```
gactcacaaa ctgtatctca tacacgagtg aacactgaaa acaaagaata cttgacgctg     60
aatataattt tgttttttac aatttatact ttcaaatgta ttttccttaa aatccacatg    120
aacatacttg gcaagttcca acaaattaat taaaaaaatt aggaagtgaa aattgttgac    180
aataacaatt cactctaaat tacccactgg atattacaaa atagtctttt atattaatta    240
caatatatac aaaaatacat acatctatat caaaatgcca tacaaaaatt caataagaat    300
attacaagat attaataact tttaaaatca tcgccct                              337
```

<210> SEQ ID NO 55
<211> LENGTH: 365
<212> TYPE: DNA
<213> ORGANISM: Strongylocentrotus purpuratus

<400> SEQUENCE: 55

```
aggaaccccc cacttggaat tccatatcac ggtgttaaat actaactcta cacaaagcag      60
cttttttccc acgagtaatt ccattccgaa aagaaaggtt cattttaacc acgatttgt      120
cgctcttcca aacagacctt tggatttagg agaccttaat ggaacttcta ttgatttcct     180
aaactatagc ctttgtacgc aggaagatta cggtgtgcag agaggggta caaaaggggt      240
tcacatgggt gcgtgaaaga ggtgcaatag acaagatcct ccttctaaaa gcgtaaacct     300
cttaacacaa gccggctaat cgcggggaca acacggtaac taaaaagcaa agttgtttct     360
tagag                                                                 365
```

<210> SEQ ID NO 56
<211> LENGTH: 358
<212> TYPE: DNA
<213> ORGANISM: Strongylocentrotus franciscanus

<400> SEQUENCE: 56

```
aggaaccccc acttggaatt ccatatcacg gtgttaaata ctaactcaat acaaagcagc      60
ttttttccca cgtgtaattc cgtgcccaaa agaaaggttc attttaacca cgattttttt     120
cgccattcga aacaaaccat tggatttagg agaccttaat ggaacttcta ttgatttcca     180
aaactatagc ctttgtacgc tggaagatta cagtgtccgg agaggggtg caaaggggggt     240
tctcaggggt gcgtgaaaga ggtgcaatag aagatccctt atgaaagcgt aaacctctta     300
acacaagccg gctaatcgcg aggacaacac gggaactaag caaagttgtt tcttagag      358
```

<210> SEQ ID NO 57
<211> LENGTH: 668
<212> TYPE: DNA
<213> ORGANISM: Strongylocentrotus purpuratus

<400> SEQUENCE: 57

```
agatgtgtat caattactat ctcctgctgt gaggctaaca aaagttgaga gctgaccaga      60
cacttgttga cgattcgaac ttctcaaaag ctaatgaagt ttatcagagt tgtagctctt     120
ataaattaca tcgacacacc tttgacttgt ctcctcatca aaaagagca taaatgatac      180
cttgacatga cagctggatg acggcttgcc attggagcgg cgagcataat aaggcatgag     240
tggtccaatg agaatgcagc tcatgttcgc atgaatagat ccgtgggatg atcaaagcaa     300
taggcgcatc gctattgttt tggcggctaa attgggggca cttttgttcg catcgtctgc     360
tctttgcaag gacgcgctct cgtgagcaag agaagaatag atcgcccacc gagctttcaa     420
tttgcaggaa caaaggggga tttcaggctt tctcaaagtt tgggtagcgt ttctttaaac     480
ttcctttttt caaactggaa cctaaagtga cctcgaggcg gtagctggtt tgaaaaggaa     540
ggagtaagcg aacaaaaaga tgatgaagcg taagagcatg catttagaca gatattcaat     600
cactaataat agtttaagat taaagattaa actctggata gagctttctg acgagagttg     660
tatgcagt                                                              668
```

<210> SEQ ID NO 58
<211> LENGTH: 686
<212> TYPE: DNA
<213> ORGANISM: Strongylocentrotus franciscanus

<400> SEQUENCE: 58

```
cgatgtgtat caattactat ctccagctgt gaggcaatca caatttgaga actgacgaga      60
```

| | |
|---|---:|
| cacttgttga cgattcgaac ttccaagaag gtaatgaagt ttctcctgag ttgtagctct | 120 |
| tataaatgac aacgacacac ctttatcttg tcttctcatt aaaaagagca taaatgatac | 180 |
| cttgacatga cagctcgatg aaggcttgcc attggagcgg tgagcataat aaggcatgag | 240 |
| tgggccaatg agaatgcagc ttatgttcgc atgaatagac cgtgggatg atcaaagcaa | 300 |
| taggcgcatc ggccatcgct attgttttgg cggttaaatt gggggcactt ttgttcgcat | 360 |
| cgtctgctct ttgcaaggac gcgctctcgt gagcaataga agaatagatc gcccaccgcg | 420 |
| ctttcaattt gcaggaacaa aaggaggatt tcaggctttc taaaagtttg ggtagcgttt | 480 |
| cttaaactt ccctttttca gactgaaatc taaagtgacc tcgaggcagt agctggtttg | 540 |
| aaaaggaagg agaaagggaa caaaacgatg atgaagcgta agagcatgca tttagacaga | 600 |
| tattcaatca cttaatagtt taagataaag attaaactct cgatagagct ttctgaagag | 660 |
| agagggaga aagagttgta tacagt | 686 |

<210> SEQ ID NO 59
<211> LENGTH: 3245
<212> TYPE: DNA
<213> ORGANISM: Strongylocentrotus purpuratus

<400> SEQUENCE: 59

| | |
|---|---:|
| tacatgttat tgaaaactgt catattccaa taaccgttcc ctttataaat ataatcgctc | 60 |
| gtgatgtaat tacgacaaac cccgatgacc aatttatgtg caaaaggcgt aaaggtgtct | 120 |
| tcatttaatt cattttctat cagtgggtcc agaaattcca ccgcgtacgt tgtctcttga | 180 |
| catttagcag acgtggtgtt ttatagtgta cgactacata acggcgttca atcaacatct | 240 |
| tcaaggctaa dacaggggct aagatttgga ccaagcatta cttcgtttcg tcacatgggt | 300 |
| tataattaaa gagcactaaa aggtgcattg acattgtcga tacccggggt cgataccta | 360 |
| tatacctcgc actatgtaca gatgtaggct tactttggtc ctaagctgca cccgctatgc | 420 |
| agcagtgatc agatatcatc ctcctaactc gaatataacg gtgatcacca gtagtgtact | 480 |
| ttcttccctc tcattagcac tctgtaccag tcagcaggtg taggatactc aatgttaaat | 540 |
| acacatttta agtggtggtg gcggactaaa agcaaatggt gttgatttag caattaccat | 600 |
| tgatgatgca gaataacatc gtcaattatt ttgaaatata ttacttatat gcgatcgatt | 660 |
| ttaaatgggt tctggggacc tggtcgaacc atctgcaaga atatatcaag aaaaatacca | 720 |
| tcatggcaaa taacacagac ataataccgc gtgagtccaa aaaaaagtac acactagaaa | 780 |
| attggtaatt attttaaaa tcatctatga acagtaaatt attacacatc ttatgaaaga | 840 |
| gtgttttatc ccgaatcatt tagtatcatt ttgtgtggtt cgtgttcacg cttggatgaa | 900 |
| tgtaggaggc attgttacg agagagagtg taaaaatcga cttgcgctaa agttgcttat | 960 |
| ctgatgtttg aataaaacaa tggggatttg ggtattaatt cggtctttac agatccaaat | 1020 |
| aacatcccta acaaaatcaa caatgccaca catatcaaat atgaatatca aatatcaaca | 1080 |
| aacatttgtg cgcgtgtgtg catgagtgtg actttgcttc tgcaaaaagc atatgcaata | 1140 |
| catttcagtt gatacattca attcattctc tcactccgct aatcccaaca tataataata | 1200 |
| catactgtag gcattacttt ggcgcaagtc gattttagca ctcttcttct tcttattctt | 1260 |
| cttcttccag ttaagtgcag cttcaaggtg atgaagataa tcgcactggt tgcgaacaat | 1320 |
| gccatccaag cgcgaacaca taccacacaa aaatgatacc aaatgatttg tgataaaaca | 1380 |
| ctctttcata ataataattt actgttcata gatgattta aaaataatta gcaatttttct | 1440 |
| aggtgtaaac tttgtttga ctcacacggt atatcagata gatcctaata ctagctgagt | 1500 |

```
cttcatcctc tctttctctt ttgtcgtccg ggtaatgatg tgtatatagt gtattatgta    1560
tagacgaaaa tagattccat tccagttatt cataccacat tctaagcgat cggaatgaaa    1620
ttaaacagtt ttcttttttg gtctcgttta tgaaaggtgc aagccttttta acatgcacag   1680 tagacctgtt tactactttt tatgcaaact tctcgaagaa aagtttccct tgacaacaca    1740
aaagcttgcc aaacatagca acagttagtg tatgcaaagg gaattacatc tatagaaatc    1800
tcattatgta tagcaagtga atctaaaaca tgttgttagt aactagggat taaggattaa    1860
attatttcct attaaaaaag gtgtatttgt cattggtaaa agtacaatcg tcttttactg    1920
ttttgttggt ctaatgtata ttcaggcttt tggttaaccg agtcagtctt ttgttcgaca    1980
agaaaatgct gttttcgagt ctataaagag taagaccgct ttaaaggacg ttctgccact    2040
ggcatgttga ctgtaaggtt cttgagcttg gtgtgtcttt ttataggaa acaatgttta     2100 ctggttgaca ccctgaaagg tgcttctact gaaaaggatc agatcacttc ttgtaaactt    2160
ctcgggatac cattttttttt gacagagaag agatataatg aatgaagatg ctataagctt   2220
aagttcaact gattaacaca acaataagtg tgacacccca acccgccccc ttctatatct    2280
ctgtatgtct catttctttc cgctatgtcg ctctctctca ctgtctgact caccctctct    2340
caccctctcc cctgtctcca cttctctctc tgtaatatgt ctcatttatg tcgctctctc    2400
tctctctcat tgtctttctc tgtctaactc accctctccc ctgtctccac ttctctctct    2460
ctgtaatatg tctcatttat gtcgctctct ctcaccgtct ttctctgtct aactcatcct    2520 ctccctgtc tccacttctc tctctgtaat atgtctcatt tatgttgctc tctctctcac     2580
tgtctttctc tgtctaactc accctctccc ctgtctccac ttctctctct ataatatgtc    2640
tcatttatgt cgctctctct ctcactgtct ttctctgt ctaactcacc ctctcccttg      2700
tctccacttc tctctctgta atatgtctca tttatgtcgc tctctctcac tgtctttctc    2760
tgtctaactc accctctccc ctgtctccac ttctctctct gtaatatgtc tcatttatgt    2820
cgctctctct ctcagtgtct ttctctgtct aactcaccct ctccctgtc tccacttctt    2880 tctctgtaat atgtctcatt tatgtcgctc tctcactg tctttctctg tctaactcac     2940
tctctcccct gtctccactt ctctctgtaa tatgtctcat ttatgtcgct ctctctcact    3000
gtctttctct gtctaactca ccctctcccc tgtctccact tctctctctg taatatgtct    3060
catttatgtc gctctctctc actgtctttc tctgtctaac tcccctctc cctgtctcc     3120 acttctctct ctgtatgact cattatgttg ccccgctct ttatctctat atcttactct    3180
ctctctctct tgcttactct tctttacata actattactg catcaatttg tttaaattat    3240
atacg                                                                3245
```

<210> SEQ ID NO 60
<211> LENGTH: 2710
<212> TYPE: DNA
<213> ORGANISM: Strongylocentrotus franciscanus

<400> SEQUENCE: 60

```
tacgtgttag tgattactat catattccaa caaccatcca ctccattaat acaatcgctt      60
acgcgtaatg taattatacg acaaactccg atgatcaatt tctgtgcaaa aggcttaaag     120
acgtctagac ttcattaaat tcacttgccg atcggtggaa gggtccagaa atccatcgca    180
ttattatatt ccaccgaagc agacgtggtg tttcaccgat tacgactgta taacggcgtt    240
cggtcaacat cctcaaggcc aagatttgga ccaaacatta ctttgtttca tcattaaaga    300
```

```
ccactaaaag gtgcactaac attgacgata ccctacatgt ctcgcacatg tacagtaagt    360
tgtaggctta cttttggtcct aagctgcacc cacaatgcag caatgattag ctctcatcct   420
cctaactaga aaataatggt gatctccagg aatgtaattt cttccctctc attagcaatc    480
tgcaccagtc tgcatggagg agactcaatg gaaaattcac cttttaagtg gcaacctgat    540
ggctaactaa aagcaaatgg tgttgatctt gcaattacca ttgatgacgc agaataacat    600
cgtcaattat tttgaaacat atttcttaca cgatcgattt ttaaatggat tctaaggacc    660
tggccgaacc atcagcaaga gatgagaaat ggtttgcaac caaacctcaa gaacatatca    720
agaacaaaat aagatattct tattcataag tgcaaaataa cacgtggtat atgataacga    780
tctcaaagat ggatcgttat gctaacggag ccatcctcct ctctttctct ctcgtcgtcc    840
tggttatcat gctcagtgta taccttaaag gcaatccaa cccttgtatt aagttgattt    900
gtatgaaagc agaaaaataa cagaagtagg atggcaaaag tttgaaatga atcggaccaa    960
tagtaaggaa gttatgaatg tttgaaatgt gagatcacta agtctatgcg aatctcaaat   1020
tggtagtttg gtcagtggat tgtgacgtag aacaaggact agtctcccat ttgccgtgta   1080
caaaaatatc attaatttct gttttctcg taagttcctt ctcccttgag gcactactaa    1140
aaatatatta tagatagcat attagtatag gtcctctaaa aagaatagac cctcctgagc   1200
catgatcttt tgaaaaattg aaattttttag tcattttata atatgttgga acagatgaga   1260
aagtattccg acactacatc acattgactt taccgcttca tacgtatagt gattgcaacc   1320
ttcaaacatt cataactttt tcatatttag tcagatttaa ttgaaacttg aatcagtttg    1380
cttctctgat ttttctgctt tcttaagag tagttgtcta tttggttgg atatcccttc      1440 aaggagacga gtaatgaaat agatttttc agataacttt ggacgtttgt aaagtattac    1500
aaaatttgtt tatacatgta ccagaatcca agcgatcgga atgaaatgaa acagttttct   1560 tttttattc ccgtttatga aaggtgcaat cagccttttc acatgcacaa tcgacctgtt    1620
tactacttgt tatgcaaact ttttgaaaaa aatttccct tgacacccca aaagcttggc     1680
aaacatagca acagttagcg tatgcaaagt gaattatatc tatagaaatg ccattaaata   1740
taactagtga atctaataca cagggattaa ggagaacatg cataattta aacatattta     1800 tgcatgtcat tggtaaaagt acaatcgtct tgaactattt gtaggtccac ggtaaattca   1860
ggcttttggt taaccaattc ggtcttttgt tcgagtttga aagagaataa gaacgcttta   1920
agggacgtcc tgccactggt ttgttgactc taaggttttt gagcttgcat ggtgtgtctg   1980 tttttaggg aaacaatgtt tactggttgg cactttgaaa ggtgcttta ctgaaaagga     2040 tacgatcact ttttgtaaac ttttccggga accatttgtt attattgaa ttgagagggt     2100 aagcttagtt caacggatta acacaacaat tattgtggaa ccccccccccc tctctctctc   2160 tctctctctc tctctgtatg tctcattctg tcccctcatg tctcccttc tctctctgta    2220 tgtctcattc tgccctgtc tcccttctc tctctgtatg tctcattctg tcctctgtct    2280 cgacccctc tctctctgta agtctcattc tgtcccctgt ctcccttct ctctctgtat     2340 gtctcattct gtcctctgta tgtctcattc tctctcttta tatctcattc tgtcccctgt   2400
ctccctttct ctctctgtat gtctcattct gtcctctgta tgtctcattc tctctcttta   2460
tatctcattc tgccctgtc tcccttctct ctctgtatgt ctcattctgt cctctgtatg   2520
tctcattctc tctctttata tctcattctg tcgtccactc tctttatctc cttctcttac    2580
tcttctttac atatgactgc agcaatgaat gatgtctata aaaatataa aaatgatgat    2640 gaagatggtg atggtgatga ccctgattat aaagttttac acaacatacg ttttagttta   2700
```
atcacacacg                                                              2710

<210> SEQ ID NO 61
<211> LENGTH: 352
<212> TYPE: DNA
<213> ORGANISM: Strongylocentrotus purpuratus

<400> SEQUENCE: 61
attatgatca cattaatttt gtcaacttta ttgataataa aaacacgtat tttgggtaga     60
ttagtgcaag tttagttgtc ccgtatataa atcaacataa agcttaagaa tattataatc    120
atccagtttc tattacaaag taagttagag agtccttttta aaagagagag agactgtatt   180
tatacaaggc tggtgttctg tacacagtct taatgtgagt agtcatagca tagacaaagc    240
atccaactta gtggacatta aaaagttcat cttcctcaga gttcaaagat atttgggacc    300
tacagcctcg atccaacggg ctggcacgtc cgcctggtca cagttcgccg ac            352

<210> SEQ ID NO 62
<211> LENGTH: 337
<212> TYPE: DNA
<213> ORGANISM: Strongylocentrotus franciscanus

<400> SEQUENCE: 62
tcaattaact tattaacatt tgataacgt taataatgat gcaaattatc atctttatcg      60
atacaacata catttgtttt ggtagagtag tgcaagtttc gttgtttcct tgaaattatc    120
atagtttcaa tttcaaaata gattagaaaa tcctttttgaa agagagagac taaaatatac   180
aaagtgttct gtatacagtc ttaatgagag cagtcttaaa atagacaaag cgtccaactt    240
ggtggacatt aaaagagttcc tcagagttca aagaccttcg gggacctaca gcatcgagcc   300
gacgggctga cacgtccgcc tggtaacagt cgccgac                             337

<210> SEQ ID NO 63
<211> LENGTH: 1158
<212> TYPE: DNA
<213> ORGANISM: Strongylocentrotus purpuratus

<400> SEQUENCE: 63
aaacgaagtt gcagttgcag ctggacgtaa tgacgacttg agtcttacgg atcaccatcc     60
cgcagctcct acacagtctg ctacagctct gcttcaccca tcggaacgat gaaggcgacg    120
tcgaatcctt ggtcaatgat gacgatgatg atacctcggt gacatcctct cgcaccatgc    180
actccctgcc cgcagtcccg gtgacaccga tggtgaggtt ggcacggcag tagtcggggg    240
actggtccag gaaaacgagg tcgcgacggt tgtgcgatgc gctcactacg gcttgaggga    300
agcgatcttc agcgctgttg ccgtcgatga gtttcccacg aacgaagtcg acgcgtacgg    360
cctggaagta cttgcgcttg atctcgtccc cgatgacacg gaagtttgcg acgtggttcc    420
agcaggtctg tagagagcag gagccggaga cgccatgaca cttacaggtt cgttggaggg    480
tctgtttgac agcctgtcaa caataagaag aaataaacag ttagtcaaat tgaatacgaa    540
ttatacatca ttaagcgtca ataaactaag actaagattt tgtttaact agcaacagta    600
aacatattcc cccctttttc ccccattcca caaggttcct ttattaaaca atgtcgctca    660
caatgtatac aaggaaagat atacacatgc agaatttaaa aatgatattc ttggccattc    720
aaaatatgat aagaacatac atttatatat atatataa gttacaaatt gcaatttttt     780
aaacatcaca gatttactcg gcaaaataaa tttagaagaa atgaacaata cataattcat    840

| aaaacaacta aaattatggt tattttaata aagaaaaaaa aggttatacg caaatagtat | 900 |
| gaattggctg gtaattatgc actttgagag tctgactttc ataaagtctt accatttcaa | 960 |
| aattaaaaac gagttatcac ttgatatttg tgaaaatgct tcactcttgg acaattttga | 1020 |
| gaatgaattt catgaagtta tgctaacagt tgaattaact tctttttttt aagaagagag | 1080 |
| aaatagacca ctggtgattc gatatcctgg gaataagaat tgcacttcga cgtcactttt | 1140 |
| ggtactcacc tttctgcc | 1158 |

<210> SEQ ID NO 64
<211> LENGTH: 1301
<212> TYPE: DNA
<213> ORGANISM: Strongylocentrotus franciscanus

<400> SEQUENCE: 64

| aaacgaagtt gcagttgcag ctggatgtga tgacgacttc agtcttacga atcaccatcc | 60 |
| cgcagctcct acacagtctg ctacaactct gtttcaccca tcggaaggat gaaggcgacg | 120 |
| tcgagtcctt ggtcaaagat gacgatgatg atgcctcggt gacatcttct cgcaccatgc | 180 |
| actccctgcc ggcagttccg gtgacaccga tggtgaggtt ggcacggcag tagtcggggg | 240 |
| actggtccag gaaaacgagg tcgcgacggt tgtgcgatac ggtcatgacg gcacgaggga | 300 |
| agcgatcttc agcacggttg ccgtcgatga gtttaccgct gacgaagtcg acgcgtacgg | 360 |
| ccttgaagta cttccgcttg atctcgtccc cgatgacacg gaaggttgcg acgtggttcc | 420 |
| agcaggtctg gagggagcag gagccggaga cgccgtgaca cttacaagtt cgctgaagtg | 480 |
| tctgtttgac agcctgtcaa caataagcag aaagaaacag tttacaaaaa taaacaagac | 540 |
| taagttttta aaaactagca acagttaaca tcataaaaac aacaaaaaac agaatttatg | 600 |
| caaatacact gaattggctg atgattatgc cctctgagag tttaaaggga tccggtaact | 660 |
| ttgtctcaga ttctgaaaca aaattctgga tttagctcat gatgcaatga taatcataaa | 720 |
| cctttaggtc agtcaggaac cccatgactt ttacaagctg atcgcctgtc tgattatcaa | 780 |
| gatatttatg attggaatta caaattttga aaaccgttcg cctgatggtt ttcataacac | 840 |
| tatagtctat tagggaaaac gagtatggta aaaccggtca atcaaagatt tttactttt | 900 |
| tgaggcactt cttgatcatt ttgaagcgca attttttag ggcttcatta ttacaccata | 960 |
| tcacagacac taataacatg tagggccgtg tatctcagat ttaacactgt taaacgatcc | 1020 |
| ctttaataaa gtattacccc aactataccc tgattatatc tcaccatttc aaaattgcag | 1080 |
| taatcaattg atattcgtga aaatacttca ctcttggtca attttgagga ggaatttcat | 1140 |
| gaagttatgc taacagttaa atgatttta ttttgtaata taaagaaata gaccataaag | 1200 |
| gaatgtaaaa tattgttcta tcgtgtccca ctagtgttaa ttcgatgttc tgagaataag | 1260 |
| attcgcattt cgacgtcact ttcggtactc acctttctgc c | 1301 |

<210> SEQ ID NO 65
<211> LENGTH: 569
<212> TYPE: DNA
<213> ORGANISM: Strongylocentrotus purpuratus

<400> SEQUENCE: 65

| ctgaaaaata tcacagaaat taaataagtt atagattgaa cttgaagctg aattaacaac | 60 |
| gctaatcatt aagcaaacaa aagtattgaa caacaaatat attccttgca tcaaacacaa | 120 |
| tcgagtttgt gaaacaaaaa atcgatgcag tgggtgcaga aattctcgac ctttctagtc | 180 |
| gtgtatttag tatattttca ggactgtgaa taaaaaacga ctgtgctaat tatataccac | 240 |

```
aaagtatgga ctgattgtcg aaaatgaagg ggtttcttaa taaatgactg atctgttatc    300
catagatgat aataataatg ataataagga ttaacacgat cacaactatt tacgaaaaat    360
caacctgagg aattttcaat aacctcgcac tgggtcacgt tttgtattta gcgaacatta    420
caatgacgca attattacgt tatccgaaca tgatgctatg agacatacag tacgatatcg    480
gaatcgccat tgatgtgttg attattcatt tataatttaa acaattgaaa aaaaatcttt    540
aaaaaacctc tccaaaaaaa aaaaacgta                                      569

<210> SEQ ID NO 66
<211> LENGTH: 469
<212> TYPE: DNA
<213> ORGANISM: Strongylocentrotus franciscanus

<400> SEQUENCE: 66
ctgaaaaata acatagaaat aagttataga ttgaacttgt agatgaaatt acaacgatta     60
tcatgaagca aaaaaagta ctgaacctgg tattgaaaaa tagatattcc tggcctaaaa    120
cgcggtcaat ttatgaaaca aaaaatgatg cagtgggtgc agaaattctt ggcgtttcta    180
ctcaacatgc atctaggatg catgagtcta agttcttgt gcttaaccac aaaatgtgga     240
ccgaatgtcg agaaattaag ggtgtctaaa taaatgacag atctaatatt catagaggac    300
taatcaacta ctttgattgt tggcgtgaaa ggaaagacaa atgataataa cgatgaacac    360
gatcgcaact actttcgaaa ttgggtaatg gaattgctct tgaattgata gttaaatgtt    420
gttgattaac tttattttt ttaaagataa actataacaa aaaaacgta                469

<210> SEQ ID NO 67
<211> LENGTH: 476
<212> TYPE: DNA
<213> ORGANISM: Strongylocentrotus purpuratus

<400> SEQUENCE: 67
tgaaagaaga gaaagaaaac acagggttaa attatatgca actcagtcat ggcgggggat     60
aactcgataa agttaaacat actagataaa acagaattg cagtgtattc atatcaatat    120
tcacaatacc atatattaca ttcataaata ttttcttta taacaagttg atgcgaacta    180
ttttgtcata tttcgtttag acttgcatat ttctgtagga cttttaaca ttttaacatc     240 cgctgtacgc attcctattt catacatacc tacctctgaa ttttaaagat aacctataat    300
tatttagaaa attacacaat gaaatataaa actttaatag gtcattgttg ttgaacatcg    360
tgtgctcgat ctccgaagtg aaaataccc ccccccccc atctgaatta acatcatatt     420 ttattttca ggggcggaat catgatcagg acaaagggc acacaatttc gataat        476

<210> SEQ ID NO 68
<211> LENGTH: 446
<212> TYPE: DNA
<213> ORGANISM: Strongylocentrotus franciscanus

<400> SEQUENCE: 68
tgaagagaaa gtaacacctt tgttagattt aatgcaactc ataacggggg atatcacgac     60
aaagtaagac atactaaata aaaacagaat taaagtgtat tcatatcaat attcacaata    120 ccatattta cattcatata tattttcttt ttttaacaa gctgatgcga acttttaaa    180 tatttcgtta agacttgtat atttctgtag agcttgtaaa atcatgacat ccgcattaca    240
catccctatt tcatacatac cttcctctaa tttaattttt tgattatttt agaagataat    300
```

```
gcaatgaaag ataaactttg ataggacatt gttgtaaaga atcttttgac ttgcacccaa    360
taaatgaaca tcgcgtgctt gatcttgtaa ttacaaacta gtccaaaaaa aaaatcttgg    420
aaccagcggg atttgaacct gagatc                                        446
```

<210> SEQ ID NO 69
<211> LENGTH: 821
<212> TYPE: DNA
<213> ORGANISM: Strongylocentrotus purpuratus

<400> SEQUENCE: 69

```
tgcaagggga gaaaagaaa gagatttaaa ggtcagcatg tatgtcatta cttaaagttt     60
caaacaatgt atccacgttc ctcgataatt gattaagata ttatataagt gttatataga   120
atgattacga tatttgtcat tcttttacca aatagcctgg atttgtttta cttctttttt   180
taaataggac atttctgata gtgagatatc acccaaaaat gtagcaaacg attccaacga   240
atacagagta tacgcaaaca aaatatata agcctccata taagagggaa aagaagaaaa    300
ggagtaaact gtcatagacc ggaaattaaa cataaagtca acattaaaca gaaaacagaa   360
gattgtcttt taggagaaat ttcgatattc ccagcagggg cgtagattat tactgcgctt   420
ttgagaaggc tcaagaagag tatcttaaat gcactcttag taaactgaga atacatcgtg   480
cctaatatca atagcatga acacaatgta ggtctaataa catttgttct cctatattag   540
taaggtctgg ctgacttatt tcttccaca attttgcaga cactattctc tctttctgta    600
tgtactacct ggtttcgtcg cttaaatatc cattccagat ttgtaaaggc cgtattaaca   660 aaaaggtcc cttcctatgc atacacaaac tctgacaaaa tttgctttaa aaacacgttc    720
aagtttgtca ttaactacat attaattcga accaaggctt gtaactatat agcaggcaaa   780
cgtattactg acatttttag aagaatgtga tttccttagg a                       821
```

<210> SEQ ID NO 70
<211> LENGTH: 632
<212> TYPE: DNA
<213> ORGANISM: Strongylocentrotus franciscanus

<400> SEQUENCE: 70

```
tggaaaggga gaacaagaat gagaaatatc ggtcagcatt tcttgcatta ctatagtcta    60
tacatgtagt ttcaaacaat gtatccatgt ttctcgataa taaacaaagg tcatgtaaaa   120
agatggtctt cagaataata atgttatttg acattcttgt aacaaatagt tctgttcttc   180
atttgtgaaa tatcagcaaa agaattaaac gggcactata ttccggagga tttgcaacat   240
tcctagtagg ggcgtacatt actactgcac tttcgagaag gttcaagaaa aggacattaa   300
atgctctctt agtaaactga attaaataca tcgtgcgtaa catataggaa tagacatgaa   360
cacaaagtag gatttaattg gaatgtgtaa catttgtaag cctagattat tagtgcctgg   420
ttgacttgtt tccttctcta attttgcaga catattttt ctttctttct gtactacatg    480
tatctggtta gatctgtcat cggatagaat aagtggagcc aagacacatc ttgtgtcgta   540
taaaagtact ttaaatatat atatatatat agcagtccct acatattact taaatattca   600
aaagaatgtg atttcgttga aacacactat ga                                 632
```

<210> SEQ ID NO 71
<211> LENGTH: 340
<212> TYPE: DNA
<213> ORGANISM: Strongylocentrotus purpuratus

<400> SEQUENCE: 71

```
gtcaccggct aattaaagtt gagagtttgt ggtctgatta tattgatact cgggttctaa    60
aggcccatta cggttttaa ttaagaggga gagtaaaaag cagtaaggga tgatacgtgc   120
ttgaacaagt tatcttaaga tgaatcagaa tgttgtgctt ttgaaagcct tgacgtcatc   180
atgggagggg attgcaaaca ctgacaggaa accctatttc cgcatgaaaa tcgaaagaga   240
aagaaacttt cagctttatt acttttaga aatcccaaat taccgagtaa ttaaaagggg   300
tgatattgaa cgatttgcaa agtaaagtgt ttttcttacc                         340

<210> SEQ ID NO 72
<211> LENGTH: 390
<212> TYPE: DNA
<213> ORGANISM: Strongylocentrotus franciscanus

<400> SEQUENCE: 72
gtcaccggct aattaaagtt gagagcgatg acagtttgtg gtctgattat attgatactc    60
gttctaaagg cccattacgg ttattaatta agagggaggg taaaaagcag aagggatga   120 tacgtgcttg aacaagttat gttgggataa atgttatgct tttgaaagcc tttacgtcat   180
cctggtcatg ggatgggacg ggaatattaa caatgacaag aaaaaacggg gtttcgcatg   240
aaaatcgaaa agggcctctt aaatatttag taatgaataa ttcattagta atgaataatt   300
cattacttga caaagaatga ggaggattgg gtgaattgtt gaattgtatg ttaattaagt   360 tttttttaa tttaaagtat tttccttacc                                     390

<210> SEQ ID NO 73
<211> LENGTH: 903
<212> TYPE: DNA
<213> ORGANISM: Strongylocentrotus purpuratus

<400> SEQUENCE: 73
ttaaaagact tggagtgtac gattaagagc tttctaagta tctaatacct ccgtttcttt    60
cacagcaaat gggacgcttt attgtccgat aagaaaacac tcctttacaa attaccattt   120
gtaaaaaggg taatttgtcg atatcttact ctgctcggtt gaatattgta agaggaattt   180
attgatgaag gcctgcttga cacttgtgtt catcgtgtgc tgtgctattc gtaaacttat   240
cgatatgaga gacttaatat taagacttgt aggtgtataa cacggtgccc attttttgtaa   300 tcatagttcc tcaatccaca ttttgtttat tcataactgc atccatacta caaagtttgt   360
atacgcgcct attgataatg tgccatattc gtcatcattt tattcgagtt gcatcgtatc   420
ccgttaaatg tccccgttat gatcgttcta tggacaattc aacagtttga gaaagatttg   480
ttgttggaat tcagtgaaat ttcagtttaa acatatttat tcatgaagct gtctctcagc   540
tagaagaaaa agaatattgt tggtatgatg ggataatgat tacaaaatta ttaatgacga   600
aatttcacat ggttttaaat attaagtgta taagtgctat tgtgtatacc gtattgtata   660
atcgtataac aaaaaactcg cattaatgga agtaaaatcg taatgttaga atatgaagaa   720
tataaagtat acatattttt aagaagttgg ccgtgaaggc aggtagaaaa tcataactga   780
tttgtcaata cataaaaaca agcaggataa gaataatatt gaaatatata aagggaatc   840 gttgcaaaaa taccagaccg attatcccaa agcattttaa aattcaacta attattgtaa   900
agt                                                                 903

<210> SEQ ID NO 74
<211> LENGTH: 803
<212> TYPE: DNA
```

<213> ORGANISM: Strongylocentrotus franciscanus

<400> SEQUENCE: 74

```
ttaaaagact tggagtgtac gattaagagc tttctaagta tctaatacct ccgtttcttt      60
cataccaaat gggacgcttt attgtctgat aagaaaacac tcctttacaa attaccattt     120
gtaaataggg taatttgtcg atacctcact cggctcggct gagtatccca agatgaattg     180
atgaaggctg cttgacactt gtgttcaatg tatgctacgc tatttgtaaa cttatcgata     240
tgaaagactt actattaaga ctggtaggtg tataaaataa gagtttgaga aagcattttg     300
ttttaaatgg aattgaagtg aaatttcagt ttgaacttat ttattcatga agttgtctct     360
cagctaagaa atgaacaata ggttttgttt ttgtggtggt atgatgtgat aattattaca     420
aatgattaat gacaacattt cacatggttt taaataataa acctgaaagt gctattgaat     480
cctgaaccat tattagtgcg attaaataat aaacataatg ctgcagccaa tgctaaaata     540
cagacagtag agaatatcat ataataaaac ttacattaat ggaagtaaaa ttataatttt     600
gtgtagaata tgaagaatat gaaatatata tttttaagaa gtttgccgtg aagactggta     660
aaaaatcata acggatattt caatttaaac aaatcaagcg gagtaagaat aatattgaaa     720
tatacagaag gggttcgttt atgaataaat accaaaccga ttattccaaa gcactttaaa     780
atttcaacca attagtgtaa agt                                             803
```

<210> SEQ ID NO 75
<211> LENGTH: 690
<212> TYPE: DNA
<213> ORGANISM: Strongylocentrotus purpuratus

<400> SEQUENCE: 75

```
ttgtaaaatt attatatttc ttacctgtgg gcattgaccg cgccacggcc aaaaccgcga      60
acagcaaaat atttaacctc atcatcgtct caaaaattag caatattatg acctgtcctc     120
gaccagtctt tctctatttta accctccgct cttgatgagg ggggtaaagt tacacccctt     180
tgtctttgat agcacaatca ggagacgaaa ctcaaacagt ttaacccggg gatgtgataa     240
ctttgagatg atgtaatcac ttggtagttt aatcacttaa tcctacgcga tgataatggt     300
atgatcattt tggtcaatat ttttgagacg ttgcgattta cgacgtttct tagaagtaag     360
ggcgatttaa gaggaaatta cgcttttgtt acattgtttg atgaagttta aatgcatttg     420
tcagatgttt gtgtttacgg gcattaaatc ttgcgtggaa acaaaggacg ttcagttcca     480
ggtatattcg gggtttttatc tcatcggaat cgactgaaaa acatccaaaa ttaatttgaa     540
aaaccaacaa agttaaagtc tttattcatg ataacatttc tgaattagaa gtgccctctt     600
catttgttat ttgatataca aaaacaactc cgaattggaa atccaaaccc cttctccata     660
agccacgttt tgagtgtggg tgtacattag                                      690
```

<210> SEQ ID NO 76
<211> LENGTH: 679
<212> TYPE: DNA
<213> ORGANISM: Strongylocentrotus purpuratus

<400> SEQUENCE: 76

```
ttgtaaaatt attatatttc ttacctgtgg gcattgaccg cgccacggcc aaaaccgcga      60
acagcaaaat atttaacctc ctcatcgtct caaaaattag caatattatg acctgtcctc     120
gaccagtctt tctctatttta accctccgct cttgatgagg ggggtaaagt tacacccctt     180
tgtctttgat agcacaatcc aaaactcaaa cagtttaacc tgggatgcga aactttgaa      240
```

| | |
|---|---|
| atgatgtaat ctcttggtag cttgatcact taatcctccg cgatgataat ggcgtgatca | 300 |
| ttttggtcaa tattttgag acgttgcgat ttacgacgtt cttagaagta agggcgattt | 360 |
| aagaggaatt acgcttttgt tacatggttt gatgaagttt aatgcatttg tcagatgttt | 420 |
| gtgtttacgg gcattaaatc tttcgtggaa acaaagaacg ttcagttcca ggtatattcg | 480 |
| gggtttatc tcatcggaat cgactgaaaa acatccgaaa ttaatttgaa aaaccaacaa | 540 |
| agttaaagtc tttattcatg ataacgtttc tgaattagaa gtgccctctt catttgttat | 600 |
| ttgatataca aaaacaaccc cgaattggaa atccaaaccc ttctccataa gccacgtttt | 660 |
| gagtgtgagt gtacattag | 679 |

<210> SEQ ID NO 77
<211> LENGTH: 690
<212> TYPE: DNA
<213> ORGANISM: Strongylocentrotus purpuratus

<400> SEQUENCE: 77

| | |
|---|---|
| ttgtaaaatt attatatttc ttacctgtgg gcattgaccg cgccacggcc aaaaccgcga | 60 |
| acagcaaaat atttaacctc atcatcgtct caaaaattag caatattatg acctgtcctc | 120 |
| gaccagtctt tctctattta accctccgct cttgatgagg ggggtaaagt tacaccccctt | 180 |
| tgtctttgat agcacaatca ggagacgaaa ctcaaacagt ttaacccggg gatgtgataa | 240 |
| ctttgagatg atgtaatcac ttggtagttt aatcacttaa tcctacgcga tgataatggt | 300 |
| atgatcattt tggtcaatat ttttgagacg ttgcgattta cgacgtttct tagaagtaag | 360 |
| ggcgatttaa gaggaaatta cgcttttgtt acattgtttg atgaagttta aatgcatttg | 420 |
| tcagatgttt gtgtttacgg gcattaaatc ttgcgtggaa acaaaggacg ttcagttcca | 480 |
| ggtatattcg gggttttatc tcatcggaat cgactgaaaa acatccaaaa ttaatttgaa | 540 |
| aaaccaacaa agttaaagtc tttattcatg ataacatttc tgaattagaa gtgccctctt | 600 |
| catttgttat ttgatataca aaaacaactc cgaattggaa atccaaaccc cttctccata | 660 |
| agccacgttt tgagtgtggg tgtacattag | 690 |

<210> SEQ ID NO 78
<211> LENGTH: 679
<212> TYPE: DNA
<213> ORGANISM: Strongylocentrotus purpuratus

<400> SEQUENCE: 78

| | |
|---|---|
| ttgtaaaatt attatatttc ttacctgtgg gcattgaccg cgccacggcc aaaaccgcga | 60 |
| acagcaaaat atttaacctc ctcatcgtct caaaaattag caatattatg acctgtcctc | 120 |
| gaccagtctt tctctattta accctccgct cttgatgagg ggggtaaagt tacaccccctt | 180 |
| tgtctttgat agcacaatcc aaaactcaaa cagtttaacc tgggatgcga taactttgaa | 240 |
| atgatgtaat ctcttggtag cttgatcact taatcctccg cgatgataat ggcgtgatca | 300 |
| ttttggtcaa tattttgag acgttgcgat ttacgacgtt cttagaagta agggcgattt | 360 |
| aagaggaatt acgcttttgt tacatggttt gatgaagttt aatgcatttg tcagatgttt | 420 |
| gtgtttacgg gcattaaatc tttcgtggaa acaaagaacg ttcagttcca ggtatattcg | 480 |
| gggtttatc tcatcggaat cgactgaaaa acatccgaaa ttaatttgaa aaaccaacaa | 540 |
| agttaaagtc tttattcatg ataacgtttc tgaattagaa gtgccctctt catttgttat | 600 |
| ttgatataca aaaacaaccc cgaattggaa atccaaaccc ttctccataa gccacgtttt | 660 |

| | |
|---|---:|
| gagtgtgagt gtacattag | 679 |

<210> SEQ ID NO 79
<211> LENGTH: 1197
<212> TYPE: DNA
<213> ORGANISM: Strongylocentrotus purpuratus

<400> SEQUENCE: 79

| | |
|---|---:|
| tcggatatcg tgacattaat tttataatat atcatgacat ttttgctgca tattttgcgg | 60 |
| taccggaaga tggtgatttt aacatgggga taaagatatt gcatcaagat ttgcacaagc | 120 |
| tcttattcta atatccaccc ttgccccccc cccccatctg ctccctctc actcctgtt | 180 |
| tctttcttcg tcgtcgttct tcttattcgt cttctccttt tcccctttgt acatatccct | 240 |
| ttctttatcc tctctctctc tctctccccc gtttccatct acacctccct ctgtttctgt | 300 |
| ttctgtatct cactcttgtt tcttacactg acccagttcg cactccctct ttattttcc | 360 |
| ttcacccaca ctcgatctct ctctctcctg ctctatatct ctctgtatat ctgtctctat | 420 |
| gtgtgtgtgg gtgtgtgtgt gtgtgtgtgt gtgcgtgctc tcacctcagc attcttgtgg | 480 |
| ggttttaatg tgcgcttcac atacccttg tgaggcattt tactttgtgg ggtaattttt | 540 |
| caggacccca cagagtaaag tctttcaaat gactgtatat tcggtgtcct atgctgcggg | 600 |
| gcattagaag tggtaccca taaatgactt tttgtgagcg tgtgctaaaa cttgcacact | 660 |
| tttttatggg taacatcgta agcacaccgc cgggttgtta tcgccaggtt gtacataccc | 720 |
| cactagtagg ggaccacaag gtatatctgg aacgcacaga ataccccac aatcaggtgc | 780 |
| cccacaaagg ccctgatgtg agaatgcgtg tgtgcgcgtg tgtttgtgtg tgtgtctctc | 840 |
| tctctctctc tctctctcac tctctaagta tatctatctc cttccccatt ttctctttcc | 900 |
| ccctctgaaa tattgataaa aagaatacat aatttgggtt ttctgttgta cgcagaaaaa | 960 |
| cccctaaatg tcgtattctt tcacaaatat tcgacttcga actcatttcc ttgcagaaat | 1020 |
| gtgtctctaa tcacatcctc ctaatacatt tatgatacaa ttttattta gggaaaatgt | 1080 |
| tgtcgtcaaa atgtatgggg ctcccaacgc ttcaaagggg cttaaagtt atcatatgaa | 1140 |
| tgtaacctaa accttctgaa aataatcatg atattgggca ctgctgggat gatttta | 1197 |

<210> SEQ ID NO 80
<211> LENGTH: 1033
<212> TYPE: DNA
<213> ORGANISM: Strongylocentrotus purpuratus

<400> SEQUENCE: 80

| | |
|---|---:|
| tcggatatcg tgacattaat ttatgatata tgatgacatt tttgcttcat attttgcggt | 60 |
| accggaagat ggtgagttta acatgaggat aaagatattg catcaagatt tgcgcaagct | 120 |
| cttgttctaa tatacacatt gcccccccc catctgctcc cctctcact ccctgtttct | 180 |
| tcttcttctt cttcttcttc ttcttcttct tcttcttctt cttcttctac ttcttctttt | 240 |
| tcttcttcct cctcctattt tattcttctt ctttttagtc ttcttcttct tcttcctctt | 300 |
| cttcttcttg ttcttctcct tcttcttctt cttgttcttc ttgttcttgt tcttgttctt | 360 |
| cttcttcttc ttcttaatcg tcttctccct ttccccttg tacatacatg tatatccttt | 420 |
| tcgttatcct ctctctctcc cccgtttcca tttacatctc cctctgtttc tgtttctgta | 480 |
| tctcactctt tttcttaca ctgacccatt cgcactccct ctttctcttt ccttcacaca | 540 |
| cacactcgat ctctctctct ctctctcctg ctctttatct gtgtgtgtgt gtgtctctct | 600 |
| atgtgtgtgg ggggaggggt gtgtgtatct ctctcactct ctaagtatct atctccttcc | 660 |

```
ccattctctc tttctcccac tctcagtctc tcacacacac cctctgagta tctacctcct        720
tccccatttt ctcttcgccc tctcaaatat tgataaaaag aatacataat ttgggttttt        780
tgttgtacgc caacaaaaaa attgcattct ttcatatata ttcgacttca aacacatttg        840
ttttgaaaat tcttgcagaa atgcgtctca aatgacattc tctttataca ttataataca        900
atttaagcga aattttgtcg tcaaatgtat gaggctccca acgcttcagc tagaggggct        960
ttaaagttat atgaatgtaa cctaaacctt ctgaattacg gtcatggtat tgggcactgc       1020
tgtgatcatt tta                                                          1033

<210> SEQ ID NO 81
<211> LENGTH: 1198
<212> TYPE: DNA
<213> ORGANISM: Strongylocentrotus purpuratus

<400> SEQUENCE: 81
tcggatatcg tgacattaat tttataatat atcatgacat ttttgctgca tattttgcgg         60
taccggaaga tggtgatttt aacatgggga taaagatatt gcatcaagat ttgcacaagc        120
tcttattcta atatccaccc ttgcccccccc ccccatctg ctccctctc actccctgtt         180 tctttcttcg tcgtcgttct tcttattcgt cttctccttt tcccctttgt acatatccct        240
ttctttatcc tctctctctc tctctccccc gtttccatct cacctccct ctgtttctgt         300 ttctgtatct cactcttgtt tcttacactg acccagttcg cactccctct ttatttttcc        360
ttcacccaca ctcgatctct ctctctcctg ctctatatct ctctgtatat ctgtctctat        420
gtgtgtgtgg gtgtgtgtgt gtgtgtgtgt gtgcgtgctc tcacctcagc attcttgtgg        480
ggttttaatg tgcgcttcac ataccccttg tgaggcattt tactttgtgg ggtaattttt        540 caggaccccca cagagtaaag tctttcaaat gactgtatat tcggtgtcct atgctgcggg       600
gcattagaag tggtaccccca taatgactt tttgtgagcg tgtgctaaaa cttgcacact        660
tttttatggg taacatcgta agcacaccgc cgggttgtta tcgccaggtt gtacatacccс       720 cactagtagg ggaccacaag gtatatctgg aacgcacaga aataccccac aatcaggtgc        780
cccacaaagg ccctgatgtg agaatgcgtg tgtgcgcgtg tgtttgtgtg tgtgtctctc        840
tctctctctc tctctctcac tctctaagta tatctatctc cttccccatt ttctcttttcc       900 ccctctgaaa tattgataaa aagaatacat aatttgggtt ttctgttgta cgcagaaaaa        960
cccctaaatg tcgtattctt tcacaaatat tcgacttcga actcatttcc ttgcagaaat       1020
gtgtctctaa tcacatcctc ctaatacatt tatgatacaa ttttatttta gggaaaatgt       1080
tgtcgtcaaa atgtatgggg ctcccaacgc ttcaaagggg ctttaaagtt atcatatgaa       1140
tgtaacctaa accttctgaa ataatcatg atattgggca ctgctgggat gattttat         1198

<210> SEQ ID NO 82
<211> LENGTH: 837
<212> TYPE: DNA
<213> ORGANISM: Strongylocentrotus purpuratus

<400> SEQUENCE: 82
tcggatatcg tgacattaat ttataatata tcatgacatt tttgctgcat attttgcggt         60
accggaagat ggtgatttta acatggggat aaagatattg catcaagatt tgcacaagct        120
cttattctaa tatccacctt gcccccccccс ccatctgctc cctctcact ccctgtttct        180 tcttcgtcgt cttcttctta ttcgtcttct cctttttcccс tttgtacata tccctttctt        240
```

```
tatcctctct ctctctctcc cccgtttcca tctacacctc cctctgtttc tgtttctgta    300
tctcactctt ttttcttaca ctgacccagt tcgcactccc tctttatttt tccttcaccc    360
acactcgatc tctctctctc ctgctctata tctctctgta tatctgtctc tatgtgtgtg    420
tgggtgtgtg tgtgtgtgtg tgtgtgtgcg tgtgtgcgcg tgtgcgtgtg tgtgtgtgtg    480
tctctctctc tctctctctc tctcactctc taagtatatc tatctccttc cccatttttct   540 ctttccccct ctcaaatttt gataaaaaga atacataatt tgggttttct gttgtacgca    600
gaaaacctaa atgtcgtatt ctttcacaaa tattcgactt cgaacacatt ccttgcagaa    660
atgtgtctct aatcacatcc tcctaataca ttatgataca atttatttta aggaaaatgt    720
tgtcgtcaaa tgtatggggc tcccaacgct tcaaaggggc tttaaagtta tcatatgaat    780
gtaacctaaa ccttctgaaa ataatcatga tattgggcac tgctgggatg attttat      837
```

<210> SEQ ID NO 83
<211> LENGTH: 1197
<212> TYPE: DNA
<213> ORGANISM: Strongylocentrotus purpuratus

<400> SEQUENCE: 83

```
tcggatatcg tgacattaat tttataatat atcatgacat ttttgctgca tattttgcgg    60
taccggaaga tggtgatttt aacatgggga taaagatatt gcatcaagat ttgcacaagc    120
tcttattcta atatccaccc ttgcccccccc cccccatctg ctcccctctc actccctgtt    180
tctttcttcg tcgtcgttct tcttattcgt cttctccttt tcccctttgt acatatccct    240
ttctttatcc tctctctctc tctctccccc gtttccatct acacctccct ctgtttctgt    300
ttctgtatct cactcttgtt tcttacactg acccagttcg cactccctct ttattttttcc   360 ttcacccaca ctcgatctct ctctctcctg ctctatatct ctctgtatat ctgtctctat    420
gtgtgtgtgg gtgtgtgtgt gtgtgtgtgt gtgcgtgctc tcacctcagc attcttgtgg    480
ggttttaatg tgcgcttcac ataccccttg tgaggcattt tactttgtgg ggtaattttt    540 caggaccccca cagagtaaag tctttcaaat gactgtatat tcggtgtcct atgctgcggg   600
gcattagaag tggtacccca taaatgactt tttgtgagcg tgtgctaaaa cttgcacact    660
tttttatggg taacatcgta agcacaccgc cgggttgtta tcgccaggtt gtacataccc    720
cactagtagg ggaccacaag gtatatctgg aacgcacaga aataccccac aatcaggtgc    780
cccacaaagg ccctgatgtg agaatgcgtg tgtgcgcgtg tgtttgtgtg tgtgtctctc    840
tctctctctc tctctctcac tctctaagta tatctatctc cttccccatt ttctctttcc    900
ccctctgaaa tattgataaa aagaatacat aatttggggt ttctgttgta cgcagaaaaa    960
cccctaaatg tcgtattctt tcacaaatat tcgacttcga actcatttcc ttgcagaaat    1020
gtgtctctaa tcacatcctc ctaatacatt tatgatacaa ttttatttta gggaaaatgt    1080
tgtcgtcaaa atgtatgggg ctcccaacgc ttcaaagggg ctttaaagtt atcatatgaa    1140
tgtaacctaa accttctgaa aataatcatg atattgggca ctgctgggat gatttta      1197
```

<210> SEQ ID NO 84
<211> LENGTH: 841
<212> TYPE: DNA
<213> ORGANISM: Strongylocentrotus purpuratus

<400> SEQUENCE: 84

```
tcggatatcg tgacattaat ttataatata tgatgacatt tttgcttcat attttgccgt    60
accggaagat agagatgtta acatggggat aaagatattg catcaagatt tgcacaagct    120
```

```
cttgttctaa tatccacctt gcccccccc cccatctac tccctctca ctccctgttt    180 cttcttcttc gtcttcttct tattcgtctt ctccttttcc cctttgtaca ttttatgtc    240 attttctta tcctctctct ctctccctcg tttccatgta caccttcctc tgtttctgtt    300
tctgtatctc actctttttt cttacactga cccagttcgc actccctctt tattttcct    360 tcacccacac tcgatctctc tctctctctc ctgctctata tctctctgta tatctctctc    420
tatgtgtgtg tgggtgtgtg tgtgtgtgtg tgtgtgcgcg cgcgtgtgtg tgtgtgtgtg    480
tgtgtgtgtg tctctctctc tctctctcac tctctaagta tatctatctc cttccccatt    540
ttctctttcc ccctctcaaa tattgataaa aagaatacat aatttgggtt ttctgttgta    600
cgcagaaaac ctaaatgtcg tattccttca caaatattcg acttcgaaca cattccttgc    660
agaaatgtgt ctctaatcac atcctcctaa tacattatga tacaatttta tttaaggaaa    720
atgttgtcgt caaatgtatg gggctcccaa cgcttcaaag gggctttaaa gttatcatat    780
gaatgtaacc taaaccttct gaattacggt catgatattg ggcactgctg ggatgatttt    840
a                                                                    841

<210> SEQ ID NO 85
<211> LENGTH: 1197
<212> TYPE: DNA
<213> ORGANISM: Strongylocentrotus purpuratus

<400> SEQUENCE: 85
tcggatatcg tgacattaat tttataatat atcatgacat ttttgctgca tattttgcgg     60
taccggaaga tggtgatttt aacatgggga taaagatatt gcatcaagat ttgcacaagc    120
tcttattcta atatccaccc ttgcccccccc cccccatctg ctccctctc actccctgtt    180 tcttttcttcg tcgtcgttct tcttattcgt cttctccttt tccctttgt acatatccct    240 ttctttatcc tctctctctc tctctccccc gtttccatct acacctccct ctgtttctgt    300
ttctgtatct cactcttgtt tcttacactg acccagttcg cactccctct ttattttttcc    360 ttcacccaca ctcgatctct ctctctcctg ctctatatct ctctgtatat ctgtctctat    420
gtgtgtgtgg gtgtgtgtgt gtgtgtgt gtgcgtgctc tcacctcagc attcttgtgg    480
ggttttaatg tgcgcttcac ataccccttg tgaggcattt tactttgtgg ggtaattttt    540
caggacccca cagagtaaag tctttcaaat gactgtatat tcggtgtcct atgctgcggg    600
gcattagaag tggtacccca taaatgactt tttgtgagcg tgtgctaaaa cttgcacact    660
tttttatggg taacatcgta agcacaccgc cgggttgtta tcgccaggtt gtacataccc    720
cactagtagg ggaccacaag gtatatctgg aacgcacaga ataccccac aatcaggtgc    780 cccacaaagg ccctgatgtg agaatgcgtg tgtgcgcgtg tgtttgtgtg tgtgtctctc    840
tctctctctc tctctctcac tctctaagta tatctatctc cttccccatt ttctctttcc    900
ccctctgaaa tattgataaa aagaatacat aatttgggtt ttctgttgta cgcagaaaaa    960
cccctaaatg tcgtattctt tcacaaatat tcgacttcga actcatttcc ttgcagaaat   1020
gtgtctctaa tcacatcctc ctaatacatt tatgatacaa ttttattta gggaaaatgt   1080 tgtcgtcaaa atgtatgggg ctcccaacgc ttcaaagggg ctttaaagtt atcatatgaa   1140
tgtaacctaa accttctgaa aataatcatg atattgggca ctgctgggat gatttta      1197

<210> SEQ ID NO 86
<211> LENGTH: 895
<212> TYPE: DNA
```

<213> ORGANISM: Strongylocentrotus purpuratus

<400> SEQUENCE: 86

```
tcggatatcg tgacattaat ttataatata tgatgacatt tttgcttcat attttgccgt      60
accggaagat ggtgatgtta acatgggaat aaagatattg catcaagatt tgcacaagct     120
cttgttctaa tatccacctc cccccccca tctgctcccc tctcactccc tgtttcttct     180
tcttcgtctt cttcttattc gtcttctcct tttcccttt gtacatatat cattttattt     240
atcctctctc tctctctctc tccctcattt ccatttacac cttcctctgt ttctgtttct     300
gtatctcact cttttcttta cactgaccca gttcgcactc cctctttatt tttccttcac     360
ccacactctc tctctctctc tctctctctc tcctgctc tatatctctc tgtatatctg     420
tctctatgtg tgtgtgagtg tgtgtgtgtg tgtgtgtg tgcgtgtgtc tctctctctc     480
tctcactctc taagtatata tctccttccc tattctctct ttctcccgct ctctctctct     540
ttctctcact ctctaagtat atctatctcc ttccccattt tttctttccc cctttctct     600
ttccccctct caaatattga taaaaggaat acataatttg ggttttctgt tgtacgcaga     660
aaatctaaat gtcgtaatcc ttcgcaaata ttcgacttcg aacacattcc ttgcagaaat     720
gtgtctcaaa tcacatcctc ctaatacatt atgatacaat tttatttaag gaaaatgttg     780
tcgtcaaatg tatggggctc ccaacgcttc aaagggcttt aaagttatc atatgaatgt     840
aacctaaacc ttctgaatta cggtcatgat attgggcact gctgggatga tttta          895
```

<210> SEQ ID NO 87
<211> LENGTH: 1197
<212> TYPE: DNA
<213> ORGANISM: Strongylocentrotus purpuratus

<400> SEQUENCE: 87

```
tcggatatcg tgacattaat tttataatat atcatgacat ttttgctgca tattttgcgg      60
taccggaaga tggtgatttt aacatgggga taaagatatt gcatcaagat ttgcacaagc     120
tcttattcta atatccaccc ttgccccccc ccccatctg ctcccctctc actccctgtt     180
tctttcttcg tcgtcgttct tcttattcgt cttctccttt tcccctttgt acatatccct     240
ttctttatcc tctctctctc tctctccccc gtttccatct acacctccct ctgtttctgt     300
ttctgtatct cactcttgtt tcttacactg acccagttcg cactccctct ttattttcc     360
ttcacccaca ctcgatctct ctctctcctg ctctatatct ctctgtatat ctgtctctat     420
gtgtgtgtgg gtgtgtgtgt gtgtgtgtgt gtgcgtgctc tcacctcagc attcttgtgg     480
ggttttaatg tgcgcttcac ataccccttg tgaggcattt tactttgtgg ggtaattttt     540
caggaccccca cagagtaaag tctttcaaat gactgtatat tcggtgtcct atgctgcggg     600
gcattagaag tggtacccca taaatgactt tttgtgagcg tgtgctaaaa cttgcacact     660
tttttatggg taacatcgta agcacaccgc cgggttgtta tcgccaggtt gtacataccc     720
cactagtagg ggaccacaag gtatatctgg aacgcacaga aataccccac aatcaggtgc     780
cccacaaagg ccctgatgtg agaatgcgtg tgtgcgcgtg tgtttgtgtg tgtgtctctc     840
tctctctctc tctctctcac tctctaagta tatctatctc cttccccatt ttctctttcc     900
ccctctgaaa tattgataaa aagaatacat aatttgggtt ttctgttgta cgcagaaaaa     960
ccctaaatg tcgtattctt tcacaaatat tcgacttcga actcatttcc ttgcagaaat    1020
gtgtctctaa tcacatcctc ctaatacatt tatgataaca ttttatttta gggaaaatgt    1080
tgtcgtcaaa atgtatgggg ctcccaacgc ttcaaagggg ctttaaagtt atcatatgaa    1140
```
tgtaacctaa accttctgaa ataatcatg atattgggca ctgctgggat gatttta        1197

<210> SEQ ID NO 88
<211> LENGTH: 882
<212> TYPE: DNA
<213> ORGANISM: Strongylocentrotus purpuratus

<400> SEQUENCE: 88
tcggatatcg tgacattaat ttataatata tgatgacatt tttgcttcat attttgccgt     60
accggaagat agagatacat gggaataaag atattgcatc aagagttgca caagctcttg    120
ttctaatatc taccttgccc cccccccccc atctgctccc ctctcactcc ctgtgtcttc    180
ttcttcgtct tcttcttatt cgtcttctcc ttttcccctt tgtacatata tcattttctt    240
tatcctctct ctctctccct cgtttccatt tacaccttcc tctgtttctg tttctgtatc    300
tcactctttt tcttacactg acccagttcg cactccctct ttattttttcc ttcacccaca    360 ctcgatctct ctctcctgct ctatatctct ctgtatatct gtctctatgt gtgtgtgggt    420
gtatgtgtgt gtgtgtctct ctctctctct ctctctctct ctctctctct ctctctctct    480
cacactctct aagtattatc tccttccaca ttctctcttt ctcccgctct ctctctctca    540
cacacactct ctgagtatct acctccttcc ccattttttc ttccccccctc tcaaatattg    600 attaaaagaa tacataattt gggtttttg ttgtacgcca aaaaacaaaa ttgtgtattc     660
tttcataaat attcgacttc aaacacattt gttttgaaaa ttcttgcaga aatgcgtctc    720
aaatgacatc ttctttatac attatgatac aatttaagcg aaatgttttc gtcaaagcta    780
tggggctcct aacgcctcag agggtcttaa agttatcatt tgaatgtaac ctaaactttc    840
tgaattacgg tcatggtttt gggcactgct gggatgattt ta                      882

<210> SEQ ID NO 89
<211> LENGTH: 1197
<212> TYPE: DNA
<213> ORGANISM: Strongylocentrotus purpuratus

<400> SEQUENCE: 89
tcggatatcg tgacattaat tttataatat atcatgacat ttttgctgca tattttgcgg     60
taccggaaga tggtgatttt aacatgggga taaagatatt gcatcaagat ttgcacaagc    120
tcttattcta atatccaccc ttgcccccccc ccccatctg ctcccctctc actccctgtt    180
tctttcttcg tcgtcgttct tcttattcgt cttctccttt tcccctttgt acatatccct    240
ttctttatcc tctctctctc tctctccccc gtttccatct acacctccct ctgtttctgt    300
ttctgtatct cactcttgtt tcttacactg acccagttcg cactccctct ttattttttcc    360 ttcacccaca ctcgatctct ctctcctg ctctatatct ctctgtatat ctgtctctat    420
gtgtgtgtgg gtgtgtgtgt gtgtgtgtgt gtgcgtgctc tcacctcagc attcttgtgg    480
ggttttaatg tgcgcttcac ataccccttg tgaggcattt tactttgtgg ggtaattttt    540 caggaccccca cagagtaaag tctttcaaat gactgtatat tcggtgtcct atgctgcggg    600
gcattagaag tggtacccca taaatgactt tttgtgagcg tgtgctaaaa cttgcacact    660
tttttatggg taacatcgta agcacaccgc cgggttgtta tcgccaggtt gtacataccc    720
cactagtagg ggaccacaag gtatatctgg aacgcacaga aatacccac aatcaggtgc    780 cccacaaagg ccctgatgtg agaatgcgtg tgtgcgcgtg tgtttgtgtg tgtgtctctc    840
tctctctctc tctctctcac tctctaagta tatctatctc cttccccatt ttctctttcc    900

```
ccctctgaaa tattgataaa aagaatacat aatttgggtt ttctgttgta cgcagaaaaa      960
cccctaaatg tcgtattctt tcacaaatat tcgacttcga actcatttcc ttgcagaaat     1020
gtgtctctaa tcacatcctc ctaatacatt tatgatacaa ttttatttta gggaaaatgt     1080
tgtcgtcaaa atgtatgggg ctcccaacgc ttcaaagggg ctttaaagtt atcatatgaa     1140
tgtaacctaa accttctgaa ataatcatg atattgggca ctgctgggat gatttta        1197
```

<210> SEQ ID NO 90
<211> LENGTH: 853
<212> TYPE: DNA
<213> ORGANISM: Strongylocentrotus purpuratus

<400> SEQUENCE: 90

```
tcggatatcg tgacattaat ttataatata tgatgacatt tttgcttcat attttgcggt       60
accggaagat ggtgatttta acatggggat aaagatattg catcaagatt gcacaagct      120 cttgttctaa tatccaccct tgccccccccc ccatctgctc cctctcact ccctgtttct     180 tcttcttcgt cttcttctta ttcgtcttct ccttttcccc tttgtacata tcatttttc     240 tttatcctct ctctctctcc ctcgtttcca tttacacctc cctctgtttc tgtatctcac    300
tcttttttct tacactgacc cagttcgcac tccctcttta ttttccttc acccacactc     360 gatctctctc tctctcctgc tctatatctc tctgtatatc tgtctctatg tgtgtgtggg    420
tgtgtgtgtg cgtgtgtgtg ggtgtgtgtg tgcgtgtgtg tgggtgtgtg tgtgtgtgtg    480
tgtgtgtctc tctctctctc tctctctctc tctctctctc actctctaag tatatctatc    540
tccttcccca ttttctcttt ccccctctca atattgata aaaagaatac ataatttggg     600
ctttctgttg tacgcagaaa accaaaatgt cgtattcctt cacaaatatt cgacttcgaa    660
cacattcctt gcagaaatgt gtctctaatc acatcctcct aatacattat gatacaattt    720
tatttaagga aaatgttgtc gtcaaatgta tggggctccc aacgcttcaa aggagcttta    780
aagttatcat atgaatgtaa cctaaacctt ctgaattacg gtcatgatat tgggcactgc    840
tgggatgatt tta                                                       853
```

<210> SEQ ID NO 91
<211> LENGTH: 1197
<212> TYPE: DNA
<213> ORGANISM: Strongylocentrotus purpuratus

<400> SEQUENCE: 91

```
tcggatatcg tgacattaat tttataatat atcatgacat ttttgctgca tattttgcgg      60
taccggaaga tggtgatttt aacatgggga taaagatatt gcatcaagat tgcacaagc     120 tcttattcta atatccaccc ttgcccccccc ccccatctg ctccctctc actccctgtt     180 tctttcttcg tcgtcgttct tcttattcgt cttctccttt tcccctttgt acatatccct    240
ttctttatcc tctctctctc tctctccccc gtttccatct acacctccct ctgtttctgt    300
ttctgtatct cactcttgtt tcttacactg acccagttcg cactccctct ttattttcc    360 ttcacccaca ctcgatctct ctctctcctg ctctatatct ctctgtatat ctgtctctat    420
gtgtgtgtgg gtgtgtgtgt gtgtgtgtgt gtgcgtgctc tcacctcagc attcttgtgg    480
ggttttaatg tgcgcttcac ataccccttg tgaggcattt tactttgtgg ggtaattttt    540 caggaccccca cagagtaaag tctttcaaat gactgtatat tcggtgtcct atgctgcggg   600
gcattagaag tggtacccca taaatgactt tttgtgagcg tgtgctaaaa cttgcacact    660 ttttttatggg taacatcgta agcacaccgc cgggttgtta tcgccaggtt gtacatacccc  720
```

```
cactagtagg ggaccacaag gtatatctgg aacgcacaga aatacccac  aatcaggtgc       780 cccacaaagg ccctgatgtg agaatgcgtg tgtgcgcgtg tgtttgtgtg tgtgtctctc       840
tctctctctc tctctctcac tctctaagta tatctatctc cttccccatt ttctcttttcc      900 ccctctgaaa tattgataaa aagaatacat aatttgggtt ttctgttgta cgcagaaaaa       960
cccctaaatg tcgtattctt tcacaaatat tcgacttcga actcatttcc ttgcagaaat      1020
gtgtctctaa tcacatcctc ctaatacatt tatgatacaa ttttatttta gggaaaatgt      1080
tgtcgtcaaa atgtatgggg ctcccaacgc ttcaaagggg ctttaaagtt atcatatgaa      1140
tgtaacctaa accttctgaa ataatcatg  atattgggca ctgctgggat gatttta        1197
```

<210> SEQ ID NO 92
<211> LENGTH: 1002
<212> TYPE: DNA
<213> ORGANISM: Strongylocentrotus purpuratus

<400> SEQUENCE: 92

```
tcggatatcg tgacattaat ttatgatata tgatgacatt tttgcttcat attttgccgt        60
accggaagat agagatgtta acatggggat aaagatattg catcaagatt tgcacaagct       120
cttgttctaa tatccacctg cccccccccc caatctgctc ccctctcact ccctgtttat       180
ccttcttctt ctacttcttc ttcttctact tcttcttctt cttcttctac ttcttctttt       240
tcttcttcct cctcctattt ttcttcttct tcttctcctc cttcttcttc tttttcttct       300
tcttcttctt cttcttctcc ttcttcttct tcttcttctt cttcttcttc ttcttctttt       360
tcttaatcgt cttctccctt tccccttttgt acatatatcc ctttcgttat ccttcctctc      420
tctctcctcc gtttccatct acacctccct ctgtttctgt ttctgtatct cactcttttt       480
tcttacactg acccagtttg cactccctct ttatttttcc ttcacccaca ctctctctct       540
ctctctctct ctctcctgct ctatatctct ctgtatatat gtctctatgt gtgtgtgggt       600
gtgtgtgtgt gtgtgtgtgt gcgcgcgcgc gcgtgtgtgt gtgtgtgtgt gtctctctct       660
ctccctctca ctctctaagt atatttatct ccttcccat  tttctctttc cccctctcaa       720
atattgataa aagaatgca  taatttgggt tttctgttgt acgcagaaaa cctaaatgtc       780
gtattccttc acaaatattc gacttcgaac acattccttg ctgaaatgtg tctctaatca       840
catcctccta atacattatg atacaatttt atttaaggaa aatgttgtcg tcaaatgtat       900
ggggctccca acgcttcaaa ggggctttaa agttatcata tgaatgtaac ccaaaccttc       960
tgaattacgg tcatgatatt gggcactgct ggatgatttt ta                         1002
```

<210> SEQ ID NO 93
<211> LENGTH: 1197
<212> TYPE: DNA
<213> ORGANISM: Strongylocentrotus purpuratus

<400> SEQUENCE: 93

```
tcggatatcg tgacattaat tttataatat atcatgacat ttttgctgca tattttgcgg        60
taccggaaga tggtgatttt aacatgggga taaagatatt gcatcaagat tgcacaagc       120 tcttattcta atatccaccc ttgcccccccc ccccatctg  ctccctctc  actccctgtt      180 tctttcttcg tcgtcgttct tcttattcgt cttctccttt tccccttttgt acatatccct      240 ttctttatcc tctctctctc tctcccccc  gtttccatct acacctccct ctgtttctgt       300
ttctgtatct cactcttgtt tcttacactg acccagttcg cactccctct ttattttttcc      360
```

```
ttcacccaca ctcgatctct ctctctcctg ctctatatct ctctgtatat ctgtctctat    420
gtgtgtgtgg gtgtgtgtgt gtgtgtgtgt gtgcgtgctc tcacctcagc attcttgtgg    480
ggttttaatg tgcgcttcac atacccctttg tgaggcattt tactttgtgg ggtaattttt    540
caggacccca cagagtaaag tctttcaaat gactgtatat tcggtgtcct atgctgcggg    600
gcattagaag tggtacccca taaatgactt tttgtgagcg tgtgctaaaa cttgcacact    660
tttttatggg taacatcgta agcacaccgc cgggttgtta tcgccaggtt gtacataccc    720
cactagtagg ggaccacaag gtatatctgg aacgcacaga atacccac aatcaggtgc    780 cccacaaagg ccctgatgtg agaatgcgtg tgtgcgcgtg tgtttgtgtg tgtgtctctc    840
tctctctctc tctctctcac tctctaagta tatctatctc cttccccatt ttctctttcc    900
ccctctgaaa tattgataaa aagaatacat aatttgggtt ttctgttgta cgcagaaaaa    960
cccctaaatg tcgtattctt tcacaaatat tcgacttcga actcatttcc ttgcagaaat   1020
gtgtctctaa tcacatcctc ctaatacatt tatgatacaa tttatttta gggaaaatgt   1080 tgtcgtcaaa atgtatgggg ctcccaacgc ttcaaagggg cttaaagtt atcatatgaa   1140 tgtaacctaa accttctgaa aataatcatg atattgggca ctgctgggat gattta       1197

<210> SEQ ID NO 94
<211> LENGTH: 843
<212> TYPE: DNA
<213> ORGANISM: Strongylocentrotus purpuratus

<400> SEQUENCE: 94
tcggatatcg tgacattaat ttatgatata taatgacatt tttgcttcat attttgcggt     60
accggaagat ggtgatttta acatggggat aaagatattg catcaagatt tgcacaagct    120
cttgttctaa tatccacctt gccccccccc ccatctgctc ccctctcact ccctgtttct    180
tcttcgtcgt cttcttctta ttcgtcttct ccttttcccc tttgtacata tatcattttc    240
tttatcctct ctctctctcc ctcgtttcca tttacacctt cctctgtttc tgtttctgta    300
tctcactctt ttttcttaca ctgacccagt tcgcactccc tctttatttt tccttcacca    360
cactcgatct ctctctctct ctcctgctct atatctctct gtatatctgt ctctatgtgt    420
gtgtgggtgt gtgtgtgtgt gtgtgcgcgc gtgtgtgcgt gtgtgtgtgt gtgtgtgtgt    480
gtgtgcgcgc gtgtgtgtgc gtgtgtgtgt gtgtgtgtgt ctctctctct cactctctaa    540
gtatatcttt ccccctctca aatattgata aaaagaatac ataatttggg ttttctgttg    600
tacgcagaaa acctaaatgt cgtattcctt cacaaatatt cgacttcgaa cacattcctt    660
gcagaaatgt gtctctaatc acatcctcct aatacattat gatacaattt tatttaagga    720
aaatgttgtc gtcaaatgta tggggctccc aacgcttcaa aggggcttta aagttatcat    780
atgaatgtaa cctaaacctt ctgaattacg gtcatgatat tgggcactgc tgggatgatt    840
tta                                                                  843

<210> SEQ ID NO 95
<211> LENGTH: 1197
<212> TYPE: DNA
<213> ORGANISM: Strongylocentrotus purpuratus

<400> SEQUENCE: 95
tcggatatcg tgacattaat tttataatat atcatgacat ttttgctgca tattttgcgg     60
taccggaaga tggtgatttt aacatgggga taaagatatt gcatcaagat ttgcacaagc    120
tcttattcta atatccaccc ttgccccccc ccccccatctg ctccctctc actccctgtt    180
```

```
tctttcttcg tcgtcgttct tcttattcgt cttctccttt tccccttttgt acatatccct      240 ttctttatcc tctctctctc tctctccccc gtttccatct acacctccct ctgtttctgt      300
ttctgtatct cactcttgtt tcttacactg acccagttcg cactccctct ttatttttcc      360
ttcacccaca ctcgatctct ctctctcctg ctctatatct ctctgtatat ctgtctctat      420
gtgtgtgtgg gtgtgtgtgt gtgtgtgtgt gtgcgtgctc tcacctcagc attcttgtgg      480
ggttttaatg tgcgcttcac ataccccttg tgaggcattt tactttgtgg ggtaattttt      540 caggaccccca cagagtaaag tctttcaaat gactgtatat tcggtgtcct atgctgcggg     600
gcattagaag tggtaccccca taaatgactt tttgtgagcg tgtgctaaaa cttgcacact     660 ttttttatggg taacatcgta agcacaccgc cgggttgtta tcgccaggtt gtacatacccc    720 cactagtagg ggaccacaag gtatatctgg aacgcacaga aataccccac aatcaggtgc     780 ccccacaaagg ccctgatgtg agaatgcgtg tgtgcgcgtg tgtttgtgtg tgtgtctctc     840
tctctctctc tctctctcac tctctaagta tatctatctc cttccccatt ttctctttcc      900
ccctctgaaa tattgataaa aagaatacat aatttgggtt ttctgttgta cgcagaaaaa     960 ccccctaaaatg tcgtattctt tcacaaatat tcgacttcga actcatttcc ttgcagaaat    1020
gtgtctctaa tcacatcctc ctaatacatt tatgatacaa ttttatttta gggaaaatgt     1080
tgtcgtcaaa atgtatgggg ctcccaacgc ttcaaagggg ctttaaagtt atcatatgaa     1140
tgtaacctaa accttctgaa aataatcatg atattgggca ctgctgggat gattttta       1197
```

<210> SEQ ID NO 96
<211> LENGTH: 951
<212> TYPE: DNA
<213> ORGANISM: Strongylocentrotus purpuratus

<400> SEQUENCE: 96

```
tcggatatcg tgacattaat ttatgatata tgatgacatt tttgcttcat atttcgcggt       60
accggaaaat actagtagtg attttaacat gggaataaag atattgcatc aagatttgca      120
cgagctcttg tttcaatatc cactttgccc ccccccccc catctgctcc cctctcactc       180
cctgtttatc cttcttcttc tacttcttct ttttcttctt cctcctccta ttttttcttct    240 tcttcttctt ctcctccttc ttcttcttct tcttcttctt cttcttcttc ttcttcttct      300
tcttcttctt aatcgtcttc tcccttcccc cttgtacat atatccctt cttttatccta      360 tctcccccc ccccgtttc catctacacc tccctctgtt tctgtttctg tatctcactc       420
ttttttctta cactgaccca gttcgcactc cctctttatt tttccttcac ccacactcga     480
tctctctctc tcctgctcta tatctctctg tatatctgtc tctatgtgtg tgtgggtgtg     540
tgtgcgtgtg tgcgtgtgtg tgtgtgtgcg cgcgcgcgtg tgtttgtgtg tgtgtgtgtg     600
tctctctctc tccctctcac tctctaagta tatttatctc cttccccatt ttctctttcc     660
ccctctcaaa tattgataaa aagaatacat aatttgggtt ttctgttgta cgcagaaaac     720
ctaaatgtcg tattccttca caaatattcg acttcgaaca cattccttgc agaaatgtgt     780
ctctaatcac atcctcctaa tacattatga tacaatttta tttaaggaaa atgttgtcgt     840
caaatgtatg gggctcccaa cgcttcaaag gggctttaaa gttatcatat gaatgtaacc     900
taaaccttct gaattacggt catgatattg ggcactgctg ggatgatttt a              951
```